United States Patent
Ehrich et al.

(10) Patent No.: US 10,738,358 B2
(45) Date of Patent: Aug. 11, 2020

(54) PROCESSES AND COMPOSITIONS FOR METHYLATION-BASED ENRICHMENT OF FETAL NUCLEIC ACID FROM A MATERNAL SAMPLE USEFUL FOR NON-INVASIVE PRENATAL DIAGNOSES

(71) Applicant: Sequenom, Inc., San Diego, CA (US)

(72) Inventors: Mathias Ehrich, San Diego, CA (US); Anders Olof Herman Nygren, San Diego, CA (US)

(73) Assignee: Sequenom, Inc., San Diego, CA (US)

(*) Notice: Subject to any disclaimer, the term of this patent is extended or adjusted under 35 U.S.C. 154(b) by 282 days.

(21) Appl. No.: 14/735,477

(22) Filed: Jun. 10, 2015

(65) Prior Publication Data

US 2015/0275304 A1 Oct. 1, 2015

Related U.S. Application Data

(63) Continuation of application No. 13/801,384, filed on Mar. 13, 2013, now abandoned, which is a continuation of application No. 12/561,241, filed on Sep. 16, 2009, now Pat. No. 8,476,013.

(60) Provisional application No. 61/192,264, filed on Sep. 16, 2008.

(51) Int. Cl.
| | | |
|---|---|---|
| *C12Q 1/68* | (2018.01) | |
| *C12Q 1/6883* | (2018.01) | |
| *C12Q 1/6804* | (2018.01) | |
| *C12Q 1/6809* | (2018.01) | |
| *C12Q 1/6888* | (2018.01) | |
| *C12Q 1/6806* | (2018.01) | |
| *C12Q 1/6879* | (2018.01) | |
| *G01N 33/53* | (2006.01) | |

(52) U.S. Cl.
CPC ......... *C12Q 1/6883* (2013.01); *C12Q 1/6804* (2013.01); *C12Q 1/6806* (2013.01); *C12Q 1/6809* (2013.01); *C12Q 1/6879* (2013.01); *C12Q 1/6888* (2013.01); *G01N 33/5308* (2013.01); *C12Q 2600/154* (2013.01); *G01N 2800/385* (2013.01)

(58) Field of Classification Search
None
See application file for complete search history.

(56) References Cited

U.S. PATENT DOCUMENTS

| | | |
|---|---|---|
| 4,109,496 A | 8/1978 | Allemann et al. |
| 4,179,337 A | 12/1979 | Davis et al. |
| 4,458,066 A | 7/1984 | Caruthers et al. |
| 4,469,863 A | 9/1984 | Ts'o et al. |
| 4,522,811 A | 6/1985 | Eppstein et al. |
| 4,656,127 A | 4/1987 | Mundy |
| 4,676,980 A | 6/1987 | Segal et al. |
| 4,683,195 A | 7/1987 | Mullis et al. |
| 4,683,202 A | 7/1987 | Mullis |
| 4,851,331 A | 7/1989 | Vary et al. |
| 4,868,103 A | 9/1989 | Stavrianopoulos et al. |
| 4,873,316 A | 10/1989 | Meade et al. |
| 4,965,188 A | 10/1990 | Mullis et al. |
| 5,048,530 A | 9/1991 | Hurwitz |
| 5,075,212 A | 12/1991 | Rotbart |
| 5,118,937 A | 6/1992 | Hillenkamp et al. |
| 5,210,015 A | 5/1993 | Gelfand et al. |
| 5,272,071 A | 12/1993 | Chappel et al. |
| 5,283,317 A | 2/1994 | Saifer et al. |
| 5,487,972 A | 1/1996 | Gelfand et al. |
| 5,492,806 A | 2/1996 | Drmanac et al. |
| 5,525,464 A | 6/1996 | Drmanac et al. |
| 5,536,821 A | 7/1996 | Agrawal et al. |
| 5,541,306 A | 7/1996 | Agrawal et al. |
| 5,547,835 A | 8/1996 | Koster |
| 5,589,330 A | 12/1996 | Shuber |
| 5,605,798 A | 2/1997 | Koster |
| 5,614,622 A | 2/1997 | Iyer et al. |
| 5,631,169 A | 5/1997 | Lakowicz et al. |
| 5,637,683 A | 6/1997 | Usher et al. |
| 5,637,684 A | 6/1997 | Cook |
| 5,656,493 A | 8/1997 | Mullis et al. |
| 5,679,524 A | 10/1997 | Nikiforov et al. |
| 5,691,141 A | 11/1997 | Koster |
| 5,695,940 A | 12/1997 | Drmanac et al. |
| 5,700,922 A | 12/1997 | Cook |
| 5,717,083 A | 2/1998 | Cook et al. |
| 5,719,262 A | 2/1998 | Buchardt et al. |
| 5,720,928 A | 2/1998 | Schwartz |
| 5,739,308 A | 4/1998 | Kandimalla et al. |
| 5,739,314 A | 4/1998 | Roy et al. |
| 5,766,849 A | 6/1998 | McDonough et al. |
| 5,773,601 A | 6/1998 | Agrawal |
| 5,786,146 A | 7/1998 | Herman et al. |
| 5,834,189 A | 11/1998 | Stevens et al. |
| 5,849,483 A | 12/1998 | Shuber |
| 5,849,497 A | 12/1998 | Steinman |
| 5,849,542 A | 12/1998 | Reeve et al. |
| 5,849,546 A | 12/1998 | Sousa et al. |
| 5,851,770 A | 12/1998 | Babon et al. |

(Continued)

FOREIGN PATENT DOCUMENTS

| | | |
|---|---|---|
| AU | 2009293232 B2 | 9/2015 |
| AU | 2010295968 B2 | 12/2015 |

(Continued)

OTHER PUBLICATIONS

Adinolfi et al., "Rapid detection of aneuploidies by microsatellite and the quantitative fluorescent polymerase chain reaction." Prenat Diagn. Dec. 1997;17(13):1299-311.

(Continued)

*Primary Examiner* — Jehanne S Sitton
(74) *Attorney, Agent, or Firm* — Kilpatrick Townsend & Stockton LLP

(57) ABSTRACT

Provided are compositions and processes that utilize genomic regions differentially methylated between a mother and her fetus to separate, isolate or enrich fetal nucleic acid from a maternal sample. The compositions and processes described herein are useful for non-invasive prenatal diagnostics, including the detection of chromosomal aneuploidies.

9 Claims, 32 Drawing Sheets

Specification includes a Sequence Listing.

(56) References Cited

U.S. PATENT DOCUMENTS

| | | |
|---|---|---|
| 5,869,242 A | 2/1999 | Kamb |
| 5,876,934 A | 3/1999 | Duthie et al. |
| 5,886,165 A | 3/1999 | Kandimalla et al. |
| 5,891,625 A | 4/1999 | Buchardt et al. |
| 5,908,755 A | 6/1999 | Kumar et al. |
| 5,912,118 A | 6/1999 | Ansorge et al. |
| 5,928,906 A | 7/1999 | Koster et al. |
| 5,929,226 A | 7/1999 | Padmapriya et al. |
| 5,952,174 A | 9/1999 | Nikiforov et al. |
| 5,955,599 A | 9/1999 | Iyer et al. |
| 5,958,692 A | 9/1999 | Cotton et al. |
| 5,962,674 A | 10/1999 | Iyer et al. |
| 5,976,802 A | 11/1999 | Ansorge et al. |
| 5,977,296 A | 11/1999 | Nielsen et al. |
| 5,981,186 A | 11/1999 | Gabe et al. |
| 5,998,143 A | 12/1999 | Ellis et al. |
| 6,004,744 A | 12/1999 | Goelet et al. |
| 6,013,431 A | 1/2000 | Soderlund et al. |
| 6,013,499 A | 1/2000 | Narumiya et al. |
| 6,017,702 A | 1/2000 | Lee et al. |
| 6,018,041 A | 1/2000 | Drmanac et al. |
| 6,024,925 A | 2/2000 | Little et al. |
| 6,043,031 A | 3/2000 | Koster et al. |
| 6,045,996 A | 4/2000 | Cronin et al. |
| 6,046,005 A | 4/2000 | Ju et al. |
| 6,057,134 A | 5/2000 | Lader et al. |
| 6,057,143 A | 5/2000 | Lader et al. |
| 6,087,095 A | 7/2000 | Rosenthal et al. |
| 6,107,037 A | 8/2000 | Sousa et al. |
| 6,110,684 A | 8/2000 | Kemper et al. |
| 6,117,992 A | 9/2000 | Iyer |
| 6,136,541 A | 10/2000 | Gulati |
| 6,140,053 A | 10/2000 | Koster |
| 6,140,054 A | 10/2000 | Wittwer et al. |
| 6,140,482 A | 10/2000 | Iyer et al. |
| 6,142,681 A | 11/2000 | Gulati |
| 6,143,496 A | 11/2000 | Brown et al. |
| 6,156,501 A | 12/2000 | McGall et al. |
| 6,183,958 B1 | 2/2001 | Stanton, Jr. |
| 6,194,144 B1 | 2/2001 | Koster |
| 6,194,180 B1 | 2/2001 | Joyce |
| 6,197,506 B1 | 3/2001 | Fodor et al. |
| 6,210,574 B1 | 4/2001 | Sammons et al. |
| 6,210,891 B1 | 4/2001 | Nyren et al. |
| 6,214,556 B1 | 4/2001 | Olek et al. |
| 6,214,560 B1 | 4/2001 | Yguerabide et al. |
| 6,223,127 B1 | 4/2001 | Berno |
| 6,225,625 B1 | 5/2001 | Pirrung et al. |
| 6,229,911 B1 | 5/2001 | Balaban et al. |
| 6,239,273 B1 | 5/2001 | Pease et al. |
| 6,251,638 B1 | 6/2001 | Umansky et al. |
| 6,258,538 B1 | 7/2001 | Koster et al. |
| 6,258,540 B1 | 7/2001 | Lo et al. |
| 6,297,028 B1 | 10/2001 | Taniguchi et al. |
| 6,326,174 B1 | 12/2001 | Joyce et al. |
| 6,368,834 B1 | 4/2002 | Senapathy et al. |
| 6,440,706 B1 | 8/2002 | Vogelstein et al. |
| 6,468,748 B1 | 10/2002 | Monforte et al. |
| 6,610,492 B1 | 8/2003 | Stanton, Jr. et al. |
| 6,664,056 B2 | 12/2003 | Lo et al. |
| 6,723,513 B2 | 4/2004 | Lexow |
| 6,759,217 B2 | 7/2004 | Kopreski |
| 6,818,394 B1 | 11/2004 | O'Donnell-Maloney et al. |
| 6,884,586 B2 | 4/2005 | Van Ness et al. |
| 6,916,634 B2 | 7/2005 | Kopreski |
| 6,927,028 B2 | 8/2005 | Dennis et al. |
| 6,929,911 B2 | 8/2005 | Oefner et al. |
| 7,081,339 B2 | 7/2006 | Slepnev |
| 7,169,314 B2 | 1/2007 | Unger et al. |
| 7,244,567 B2 | 7/2007 | Chen et al. |
| 7,253,259 B2 | 8/2007 | Otagiri et al. |
| 7,285,422 B1 | 10/2007 | Little et al. |
| 7,468,249 B2 | 12/2008 | Xie et al. |
| 7,655,399 B2 | 2/2010 | Cantor et al. |
| 7,709,194 B2 | 5/2010 | Lo et al. |
| 7,709,262 B2 | 5/2010 | Cantor et al. |
| 7,754,428 B2 | 7/2010 | Lo et al. |
| 7,785,798 B2 | 8/2010 | Cantor et al. |
| 7,901,884 B2 | 3/2011 | Lo et al. |
| 8,195,415 B2 | 6/2012 | Fan et al. |
| 8,476,013 B2 | 7/2013 | Ehrich et al. |
| 8,962,247 B2 | 2/2015 | Ehrich et al. |
| 9,074,013 B2 | 7/2015 | Rehli |
| 9,249,464 B2 | 2/2016 | Rehli |
| 9,926,593 B2 | 3/2018 | Ehrich et al. |
| 2001/0008615 A1 | 7/2001 | Little et al. |
| 2001/0051341 A1 | 12/2001 | Lo et al. |
| 2002/0006621 A1 | 1/2002 | Bianchi |
| 2003/0022207 A1 | 1/2003 | Balasubramanian et al. |
| 2003/0082600 A1 | 5/2003 | Olek et al. |
| 2003/0087276 A1 | 5/2003 | Kopreski |
| 2003/0096426 A1 | 5/2003 | Little et al. |
| 2003/0180748 A1 | 9/2003 | Braun et al. |
| 2003/0180779 A1 | 9/2003 | Lofton-Day et al. |
| 2003/0211483 A1 | 11/2003 | Schroeder et al. |
| 2003/0211522 A1 | 11/2003 | Landes et al. |
| 2004/0014105 A1 | 1/2004 | Schroeder et al. |
| 2004/0081993 A1 | 4/2004 | Cantor et al. |
| 2004/0115684 A1 | 6/2004 | Costa |
| 2004/0137470 A1 | 7/2004 | Dhallan |
| 2004/0203037 A1 | 10/2004 | Lo et al. |
| 2005/0037388 A1 | 2/2005 | Antonarakis et al. |
| 2005/0059003 A1 | 3/2005 | Enoki et al. |
| 2005/0064406 A1 | 3/2005 | Zabarovsky et al. |
| 2005/0064428 A1 | 3/2005 | Berlin |
| 2005/0069879 A1 | 3/2005 | Berlin |
| 2005/0079521 A1 | 4/2005 | Beaulieu et al. |
| 2005/0112590 A1 | 5/2005 | Van Den Boom et al. |
| 2005/0009059 A1 | 7/2005 | Shapero et al. |
| 2005/0019762 A1 | 7/2005 | Olek |
| 2005/0153316 A1 | 7/2005 | Jeddeloh et al. |
| 2005/0153347 A1 | 7/2005 | Shapero et al. |
| 2005/0164241 A1 | 7/2005 | Hahn et al. |
| 2005/0266473 A1 | 12/2005 | Zhang et al. |
| 2005/0272070 A1 | 12/2005 | Ehrich et al. |
| 2005/0287592 A1 | 12/2005 | Kless |
| 2006/0019278 A1 | 1/2006 | Lo et al. |
| 2006/0094039 A1 | 5/2006 | Rosenfeld et al. |
| 2006/0136142 A1 | 7/2006 | Berlin et al. |
| 2006/0160105 A1 | 7/2006 | Dhallan |
| 2006/0166228 A1 | 7/2006 | Page et al. |
| 2006/0210992 A1 | 9/2006 | van den Boom |
| 2006/0252068 A1 | 11/2006 | Lo et al. |
| 2006/0252071 A1 | 11/2006 | Lo et al. |
| 2007/0048755 A1 | 3/2007 | De Fiore |
| 2007/0059707 A1 | 3/2007 | Cantor et al. |
| 2007/0065823 A1 | 3/2007 | Dressman et al. |
| 2007/0111233 A1 | 5/2007 | Bianchi et al. |
| 2007/0202525 A1 | 8/2007 | Quake et al. |
| 2007/0207466 A1 | 9/2007 | Cantor et al. |
| 2007/0212689 A1 | 9/2007 | Bianchi et al. |
| 2007/0243549 A1 | 10/2007 | Bischoff |
| 2007/0275402 A1 | 11/2007 | Lo et al. |
| 2008/0020390 A1 | 1/2008 | Mitchell et al. |
| 2008/0070792 A1 | 3/2008 | Stoughton et al. |
| 2008/0096766 A1 | 4/2008 | Lee |
| 2008/0299562 A1 | 12/2008 | Oeth |
| 2008/0305479 A1 | 12/2008 | Van Den Boom |
| 2009/0026082 A1 | 1/2009 | Rothberg et al. |
| 2009/0029377 A1 | 1/2009 | Lo et al. |
| 2009/0061425 A1 | 3/2009 | Lo et al. |
| 2009/0111712 A1 | 5/2009 | Van Den Boom |
| 2009/0142755 A1 | 6/2009 | Albitar |
| 2009/0202984 A1 | 8/2009 | Cantor |
| 2009/0317817 A1 | 12/2009 | Oeth et al. |
| 2009/0317818 A1 | 12/2009 | Ehrich et al. |
| 2010/0105049 A1 | 4/2010 | Ehrich et al. |
| 2010/0184046 A1 | 7/2010 | Klass et al. |
| 2010/0203529 A1 | 8/2010 | Kuslich et al. |
| 2010/0216153 A1 | 8/2010 | Lapidus et al. |
| 2010/0227320 A1 | 9/2010 | Fu |
| 2010/0240054 A1 | 9/2010 | Bischoff |
| 2010/0273165 A1 | 10/2010 | Ehrich et al. |
| 2010/0279295 A1 | 11/2010 | Roy et al. |

(56) References Cited

U.S. PATENT DOCUMENTS

| | | |
|---|---|---|
| 2011/0033851 A1 | 2/2011 | Rand |
| 2011/0039724 A1 | 2/2011 | Lo et al. |
| 2011/0105353 A1 | 5/2011 | Lo et al. |
| 2011/0151460 A1 | 6/2011 | Klass et al. |
| 2011/0177517 A1 | 7/2011 | Rava et al. |
| 2011/0178719 A1 | 7/2011 | Rabinowirz et al. |
| 2011/0201507 A1 | 8/2011 | Rava et al. |
| 2011/0212846 A1 | 9/2011 | Spier |
| 2011/0224087 A1 | 9/2011 | Quake et al. |
| 2011/0244451 A1 | 10/2011 | Cantor et al. |
| 2011/0276277 A1 | 11/2011 | Lo et al. |
| 2011/0288780 A1 | 11/2011 | Rabinowirz et al. |
| 2012/0065076 A1 | 3/2012 | Peters et al. |
| 2012/0184449 A1 | 7/2012 | Hixson et al. |
| 2012/0264618 A1 | 10/2012 | Nygren |
| 2012/0276542 A1 | 11/2012 | Nygren |
| 2012/0277119 A1 | 11/2012 | Ehrich et al. |
| 2012/0282613 A1 | 11/2012 | Patsalis et al. |
| 2013/0012399 A1 | 1/2013 | Myers et al. |
| 2013/0085681 A1 | 4/2013 | Deciu et al. |
| 2013/0130923 A1 | 5/2013 | Ehrich et al. |
| 2013/0143211 A1 | 6/2013 | Ehrich et al. |
| 2013/0150249 A1 | 6/2013 | Ehrich et al. |
| 2013/0230858 A1 | 9/2013 | Cantor et al. |
| 2013/0295564 A1 | 11/2013 | Ehrich et al. |
| 2013/0296180 A1 | 11/2013 | Ehrich et al. |
| 2013/0310260 A1 | 11/2013 | Kim et al. |
| 2015/0267263 A1 | 9/2015 | Rehli |
| 2015/0275304 A1 | 10/2015 | Ehrich et al. |
| 2016/0145685 A1 | 5/2016 | Jensen et al. |
| 2016/0201113 A1 | 7/2016 | Rehli |
| 2017/0058350 A1 | 3/2017 | Tynan et al. |
| 2017/0314071 A1 | 11/2017 | Ehrich et al. |

FOREIGN PATENT DOCUMENTS

| | | |
|---|---|---|
| AU | 2015252141 A1 | 12/2015 |
| AU | 2013290102 B2 | 2/2019 |
| CA | 2737200 A1 | 3/2010 |
| CA | 2774342 C | 1/2019 |
| EP | 0264166 | 4/1988 |
| EP | 0401384 | 12/1990 |
| EP | 1373561 | 2/2009 |
| EP | 1524321 | 4/2009 |
| EP | 2271772 B1 | 7/2014 |
| EP | 2872648 A1 | 5/2015 |
| EP | 2329021 B1 | 8/2016 |
| EP | 3103871 A1 | 12/2016 |
| EP | 2478119 B1 | 7/2017 |
| EP | 3330382 A1 | 6/2018 |
| JP | 2005-514956 | 5/2005 |
| JP | 2006-508632 A | 3/2006 |
| JP | 2007-505641 | 3/2007 |
| JP | 2007508017 A | 4/2007 |
| JP | 2008-521389 | 6/2008 |
| JP | 2008518639 A | 6/2008 |
| JP | 2009-529330 | 8/2009 |
| JP | 2010-534068 A | 11/2010 |
| JP | 5727375 | 6/2015 |
| JP | 2015-126748 | 7/2015 |
| JP | 5873434 | 3/2016 |
| JP | 5923571 | 5/2016 |
| JP | 6039034 B2 | 12/2016 |
| JP | 2017000165 A | 1/2017 |
| JP | 6447765 B1 | 3/2018 |
| JP | 6513622 B2 | 5/2019 |
| WO | WO 91/006667 | 5/1991 |
| WO | WO 94/010300 | 5/1994 |
| WO | WO 97/012058 | 4/1997 |
| WO | WO 97/035589 | 10/1997 |
| WO | WO 97/037041 | 10/1997 |
| WO | WO 98/020020 | 5/1998 |
| WO | WO 98/022489 | 5/1998 |
| WO | WO 98/039352 | 9/1998 |
| WO | WO 98/039474 | 9/1998 |
| WO | WO 98/054364 | 12/1998 |
| WO | WO 99/057318 | 5/1999 |
| WO | WO 00/052625 | 9/2000 |
| WO | WO 00/056746 | 9/2000 |
| WO | WO 00/066771 | 11/2000 |
| WO | WO 00/075372 | 12/2000 |
| WO | WO 01/014398 | 3/2001 |
| WO | WO 01/020039 | 3/2001 |
| WO | WO 01/025485 | 4/2001 |
| WO | WO 01/027326 | 4/2001 |
| WO | WO 01/027327 | 4/2001 |
| WO | WO 01/027329 | 4/2001 |
| WO | WO 01/029259 | 4/2001 |
| WO | WO 02/018616 | 3/2002 |
| WO | WO 02/086163 | 10/2002 |
| WO | WO 03/000919 | 1/2003 |
| WO | WO 2003/020974 | 3/2003 |
| WO | WO 03/057909 | 7/2003 |
| WO | WO 03/062441 | 7/2003 |
| WO | 03/074723 A2 | 9/2003 |
| WO | WO 03/080863 | 10/2003 |
| WO | WO 04/013284 | 2/2004 |
| WO | WO 04/076653 | 9/2004 |
| WO | WO 04/079011 | 9/2004 |
| WO | WO 2004/078999 | 9/2004 |
| WO | WO 05/012578 | 2/2005 |
| WO | WO 05/021793 | 3/2005 |
| WO | WO 05/023091 | 3/2005 |
| WO | WO 05/035725 | 4/2005 |
| WO | WO 05/040399 | 5/2005 |
| WO | WO 05/098050 | 10/2005 |
| WO | WO 2005/118852 | 12/2005 |
| WO | WO 06/056480 | 6/2006 |
| WO | WO 06/097049 | 9/2006 |
| WO | WO 06/097051 | 9/2006 |
| WO | WO 07/016668 | 2/2007 |
| WO | WO 07/028155 | 3/2007 |
| WO | WO 07/092473 | 8/2007 |
| WO | WO 07/100911 | 9/2007 |
| WO | WO 07/121276 | 10/2007 |
| WO | WO 07/132166 | 11/2007 |
| WO | WO 07/132167 | 11/2007 |
| WO | WO 07/140417 | 12/2007 |
| WO | WO 07/147063 | 12/2007 |
| WO | WO 08/098142 | 8/2008 |
| WO | WO 08/103761 | 8/2008 |
| WO | WO 08/103763 | 8/2008 |
| WO | WO 08/118988 | 10/2008 |
| WO | WO 08/157264 | 12/2008 |
| WO | WO 09/032779 | 3/2009 |
| WO | WO 09/032781 | 3/2009 |
| WO | WO 09/039507 | 3/2009 |
| WO | WO 2009/030100 | 3/2009 |
| WO | WO 09/046445 | 4/2009 |
| WO | WO 09/091934 | 7/2009 |
| WO | WO 09/114543 | 9/2009 |
| WO | WO 10/004265 | 1/2010 |
| WO | WO 10/033639 | 3/2010 |
| WO | WO 10/065470 | 6/2010 |
| WO | WO 10/115016 | 10/2010 |
| WO | WO 2011/018600 | 2/2011 |
| WO | WO 11/034631 | 3/2011 |
| WO | 2011/054936 A1 | 5/2011 |
| WO | 2011/057094 A1 | 5/2011 |
| WO | WO 11/087760 | 7/2011 |
| WO | WO 11/091063 | 7/2011 |
| WO | WO 11/092592 | 8/2011 |
| WO | WO 11/142836 | 11/2011 |
| WO | WO 11/143659 | 11/2011 |
| WO | 2012/012703 A2 | 1/2012 |
| WO | WO 12/118745 | 9/2012 |
| WO | WO 12/149339 | 11/2012 |
| WO | WO 13/052913 | 4/2013 |
| WO | WO 13/055817 | 4/2013 |
| WO | 2013176958 A1 | 11/2013 |
| WO | 2013177086 A1 | 11/2013 |
| WO | WO 14/011928 | 1/2014 |

(56) References Cited

FOREIGN PATENT DOCUMENTS

| | | |
|---|---|---|
| WO | WO 14/168711 | 10/2014 |
| WO | WO 15/138774 | 9/2015 |
| WO | 2017045654 A1 | 3/2017 |

OTHER PUBLICATIONS

Agresti, Categorical Data Analysis, 2nd Ed. 2002. Wiley.
Altschul et al., "Basic local alignment search tool." J Mol Biol. Oct. 5, 1990;215(3):403-10.
Altschul et al., "Gapped BLAST and PSI-BLAST: a new generation of protein database search programs." Nucleic Acids Res. Sep. 1, 1997;25(17):3389-402.
Amicucci et al., Clin. Chem. 46:301-302, 2000.
Amir et al., Nature Genet. 23:185-88 (1999).
Anantha et al., "Porphyrin binding to quadrupled T4G4." Biochemistry. Mar. 3, 1998;37(9):2709-14.
Anders et al., Clin Chem, Oct. 2010, 56(10):1627-1635, Epub Aug. 20, 2010.
Anderson, S., "Shotgun DNA sequencing using cloned Dnase I-generated fragments," Nucl. Acids Res. 9:3015-3027 (1981).
Antonarakis et al., Am J Hum Genet. Mar. 1992;50(3):544-50.
Antonarakis et al., Nat Genet. Feb. 1993;3(2):146-50.
Aoki E. et al., "Methylation status of the p15INK4B gene in hematopoietic progenitors and peripheral blood cells in myelodysplastic syndromes", Leukemia 14(4):586-593 (2000).
Armour et al., "Measurement of locus copy number by hybridisation with amplifiable probes." Nucleic Acids Res. Jan. 15, 2000;28(2):605-9.
Armour et al., "The detection of large deletions or duplications in genomic DNA." Hum Mutat. Nov. 2002;20(5):325-37.
Asimakopoulos FA et al., "ABL 1 methylation is a distinct molecular event associated with clonal evolution of chronic myeloid leukemia" Blood 94(7):2452-2460 (1999.
Aston et al. (1999) Methods Enzymol. 303:55-73.
Aston et al. (1999) Trends Biotechnol. 17(7):297-302.
Ausubel et al., Current Protocols in Molecular Biology (Ausubel et al., eds., 1994).
Banerji et al., "A lymphocyte-specific cellular enhancer is located downstream of the joining region in immunoglobulin heavy chain genes." Cell. Jul. 1983;33(3):729-40.
Bartel et al., Biotechniques 14: 920-924 (1993).
Batey et al. (1992) Nucl. Acids Res. 20, 4515-4523.
Batey et al. (1996) Nucl. Acids Res. 24, 4836-4837.
Batzer et al., Nucleic Acid Res. 19:5081 (1991).
Beaucage & Caruthers, Tetrahedron Lett. 22: 1859-1862 (1981).
Beaudet, "Progress toward noninvasive prenatal diagnosis" Clin. Chem. (2011) 57(6):802-804.
Beckman Coulter, Introduction to Capillary Electrophoresis, Beckman Coulter 1991.
Benson G. Tandem repeats finder: a program to analyze DNA sequences. Nucleic Acids Res. Jan. 15, 1999;27(2):573-80.
Bianchi, 'Fetal cells in the mother: from genetic diagnosis to diseases associated with fetal cell microchimerism', In: European Journal of Obstetrics & Gynecology and Reproductive Biology, Sep. 2000, vol. 92(I), pp. 103-108.
Bock et al., "CpG island methylation in human lymphocytes is highly correlated with DNA sequence, repeats, and predicted DNA structure" PLOS Genetics (2006) 2(3):e26.
Boguski et al., "Identification of a cytidine-specific ribonuclease from chicken liver." J Biol Chem. Mar. 10, 1980;255(5):2160-3.
Boom et al. (1990), J. Clin. Microbiol. 28: 495-503.
Boom et al. (1991), J. Clin. Microbiol. 29: 1804-1811.
Boyer, L.A. et al. Polycomb complexes repress developmental regulators in murine embryonic stem cells. Nature 441, 349-53 (2006).
Braslaysky et al., "Sequence information can be obtained from single DNA molecules." Proc Natl Acad Sci U S A. Apr. 1, 2003;100(7):3960-4. Epub Mar. 21, 2003.

Brizot et al., "Maternal serum hCG and fetal nuchal translucency thickness for the prediction of fetal trisomies in the first trimester of pregnancy." Br J Obstet Gynaecol. Feb. 1995;102(2):127-32.
Bullinger et al., "Use of gene-expression profiling to identify prognostic subclasses in adult acute myeloid leukemia." N Engl J Med. Apr. 15, 2004;350(16):1605-16.
Burlingame et al. Anal. Chem. 70:647R-716R (1998).
Burnier et al., "Cell-derived microparticles in haemostasis and vascular medicine," Thromb Haemost 2009, 101:439-451.
Byrne et al., "Multiplex gene regulation: a two-tiered approach to transgene regulation in transgenic mice." Proc Natl Acad Sci U S A. Jul. 1989;86(14):5473-7.
Calame et al., "Transcriptional controlling elements in the immunoglobulin and T cell receptor loci." Adv Immunol. 1988;43:235-75.
Caliper LifeSciences, Products and Contract Services, LabChip GX 2010, printed from the internet on Mar. 15, 2011 (http://www.caliperl.com/products/labchip-gx.htm).
Camper et al., "Postnatal repression of the alpha-fetoprotein gene is enhancer independent." Genes Dev. Apr. 1989;3(4):537-46.
Cell Death Detection ELISA PLUS Cat. No. 11 774 425 001 "Detection of Post-translational Modifications on Native Intact Nucleosomes by ELISA," Version 11.0, Roche, Content Version: Sep. 2010, pp. 1-19.
Chan et al. (2004) Clin. Chem. 50:88-92.
Chan et al., "Hypermethylated RASSFIA in Maternal Plasma: A Universal Fetal DNA Marker that Improves the Reliability of Noninvasive Prenatal Diagnosis" Clin. Chem. (2006) 52:2211-2218.
Chan et al., Oncogene 22:924-934 (2003.
Chang et al., "LIBSVM: a library for Support Vector Machines," 2001.
Chen et al., "Fluorescence energy transfer detection as a homogeneous DNA diagnostic method." Proc Natl Acad Sci U S A. Sep. 30, 1997;94(20):10756-61.
Chen et al., "Template-directed dye-terminator incorporation (TDI) assay: a homogeneous DNA diagnostic method based on fluorescence resonance energy transfer." Nucleic Acids Res. Jan. 15, 1997;25(2):347-53.
Cheson et al, "Report of the National Cancer Institute-sponsored workshop on definitions of diagnosis and response in acute myeloid leukemia" J Clin Oncol 8:813-819, 1990.
Cheung et al. (1994) J. Clin. Microbiol. 32: 2593-2597.
Chirgwin et al. (1979) Biochem. 18: 5294-5299.
Chitty, L. Br Med Bull 54:839-856 (1998).
Chiu et al., "Effects of blood-processing protocols on fetal and total DNA quantification in maternal plasma." Clin Chem. Sep. 2001;47(9):1607-1613.
Chiu et al., Lancet 360:998-1000, 2002.
Chomczynski and Mackey (1995, Anal. Biochem. 225: 163-164).
Chomczynski and Mackey (1995, Biotechniques 19: 942-945).
Chomczynski and Sacchi (1987, Analytical Biochem. 162: 156-159).
Chomczynski, (1993, Biotech. 15: 532-537).
Chow, K.C., et al., Mass Spectrometric detection of a SNP panel as an internal positive control for fetal DNA analysis in maternal plasma. Clin. Chem. 53, 141-142 (2007).
Chu et al, "A novel approach toward the challenge of accurately quantifying fetal DNA in maternal plasma," Prenatal Diagnosis, 2010; 30:1226-1229.
Colella et al. Biotechniques. Jul. 2003;35(1):146-50.
Costa et al., N. Engl. J. Med. 346:1502, 2002.
Costello et al., Restriction Landmark Genomic Scanning (RLGS): Analysis of CpG Islands in genomes by 2D Gel Electrophoresis, Methods in Molecular Biology, DNA Methylation, 2 Methods and Protocols, v.: 507, 2nd eds., pp. 131-148 (2000).
Cross et al., "Purification of CpG islands using a methylated DNA binding column" Nature Genetics (1994) 6(3):236-244.
Cruikshank et al., "A lipidated anti-Tat antibody enters living cells and blocks HIV-1 viral replication." J. Acquired Immune Deficiency Syndromes and Human Retrovirology Mar. 1, 1997;14(3):193-203.
Current Protocols in Molecular Biology, John Wiley & Sons, N.Y., 6.3.1-6.3.6 (1989).

(56) References Cited

OTHER PUBLICATIONS

Dai et al., "Detection of Post-translational Modifications on Native Intact Nucleosomes by ELISA," Journal of Visualized Experiments, 2011, pp. 1-4.
D'Alton., "Prenatal diagnostic procedures." Semin Perinatol. Jun. 1994;18(3):140-62.
Das, R. et al. Proc Natl Acad Sci U S A 103, 10713-6 (2006).
Davison., "Sedimentation of deoxyribonucleic acid isolated under low hydrodynamic shear." Nature. Mar. 26, 1960;185:918-20.
Davison., "The Effect of Hydrodynamic Shear on the Deoxyribonucleic Acid From T(2) and T(4) Bacteriophages." Proc Natl Acad Sci U S A. Nov. 1959;45(11):1560-8.
Dayie et al. (1998) J. Mag. Reson. 130, 97-101 (1998).
Dear, "One by one: Single molecule tools for genomics." Brief Funct Genomic Proteomic. Jan. 2003;1(4):397-416.
Deininger, P. L. "Random subcloning of sonicated DNA: application to shotgun DNA sequence analysis," Anal. Biochem. 129(1):216-223 (1983).
Dembo et al., 1994, Ann. Prob. 22: 2022-2039.
Ding C, Cantor CR (2003) A high-throughput gene expression analysis technique using competitive PCR and matrix-assisted laser desorption ionization time-of-flight MS. Proc Natl Acad Sci U S A 100:3059-3064.
Donis-Keller et al., Nucl. Acids Res. 4:2527-2537 (1977).
Donis-Keller., "Phy M: an RNase activity specific for U and A residues useful in RNA sequence analysis." Nucleic Acids Res. Jul. 25, 1980;8(14):3133-42.
Dupont JM, Tost J, Jammes H, and Gut IG. Anal Biochem, Oct. 2004; 333(1): 119-27.
Eads et al., Cancer Res. 59:2302-2306, 1999.
Eckhardt, F. et al. Nat Genet 38, 1378-85 (2006).
Edlund et al., "Cell-specific expression of the rat insulin gene: evidence for role of two distinct 5' flanking elements." Science. Nov. 22, 1985;230(4728):912-6.
Egger et al., "Reverse transcription multiplex PCR for differentiation between polio- and enteroviruses from clinical and environmental samples." J Clin Microbiol. Jun. 1995;33(6):1442-7.
Ehrich et al., "Noninvasive detection of fetal trisomy 21 by sequencing of DNA in maternal blood: a study in a clinical setting," Reports of Major Impact, American Journal of Obstetrics and Gyenocology, Mar. 2011, 205e1-205e11.
Ehrich et al., A new method for accurate assessment of DNA quality after bisulfite treatment, Nucl. Acids Res. (2007) 35(5): e29 1-8.
Ehrich M, et al. (2005) Quantitative high-throughput analysis of DNA methylation patterns by base specific cleavage and mass spectrometry. Proc Natl Acad Sci U S A 102:15785-15790.
Ehrich M, et al. (2008) Cytosine methylation profiling of cancer cell lines. Proc Natl Acad Sci U S A 105:4844-48.
Eiben et al., "First-trimester screening: an overview." J Histochem Cytochem. Mar. 2005;53(3):281-3.
Ernani et al., Agilent's SureSelect Target Enrichment System: Bringing Cost and Process Efficiency to Next-Generation Sequencing Product Note, Agilent Technologies, Mar. 16, 2009.
Eva and Aaronson, Nature, 316:273-275, 1985.
Extended European Search Report dated Apr. 22, 2013 in European Application No. EP10843520 filed: Dec. 20, 2010 based on International Application No. PCT/US2010/061319.
Extended European Search Report dated Jan. 4, 2012 in European Application No. EP10817598.5 filed: Mar. 18, 2010.
Extended European Search Report dated: Apr. 19, 2012 in European Application No. EP 09815148 filed: Sep. 16, 2009.
Fajkusova L. et al., "Detailed Mapping of Methylcytosine Positions at the CpG Island Surrounding the Pa Promoter at the bcr-abl Locus in CML Patients and in Two Cell Lines, K562 and BV173" Blood Cells Mol. Dis. 26(3):193-204 (2000).
Fan et al., "Noninvasive diagnosis of fetal aneuploidy by shotgun sequencing DNA from maternal blood." Proc Natl Acad Sci U S A. Oct. 21, 2008;105(42):16266-71. Epub Oct. 6, 2008.
Fan et al., "Working Set Selection Using the Second Order Information for Training SVM" Journal of Machine Learning Research 6 (2005) 1889-1918.
Fan et al., "Analysis of the size distributions of fetal and maternal cell-free DNA by paired-end sequencing" Clinical Chemistry (2010) 56(8):1279-1286.
Fan, Hei-Mun Christina, "Molecular Counting: From Noninvasive Prenatal Diagnostics to Whole-Genome Haplotyping" Dissertation, Stanford University, Nov. 2010.
Feinberg., "Methylation meets genomics." Nat Genet. Jan. 2001;27(1):9-10.
Ferguson-Smith, "Placental mRNA in maternal plasma: Prospects for fetal screening", PNAS vol. 100, No. 8, 4360-4362 Apr. 15, 2003.
Fournie et al. (1986 Anal. Biochem. 158: 250-256).
Frommer et al. Proc. Natl. Acad. Sci. USA 89:1827-1831, (1992).
Futreal, P.A. et al. Nat Rev Cancer 4, 177-83 (2004).
Gardiner-Garden et al., "CpG islands in vertebrate genomes." J Mol Biol. Jul. 20, 1987;196(2):261-82.
Gebhard C, Schwarzfischer L, Pham TH, Andreesen R, Mackensen A, Rehli M (2006) Rapid and sensitive detection of CpG-methylation using methyl-binding (MB)-PCR. Nucleic Acids Res 34:e82.
Gebhard C, Schwarzfischer L, Pham TH, Schilling E, Klug M, Andreesen R, Rehli M (2006) Genomewide profiling of CpG methylation identifies novel targets of aberrant hypermethylation in myeloid leukemia. Cancer Res 66:6118-6128.
Giles et al., "Acute myeloid leukemia." Hematology Am Soc Hematol Educ Program. 2002:73-110.
Go et al. Clin Chem. Dec. 2007;53(12):2223-4.
Go et al., "Non-invasive aneuploidy detection using free fetal DNA and RNA in maternal plasma: recent progress and future possibilities" Human Reproduction Update (2011) 17(3):372-382.
Goeddel, Gene Expression Technology: Methods in Enzymology 185, Academic Press, San Diego, CA (1990).
Gonzalgo & Jones, Nucleic Acids Res. 25:2529-2531, 1997.
Gottesman, S., Gene Expression Technology: Methods in Enzymology, Academic Press, San Diego, California 185: 119-129 (1990).
Grompe et al., Proc. Natl. Acad. Sci. USA 86: 5855-5892 (1989.
Grompe., "The rapid detection of unknown mutations in nucleic acids." Nat Genet. Oct. 1993;5(2):111-7.
Grunau et al., "Bisulfite genomic sequencing: systematic investigation of critical experimental parameters." Nucleic Acids Res. Jul. 1, 2001;29(13):E65-5.
Gupta et al., "Use of specific endonuclease cleavage in RNA sequencing." Nucleic Acids Res. Jun. 1977;4(6):1957-78.
Haase et al., Methods in Virology, pp. 189-226, 1984.
Haddow, et al.,"'Screening of maternal serum for fetal Down's syndrome in the first trimester", In: The New England Journal of Medicine, Apr. 2, 1998, Vol.338(14), pp. 955-961.
Hage & Tweed, J. Chromatogr. B Biomed. Sci. Appl. Oct. 10; 699 (1-2): 499-525 (1997).
Hahn et al., (2011) Placenta 32 Suppl: S17-S20.
Hahner et al., "Matrix-assisted laser desorption/ionization mass spectrometry (MALDI) of endonuclease digests of RNA." Nucleic Acids Res. May 15, 1997;25(10):1957-64.
Hames and Higgins eds., Nucleic Acid Hybridization: A Practical Approach, IRL Press, 1985.
Hannish, J. And M. McClelland, "Activity of DNA modification and restriction enzymes in KGB, a potassium glutamate buffer," Gene Anal. Tech 5:105 (1988.
Harris et al., "Single-molecule DNA sequencing of a viral genome." Science. Apr. 4, 2008;320(5872):106-9.
Hart et al., J.Biol.Chem., 269:62-65, 1994.
Hasan et al., Nucl. Acids Res. 24:2150-2157 (1996).
Heegaard, J Mol. Recognit. Winter; 11(1-6): 141-8 (1998).
Hennig et al (2007) J. Am. Chem. Soc. 129, 14911-14921.
Herman et al. Proc. Nat. Acad. Sci. USA 93:9821-9826, 1996.
Hershey, A. D. And Burgi, E. J. Mol. Biol, 2:143-152 (1960.
Hill, Craig, "Gen-Probe Transcription-Mediated Amplification: System Principles," Jan. 1996 httl://www.gen-probe.com/pdfs/tma_whiteppr.pdf.

(56) References Cited

OTHER PUBLICATIONS

HiSeq 2000 Sequencing System Specification Sheet, Illumina Inc. 2010.
Homer, J. et al., Prenat Diagn 23:566-571 (2003).
Hook, E. B. Lancet 2:169-172 (1981).
Hromandnikova, et al., "Quantification of Fetal and Total Circulatory DNA in Maternal Plasma Samples Before and After Size Fractionation by Agarose Gel Electrophoresis,"DNA and Cell Biology, vol. 25, No. 11, 2006, pp. 635-640.
Hu, D. G. et al., "Aneuploidy detection in single cells using DNA array-based comparative genomic hybridization", Mol Hum Reprod 10: 283-289, (2004).
Hua et al., "Quantitative methylation analysis of multiple genes using methylation-sensitive restriction enzyme-based quantitative PCR for the detection of hepatocellular carcinoma" Experimental and Molecular Pathology (2011) 91:455-460.
Huang et al., "Mechanism of ribose 2'-group discrimination by an RNA polymerase." Biochemistry. Jul. 8, 1997;36(27):8231-42.
Hulten et al., "Rapid and simple prenatal diagnosis of common chromosome disorders: advantages and disadvantages of the molecular methods FISH and QF-PCR." Reproduction. Sep. 2003;126(3):279-97.
Hunkapiller et al., "A microchemical facility for the analysis and synthesis of genes and proteins." Nature. Jul. 12-18, 1984;310(5973):105-11.
Hyrup et al., "Peptide nucleic acids (PNA): synthesis, properties and potential applications." Bioorg Med Chem. Jan. 1996;4(1):5-23.
Imai et al., 1992, J. Virol. Methods 36: 181-184).
Imamura et al., "Prenatal diagnosis of adrenoleukodystrophy by means of mutation analysis." Prenat Diagn. Mar. 1996;16(3):259-61.
Innis et al., PCR Protocols: A Guide to Methods and Applications, Innis et al., eds, 1990.
International Preliminary Report on Patentability dated Dec. 30, 2009 in International Application No. PCT/US2008/066791 filed on Jun. 12, 2008.
International Preliminary Report on Patentability dated Feb. 18, 2010 in International Application No. PCT/US2008/54470 filed on Feb. 20, 2008.
International Preliminary Report on Patentability dated Jul. 5, 2012 in International Application No. PCT/US2010/061319 filed on Dec. 20, 2010.
International Preliminary Report on Patentability dated Mar. 29, 2012 in International Application No. PCT/US2010/027879 filed on Mar. 18, 2010.
International Preliminary Report on Patentability dated Sep. 3, 2009 in International Application No. PCT/US2008/54468 filed on Feb. 20, 2008.
International Preliminary Report on Patentability dated Mar. 31, 2011 in International Application No. PCT/US2009/057215 filed on Sep. 16, 2009 and published as: WO 10/033639 on Mar. 25, 2010.
International Preliminary Report on Patentability, dated Sep. 23, 2010 in International application No. PCT/US2009/036683 filed on: Mar. 10, 2009 and published as WO 09/114543 on Sep. 17, 2009.
International Search Report and Written Opinion dated Aug. 18, 2008 in International Application No. PCT/US2008/54470 filed on Feb. 20, 2008.
International Search Report and Written Opinion dated Dec. 22, 2008 in International Application No. PCT/US2008/066791 filed on Jun. 12, 2008.
International Search Report and Written Opinion dated Jan. 10, 2012 in International Application No. PCT/US2012/035479 filed on Apr. 27, 2012.
International Search Report and Written Opinion dated Sep. 21, 2011 in International Application No. PCT/US2010/061319 filed on Dec. 20, 2010.
International Search Report and Written Opinion dated Sep. 23, 2008 in International Application No. PCT/US2008/54468 filed on Feb. 20, 2008.
International Search Report and Written Opinion dated Jul. 1, 2013 in International Application No. PCT/US2013/028699, filed on Mar. 1, 2013.
International Search Report and Written Opinion dated Jul. 16, 2013 in International Application No. PCT/US2013/041906, filed on May 20, 2013.
International Search Report and Written Opinion dated Dec. 29, 2010 in International Application No. PCT/US2009/057215 filed on Sep. 16, 2009 and published as: WO 10/033639 on Mar. 25, 2010.
International Search Report and Written Opinion dated Dec. 30, 2010 in International Application No. PCT/US2010/027879 filed on Mar. 18, 2010.
International Search Report and Written Opinion, dated Feb. 24, 2010 in International application No. PCT/US2009/036683 filed on: Mar. 10, 2009 and published as WO 09/114543 on Sep. 17, 2009.
Invitation to Pay Additional Fees and Partial International Search Report dated Dec. 28, 2009 in International application No. PCT/US2009/036683 filed on: Mar. 10, 2009 and published as WO 09/114543 on Sep. 17, 2009.
International Search Report and Written Opinion dated Oct. 23, 2013 in International Application No. PCT/US2013/050145, filed on Jul. 11, 2013.
International Preliminary Report on Patentability dated Nov. 7, 2013 in International Application No. PCT/US2012/035479, filed on Apr. 27, 2012 and published as WO 2012/149339 on Nov. 1, 2012.
International Search Report and Written Opinion dated Jul. 30, 2014 in International Application No. PCT/US2014/025132, filed on Mar. 13, 2014.
International Preliminary Report on Patentability dated Sep. 12, 2014 in International Application No. PCT/US2013/028699, filed on Mar. 1, 2013 and published as WO 2013/131021 on Sep. 6, 2013.
Issa., "CpG island methylator phenotype in cancer." Nat Rev Cancer. Dec. 2004;4(12):988-93.
Iverson et al., 1981, Prenat. Diagn. 9: 31-48.
Iwabuchi et al., Oncogene 8: 1693-1696 (1993.
Jensen et al., "Detection of microdeletion 22q11.2 in a fetus by next-generation sequencing of maternal plasma" Clin Chem (2012) 58:1148-1151.
Jensen et al., "High-throughput massively parallel sequencing for fetal aneuploidy detection from maternal plasma" PLoS One (2013) 8:e57381.
Jing et al. (1998) Proc Natl Acad Sci USA. 95(14):8046-51.
Johansen et al., "An investigation of methods for enriching trophoblast from maternal blood." Prenat Diagn. Oct. 1995;15(10):921-31.
Jurinke, C., et al., "MALDI-TOF mass spectrometry: a versatile tool for high-performance DNA analysis." Mol. Biotechnol. 26, 147-164 (2004).
Kalinina et al., "Nanoliter scale PCR with TaqMan detection." Nucleic Acids Res. May 15, 1997;25(10):1999-2004.
Kaneko et al., Gut 52:641-646 (2003).
Karlin et al., "Methods for assessing the statistical significance of molecular sequence features by using general scoring schemes." Proc Natl Acad Sci U S A. Mar. 1990;87(6):2264-8.
Kent, "BLAT—the BLAST-like alignment tool." Genome Res. Apr. 2002;12(4):656-64.
Kessel et al., "Murine developmental control genes." Science. Jul. 27, 1990;249(4967):374-9.
Kidd JM et al. Mapping and sequencing of structural variation from eight human genomes. Nature. May 1, 2008;453 (7191):56-64).
Kitzman et al., "Noninvasive Whole-Genome Sequencing of a Human Fetus" Science Translation Medicine (2012) 4(137-140):115-122.
Kriegler, Gene Transfer and Expression: A Laboratory Manual (1990).
Kristensen et al., "PCR-Based Methods for Detecting Single-Locus DNA Methylation Biomarkers in Cancer Diagnostics, Prognostics, and Response to Treatement", Clinical Chemistry, Washington DC, vol. 55, No. 8., Aug. 1, 2009, pp. 1471-1483.
Krueger and Andrews, "Bismark: a flexible aligner and methylation caller for Bisulfite-Seq applications" Bioinformatics (2011) 27:1571-1572.

(56) References Cited

OTHER PUBLICATIONS

Kuchino et al., "Enzymatic RNA sequencing." Methods Enzymol. 1989;180:154-63.

Kuhn et al., "DNA Helicases" Cold Spring Harb Symp Quant Biol. 1979;43 Pt 1:63-7.

Kulkarmi et al., "Global DNA methylation patterns in placenta and its association with maternal hypertension in pre-eclampsia," (2011) DNA Cell Biol. 30(2):79-84.

Kumps et al., "RMeseuarlcthi aprtilcelex Amplicon Quantification (MAQ), a fast and efficient method for the simultaneous detection of copy number alterations in neuroblastoma," BMC Genomics 2010, 11:298, pp. 1-10.

Lai et al. (1999) Nat Genet. 23(3):309-13.

Laird, P.W. Nature Reviews Cancer 3, 253-266 (2003).

Langmead et al., "Ultrafast and memory-efficient alignment of short DNA sequences to the human genome" Genome Biol. (2009) 10(3):R25.

Larkin et al., "Clustal W and Clustal X version 2.0." Bioinformatics. Nov. 1, 2007;23(21):2947-8. Epub Sep. 10, 2007.

Lee et al., Fetal Nucleic Acids in Maternal Plasma, In:Fetal and Maternal Medicine Review, 2006, vol. 17,(2), pp. 125-137.

Lee TI, et al. (2006) Control of developmental regulators by Polycomb in human embryonic stem cells. Cell 125:301-313).

Leung et al., "An efficient algorithm for identifying matches with errors in multiple long molecular sequences." J Mol Biol. Oct. 20, 1991;221(4):1367-78.

Li et al. Nucl. Acids Res. 23:4495-4501 (1995).

Li et al., Dynamic Distribution of Linker Histone H1.5 in Cellular Differentiation, PLOS Genetics, vol. 8, Issue 8, e1002879, Aug. 2012, pp. 1-13.

Li et al., "Size separation of circulatory DNA in maternal plasma permits ready detection of fetal DNA polymorphisms." Clin Chem. Jun. 2004;50(6):1002-11. Epub Apr. 8, 2004.

Li et al., "Targeted mutation of the DNA methyltransferase gene results in embryonic lethality." Cell. Jun. 12, 1992;69(6):915-26.

Li, Y., et al., Genotyping fetal paternally inherited SNPs by MALDI-TOF MS using cell-free fetal DNA in maternal plasma: Influence of size fractionation. Electrophoresis 27, 3889-3896 (2006).

Li et al., "Mapping short DNA sequencing reads and calling variants using mapping quality scores" Genome Res. (2008) 18(11):1851-1858.

Lingbeek, M.E., Bruggeman, S.W. & van Lohuizen, M. Cell 118, 409-18 (2004).

Little, et al. Nat Med 3:1413-6 (1997).

Litz C. E. et al., "Methylation status of the major breakpoint cluster region in Philadelphia chromosome negative leukemias" Leukemia 6(1):35-41 (1992).

Liu et al., "Quantification of regional DNA methylation by liquid chromatography/tandem mass spectrometry", Analytical Biochemistry, Academic Press Inc, New York, vol. 391, No. 2, Aug. 15, 2009, pp. 106-113.

Liu et al., "The ribosomal small-subunit protein S28 gene from Helianthus annuus (asteraceae) is down-regulated in response to drought, high salinity, and abscisic acid," American Journal of Botany, vol. 90, No. 4., Apr. 1, 2003, pp. 526-531.

Lo and Chiu, "Prenatal diagnosis: progress through plasma nucleic acids" Nature Reviews Genetics (2007) 8:71-77.

Lo et al. (Nat Med. Feb. 2007;13(2):218-23).

Lo et al., "Maternal Plasma DNA Sequencing Reveals the Genome-Wide Genetic and Mutational Profile of the Fetus," Prenatal Diagnosis, Science Translational Medicine, Dec. 8, 2010, vol. 2, Issue 61, 1-13 Lo et al. (2010).

Lo et al., "Presence of fetal DNA in maternal plasma and serum." Lancet. Aug. 16, 1997;350(9076):485-7.

Lo et al., "Quantitative analysis of fetal DNA in maternal plasma and serum: implications for noninvasive prenatal diagnosis." Am J Hum Genet. Apr. 1998;62(4):768-75.

Lo et al., Clin. Chem. 45:1747-1751, 1999.

Lo et al., Clin. Chem. 45:184-188, 1999.

Lo et al., N. Engl. J. Med. 339:1734-1738 (1998).

Lo, "Recent advances in fetal nucleic acids in maternal plasma." J Histochem Cytochem. Mar. 2005;53(3):293-6.

Lun et al., "Microfluidics digital PCR reveals a higher than expected fraction of fetal DNA in maternal plasma." Clin Chem. Oct. 2008;54(10):1664-72. Epub Aug. 14, 2008.

Lun et al., "Noninvasive prenatal diagnosis of monogenic diseases by digital size selection and relative mutation dosage on DNA in maternal plasma," PNAS, vol. 105, No. 50, Dec. 16, 2008, pp. 19920-19925.

Madura et al., J. Biol. Chem. 268: 12046-12054 (1993).

Majlessi et al., Nucleic Acids Research, 26(9):2224-2229, (1998).

Malik et al., "Polyethylene glycol (PEG)-modified granulocyte-macrophage colony-stimulating factor (GM-CSF) with conserved biological activity." Exp Hematol. Sep. 1992;20(8):1028-35.

Mann et al., "Development and implementation of a new rapid aneuploidy diagnostic service within the UK National Health Service and implications for the future of prenatal diagnosis." Lancet. Sep. 29, 2001;358(9287):1057-61.

Mann, K. Methods Mol Med 92:141-156 (2004).

Mao and Williamson (1999) Nucl. Acids Res. 27, 4059-4070.

Marais et al., EMBO J. 14: 3136-3145 (1995).

Marais et al., J. Biol. Chem. 272: 4378-4383 (1997.

Margulies et al., "Genome sequencing in microfabricated high-density picolitre reactors." Nature. Sep. 15, 2005;437(7057):376-80. Epub Jul. 31, 2005.

Mason et al., EMBO J. 18: 2137-2148 (1999.

McClelland, M. et al., "A single buffer for all restriction endonucleases," Nucl. Acids Res. 16:364 (1988).

McConnell, H. M. et al., Science 257: 1906-1912 (1992)).

Meller A. 2007 Clin Chem 53: 1996-2001.

Metzker M., Nature Rev 11:31-46 (2010).

Meyers & Miller, CABIOS 4: 11-17 (1989).

Millipore, QIA25 Nucleosome ELISA Kit, Information Brochure, Calbiochem, Feb. 26, 2013.

Mito, Y., Henikoff, J.G. & Henikoff, S. Nat Genet 37, 1090-7 (2005.

Molecular Cloning of PCR Products, Unit 15.4, Current Protocols in Molecular Biology, (2001 John Wiley & Sons, Inc.) 15.4.1-15.4.11, Supplement 56.

Moudrianakis E. N. and Beer M., Proc Natl Acad Sci USA. Mar. 1965; 53:564-71.

Mouliere et al., "High Fragmentation Characterizes Tumour-Derived Circulating DNA," PLoS One, Sep. 2011, vol. 6, Issue 9, e23438, 1-10.

Nakamaye et al., Nucl. Acids Res. 23:9947-9959(1988).

Nakano et al. "Single-molecule PCR using water-in-oil emulsion;" Journal of Biotechnology 102 (2003) 117-124.

NCBI dbSNP cluster report record for rs16139, accessed Sep. 16, 2013.

Needham-VanDevanter et al., "Characterization of an adduct between CC-1065 and a defined oligodeoxynucleotide duplex." Nucleic Acids Res. Aug. 10, 1984; 12(15):6159-68.

Needleman et al., "A general method applicable to the search for similarities in the amino acid sequence of two proteins." J Mol Biol. Mar. 1970;48(3)444-453.

Ng et al. , 2003, Proc. Natl. Acad. Sci. USA 100 : 4748-4753.

Ng et al., 2002, Clin. Chem. 48: 1212-1217.

Nicolaides et al., "One-stop clinic for assessment of risk of chromosomal defects at 12 weeks of gestation." J Matern Fetal Neonatal Med. Jul. 2002;12(1):9-18.

Nicolaides, K. H. et al., Prenat Diagn 22:308-315 (2002)).

Nicolaidis et al., "Origin and mechanisms of non-disjunction in human autosomal trisomies." Hum Reprod. Feb. 1998;13(2):313-9.

Nishizuka et al., "Proteomic profiling of the NCI-60 cancer cell lines using new high-density reverse-phase lysate microarrays." Proc Natl Acad Sci U S A. Nov. 25, 2003;100(24):14229-34. Epub Nov. 17, 2003.

Nolte, "Branched DNA signal amplification for direct quantitation of nucleic acid sequences in clinical specimens." Adv Clin Chem. 1998;33:201-35.

Nosaka, K. et al., "Increasing methylation of the CDKN2A gene is associated with the progression of adult T-cell leukemia", Cancer Res. 60(4):1043-1048 (2000).

(56) References Cited

OTHER PUBLICATIONS

Nygren et al., "Quantification of Fetal DNA by Use of Methylation-Based DNA Discrimination," Clinical Chemistry, 56:10, pp. 1627-1635.
Oefner, P. J. et al., "Efficient random subcloning of DNA sheared in a recirculating point-sink flow system," Nucl. Acids Res. 24(20):3879-3886 (1996).
Oeth et al., "Qualitative and quantitative genotyping using single base primer extension coupled with matrix-assisted laser desorption/ionization time-of-flight mass spectrometry (MassARRAY)." Methods Mol Biol. 2009;578:307-43.
Oeth, P. et al., (iPLEX™ Assay: Increased Plexing Efficiency and Flexibility for MassARRAY® System through single base primer extension with mass-modified Terminators. Sequenom Application Note (2005).
Ohm, J.E. et al. A stem cell-like chromatin pattern may predispose tumor suppressor genes to DNA hypermethylation and heritable silencing. Nat Genet 39, 237-42 (2007).
Ohtsuka et al., J. Biol. Chem. 260:2605-2608 (1985).
Okano et al., "DNA methyltransferases Dnmt3a and Dnmt3b are essential for de novo methylation and mammalian development." Cell. Oct. 29, 1999;99(3):247-57.
Old RW, "Candidate epigenetic biomarkers for non-invasive prenatal diagnosis of Down syndrom," Reprod Biomed. Online 2007, vol. 15, No. 2, pp. 227-235.
Olek et al., "A modified and improved method for bisulphite based cytosine methylation analysis." Nucleic Acids Res. Dec. 15, 1996;24(24):5064-6.
Oligonucleotides and Analogues, A Practical Approach, F. Eckstein, editor, IRL Press, Oxford, 1991.
Orita et al., Proc. Natl. Acad. Sci. U.S.A 86: 27776-2770 (1989.
Osborne, et al., Curr. Opin. Chem. Biol.1(1): 5-9 (1997.
Oudejans et al., 2003, Prenatal Diagnosis 23: 111-116.
Padilla et al., "Efficient synthesis of nucleic acids heavily modified with non-canonical ribose 2'-groups using a mutantT7 RNA polymerase (RNAP)." Nucleic Acids Res. Mar. 15, 1999;27(6):1561-3.
Palomaki et al., "Maternal serum screening for Down syndrome in the United States: a 1995 survey." Am J Obstet Gynecol. May 1997;176(5):1046-51.
Palomaki et al., "DNA sequencing of maternal plasma to detect Down syndrome: an international clinical validation study" Genet Med (2011) 13:913-920, and Expanded Methods Appendix A, pp. 1-65.
Pandya et al., "Screening for fetal trisomies by maternal age and fetal nuchal translucency thickness at 10 to 14 weeks of gestation." Br J Obstet Gynaecol. Dec. 1995;102(12):957-62.
Papageorgiou et al., "Sites of differential DNA methylation between placenta and peripheral blood: molecular markers for noninvasive prenatal diagnosis of aneuploidies" The American Journal of Pathology (2009) 174(5):1609-1618.
Papageorgiou et al., "Fetal-specific DNA methylation ratio permits noninvasive prenatal diagnosis of trisomy 21" Nature Medicine (2011) 17:510-513.
Patel, D. J., Curr. Opin. Chem. Biol. Jun;1(1): 32-46 (1997).
Paulin, R. et al. in Nucleic Acids Res. 26:5009-5010, 1998.
Pearson & Reanier, J. Chrom. 255: 137-149 (1983).
Pearson, 1988, Proc. Natl. Acad. Sci. USA 85(5): 2444-2448.
Perry-O'Keefe et al., "Peptide nucleic acid pre-gel hybridization: an alternative to southern hybridization." Proc Natl Acad Sci U S A. Dec. 10, 1996;93(25)14670-5.
Pertl et al., "Rapid molecular method for prenatal detection of Down's syndrome." Lancet. May 14, 1994;343(8907):1197-8.
Peters et al., "Noninvasive Prenatal Diagnosis of a Fetal Microdeletion Syndrome," New England Journal of Medicine, Nov. 10, 2011, pp. 1847-1848.
Petersen and Mikkelsen. Cytogenet Cell Genet. 2000;91(1-4):199-203.
Pinkert et al., Genes Dev. 1: 268-277 (1987).
Poon et al., 2000, Clin. Chem. 46: 1832-1834.
Poon et al., "Differential DNA methylation between fetus and mother as a strategy for detecting fetal DNA in maternal plasma." Clin Chem. Jan. 2002;48(1):35-41.
Porter et al., Biochemistry 34: 11963-11969 (1995).
Qu et al., "Analysis of drug-DNA binding data." Methods Enzymol. 2000;321:353-69.
Queen et al., "Immunoglobulin gene transcription is activated by downstream sequence elements." Cell. Jul. 1983;33(3):741-8.
Radding., "Homologous pairing and strand exchange in genetic recombination." Annu Rev Genet. 1982;16:405-37.
Randen et al., "Prenatal genotyping of RHD and SRY using maternal blood," Vox Sanguinis, vol. 85, No. 4, Nov. 2003, pp. 300-306.
Rashtchian (1994, PCR Methods Applic. 4: S83-S91).
Rivas, G., and Minton, A. P., Trends Biochem Sci Aug;18(8): 284-7 (1993).
Roach et al., "Association between the abnormal expression of matrix-degrading enzymes by human osteoarthritic chondrocytes and demethylation of specific CpG sites in the promoter regions" Arthritis & Rheumatism (2005) 52(10):3110-3124.
Robertson et al., Nature Rev. Genet. 1:11-19 (2000).
Robinson M. D. and T. P. Speed. "A comparison of Affymetrix gene expression arrays." BMC Bioinformatics 8:449 (2007).
Rojo et al., "Cusativin, a new cytidine-specific ribonuclease accumulated in seeds of *Cucumis sativus* L." Planta. 1994;194(3):328-38.
Rollins et al., "Large-scale structure of genomic methylation patterns." Genome Res. Feb. 2006;16(2):157-63. Epub Dec. 19, 2005.
Romero and Rotbard, Diagnostic Molecular Biology: Principles and Applications, pp. 401-406; Pershing et al, eds., Mayo Foundation, Rochester, Minn., 1993.
Roschke et al., "Karyotypic complexity of the NCI-60 drug-screening panel." Cancer Res. Dec. 15, 2003;63(24):8634-47.
Rosenberg, H. S. and Bendich, A. J. Am. Chem. Soc. 82:3198-3201 (1960).
Rossolini et al., Mol. Cell. Probes 8:91-98 (1994).
Sadri & Hornsby Nucl. Acids Res. 24:5058-5059, (1996).
Saito et al., Lancet 356:1170, 2000.
Salgame et al., "An ELISA for detection of apoptosis," Nucleic Acids Research, 1997, vol. 25, No. 3, pp. 680-681.
Sambrook and Russell, Molecular Cloning, A Laboratory Manual (3rd ed. 2001).
Sambrook et al., Molecular Biology: A laboratory Approach, Cold Spring Harbor, N. Y. 1989.
Sanchez et al, "Effects of Sulpiride on Prolactin and mRNA Levels of Steroid 5a-reductase Isozymes in Adult Rat Brain," Neurochem Res (2008) 33:820-825.
Santoro, S. W. and Joyce, G. F. "A general purpose RNA-cleaving DNA enzyme," Proc. Natl. Acad. Sci. USA 94:4262-4266 (1997).
Sargent et al., Meth. Enz. 152:432 (1988).
Sayres et al., "Cell-free fetal nucleic acid testing: A review of the technology and its applications" Obstetrical and Gynecological Survey (2011) 66(7):431-442.
Schlesinger et al., "Polycomb-mediated methylation on Lys27 of histone H3 pre-marks genes for de novo methylation in cancer." Nat Genet. Feb. 2007;39(2):232-6. Epub Dec. 31, 2006.
Schouten et al., "Relative quantification of 40 nucleic acid sequences by multiplex ligation-dependent probe amplification." Nucleic Acids Res. Jun. 15, 2002;30(12):e57.
Schriefer, L. A. et al., "Low pressure DNA shearing: a method for random DNA sequence analysis," Nucl. Acids Res. 18:7455-7456 (1990).
Schroeder et al., "The human placenta methylome" PNAS USA (2013) 110(15):6037-42.
Schuler GD, Sequence mapping by electronic PCR., Genome Res. May 1997;7(5):541-50.
Scott et al. (2004) J. Am. Chem. Soc. 126, 11776-11777.
Sekizawa et al., Clin. Chem. 47:2164-2165, 2001.
Sharma et al., "Mass spectrometric based analysis, characterization and applications of circulating cell free DNA isolated from human body fluids" International Journal of Mass Spectrometry (2011) 304:172-183.

(56) References Cited

OTHER PUBLICATIONS

Sheffield et al., "Identification of novel rhodopsin mutations associated with retinitis pigmentosa by GC-clamped denaturing gradient gel electrophoresis." Am J Hum Genet. Oct. 1991;49(4):699-706.
Silverman et al., "Methylation inhibitor therapy in the treatment of myelodysplastic syndrome." Nat Clin Pract Oncol. Dec. 2005;2 Suppl 1 :S12-23.
Simoncsits et al., "New rapid gel sequencing method for RNA." Nature. Oct. 27, 1977;269(5631):833-6.
Singer et al., Biotechniques 4:230, 1986.
Sjolander & Urbaniczk, Anal. Chem. 63: 2338-2345 (1991).
Slater et al., "Rapid, high throughput prenatal detection of aneuploidy using a novel quantitative method (MLPA)." J Med Genet. Dec. 2003;40(12):907-12.
Smith et al., "Identification of common molecular subsequences." J Mol Biol. Mar. 25, 1981;147(1):195-7.
Smith et al., "Single-step purification of polypeptides expressed in *Escherichia coli* as fusions with glutathione S-transferase." Gene. Jul. 15, 1988;67(1):31-40.
Snijders et al., "Assembly of microarrays for genome-wide measurement of DNA copy number." Nat Genet. Nov. 2001;29(3):263-4.
Snijders et al., "First-trimester ultrasound screening for chromosomal defects." Ultrasound Obstet Gynecol. Mar. 1996;7(3):216-26.
Snijders et al., "UK multicentre project on assessment of risk of trisomy 21 by maternal age and fetal nuchal-translucency thickness at 10-14 weeks of gestation. Fetal Medicine Foundation First Trimester Screening Group." Lancet. Aug. 1, 1998;352(9125):343-6.
Soni et al., "Progress toward ultrafast DNA sequencing using solid-state nanopores." Clin Chem. Nov. 2007;53(11):1996-2001. Epub Sep. 21, 2007.
Sousa et al., "A mutant T7 RNA polymerase as a DNA polymerase." EMBO J. Sep. 15, 1995;14(18):4609-21.
Spetzler et al, Enriching for Rare Subpopulations of Circulating Microvesicles by the Depletion of Endothelial-and Leukocyte-Derived Microvesicles, Caris Life Sciences, Carisome Posters, Papers, Abstracts and Presentations, American Academy of Cancer Research (AACR 2011).
Stanssens et al., "High-throughput MALDI-TOF discovery of genomic sequence polymorphisms." Genome Res. Jan. 2004;14(1):126-33.
Staunton et al., "Chemosensitivity prediction by transcriptional profiling." Proc Natl Acad Sci U S A. Sep. 11, 2001;98(19)10787-92.
Strathdee, et al., Am. J. Pathol. 158:1121-1127 (2001).
Strohmeier, Fred, "A New High-Performance Capillary Electrophoresis Instrument," 10-19, Hewlett-Packard Journal, Jun. 1995.
Supplementary European Search Report dated Jul. 14, 2011 for European Application No. EP 09720284 filed: Mar. 10, 2009 based on internation application No. PCT/US2009/036683.
Szabo et al., Curr. Opin. Struct. Biol. 5: 699-705 (1995).
Tabor et al., "Non-Invasive Fetal Genome Sequencing: Opportunities and Challenges" American Journal of Medical Genetics Part A (2012) 158A(10):2382-2384.
Takai et al., Proc. Natl. Acad. Sci. U.S.A. 99:3740-3745, 2002.
Tang et al. (2002) Analytical Chemistry 74, 226-331.
Terme et al. "Histone H1 Variants Are Differentially Expressed and Incorporated into Chromatin during Differentiation and Reprogramming to Pluripotency," The Journal of Clinical Chemistry, vol. 286, No. 41, Oct. 14, 2011, pp. 35347-35357.
The Cancer Test, Cell Free DNA, 2007, Health Screen Inc. printed from the internet on Mar. 20, 2011 (http://www.thecancertest.com/science-of-cell-free-dna/.
The Human Genome, T. Strachan, BIOS Scientific Publishers, 1992.
The World Health Organization histological typing of lung tumours, Am J Clin Pathol 1982; 77:123-136.
Thorstenson, Y.R. et al., "An Automated Hydrodynamic Process for Controlled, Unbiased DNA Shearing," Genome Research 8:848-855 (1998).
Tolbert and Williamson (1996) J. Am. Chem. Soc. 118, 7929-7940.
Tolbert and Williamson (1997) J. Am. Chem. Soc. 119, 12100-12108.
Tong et al., "Noninvasive Prenatal Detection of Fetal Trisomy 18 by Epigenetic Allelic Ratio Analysis in Maternal Plasma: Theoretical and Empirical Considerations," Clinical Chemistry 52:12, pp. 2149-2202.
Tooke N and Pettersson M. IVDT. Nov. 2004; 41.
Tost et al., Nucl. Acids Res. 37:e50 (2003).
Toyota et al., "Methylation profiling in acute myeloid leukemia." Blood. May 1, 2001;97(9):2823-9.
Toyota et al., Cancer Res. 59:2307-12, 1999.
Tsaliki et al., "MeDIP real-time qPCR of maternal peripheral blood reliably identifies trisomy 21" Prenat. Diagn. (2012) 32:996-1001.
Tsui et al., "Systemic Identification of Placental Epigenetic Signatures for the Noninvasive Prenatal Detection of Edwards Syndrome" PLOS One (2010) 5(11):e15069.
Tungwiwat et al., "Non-invasive fetal sex determination using a conventional nested PCR analysis of fetal DNA in maternal plasma," Clinica Chimica Acta, vol. 334, No. 1-2, Aug. 2003, pp. 173-177.
Tynan et al., "Fractional DNA quantification by massively parallel shotgun sequencing-implications for fetal fraction measurement in maternal plasma," (Sequenom MME) ASHG Poster, 2011.
Uhlmann, K. et al. Electrophoresis 23:4072-4079 (2002).
Valk et al., "Prognostically useful gene-expression profiles in acute myeloid leukemia." N Engl J Med. Apr. 15, 2004;350(16)1617-28.
Valk-Lingbeek et al., "Stem cells and cancer; the polycomb connection." Cell. Aug. 20, 2004;118(4):409-18.
Van der Schoot, C.E., et al., Real-time PCR of bi-allelic insertion/deletion polymorphisms can serve as a reliable positive control for cell-free fetal DNA in non-invasive prenatal genotyping [abstract] Blood 102, 93a (2003).
Veltman et al., "High-throughput analysis of subtelomeric chromosome rearrangements by use of array-based comparative genomic hybridization." Am J Hum Genet. May 2002;70(5):1269-76. Epub Apr. 9, 2002.
Venter et al., "The sequence of the human genome." Science. Feb. 16, 2001;291(5507)1304-51.
Verbeck et al. in the Journal of Biomolecular Techniques (vol. 13, Issue 2, 56-61) (2002).
Verma et al., "Rapid and simple prenatal DNA diagnosis of Down's syndrome." Lancet. Jul. 4, 1998;352(9121):9-12.
Vincenet et al., "Helicase-Dependent isothermal DNA Amplification," EMBO reports 5(8):795-800 (2004).
Vire et al., "The Polycomb group protein EZH2 directly controls DNA methylation." Nature. Feb. 16, 2006;439(7078):871-4. Epub Dec. 14, 2005.
Vogelstein et al., "Digital PCR." Proc Natl Acad Sci U S A. Aug. 3, 1999;96(16):9236-41.
Volkerding et al., Clin Chem 55:641-658 (2009).
Vu et al. "Symmetric and asymmetric DNA methylation in the human IGF2-H19 imprinted region," Genomics, Mar. 1;64(2):132-143. (2000).
Wada et al., "Codon usage tabulated from the GenBank genetic sequence data." Nucleic Acids Res. May 11, 1992;20 Suppl:2111-8.
Wald and Hackshaw, Prenat Diagn 17(9):821-829 (1997).
Wang, H. et al. BMC Genomics 7, 166 (2006.
Wapner et al., "First-trimester screening for trisomies 21 and 18." N Engl J Med. Oct. 9, 2003;349(15)1405-13.
Waterman et al., 1980, J. Mol. Biol. 147: 195-197.
Weber et al., Oncogene 19: 169-176 (2000).
Weisenberger, D.J. et al. Nat Genet 38, 787-93 (2006).
Weiss et al., "H1 variant-specific lysine methylation by G9a/KMT1C and Glp1/KMT1D," Epigenetics & Chromatin Mar. 24, 2010, 3:7, pp. 1-13.
White et al., "Detecting single base substitutions as heteroduplex polymorphisms." Genomics. Feb. 1992;12(2):301-6.
Widschwendter, M. et al. Epigenetic stem cell signature in cancer. Nat Genet 39, 157-8 (2007).
Wilkinson, In situ Hybridization, Wilkinson ed., IRL Press, Oxford University Press, Oxford 1998.
Winoto et al., "A novel, inducible and T cell-specific enhancer located at the 3' end of the T cell receptor alpha locus." EMBO J. Mar. 1989;8(3):729-33.

(56) References Cited

OTHER PUBLICATIONS

Xiong & Laird, Nucleic Acids Res. 25:2532-2534, 1997.
Yamada et al. (Genome Research 14:247-266, 2004).
Yamada et al., "Suppressive effect of epigallocatechin gallate (EGCg) on DNA methylation in mice: Detection by methylation sensitive restriction endonuclease digestion and PCR" Journal of Food, Agriculture & Environment (2005) 3(2):73-76.
Yan et al., "A novel diagnostic strategy for trisomy 21 using short tandem repeats," Electrophoresis 2006, 27,416-422.
Zahra S, et al, Plasma microparticles are not elevated in fresh plasma from patients with gynaecologicalmalignancy—An observational study, Gynecol Onco, Oct. 2011;123(1):152-156.
Zervos et al., Cell 72:223-232 (1993.
Zhang et al., "Histone H1 Depletion Impairs Embryonic Stem Cell Differentiation," PLOS Genetics, vol. 8, Issue 5, el 002691, May 2012, pp. 1-14.
Zhao et al., (2010) Pretat Diag 30(8):778-782.
Zheng et al., "Nonhematopoietically Derived DNA Is Shorter than Hematopoietically Derived DNA in Plasma: A Transplantation Model," Clin Chem 58:2, Nov. 3, 2011.
Zhong et al., Am. J. Obstet. Gynecol. 184:414-419, 2001.
Zhong et al., Prenat. Diagn. 20:795-798, 2000.
Zimmermann Lecturer, et al., 'Serum parameters and nuchal translucency in first trimester screening for fetal chromosomal abnormalities', In: BJOG: An International Journal of Obstetrics & Gynaecology, 1996, vol. l03(1O), pp. 1009-1014.
Zimmermann, B. et al., Clin Chem 48:362-363 (2002).
Zuker "Mfold web server for nucleic acid folding and hybridization prediction," Nucleic Acids Res. 31(13), 3406-3415.
Office Action dated Jan. 28, 2013 in U.S. Appl. No. 13/457,978, filed Apr. 27, 2012 and published as: 2012/0276542 on: Oct. 1, 2012.
Office Action dated Sep. 17, 2012 in U.S. Appl. No. 13/457,978, filed Apr. 27, 2012 and published as: 2012/0276542 on: Oct. 1, 2012.
Office Action dated Feb. 6, 2013 in U.S. Appl. No. 13/458,036, filed Apr. 27, 2012 and published as: 2012/0264618 on: Oct. 18, 2012.
Office Action dated Sep. 24, 2012 in U.S. Appl. No. 13/458,036, filed Apr. 27, 2012 and published as: 2012/0264618 on: Oct. 18, 2012.
Office Action dated Feb. 5, 2013 in U.S. Appl. No. 13/458,341, filed Apr. 27, 2012.
Office Action dated Sep. 17, 2012 in U.S. Appl. No. 13/458,341, filed Apr. 27, 2012.
Office Action dated Feb. 27, 2013 in U.S. Appl. No. 12/561,241, filed Sep. 16, 2009.
Office Action dated Jun. 15, 2012 in U.S. Appl. No. 12/561,241, filed Sep. 16, 2009.
Office Action dated Apr. 5, 2013 in U.S. Appl. No. 13/495,975, filed Jun. 13, 2012.
Office Action dated Apr. 5, 2013 in U.S. Appl. No. 13/517,532, filed Jun. 13, 2012.
Office Action dated Apr. 12, 2013 in U.S. Appl. No. 12/727,198, filed Mar. 18, 2010.
Office Action dated Mar. 18, 2013 in U.S. Appl. No. 12/401,493, filed Mar. 10, 2009 and published as: 2009/0317817 on: Dec. 24, 2009.
Office Action dated Jul. 19, 2011 in U.S. Appl. No. 12/401,493, filed Mar. 10, 2009 and published as: 2009/0317817 on: Dec. 24, 2009.
Office Action dated Oct. 28, 2010 in U.S. Appl. No. 12/401,493, filed Mar. 10, 2009 and published as: 2009/0317817 on: Dec. 24, 2009.
Office Action dated Aug. 13, 2013 in U.S. Appl. No. 13/517,508, filed Jun. 13, 2012 and published as US 2013-0143211 on Jun. 6, 2013.
International Search Report and Written Opinion dated Aug. 14, 2013 in International Application No. PCT/US2013/041354, filed on May 16, 2013.

Office Action dated Sep. 20, 2013 in U.S. Appl. No. 13/517,532, filed on Jun. 13, 2012 and published as US 2013-0150249 on Jun. 13, 2013.
Office Action dated Sep. 24, 2013 in U.S. Appl. No. 13/495,975, filed Jun. 13, 2012 and published as US 2012-0277119 on Nov. 1, 2012.
Office Action dated Nov. 22, 2013 in U.S. Appl. No. 12/401,493, filed Mar. 10, 2009 and published as US 2009-0317817 on Dec. 24, 2009.
Office Action dated Dec. 31, 2013 in U.S. Appl. No. 12/727,198, filed Mar. 18, 2010 and published as US 2010-0273165 on Oct. 28, 2010.
Office Action dated Jan. 7, 2014 in U.S. Appl. No. 13/517,508, filed Jun. 13, 2012 and published as US 2013-0143211 on Jun. 6, 2013.
Office Action dated Feb. 5, 2014 in U.S. Appl. No. 13/517,508, filed Jun. 13, 2012 and published as US 2013-0143211 on Jun. 6, 2013.
Office Action dated Mar. 7, 2014 in U.S. Appl. No. 13/801,384, filed Mar. 13, 2013 and published as US 2013-0296180 on Nov. 7, 2013.
Office Action dated Jun. 26, 2014 in U.S. Appl. No. 13/782,857, filed Mar. 1, 2013 and published as US 2013-0310260 on Nov. 21, 2013.
Office Action dated Aug. 8, 2014 in U.S. Appl. No. 13/782,901, filed on Mar. 1, 2013 and published as US 2013-0230858 on Sep. 5, 2013.
Office Action dated Sep. 15, 2014 in U.S. Appl. No. 12/727,198, filed Mar. 18, 2010 and published as US 2010-0273165 on Oct. 28, 2010.
Office Action dated Nov. 7, 2014 in U.S. Appl. No. 13/791,466, filed Mar. 8, 2013 and published as US 2013-0295564 on Nov. 7, 2013.
International Preliminary Report on Patentability dated Dec. 4, 2014 in International Application No. PCT/US2013/041906, filed on May 20, 2013 and published as WO 2013/177086 on Nov. 28, 2013.
Office Action dated Dec. 18, 2014 in U.S. Appl. No. 13/517,508, filed Jun. 13, 2012 and published as US 2013-0143211 on Jun. 6, 2013.
Office Action dated Dec. 22, 2014 in U.S. Appl. No. 13/801,384, filed Mar. 13, 2013 and published as US 2013-0296180 on Nov. 7, 2013.
Office Action dated Jan. 30, 2015 in U.S. Appl. No. 13/518,368, filed Feb. 6, 2013 and published as US 2013-0130923 on May 23, 2013.
International Preliminary Report on Patentability dated Jan. 22, 2015 in International Application No. PCT/US2013/050145, filed on Jul. 11, 2013 and published as WO 2014/011928 on Jan. 16, 2014.
Office Action dated Aug. 3, 2015 in U.S. Appl. No. 13/791,466, filed Mar. 8, 2013 and published as US 2013-0295564 on Nov. 7, 2013.
Office Action dated Aug. 20, 2015 in U.S. Appl. No. 13/940,162, filed Jul. 11, 2013 and published as US 2014-0093873 on Apr. 3, 2014.
International Preliminary Report on Patentability dated Sep. 24, 2015 in International Application No. PCT/US2014/025132, filed on Mar. 13, 2014 and published a WO 2014/168711 on Oct. 16, 2014.
Office Action dated Mar. 17, 2016 in U.S. Appl. No. 13/940,162, filed Jul. 11, 2013 and published as US 2014-0093873 on Apr. 3, 2014.
International Preliminary Report on Patentability dated Sep. 22, 2016 in International Application No. PCT/US2015/020250, filed on Mar. 12, 2015 and published as WO 2015/138774 on Sep. 17, 2015.
Extended European Search Report dated Nov. 14, 2016 in European Patent Application No. EP16173137.7, filed on Sep. 16, 2009.
Office Action dated Aug. 12, 2016 in U.S. Appl. No. 13/791,466, filed Mar. 8, 2013 and published as US 2013-0295564 on Nov. 7, 2013.
Australian Patent Office Application No. 2015-252141, Second Examination Report dated Oct. 3, 2017, 11 pages.
Japanese Patent Office Application No. 2015-076001, Final Office action dated Oct. 2, 2017, 4 pages.
European Patent Office Application No. 13739590.1, Office Action dated Aug. 1, 2017.

(56) References Cited

OTHER PUBLICATIONS

Japanese Patent Office No. 2015-521823, Office Action dated Jun. 28, 2017.
Japanese Patent Office No. 2016-199141, Office Action dated Jun. 16, 2017.
AU 2015252141, "First Examination Report", dated Oct. 28, 2016, 4 pages.
CA 2,737,200, "Office Action", dated Dec. 11, 2017, 3 pages.
EP 17182863.5, "Extended European Search Report", dated Feb. 26, 2018, 9 pages.
AU 2013290102, "First Examination Report", dated Apr. 19, 2018, 3 pages.
EP 13739590.1, "Office Action", dated Jun. 18, 2018, 5 pages.
JP 2015-521823, "Office Action", dated Apr. 19, 2018, 10 pages.
JP 2016-199141, "Office Action", dated May 28, 2018, 18 pages.
U.S. Appl. No. 15/261,457, Final Office Action dated Jul. 15, 2019, 15 pages.
U.S. Appl. No. 15/261,457, Non-Final Office Action dated Oct. 23, 2018, 15 pages.
U.S. Appl. No. 15/428,659, Non-Final Office Action dated Jan. 11, 2019, 9 pages.
Australian Application No. 2009293232, First Examination Report dated Mar. 11, 2014, 3 pages.
Australian Application No. 2009293232, Notice of Acceptance dated Apr. 30, 2015, 2 pages.
Australian Application No. 2010295968, First Examination Report dated Jul. 17, 2014, 4 pages.
Australian Application No. 2010295968, Notice of Acceptance dated Aug. 10, 2015, 3 pages.
Australian Application No. 2013290102, Notice of Acceptance dated Nov. 6, 2018, 3 pages.
Australian Application No. 2017251674, First Examination Report dated Sep. 14, 2018, 6 pages.
Canadian Application No. 2,737,200, Notice of Allowance dated Aug. 6, 2019, 1 page.
Canadian Application No. 2,878,979, Office Action dated Feb. 7, 2019, 4 pages.
European Application No. 09815148.3, Notice of Decision to Grant dated Jul. 14, 2016, 3 pages.
European Application No. 09815148.3, Office Action dated Nov. 13, 2014, 4 pages.
European Application No. 09815148.3, Office Action dated May 14, 2014, 5 pages.
European Application No. 09815148.3, Office Action dated Jan. 3, 2013, 7 pages.
European Application No. 10817598.5, Notice of Decision to Grant dated Jun. 29, 2017, 3 pages.
European Application No. 10817598.5, Office Action dated Jan. 29, 2014, 5 pages.
European Application No. 13739590.1, Office Action dated Feb. 1, 2016, 5 pages.
European Application No. 13739590.1, Office Action dated Nov. 26, 2018, 5 pages.
European Application No. 16173137.7, Office Action dated Jun. 26, 2019, 5 pages.
European Application No. 16173137.7, Office Action dated Oct. 1, 2018, 6 pages.
European Application No. 17182863.5, Office Action dated Jul. 19, 2019, 4 pages.
Indian Application No. 3139/DELNP/2012, First Examination Report dated Oct. 25, 2017, 8 pages.
Japanese Application No. 2011-527069, Notice of Decision to Grant dated Mar. 4, 2015, 6 pages (3 pages for the original document and 3 pages for the English translation).
Japanese Application No. 2011-527069, Office Action dated Mar. 7, 2014, 14 pages (8 pages for the original document and 6 pages for the English translation).
Japanese Application No. 2012-529756, Notice of Decision to Grant dated Dec. 24, 2015, 5 pages (3 pages for the original document and 2 pages for the English translation).
Japanese Application No. 2012-529756, Office Action dated Jul. 14, 2014, 14 pages (8 pages for the original document and 6 pages for the English translation).
Japanese Application No. 2012-529756, Office Action dated Jun. 2, 2015, 17 pages (10 pages for the original document and 7 pages for the English translation).
Japanese Application No. 2014-180865, Notice of Decision to Grant dated Apr. 1, 2016, 6 pages (3 pages for the original document and 3 pages for the English translation).
Japanese Application No. 2014-180865, Office Action dated Oct. 9, 2015, 7 pages (4 pages for the original document and 3 pages for the English translation).
Japanese Application No. 2015-005024, Office Action dated Jan. 25, 2016, 5 pages (3 pages for the original document and 2 pages for the English translation).
Japanese Application No. 2015-076001, Office Action dated Feb. 10, 2016, 6 pages (3 pages for the original document and 3 pages for the English translation).
Japanese Application No. 2015-076001, Office Action dated Nov. 11, 2016, 9 pages (5 pages for the original document and 4 pages for the English translation).
Japanese Application No. 2015-195591, Notice of Decision to Grant dated Oct. 26, 2016, 6 pages (3 pages for the original document and 3 pages for the English translation).
Japanese Application No. 2015-195591, Office Action dated Jul. 15, 2016, 6 pages (3 pages for the original document and 3 pages for the English translation).
Japanese Application No. 2017-241844, Office Action dated Oct. 19, 2018, 4 pages (2 pages for the original document and 2 pages for the English translation).
Japanese Application No. 2018-017348, Office Action dated Feb. 6, 2019, 15 pages (6 pages for the original document and 9 pages for the English translation).
Japanese Application No. 2018-017349, Office Action dated Dec. 26, 2018, 4 pages (2 pages for the original document and 2 pages for the English translation).

Fractionating DNA Based on Methylation

FIGURE 10
1. Assay Design
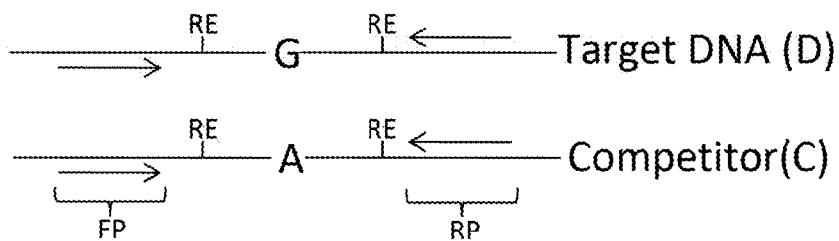
2. CCF DNA isolation     3. DNA digestion
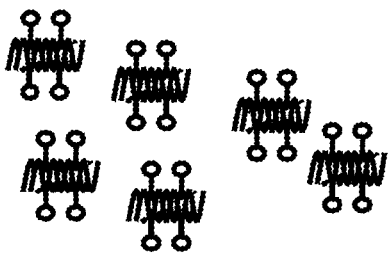
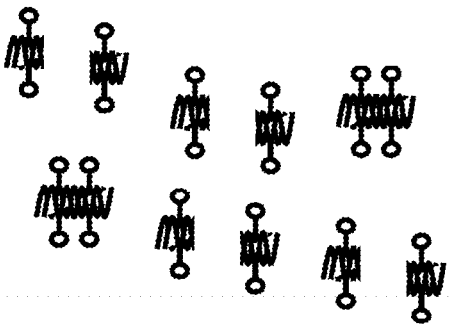
4. Addition of primers and known amount of competitor oligonucleotide Followed by PCR
5. Primer extension
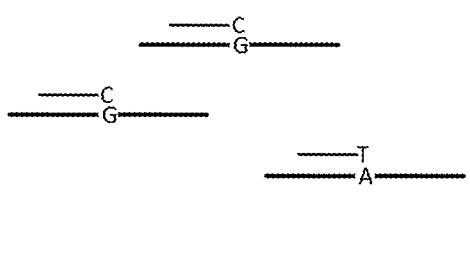
6. Analyte separation
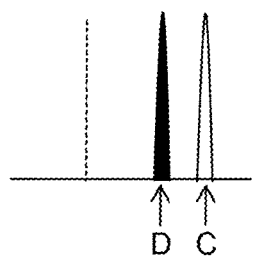

FIGURE 11
1. Selection of differentially methylated targets for specific DNA sequence capture
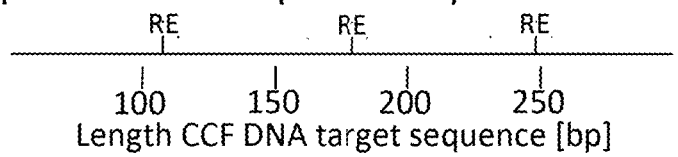
2. Distribution of CCF DNA after capture
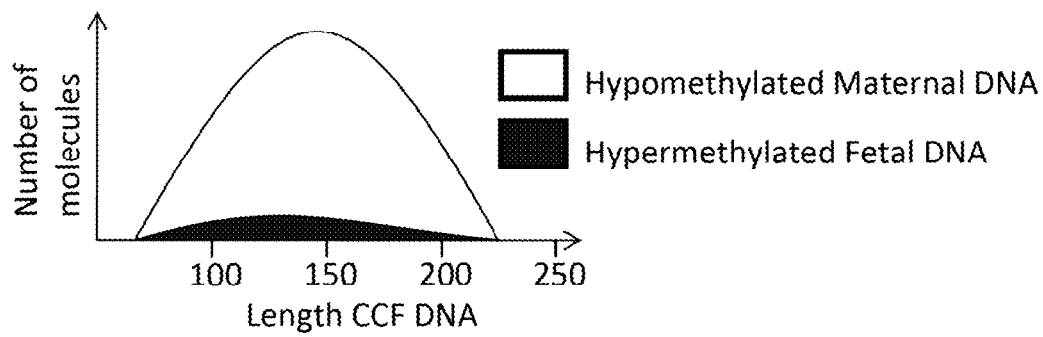
3. Distribution of CCF DNA after digestion
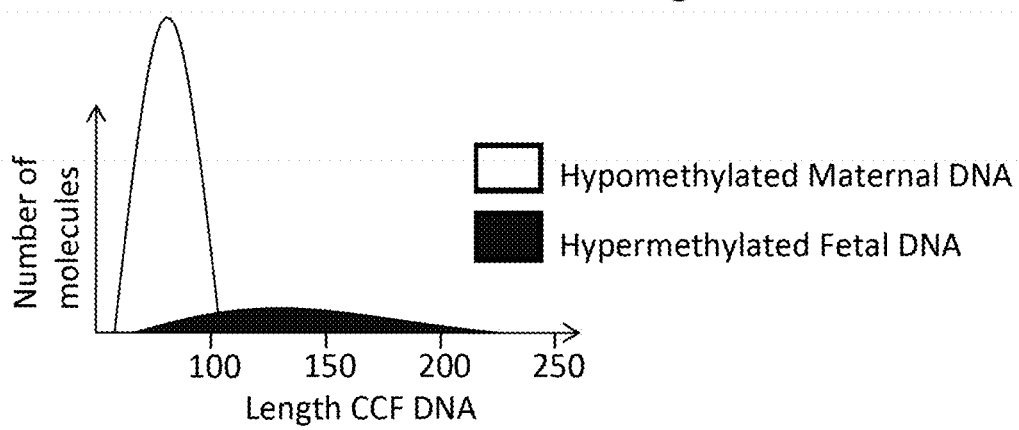
4. Quantification of non-digested DNA molecules
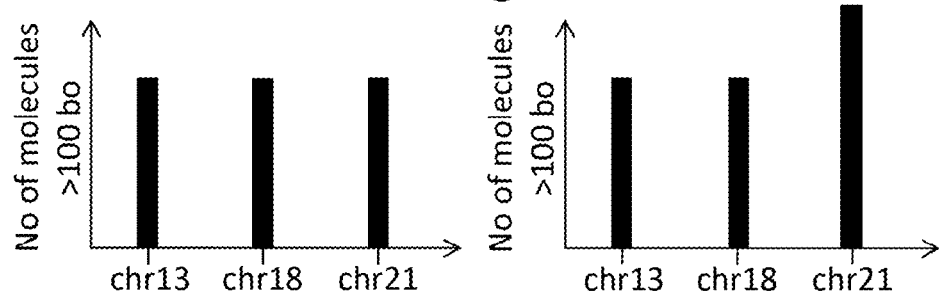

PROCESSES AND COMPOSITIONS FOR METHYLATION-BASED ENRICHMENT OF FETAL NUCLEIC ACID FROM A MATERNAL SAMPLE USEFUL FOR NON-INVASIVE PRENATAL DIAGNOSES

RELATED PATENT APPLICATION

This patent application is a continuation of U.S. patent application Ser. No. 13/801,384, filed on Mar. 13, 2013, entitled PROCESSES AND COMPOSITIONS FOR METHYLATION-BASED ENRICHMENT OF FETAL NUCLEIC ACID FROM A MATERNAL SAMPLE USEFUL FOR NON INVASIVE PRENATAL DIAGNOSES, naming Mathias Ehrich and Anders Olaf Herman Nygren as inventors, which is a continuation of U.S. patent application Ser. No. 12/561,241, filed on Sep. 16, 2009, now U.S. Pat. No. 8,476,013 issued on Jul. 2, 2013, entitled PROCESSES AND COMPOSITIONS FOR METHYLATION-BASED ENRICHMENT OF FETAL NUCLEIC ACID FROM A MATERNAL SAMPLE USEFUL FOR NON INVASIVE PRENATAL DIAGNOSES, naming Mathias Ehrich and Anders Olaf Herman Nygren as inventors, which claims the benefit of U.S. Provisional Patent Application No. 61/192,264 filed on Sep. 16, 2008, entitled PROCESSES AND COMPOSITIONS FOR METHYLATION-BASED ENRICHMENT OF FETAL NUCLEIC ACID FROM A MATERNAL SAMPLE USEFUL FOR NON INVASIVE PRENATAL DIAGNOSES, naming Mathias Ehrich as an inventor. The entire content of the foregoing patent applications is incorporated herein by reference, including all text, tables and drawings.

FIELD

Provided in certain embodiments are biomarkers. In some embodiments, biomarkers provided are useful for noninvasive detection of fetal genetic traits. Certain fetal genetic traits include but are not limited to presence or absence of fetal nucleic acid.

BACKGROUND

Non-invasive prenatal testing is becoming a field of rapidly growing interest. Early detection of pregnancy-related conditions, including complications during pregnancy and genetic defects of the fetus is of crucial importance, as it allows early medical intervention necessary for the safety of both the mother and the fetus. Prenatal diagnosis has been conducted using cells isolated from the fetus through procedures such as chorionic villus sampling (CVS) or amniocentesis. However, these conventional methods are invasive and present an appreciable risk to both the mother and the fetus. The National Health Service currently cites a miscarriage rate of between 1 and 2 percent following the invasive amniocentesis and chorionic villus sampling (CVS) tests.

An alternative to these invasive approaches has been developed for prenatal screening, e.g., to detecting fetal abnormalities, following the discovery that circulating cell-free fetal nucleic acid can be detected in maternal plasma and serum (Lo et al., Lancet 350:485-487, 1997; and U.S. Pat. No. 6,258,540). Circulating cell free fetal nucleic acid (cffNA) has several advantages making it more applicable for non-invasive prenatal testing. For example, cell free nucleic acid is present at higher levels than fetal cells and at concentrations sufficient for genetic analysis. Also, cffNA is cleared from the maternal bloodstream within hours after delivery, preventing contamination from previous pregnancies.

Examples of prenatal tests performed by detecting fetal DNA in maternal plasma or serum include fetal rhesus D (RhD) genotyping (Lo et al., N. Engl. J. Med. 339:1734-1738, 1998), fetal sex determination (Costa et al., N. Engl. J. Med. 346:1502, 2002), and diagnosis of several fetal disorders (Amicucci et al., Clin. Chem. 46:301-302, 2000; Saito et al., Lancet 356:1170, 2000; and Chiu et al., Lancet 360:998-1000, 2002). In addition, quantitative abnormalities of fetal DNA in maternal plasma/serum have been reported in preeclampsia (Lo et al., Clin. Chem. 45:184-188, 1999 and Zhong et al., Am. J. Obstet. Gynecol. 184:414-419, 2001), fetal trisomy 21 (Lo et al., Clin. Chem. 45:1747-1751, 1999 and Zhong et al., Prenat. Diagn. 20:795-798, 2000) and hyperemesis gravidarum (Sekizawa et al., Clin. Chem. 47:2164-2165, 2001).

SUMMARY

The technology provides inter alia human epigenetic biomarkers that are useful for the noninvasive detection of fetal genetic traits, including, but not limited to, the presence or absence of fetal nucleic acid, the absolute or relative amount of fetal nucleic acid, fetal sex, and fetal chromosomal abnormalities such as aneuploidy. The human epigenetic biomarkers of the technology represent genomic DNA that display differential CpG methylation patterns between the fetus and mother. The compositions and processes of the technology allow for the detection and quantification of fetal nucleic acid in a maternal sample based on the methylation status of the nucleic acid in said sample. More specifically, the amount of fetal nucleic acid from a maternal sample can be determined relative to the total amount of nucleic acid present, thereby providing the percentage of fetal nucleic acid in the sample. Further, the amount of fetal nucleic acid can be determined in a sequence-specific (or locus-specific) manner and with sufficient sensitivity to allow for accurate chromosomal dosage analysis (for example, to detect the presence or absence of a fetal aneuploidy).

In an aspect of the technology, a method is provided for enriching fetal nucleic acids from a maternal biological sample, based on differential methylation between fetal and maternal nucleic acid comprising the steps of: (a) binding a target nucleic acid, from a sample, and a control nucleic acid, from the sample, to a methylation-specific binding protein; and (b) eluting the bound nucleic acid based on methylation status, wherein differentially methylated nucleic acids elute at least partly into separate fractions. In an embodiment, the nucleic acid sequence includes one or more of the polynucleotide sequences of SEQ ID NOs: 1-89. SEQ ID NOs: 1-89 are provided in Table 4. The technology includes the sequences of SEQ ID NOs: 1-89, and variations thereto. In another embodiment, a control nucleic acid is not included in step (a).

In a related embodiment, a method is provided for enriching fetal nucleic acid from a maternal sample, which comprises the following steps: (a) obtaining a biological sample from a woman; (b) separating fetal and maternal nucleic acid based on the methylation status of a CpG-containing genomic sequence in the sample, wherein the genomic sequence from the fetus and the genomic sequence from the woman are differentially methylated, thereby distinguishing the genomic sequence from the woman and the genomic sequence from the fetus in the sample. In another embodiment, the genomic sequence is at least 15 nucleotides in length, comprising at least one cytosine, further wherein the region has (1) a genomic locus selected from Table 1; and (2) a DNA sequence of no more than 10 kb upstream and/or downstream from the locus. In embodiments, obtaining a biological sample from a woman does not limit the scope of the technology. This obtaining can refer to actually collecting a sample from a woman (e.g., a blood draw) or to receiving a sample from elsewhere (e.g., from a clinic or hospital) and performing steps of a method.

In another related embodiment, a method is provided for enriching fetal nucleic acid from a maternal sample, which comprises the following steps: (a) obtaining a biological sample from the woman; (b) digesting or removing maternal nucleic acid based on the methylation status of a CpG-containing genomic sequence in the sample, wherein the genomic sequence from the fetus and the genomic sequence from the woman are differentially methylated, thereby enriching for the genomic sequence from the fetus in the sample. Maternal nucleic acid may be digested using one or more methylation sensitive restriction enzymes that selectively digest or cleave maternal nucleic acid based on its methylation status. In another embodiment, the genomic sequence is at least 15 nucleotides in length, comprising at least one cytosine, further wherein the region consists of (1) a genomic locus selected from Table 1; and (2) a DNA sequence of no more than 10 kb upstream and/or downstream from the locus.

In another aspect of the technology, a method is provided for preparing nucleic acid having a nucleotide sequence of a fetal nucleic acid, which comprises the following steps: (a) providing a sample from a pregnant female; (b) separating fetal nucleic acid from maternal nucleic acid from the sample of the pregnant female according to a different methylation state between the fetal nucleic acid and the maternal nucleic acid counterpart, wherein the nucleotide sequence of the fetal nucleic acid comprises one or more CpG sites from one or more of the polynucleotide sequences of SEQ ID NOs: 1-89 within a polynucleotide sequence from a gene or locus that contains one of the polynucleotide sequences of SEQ ID NOs: 1-89; and (c) preparing nucleic acid comprising a nucleotide sequence of the fetal nucleic acid by an amplification process in which fetal nucleic acid separated in part (b) is utilized as a template. In another embodiment, a method is provided for preparing nucleic acid having a nucleotide sequence of a fetal nucleic acid, which comprises the following steps: (a) providing a sample from a pregnant female; (b) digesting or removing maternal nucleic acid from the sample of the pregnant female according to a different methylation state between the fetal nucleic acid and the maternal nucleic acid counterpart, wherein the nucleotide sequence of the fetal nucleic acid comprises one or more CpG sites from one or more of the polynucleotide sequences of SEQ ID NOs: 1-89 within a polynucleotide sequence from a gene that contains one of the polynucleotide sequences of SEQ ID NOs: 1-89; and (c) preparing nucleic acid comprising a nucleotide sequence of the fetal nucleic acid. The preparing process of step (c) may be a hybridization process, a capture process, or an amplification process in which fetal nucleic acid separated in part (b) is utilized as a template. Also, in the above embodiment wherein maternal nucleic acid is digested, the maternal nucleic acid may be digested using one or more methylation sensitive restriction enzymes that selectively digest or cleave maternal nucleic acid based on its methylation status. In either embodiment, the polynucleotide sequences of SEQ ID NOs: 1-89 may be within a polynucleotide sequence from a CpG island that contains one of the polynucleotide sequences of SEQ ID NOs: 1-89. The polynucleotide sequences of SEQ ID NOs: 1-89 are further characterized in Tables 1-3 herein, including the identification of CpG islands that overlap with the polynucleotide sequences provided in SEQ ID NOs: 1-89. In another embodiment, the nucleic acid prepared by part (c) is in solution. In yet another embodiment, the method further comprises quantifying the fetal nucleic acid from the amplification process of step (c).

In another aspect of the technology, a method is provided for enriching fetal nucleic acid from a sample from a pregnant female with respect to maternal nucleic acid, which comprises the following steps: (a) providing a sample from a pregnant female; and (b) separating or capturing fetal nucleic acid from maternal nucleic acid from the sample of the pregnant female according to a different methylation state between the fetal nucleic acid and the maternal nucleic acid, wherein the nucleotide sequence of the fetal nucleic acid comprises one or more CpG sites from one or more of the polynucleotide sequences of SEQ ID NOs: 1-89 within a polynucleotide sequence from a gene that contains one of the polynucleotide sequences of SEQ ID NOs: 1-89. In another embodiment, the polynucleotide sequences of SEQ ID NOs: 1-89 may be within a polynucleotide sequence from a CpG island that contains one of the polynucleotide sequences of SEQ ID NOs: 1-89. The polynucleotide sequences of SEQ ID NOs: 1-89 are characterized in Table 1 herein. In another embodiment, the nucleic acid separated by part (b) is in solution. In yet another embodiment, the method further comprises amplifying and/or quantifying the fetal nucleic acid from the separation process of step (b).

In another aspect of the technology, a composition is provided comprising an isolated nucleic acid from a fetus of a pregnant female, wherein the nucleotide sequence of the nucleic acid comprises one or more of the polynucleotide sequences of SEQ ID NOs: 1-89. In one embodiment, the nucleotide sequence consists essentially of a nucleotide sequence of a gene, or portion thereof. In another embodiment, the nucleotide sequence consists essentially of a nucleotide sequence of a CpG island, or portion thereof. The polynucleotide sequences of SEQ ID NOs: 1-89 are further characterized in Table 1. In another embodiment, the nucleic acid is in solution. In another embodiment, the nucleic acid from the fetus is enriched relative to maternal nucleic acid. In another embodiment, the composition further comprises an agent that binds to methylated nucleotides. For example, the agent may be a methyl-CpG binding protein (MBD) or fragment thereof.

In another aspect of the technology, a composition is provided comprising an isolated nucleic acid from a fetus of a pregnant female, wherein the nucleotide sequence of the nucleic acid comprises one or more CpG sites from one or more of the polynucleotide sequences of SEQ ID NOs: 1-89 within a polynucleotide sequence from a gene, or portion thereof, that contains one of the polynucleotide sequences of SEQ ID NOs: 1-89. In another embodiment, the nucleotide sequence of the nucleic acid comprises one or more CpG sites from one or more of the polynucleotide sequences of SEQ ID NOs: 1-89 within a polynucleotide sequence from a CpG island, or portion thereof, that contains one of the polynucleotide sequences of SEQ ID NOs: 1-89. The polynucleotide sequences of SEQ ID NOs: 1-89 are further characterized in Table 1. In another embodiment, the nucleic acid is in solution. In another embodiment, the nucleic acid from the fetus is enriched relative to maternal nucleic acid. Hyper- and hypomethylated nucleic acid sequences of the technology are identified in Table 1. In another embodiment, the composition further comprises an agent that binds to methylated nucleotides. For example, the agent may be a methyl-CpG binding protein (MBD) or fragment thereof.

In some embodiments, a nucleotide sequence of the technology includes three or more of the CpG sites. In another embodiment, the nucleotide sequence includes five or more of the CpG sites. In another embodiment, the nucleotide sequence is from a gene region that comprises a PRC2 domain (see Table 3). In another embodiment, the nucleotide sequence is from a gene region involved with development. For example, SOX14—which is an epigenetic marker of the present technology (See Table 1)—is a member of the SOX (SRY-related HMG-box) family of transcription factors involved in the regulation of embryonic development and in the determination of cell fate.

In some embodiments, the genomic sequence from the woman is methylated and the genomic sequence from the fetus is unmethylated. In other embodiments, the genomic sequence from the woman is unmethylated and the genomic sequence from the fetus is methylated. In another embodiment, the genomic sequence from the fetus is hypermethylated relative to the genomic sequence from the mother. Fetal genomic sequences found to be hypermethylated relative to maternal genomic sequence are provided in SEQ ID NOs: 1-59. Alternatively, the genomic sequence from the fetus is hypomethylated relative to the genomic sequence from the mother. Fetal genomic sequences found to be hypomethylated relative to maternal genomic sequence are provided in SEQ ID NOs: 60-85. Methylation sensitive restriction enzymes of the technology may be sensitive to hypo- or hyper-methylated nucleic acid.

In another embodiment, the fetal nucleic acid is extracellular nucleic acid. Generally the extracellular fetal nucleic acid is about 500, 400, 300, 250, 200 or 150 (or any number there between) nucleotide bases or less. In another embodiment, the digested maternal nucleic acid is less than about 90, 100, 110, 120, 130, 140 or 150 base pairs. In a related embodiment, the fetal nucleic acid is selectively amplified, captured or separated from or relative to the digested maternal nucleic acid based on size. For example, PCR primers may be designed to amplify nucleic acid greater than about 75, 80, 85, 90, 95, 100, 105, 110, 115 or 120 (or any number there between) base pairs thereby amplifying fetal nucleic acid and not digested maternal nucleic acid. In another embodiment, the nucleic acid is subjected to fragmentation prior to certain methods of the technology. Examples of methods of fragmenting nucleic acid, include but are not limited to sonication and restriction enzyme digestion. In some embodiments the fetal nucleic acid is derived from the placenta. In other embodiments the fetal nucleic acid is apoptotic.

In some embodiments, the present technology provides a method in which the sample is a member selected from the following: maternal whole blood, maternal plasma or serum, amniotic fluid, a chorionic villus sample, biopsy material from a pre-implantation embryo, fetal nucleated cells or fetal cellular remnants isolated from maternal blood, maternal urine, maternal saliva, washings of the female reproductive tract and a sample obtained by celocentesis or lung lavage. In certain embodiments, the biological sample is maternal blood. In some embodiments, the biological sample is a chorionic villus sample. In certain embodiments, the maternal sample is enriched for fetal nucleic acid prior to certain methods of the present technology. Examples of fetal enrichment methods are provided in PCT Publication Nos. WO/2007140417A2, WO2009/032781A2 and US Publication No. 20050164241.

In some embodiments, nucleated and anucleated cell populations are removed from the sample prior to practicing certain methods of the technology (e.g., substantially all nucleated and anucleated cell populations are removed). In some embodiments, the sample is collected, stored or transported in a manner known to the person of ordinary skill in the art to minimize degradation or the quality of fetal nucleic acid present in the sample.

The sample can be from any animal, including but not limited, human, non-human, mammal, reptile, cattle, cat, dog, goat, swine, pig, monkey, ape, gorilla, bull, cow, bear, horse, sheep, poultry, mouse, rat, fish, dolphin, whale, and shark, or any animal or organism that may have a detectable pregnancy-associated disorder or chromosomal abnormality.

In some embodiments, the sample is treated with a reagent that differentially modifies methylated and unmethylated DNA. For example, the reagent may comprise bisulfite; or the reagent may comprise one or more enzymes that preferentially cleave methylated DNA; or the reagent may comprise one or more enzymes that preferentially cleave unmethylated DNA. Examples of methylation sensitive restriction enzymes include, but are not limited to, HhaI and HpaII.

In one embodiment, the fetal nucleic acid is separated from the maternal nucleic acid by an agent that specifically binds to methylated nucleotides in the fetal nucleic acid. In another embodiment, the fetal nucleic acid is separated or removed from the maternal nucleic acid by an agent that specifically binds to methylated nucleotides in the maternal nucleic acid counterpart. In an embodiment, the agent that binds to methylated nucleotides is a methyl-CpG binding protein (MBD) or fragment thereof.

In another aspect of the technology, a method is provided for determining the amount or copy number of fetal DNA in a maternal sample that comprises differentially methylated maternal and fetal DNA. The method is performed by a) distinguishing between the maternal and fetal DNA based on differential methylation status; and b) quantifying the fetal DNA of step a). In a specific embodiment, the method comprises a) digesting the maternal DNA in a maternal sample using one or more methylation sensitive restriction enzymes thereby enriching the fetal DNA; and b) determining the amount of fetal DNA from step a). The amount of fetal DNA can be used inter alia to confirm the presence or absence of fetal nucleic acid, determine fetal sex, diagnose fetal disease or be used in conjunction with other fetal diagnostic methods to improve sensitivity or specificity. In one embodiment, the method for determining the amount of fetal DNA does not require the use of a polymorphic sequence. For example, an allelic ratio is not used to quantify the fetal DNA in step b). In another embodiment, the method for determining the amount of fetal DNA does not require the treatment of DNA with bisulfite to convert cytosine residues to uracil. Bisulfite is known to degrade DNA, thereby, further reducing the already limited fetal nucleic acid present in maternal samples. In one embodiment, determining the amount of fetal DNA in step b) is done by introducing one or more competitors at known concentrations. In another embodiment, determining the amount of fetal DNA in step b) is done by RT-PCR, primer extension, sequencing or counting. In a related embodiment, the amount of nucleic acid is determined using BEAMing technology as described in US Patent Publication No. US20070065823. In another embodiment, the restriction efficiency is determined and the efficiency rate is used to further determine the amount of fetal DNA. Exemplary differentially methylated nucleic acids are provided in SEQ ID NOs: 1-89.

In another aspect of the technology, a method is provided for determining the concentration of fetal DNA in a maternal sample, wherein the maternal sample comprises differentially methylated maternal and fetal DNA, comprising a) determining the total amount of DNA present in the maternal sample; b) selectively digesting the maternal DNA in a maternal sample using one or more methylation sensitive restriction enzymes thereby enriching the fetal DNA; c) determining the amount of fetal DNA from step b); and d) comparing the amount of fetal DNA from step c) to the total amount of DNA from step a), thereby determining the concentration of fetal DNA in the maternal sample. The concentration of fetal DNA can be used inter alia in conjunction with other fetal diagnostic methods to improve sensitivity or specificity. In one embodiment, the method for determining the amount of fetal DNA does not require the use of a polymorphic sequence. For example, an allelic ratio is not used to quantify the fetal DNA in step b). In another embodiment, the method for determining the amount of fetal DNA does not require the treatment of DNA with bisulfite to convert cytosine residues to uracil. In one embodiment, determining the amount of fetal DNA in step b) is done by introducing one or more competitors at known concentrations. In another embodiment, determining the amount of fetal DNA in step b) is done by RT-PCR, sequencing or counting. In another embodiment, the restriction efficiency is determined and used to further determine the amount of total DNA and fetal DNA. Exemplary differentially methylated nucleic acids are provided in SEQ ID NOs: 1-89.

In another aspect of the technology, a method is provided for determining the presence or absence of a fetal aneuploidy using fetal DNA from a maternal sample, wherein the maternal sample comprises differentially methylated maternal and fetal DNA, comprising a) selectively digesting the maternal DNA in a maternal sample using one or more methylation sensitive restriction enzymes thereby enriching the fetal DNA; b) determining the amount of fetal DNA from a target chromosome; c) determining the amount of fetal DNA from a reference chromosome; and d) comparing the amount of fetal DNA from step b) to step c), wherein a biologically or statistically significant difference between the amount of target and reference fetal DNA is indicative of the presence of a fetal aneuploidy. In one embodiment, the method for determining the amount of fetal DNA does not require the use of a polymorphic sequence. For example, an allelic ratio is not used to quantify the fetal DNA in step b). In another embodiment, the method for determining the amount of fetal DNA does not require the treatment of DNA with bisulfite to convert cytosine residues to uracil. In one embodiment, determining the amount of fetal DNA in steps b) and c) is done by introducing one or more competitors at known concentrations. In another embodiment, determining the amount of fetal DNA in steps b) and c) is done by RT-PCR, sequencing or counting. In another embodiment, the amount of fetal DNA from a target chromosome determined in step b) is compared to a standard control, for example, the amount of fetal DNA from a target chromosome from euploid pregnancies. In another embodiment, the restriction efficiency is determined and used to further determine the amount of fetal DNA from a target chromosome and from a reference chromosome. Exemplary differentially methylated nucleic acids are provided in SEQ ID NOs: 1-89.

In another aspect of the technology, a method is provided for detecting the presence or absence of a chromosomal abnormality by analyzing the amount or copy number of target nucleic acid and control nucleic acid from a sample of differentially methylated nucleic acids comprising the steps of: (a) enriching a target nucleic acid, from a sample, and a control nucleic acid, from the sample, based on its methylation state; (b) performing a copy number analysis of the enriched target nucleic acid in at least one of the fractions; (c) performing a copy number analysis of the enriched control nucleic acid in at least one of the fractions; (d) comparing the copy number from step (b) with the copy number from step (c); and (e) determining if a chromosomal abnormality exists based on the comparison in step (d), wherein the target nucleic acid and control nucleic acid have the same or substantially the same methylation status. In a related embodiment, a method is provided for detecting the presence or absence of a chromosomal abnormality by analyzing the amount or copy number of target nucleic acid and control nucleic acid from a sample of differentially methylated nucleic acids comprising the steps of: (a) binding a target nucleic acid, from a sample, and a control nucleic acid, from the sample, to a binding agent; (b) eluting the bound nucleic acid based on methylation status, wherein differentially methylated nucleic acids elute at least partly into separate fractions; (c) performing a copy number analysis of the eluted target nucleic acid in at least one of the fractions; (d) performing a copy number analysis of the eluted control nucleic acid in at least one of the fractions; (e) comparing the copy number from step (c) with the copy number from step (d); and (f) determining if a chromosomal abnormality exists based on the comparison in step (e), wherein the target nucleic acid and control nucleic acid have the same or substantially the same methylation status. Differentially methylated nucleic acids are provided in SEQ ID NOs: 1-89.

In another aspect of the technology, a method is provided for detecting the presence or absence of a chromosomal abnormality by analyzing the allelic ratio of target nucleic acid and control nucleic acid from a sample of differentially methylated nucleic acids comprising the steps of: (a) binding a target nucleic acid, from a sample, and a control nucleic acid, from the sample, to a binding agent; (b) eluting the bound nucleic acid based on methylation status, wherein differentially methylated nucleic acids elute at least partly into separate fractions; (c) performing an allelic ratio analysis of the eluted target nucleic acid in at least one of the fractions; (d) performing an allelic ratio analysis of the eluted control nucleic acid in at least one of the fractions; (e) comparing the allelic ratio from step c with the allelic ratio from step d; and (f) determining if a chromosomal abnormality exists based on the comparison in step (e), wherein the target nucleic acid and control nucleic acid have the same or substantially the same methylation status. Differentially methylated nucleic acids are provided in SEQ ID NOs: 1-89, and SNPs within the differentially methylated nucleic acids are provided in Table 2. The methods may also be useful for detecting a pregnancy-associated disorder.

In another aspect of the technology, the amount of maternal nucleic acid is determined using the methylation-based methods of the technology. For example, fetal nucleic acid can be separated (for example, digested using a methylation-sensitive enzyme) from the maternal nucleic acid in a sample, and the maternal nucleic acid can be quantified using the methods of the technology. Once the amount of maternal nucleic acid is determined, that amount can subtracted from the total amount of nucleic acid in a sample to determine the amount of fetal nucleic acid. The amount of fetal nucleic acid can be used to detect fetal traits, including fetal aneuploidy, as described herein.

For aspects and embodiments of the technology described herein, the methods may also be useful for detecting a pregnancy-associated disorder. In some embodiments, the sample comprises fetal nucleic acid, or fetal nucleic acid and maternal nucleic acid. In the case when the sample comprises fetal and maternal nucleic acid, the fetal nucleic acid and the maternal nucleic acid may have a different methylation status. Nucleic acid species with a different methylation status can be differentiated by any method known in the art. In an embodiment, the fetal nucleic acid is enriched by the selective digestion of maternal nucleic acid by a methylation sensitive restriction enzyme. In another embodiment, the fetal nucleic acid is enriched by the selective digestion of maternal nucleic acid using two or more methylation sensitive restriction enzymes in the same assay. In an embodiment, the target nucleic acid and control nucleic acid are both from the fetus. In another embodiment, the average size of the fetal nucleic acid is about 100 bases to about 500 bases in length. In another embodiment the chromosomal abnormality is an aneuploidy, such as trisomy 21. In some embodiments, the target nucleic acid is at least a portion of a chromosome which may be abnormal and the control nucleic acid is at least a portion of a chromosome which is very rarely abnormal. For example, when the target nucleic acid is from chromosome 21, the control nucleic acid is from a chromosome other than chromosome 21—preferably another autosome. In another embodiment, the binding agent is a methylation-specific binding protein such as MBD-Fc. Also, the enriched or eluted nucleic acid is amplified and/or quantified by any method known in the art. In an embodiment, the fetal DNA is quantified using a method that does not require the use of a polymorphic sequence. For example, an allelic ratio is not used to quantify the fetal DNA. In another embodiment, the method for quantifying the amount of fetal DNA does not require the treatment of DNA with bisulfite to convert cytosine residues to uracil.

In some embodiments, the methods of the technology include the additional step of determining the amount of one or more Y-chromosome-specific sequences in a sample. In a related embodiment, the amount of fetal nucleic acid in a sample as determined by using the methylation-based methods of the technology is compared to the amount of Y-chromosome nucleic acid present.

Methods for differentiating nucleic acid based on methylation status include, but are not limited to, methylation sensitive capture, for example using, MBD2-Fc fragment; bisulfite conversion methods, for example, MSP (methylation-sensitive PCR), COBRA, methylation-sensitive single nucleotide primer extension (Ms-SNuPE) or Sequenom MassCLEAVE™ technology; and the use of methylation sensitive restriction enzymes. Except where explicitly stated, any method for differentiating nucleic acid based on methylation status can be used with the compositions and methods of the technology.

In some embodiments, methods of the technology may further comprise an amplification step. The amplification step can be performed by PCR, such as methylation-specific PCR. In another embodiment, the amplification reaction is performed on single molecules, for example, by digital PCR, which is further described in U.S. Pat. Nos. 6,143,496 and 6,440,706, both of which are hereby incorporated by reference. In other embodiments, the method does not require amplification. For example, the amount of enriched fetal DNA may be determined by counting the fetal DNA (or sequence tags attached thereto) with a flow cytometer or by sequencing means that do not require amplification. In another embodiment, the amount of fetal DNA is determined by an amplification reaction that generates amplicons larger than the digested maternal nucleic acid, thereby further enriching the fetal nucleic acid.

For embodiments that require sequence analysis, any one of the following sequencing technologies may be used: a primer extension method (e.g., iPLEX®; Sequenom, Inc.), direct DNA sequencing, restriction fragment length polymorphism (RFLP analysis), allele specific oligonucleotide (ASO) analysis, methylation-specific PCR (MSPCR), pyrosequencing analysis, acycloprime analysis, Reverse dot blot, GeneChip microarrays, Dynamic allele-specific hybridization (DASH), Peptide nucleic acid (PNA) and locked nucleic acids (LNA) probes, TaqMan, Molecular Beacons, Intercalating dye, FRET primers, fluorescence tagged dNTP/ddNTPs, AlphaScreen, SNPstream, genetic bit analysis (GBA), Multiplex minisequencing, SNaPshot, GOOD assay, Microarray miniseq, arrayed primer extension (APEX), Microarray primer extension, Tag arrays, Coded microspheres, Template-directed incorporation (TDI), fluorescence polarization, Colorimetric oligonucleotide ligation assay (OLA), Sequence-coded OLA, Microarray ligation, Ligase chain reaction, Padlock probes, Invader™ assay, hybridization using at least one probe, hybridization using at least one fluorescently labeled probe, electrophoresis, cloning and sequencing, for example as performed on the 454 platform (Roche) (Margulies, M. et al. 2005 Nature 437, 376-380), Illumina Genome Analyzer (or Solexa platform) or SOLiD System (Applied Biosystems) or the Helicos True Single Molecule DNA sequencing technology (Harris T D et al. 2008 Science, 320, 106-109), the single molecule, real-time (SMRT™) technology of Pacific Biosciences, or nanopore-based sequencing (Soni G V and Meller A. 2007 Clin Chem 53: 1996-2001) and combinations thereof. Nanopore-based methods may include sequencing nucleic acid using a nanopore, or counting nucleic acid molecules using a nanopore, for example, based on size wherein sequence information is not determined.

The absolute copy number of one or more nucleic acids can be determined, for example, using mass spectrometry, a system that uses a competitive PCR approach for absolute copy number measurements. See for example, Ding C, Cantor C R (2003) A high-throughput gene expression analysis technique using competitive PCR and matrix-assisted laser desorption ionization time-of-flight MS. Proc Natl Acad Sci USA 100:3059-3064, and U.S. patent application Ser. No. 10/655,762, which published as US Patent Publication No. 20040081993, both of which are hereby incorporated by reference.

In some embodiments, the amount of the genomic sequence is compared with a standard control, wherein an increase or decrease from the standard control indicates the presence or progression of a pregnancy-associated disorder. For example, the amount of fetal nucleic acid may be compared to the total amount of DNA present in the sample. Or when detecting the presence or absence of fetal aneuploidy, the amount of fetal nucleic acid from target chromosome may be compared to the amount of fetal nucleic acid from a reference chromosome. Preferably the reference chromosome is another autosome that has a low rate of aneuploidy. The ratio of target fetal nucleic acid to reference fetal nucleic acid may be compared to the same ratio from a normal, euploid pregnancy. For example, a control ratio may be determined from a DNA sample obtained from a female carrying a healthy fetus who does not have a chromosomal abnormality. Preferably, one uses a panel of control samples. Where certain chromosome anomalies are known, one can also have standards that are indicative of a specific disease or condition. Thus, for example, to screen for three different chromosomal aneuploidies in a maternal plasma of a pregnant female, one preferably uses a panel of control DNAs that have been isolated from mothers who are known to carry a fetus with, for example, chromosome 13, 18, or 21 trisomy, and a mother who is pregnant with a fetus who does not have a chromosomal abnormality.

In some embodiments, the present technology provides a method in which the alleles from the target nucleic acid and control nucleic acid are differentiated by sequence variation. The sequence variation may be a single nucleotide polymorphism (SNP) or an insertion/deletion polymorphism. In an embodiment, the fetal nucleic acid should comprise at least one high frequency heterozygous polymorphism (e.g., about 2%, 3%, 4%, 5%, 6%, 7%, 8%, 9%, 10%, 11%, 12%, 13%, 14%, 15%, 16%, 17%, 18%, 19%, 20%, 25% or more frequency rate), which allows the determination of the allelic-ratio of the nucleic acid in order to assess the presence or absence of the chromosomal abnormality. A list of exemplary SNPs is provided in Table 2, however, this does not represent a complete list of polymorphic alleles that can be used as part of the technology. Any SNP meeting the following criteria may also be considered: (a) the SNP has a heterozygosity frequency greater than about 2% (preferably across a range of different populations), (b) the SNP is a heterozygous locus; and (c)(i) the SNP is within nucleic acid sequence described herein, or (c)(iii) the SNP is within about 5 to about 2000 base pairs of a SNP described herein (e.g., within about 5, 10, 15, 20, 25, 30, 40, 50, 60, 70, 80, 90, 100, 200, 300, 400, 500, 600, 700, 800, 900, 1000, 1250, 1500, 1750 or 2000 base pairs of a SNP described herein).

In other embodiments, the sequence variation is a short tandem repeat (STR) polymorphism. In some embodiments, the sequence variation falls in a restriction site, whereby one allele is susceptible to digestion by a restriction enzyme and the one or more other alleles are not. In some embodiments, the sequence variation is a methylation site.

In some embodiments, performing an allelic ratio analysis comprises determining the ratio of alleles of the target nucleic acid and control nucleic acid from the fetus of a pregnant woman by obtaining an nucleic acid-containing biological sample from the pregnant woman, wherein the biological sample contains fetal nucleic acid, partially or wholly separating the fetal nucleic acid from the maternal nucleic acid based on differential methylation, discriminating the alleles from the target nucleic acid and the control nucleic acid, followed by determination of the ratio of the alleles, and detecting the presence or absence of a chromosomal disorder in the fetus based on the ratio of alleles, wherein a ratio above or below a normal, euploid ratio is indicative of a chromosomal disorder. In one embodiment, the target nucleic acid is from a suspected aneuploid chromosome (e.g., chromosome 21) and the control nucleic acid is from a euploid chromosome from the same fetus.

In some embodiments, the present technology is combined with other fetal markers to detect the presence or absence of multiple chromosomal abnormalities, wherein the chromosomal abnormalities are selected from the following: trisomy 21, trisomy 18 and trisomy 13, or combinations thereof. In some embodiments, the chromosomal disorder involves the X chromosome or the Y chromosome.

In some embodiments, the compositions or processes may be multiplexed in a single reaction. For example, the amount of fetal nucleic acid may be determined at multiple loci across the genome. Or when detecting the presence or absence of fetal aneuploidy, the amount of fetal nucleic acid may be determined at multiple loci on one or more target chromosomes (e.g., chromosomes 13, 18 or 21) and on one or more reference chromosomes. If an allelic ratio is being used, one or more alleles from Table 2 can be detected and discriminated simultaneously. When determining allelic ratios, multiplexing embodiments are particularly important when the genotype at a polymorphic locus is not known. In some instances, for example when the mother and child are homozygous at the polymorphic locus, the assay may not be informative. In one embodiment, greater than 1, 2, 3, 4, 5, 6, 7, 8, 9, 10, 11, 12, 13, 14, 15, 16, 17, 18, 19, 20, 25, 30, 35, 40, 50, 100, 200, 300 or 500, and any intermediate levels, polynucleotide sequences of the technology are enriched, separated and/or examined according the methods of the technology. When detecting a chromosomal abnormality by analyzing the copy number of target nucleic acid and control nucleic acid, less than 3, 4, 5, 6, 7, 8, 9, 10, 11, 12, 13, or 14 polynucleotide sequences may need to be analyzed to accurately detect the presence or absence of a chromosomal abnormality. In another embodiment, the compositions or processes of the technology may be used to assay samples that have been divided into 2, 3, 4, 5, 6, 7, 8, 9, 10, 11, 12, 13, 14, 15, 16, 17, 18, 19, 20, 25, 30, 35, 40, 50, 100 or more replicates, or into single molecule equivalents. Methods for analyzing fetal nucleic acids from a maternal sample in replicates, including single molecule analyses, are provided in U.S. application Ser. No. 11/364,294, which published as US Patent Publication No. US 2007-0207466 A1, which is hereby incorporated by reference.

In a further embodiment, the present technology provides a method wherein a comparison step shows an increased risk of a fetus having a chromosomal disorder if the ratio of the alleles or absolute copy number of the target nucleic acid is higher or lower by 1 standard deviation from the standard control sequence. In some embodiments, the comparison step shows an increased risk of a fetus having a chromosomal disorder if the ratio of the alleles or absolute copy number of the target nucleic acid is higher or lower by 2 standard deviation from the standard control sequence. In some other embodiments, the comparison step shows an increased risk of a fetus having a chromosomal disorder if the ratio of the alleles or absolute copy number of the target nucleic acid is higher or lower by 3 standard deviation from the standard control sequence. In some embodiments, the comparison step shows an increased risk of a fetus having a chromosomal disorder if the ratio of the alleles or absolute copy number of the target nucleic acid is higher or lower than a statistically significant standard deviation from the control. In one embodiment, the standard control is a maternal reference, and in another embodiment the standard control is a fetal reference chromosome (e.g., non-trisomic autosome).

In some embodiments, the methods of the technology may be combined with other methods for diagnosing a chromosomal abnormality. For example, a noninvasive diagnostic method may require confirmation of the presence or absence of fetal nucleic acid, such as a sex test for a female fetus or to confirm an RhD negative female fetus in an RhD negative mother. In another embodiment, the compositions and methods of the technology may be used to determine the percentage of fetal nucleic acid in a maternal sample in order to enable another diagnostic method that requires the percentage of fetal nucleic acid be known. For example, does a sample meet certain threshold concentration requirements? When determining an allelic ratio to diagnose a fetal aneuploidy from a maternal sample, the amount or concentration of fetal nucleic acid may be required to make a diagnose with a given sensitivity and specificity. In other embodiments, the compositions and methods of the technology for detecting a chromosomal abnormality can be combined with other known methods thereby improving the overall sensitivity and specificity of the detection method. For example, mathematical models have suggested that a combined first-trimester screening program utilizing maternal age (MA), nuchal translucency (NT) thickness, serum-free beta-hCG, and serum PAPP-A will detect more than 80% of fetuses with Down's syndrome for a 5% invasive testing rate (Wald and Hackshaw, Prenat Diagn 17(9):921-9 (1997)). However, the combination of commonly used aneuploidy detection methods combined with the non-invasive free fetal nucleic acid-based methods described herein may offer improved accuracy with a lower false positive rate. Examples of combined diagnostic methods are provided in PCT Publication Number WO2008157264A2 (assigned to the Applicant), which is hereby incorporated by reference. In some embodiments, the methods of the technology may be combined with cell-based methods, wherein fetal cells are procured invasively or non-invasively.

In certain embodiments, an increased risk for a chromosomal abnormality is based on the outcome or result(s) produced from the compositions or methods provided herein. An example of an outcome is a deviation from the euploid absolute copy number or allelic ratio, which indicates the presence of chromosomal aneuploidy. This increase or decrease in the absolute copy number or ratio from the standard control indicates an increased risk of having a fetus with a chromosomal abnormality (e.g., trisomy 21). Information pertaining to a method described herein, such as an outcome, result, or risk of trisomy or aneuploidy, for example, may be transfixed, renditioned, recorded and/or displayed in any suitable medium. For example, an outcome may be transfixed in a medium to save, store, share, communicate or otherwise analyze the outcome. A medium can be tangible (e.g., paper) or intangible (e.g., electronic medium), and examples of media include, but are not limited to, computer media, databases, charts, patient charts, records, patient records, graphs and tables, and any other medium of expression. The information sometimes is stored and/or renditioned in computer readable form and sometimes is stored and organized in a database. In certain embodiments, the information may be transferred from one location to another using a physical medium (e.g., paper) or a computer readable medium (e.g., optical and/or magnetic storage or transmission medium, floppy disk, hard disk, random access memory, computer processing unit, facsimile signal, satellite signal, transmission over an internet or transmission over the world-wide web).

A CpG island may be used as the CpG-containing genomic sequence in some cases, whereas in other cases the CpG-containing genomic sequence may not be a CpG island. In some embodiments, the present technology provides a kit for performing the methods of the technology. One component of the kit is a methylation-sensitive binding agent.

BRIEF DESCRIPTION OF THE DRAWINGS

FIG. 6 discloses SEQ ID NOS 178-179, respectively, in order of appearance.

FIG. 10: Shows one embodiment of the Fetal Quantifier Method. Maternal nucleic acid is selectively digested and the remaining fetal nucleic acid is quantified using a competitor of known concentration. In this schema, the analyte is separated and quantified by a mass spectrometer.

FIG. 11: Shows one embodiment of the Methylation-Based Fetal Diagnostic Method. Maternal nucleic acid is selectively digested and the remaining fetal nucleic acid is quantified for three different chromosomes (13, 18 and 21). Parts 2 and 3 of the Figure illustrate the size distribution of the nucleic acid in the sample before and after digestion. The amplification reactions can be size-specific (e.g., greater than 100 base pair amplicons) such that they favor the longer, non-digested fetal nucleic acid over the digested maternal nucleic acid, thereby further enriching the fetal nucleic acid. The spectra at the bottom of the Figure show an increased amount of chromosome 21 fetal nucleic acid indicative of trisomy 21.

FIGS. 14 A and B: Show the results of the total copy number assay from plasma samples.

DEFINITIONS

Figure 1:
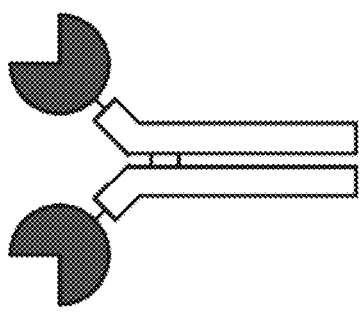
FIG. 1: Shows the design of the recombinant MBD-Fc protein used to separate differentially methylated DNA.

The term "pregnancy-associated disorder," as used in this application, refers to any condition or disease that may affect a pregnant woman, the fetus, or both the woman and the fetus. Such a condition or disease may manifest its symptoms during a limited time period, e.g., during pregnancy or delivery, or may last the entire life span of the fetus following its birth. Some examples of a pregnancy-associated disorder include ectopic pregnancy, preeclampsia, preterm labor, RhD incompatibility, fetal chromosomal abnormalities such as trisomy 21, and genetically inherited fetal disorders such as cystic fibrosis, beta-thalassemia or other monogenic disorders. The ability to enrich fetal nucleic from a maternal sample may prove particularly useful for the noninvasive prenatal diagnosis of autosomal recessive diseases such as the case when a mother and father share an identical disease causing mutation, an occurrence previously perceived as a challenge for maternal plasma-based non-trisomy prenatal diagnosis.

The term "chromosomal abnormality" or "aneuploidy" as used herein refers to a deviation between the structure of the subject chromosome and a normal homologous chromosome. The term "normal" refers to the predominate karyotype or banding pattern found in healthy individuals of a particular species, for example, a euploid genome (in humans, 46XX or 46XY). A chromosomal abnormality can be numerical or structural, and includes but is not limited to aneuploidy, polyploidy, inversion, a trisomy, a monosomy, duplication, deletion, deletion of a part of a chromosome, addition, addition of a part of chromosome, insertion, a fragment of a chromosome, a region of a chromosome, chromosomal rearrangement, and translocation. Chromosomal abnormality may also refer to a state of chromosomal abnormality where a portion of one or more chromosomes is not an exact multiple of the usual haploid number due to, for example, chromosome translocation. Chromosomal translocation (e.g. translocation between chromosome 21 and 14 where some of the 14th chromosome is replaced by extra 21st chromosome) may cause partial trisomy 21. A chromosomal abnormality can be correlated with presence of a pathological condition or with a predisposition to develop a pathological condition. A chromosomal abnormality may be detected by quantitative analysis of nucleic acid.

The terms "nucleic acid" and "nucleic acid molecule" may be used interchangeably throughout the disclosure. The terms refer to nucleic acids of any composition from, such as DNA (e.g., complementary DNA (cDNA), genomic DNA (gDNA) and the like), RNA (e.g., message RNA (mRNA), short inhibitory RNA (siRNA), ribosomal RNA (rRNA), tRNA, microRNA, RNA highly expressed by the fetus or placenta, and the like), and/or DNA or RNA analogs (e.g., containing base analogs, sugar analogs and/or a non-native backbone and the like), RNA/DNA hybrids and polyamide nucleic acids (PNAs), all of which can be in single- or double-stranded form, and unless otherwise limited, can encompass known analogs of natural nucleotides that can function in a similar manner as naturally occurring nucleotides. For example, the nucleic acids provided in SEQ ID Nos: 1-89 (see Table 4) can be in any form useful for conducting processes herein (e.g., linear, circular, supercoiled, single-stranded, double-stranded and the like) or may include variations (e.g., insertions, deletions or substitutions) that do not alter their utility as part of the present technology. A nucleic acid may be, or may be from, a plasmid, phage, autonomously replicating sequence (ARS), centromere, artificial chromosome, chromosome, or other nucleic acid able to replicate or be replicated in vitro or in a host cell, a cell, a cell nucleus or cytoplasm of a cell in certain embodiments. A template nucleic acid in some embodiments can be from a single chromosome (e.g., a nucleic acid sample may be from one chromosome of a sample obtained from a diploid organism). Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, single nucleotide polymorphisms (SNPs), and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)). The term nucleic acid is used interchangeably with locus, gene, cDNA, and mRNA encoded by a gene. The term also may include, as equivalents, derivatives, variants and analogs of RNA or DNA synthesized from nucleotide analogs, single-stranded ("sense" or "antisense", "plus" strand or "minus" strand, "forward" reading frame or "reverse" reading frame) and double-stranded polynucleotides. Deoxyribonucleotides include deoxyadenosine, deoxycytidine, deoxyguanosine and deoxythymidine. For RNA, the base cytosine is replaced with uracil. A template nucleic acid may be prepared using a nucleic acid obtained from a subject as a template.

A "nucleic acid comprising one or more CpG sites" or a "CpG-containing genomic sequence" as used herein refers to a segment of DNA sequence at a defined location in the genome of an individual such as a human fetus or a pregnant woman. Typically, a "CpG-containing genomic sequence" is at least 15 nucleotides in length and contains at least one cytosine. Preferably, it can be at least 30, 50, 80, 100, 150, 200, 250, or 300 nucleotides in length and contains at least 2, 5, 10, 15, 20, 25, or 30 cytosines. For anyone "CpG-containing genomic sequence" at a given location, e.g., within a region centering around a given genetic locus (see Table 1), nucleotide sequence variations may exist from individual to individual and from allele to allele even for the same individual. Typically, such a region centering around a defined genetic locus (e.g., a CpG island) contains the locus as well as upstream and/or downstream sequences. Each of the upstream or downstream sequence (counting from the 5' or 3' boundary of the genetic locus, respectively) can be as long as 10 kb, in other cases may be as long as 5 kb, 2 kb, 1 kb, 500 bp, 200 bp, or 100 bp. Furthermore, a "CpG-containing genomic sequence" may encompass a nucleotide sequence transcribed or not transcribed for protein production, and the nucleotide sequence can be an inter-gene sequence, intra-gene sequence, protein-coding sequence, a non protein-coding sequence (such as a transcription promoter), or a combination thereof.

As used herein, a "methylated nucleotide" or a "methylated nucleotide base" refers to the presence of a methyl moiety on a nucleotide base, where the methyl moiety is not present in a recognized typical nucleotide base. For example, cytosine does not contain a methyl moiety on its pyrimidine ring, but 5-methylcytosine contains a methyl moiety at position 5 of its pyrimidine ring. Therefore, cytosine is not a methylated nucleotide and 5-methylcytosine is a methylated nucleotide. In another example, thymine contains a methyl moiety at position 5 of its pyrimidine ring, however, for purposes herein, thymine is not considered a methylated nucleotide when present in DNA since thymine is a typical nucleotide base of DNA. Typical nucleoside bases for DNA are thymine, adenine, cytosine and guanine. Typical bases for RNA are uracil, adenine, cytosine and guanine. Correspondingly a "methylation site" is the location in the target gene nucleic acid region where methylation has, or has the possibility of occurring. For example a location containing CpG is a methylation site wherein the cytosine may or may not be methylated.

As used herein, a "CpG site" or "methylation site" is a nucleotide within a nucleic acid that is susceptible to methylation either by natural occurring events in vivo or by an event instituted to chemically methylate the nucleotide in vitro.

As used herein, a "methylated nucleic acid molecule" refers to a nucleic acid molecule that contains one or more methylated nucleotides that is/are methylated.

A "CpG island" as used herein describes a segment of DNA sequence that comprises a functionally or structurally deviated CpG density. For example, Yamada et al. (Genome Research 14:247-266, 2004) have described a set of standards for determining a CpG island: it must be at least 400 nucleotides in length, has a greater than 50% GC content, and an OCF/ECF ratio greater than 0.6. Others (Takai et al., Proc. Natl. Acad. Sci. U.S.A. 99:3740-3745, 2002) have defined a CpG island less stringently as a sequence at least 200 nucleotides in length, having a greater than 50% GC content, and an OCF/ECF ratio greater than 0.6.

The term "epigenetic state" or "epigenetic status" as used herein refers to any structural feature at a molecular level of a nucleic acid (e.g., DNA or RNA) other than the primary nucleotide sequence. For instance, the epigenetic state of a genomic DNA may include its secondary or tertiary structure determined or influenced by, e.g., its methylation pattern or its association with cellular proteins.

The term "methylation profile" "methylation state" or "methylation status," as used herein to describe the state of methylation of a genomic sequence, refers to the characteristics of a DNA segment at a particular genomic locus relevant to methylation. Such characteristics include, but are not limited to, whether any of the cytosine (C) residues within this DNA sequence are methylated, location of methylated C residue(s), percentage of methylated C at any particular stretch of residues, and allelic differences in methylation due to, e.g., difference in the origin of the alleles. The term "methylation" profile" or "methylation status" also refers to the relative or absolute concentration of methylated C or unmethylated C at any particular stretch of residues in a biological sample. For example, if the cytosine (C) residue(s) within a DNA sequence are methylated it may be referred to as "hypermethylated"; whereas if the cytosine (C) residue(s) within a DNA sequence are not methylated it may be referred to as "hypomethylated". Likewise, if the cytosine (C) residue(s) within a DNA sequence (e.g., fetal nucleic acid) are methylated as compared to another sequence from a different region or from a different individual (e.g., relative to maternal nucleic acid), that sequence is considered hypermethylated compared to the other sequence. Alternatively, if the cytosine (C) residue(s) within a DNA sequence are not methylated as compared to another sequence from a different region or from a different individual (e.g., the mother), that sequence is considered hypomethylated compared to the other sequence. These sequences are said to be "differentially methylated", and more specifically, when the methylation status differs between mother and fetus, the sequences are considered "differentially methylated maternal and fetal nucleic acid".

Figure 2:
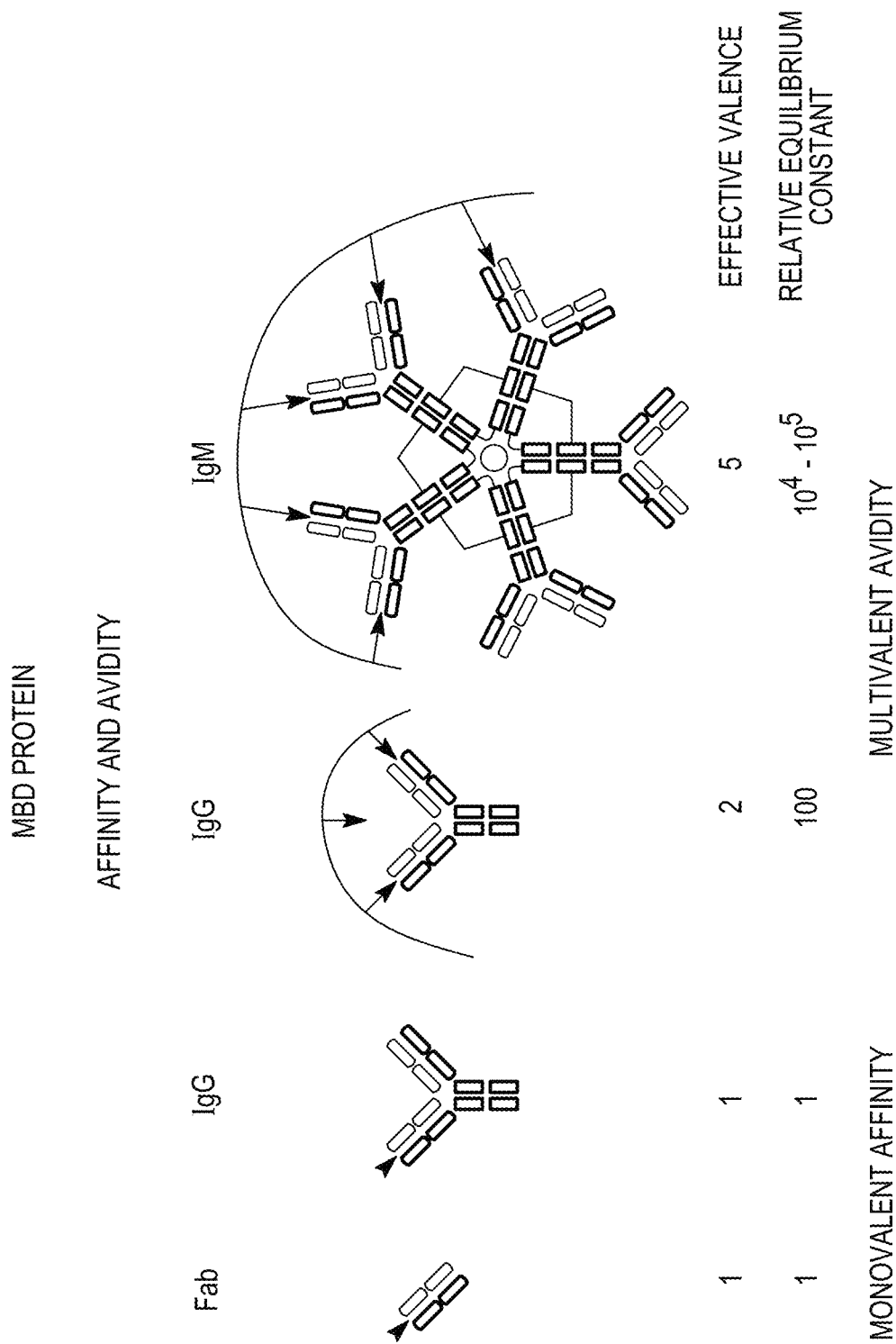
FIG. 2: Shows the methyl-CpG-binding, antibody-like protein has a high affinity and high avidity to its "antigen", which is preferably DNA that is methylated at CpG dinucleotides.

The term "agent that binds to methylated nucleotides" as used herein refers to a substance that is capable of binding to methylated nucleic acid. The agent may be naturally-occurring or synthetic, and may be modified or unmodified. In one embodiment, the agent allows for the separation of different nucleic acid species according to their respective methylation states. An example of an agent that binds to methylated nucleotides is described in PCT Patent Application No. PCT/EP2005/012707, which published as WO06056480A2 and is hereby incorporated by reference. The described agent is a bifunctional polypeptide comprising the DNA-binding domain of a protein belonging to the family of Methyl-CpG binding proteins (MBDs) and an Fc portion of an antibody (see FIG. 1). The recombinant methyl-CpG-binding, antibody-like protein can preferably bind CpG methylated DNA in an antibody-like manner. That means, the methyl-CpG-binding, antibody-like protein has a high affinity and high avidity to its "antigen", which is preferably DNA that is methylated at CpG dinucleotides. The agent may also be a multivalent MBD (see FIG. 2).

The term "polymorphism" as used herein refers to a sequence variation within different alleles of the same genomic sequence. A sequence that contains a polymorphism is considered "polymorphic sequence". Detection of one or more polymorphisms allows differentiation of different alleles of a single genomic sequence or between two or more individuals. As used herein, the term "polymorphic marker" or "polymorphic sequence" refers to segments of genomic DNA that exhibit heritable variation in a DNA sequence between individuals. Such markers include, but are not limited to, single nucleotide polymorphisms (SNPs), restriction fragment length polymorphisms (RFLPs), short tandem repeats, such as di-, tri- or tetra-nucleotide repeats (STRs), and the like. Polymorphic markers according to the present technology can be used to specifically differentiate between a maternal and paternal allele in the enriched fetal nucleic acid sample.

The terms "single nucleotide polymorphism" or "SNP" as used herein refer to the polynucleotide sequence variation present at a single nucleotide residue within different alleles of the same genomic sequence. This variation may occur within the coding region or non-coding region (i.e., in the promoter or intronic region) of a genomic sequence, if the genomic sequence is transcribed during protein production. Detection of one or more SNP allows differentiation of different alleles of a single genomic sequence or between two or more individuals.

The term "allele" as used herein is one of several alternate forms of a gene or non-coding regions of DNA that occupy the same position on a chromosome. The term allele can be used to describe DNA from any organism including but not limited to bacteria, viruses, fungi, protozoa, molds, yeasts, plants, humans, non-humans, animals, and archeabacteria.

The terms "ratio of the alleles" or "allelic ratio" as used herein refer to the ratio of the population of one allele and the population of the other allele in a sample. In some trisomic cases, it is possible that a fetus may be tri-allelic for a particular locus. In such cases, the term "ratio of the alleles" refers to the ratio of the population of any one allele against one of the other alleles, or any one allele against the other two alleles.

The term "non-polymorphism-based quantitative method" as used herein refers to a method for determining the amount of an analyte (e.g., total nucleic acid, Y-chromosome nucleic acid, or fetal nucleic acid) that does not require the use of a polymorphic marker or sequence. Although a polymorphism may be present in the sequence, said polymorphism is not required to quantify the sequence. Examples of non-polymorphism-based quantitative methods include, but are not limited to, RT-PCR, digital PCR, array-based methods, sequencing methods, nanopore-based methods, nucleic acid-bound bead-based counting methods and competitor-based methods wherein one or more competitors are introduced at a known concentration(s) to determine the amount of one or more analytes. In some embodiments, some of the above exemplary methods (for example, sequencing) may need to be actively modified or designed such that one or more polymorphisms are not interrogated.

The terms "absolute amount" or "copy number" as used herein refers to the amount or quantity of an analyte (e.g., total nucleic acid or fetal nucleic acid). The present technology provides compositions and processes for determining the absolute amount of fetal nucleic acid in a mixed maternal sample. Absolute amount or copy number represents the number of molecules available for detection, and may be expressed as the genomic equivalents per unit. The term "concentration" refers to the amount or proportion of a substance in a mixture or solution (e.g., the amount of fetal nucleic acid in a maternal sample that comprises a mixture of maternal and fetal nucleic acid). The concentration may be expressed as a percentage, which is used to express how large/small one quantity is, relative to another quantity as a fraction of 100. Platforms for determining the quantity or amount of an analyte (e.g., target nucleic acid) include, but are not limited to, mass spectrometry, digital PCR, sequencing by synthesis platforms (e.g., pyrosequencing), fluorescence spectroscopy and flow cytometry.

The term "sample" as used herein refers to a specimen containing nucleic acid. Examples of samples include, but are not limited to, tissue, bodily fluid (for example, blood, serum, plasma, saliva, urine, tears, peritoneal fluid, ascitic fluid, vaginal secretion, breast fluid, breast milk, lymph fluid, cerebrospinal fluid or mucosa secretion), umbilical cord blood, chorionic villi, amniotic fluid, an embryo, a two-celled embryo, a four-celled embryo, an eight-celled embryo, a 16-celled embryo, a 32-celled embryo, a 64-celled embryo, a 128-celled embryo, a 256-celled embryo, a 512-celled embryo, a 1024-celled embryo, embryonic tissues, lymph fluid, cerebrospinal fluid, mucosa secretion, or other body exudate, fecal matter, an individual cell or extract of the such sources that contain the nucleic acid of the same, and subcellular structures such as mitochondria, using protocols well established within the art.

Fetal DNA can be obtained from sources including but not limited to maternal blood, maternal serum, maternal plasma, fetal cells, umbilical cord blood, chorionic villi, amniotic fluid, urine, saliva, lung lavage, cells or tissues.

The term "blood" as used herein refers to a blood sample or preparation from a pregnant woman or a woman being tested for possible pregnancy. The term encompasses whole blood or any fractions of blood, such as serum and plasma as conventionally defined.

The term "bisulfite" as used herein encompasses any suitable types of bisulfites, such as sodium bisulfite, that are capable of chemically converting a cytosine (C) to a uracil (U) without chemically modifying a methylated cytosine and therefore can be used to differentially modify a DNA sequence based on the methylation status of the DNA.

As used herein, a reagent that "differentially modifies" methylated or non-methylated DNA encompasses any reagent that modifies methylated and/or unmethylated DNA in a process through which distinguishable products result from methylated and non-methylated DNA, thereby allowing the identification of the DNA methylation status. Such processes may include, but are not limited to, chemical reactions (such as a C.fwdarw.U conversion by bisulfite) and enzymatic treatment (such as cleavage by a methylation-dependent endonuclease). Thus, an enzyme that preferentially cleaves or digests methylated DNA is one capable of cleaving or digesting a DNA molecule at a much higher efficiency when the DNA is methylated, whereas an enzyme that preferentially cleaves or digests unmethylated DNA exhibits a significantly higher efficiency when the DNA is not methylated.

The terms "non-bisulfite-based method" and "non-bisulfite-based quantitative method" as used herein refer to any method for quantifying methylated or non-methylated nucleic acid that does not require the use of bisulfite. The terms also refer to methods for preparing a nucleic acid to be quantified that do not require bisulfite treatment. Examples of non-bisulfite-based methods include, but are not limited to, methods for digesting nucleic acid using one or more methylation sensitive enzymes and methods for separating nucleic acid using agents that bind nucleic acid based on methylation status.

The terms "methyl-sensitive enzymes" and "methylation sensitive restriction enzymes" are DNA restriction endonucleases that are dependent on the methylation state of their DNA recognition site for activity. For example, there are methyl-sensitive enzymes that cleave or digest at their DNA recognition sequence only if it is not methylated. Thus, an unmethylated DNA sample will be cut into smaller fragments than a methylated DNA sample. Similarly, a hyper-methylated DNA sample will not be cleaved. In contrast, there are methyl-sensitive enzymes that cleave at their DNA recognition sequence only if it is methylated. As used herein, the terms "cleave", "cut" and "digest" are used interchangeably.

The term "target nucleic acid" as used herein refers to a nucleic acid examined using the methods disclosed herein to determine if the nucleic acid is part of a pregnancy-related disorder or chromosomal abnormality. For example, a target nucleic acid from chromosome 21 could be examined using the methods of the technology to detect Down's Syndrome.

The term "control nucleic acid" as used herein refers to a nucleic acid used as a reference nucleic acid according to the methods disclosed herein to determine if the nucleic acid is part of a chromosomal abnormality. For example, a control nucleic acid from a chromosome other than chromosome 21 (herein referred to as a "reference chromosome") could be as a reference sequence to detect Down's Syndrome. In some embodiments, the control sequence has a known or predetermined quantity.

The term "sequence-specific" or "locus-specific method" as used herein refers to a method that interrogates (for example, quantifies) nucleic acid at a specific location (or locus) in the genome based on the sequence composition. Sequence-specific or locus-specific methods allow for the quantification of specific regions or chromosomes.

The term "gene" means the segment of DNA involved in producing a polypeptide chain; it includes regions preceding and following the coding region (leader and trailer) involved in the transcription/translation of the gene product and the regulation of the transcription/translation, as well as intervening sequences (introns) between individual coding segments (exons).

In this application, the terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins (i.e., antigens), wherein the amino acid residues are linked by covalent peptide bonds.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, .gamma.-carboxyglutamate, and O-phosphoserine.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

"Primers" as used herein refer to oligonucleotides that can be used in an amplification method, such as a polymerase chain reaction (PCR), to amplify a nucleotide sequence based on the polynucleotide sequence corresponding to a particular genomic sequence, e.g., one located within the CpG island CG1137, PDE9A, or CG1009 on chromosome 21, in various methylation status. At least one of the PCR primers for amplification of a polynucleotide sequence is sequence-specific for the sequence.

The term "template" refers to any nucleic acid molecule that can be used for amplification in the technology. RNA or DNA that is not naturally double stranded can be made into double stranded DNA so as to be used as template DNA.

Any double stranded DNA or preparation containing multiple, different double stranded DNA molecules can be used as template DNA to amplify a locus or loci of interest contained in the template DNA.

The term "amplification reaction" as used herein refers to a process for copying nucleic acid one or more times. In embodiments, the method of amplification includes but is not limited to polymerase chain reaction, self-sustained sequence reaction, ligase chain reaction, rapid amplification of cDNA ends, polymerase chain reaction and ligase chain reaction, 0-beta phage amplification, strand displacement amplification, or splice overlap extension polymerase chain reaction. In some embodiments, a single molecule of nucleic acid is amplified, for example, by digital PCR.

The term "sensitivity" as used herein refers to the number of true positives divided by the number of true positives plus the number of false negatives, where sensitivity (sens) may be within the range of 0 sens 1. Ideally, method embodiments herein have the number of false negatives equaling zero or close to equaling zero, so that no subject is wrongly identified as not having at least one chromosome abnormality or other genetic disorder when they indeed have at least one chromosome abnormality or other genetic disorder. Conversely, an assessment often is made of the ability of a prediction algorithm to classify negatives correctly, a complementary measurement to sensitivity. The term "specificity" as used herein refers to the number of true negatives divided by the number of true negatives plus the number of false positives, where sensitivity (spec) may be within the range of 0≤spec≤1. Ideally, methods embodiments herein have the number of false positives equaling zero or close to equaling zero, so that no subject wrongly identified as having at least one chromosome abnormality other genetic disorder when they do not have the chromosome abnormality other genetic disorder being assessed. Hence, a method that has sensitivity and specificity equaling one, or 100%, sometimes is selected.

One or more prediction algorithms may be used to determine significance or give meaning to the detection data collected under variable conditions that may be weighed independently of or dependently on each other. The term "variable" as used herein refers to a factor, quantity, or function of an algorithm that has a value or set of values. For example, a variable may be the design of a set of amplified nucleic acid species, the number of sets of amplified nucleic acid species, percent fetal genetic contribution tested, percent maternal genetic contribution tested, type of chromosome abnormality assayed, type of genetic disorder assayed, type of sex-linked abnormalities assayed, the age of the mother and the like. The term "independent" as used herein refers to not being influenced or not being controlled by another. The term "dependent" as used herein refers to being influenced or controlled by another. For example, a particular chromosome and a trisomy event occurring for that particular chromosome that results in a viable being are variables that are dependent upon each other.

One of skill in the art may use any type of method or prediction algorithm to give significance to the data of the present technology within an acceptable sensitivity and/or specificity. For example, prediction algorithms such as Chi-squared test, z-test, t-test, ANOVA (analysis of variance), regression analysis, neural nets, fuzzy logic, Hidden Markov Models, multiple model state estimation, and the like may be used. One or more methods or prediction algorithms may be determined to give significance to the data having different independent and/or dependent variables of the present technology. And one or more methods or prediction algorithms may be determined not to give significance to the data having different independent and/or dependent variables of the present technology. One may design or change parameters of the different variables of methods described herein based on results of one or more prediction algorithms (e.g., number of sets analyzed, types of nucleotide species in each set). For example, applying the Chi-squared test to detection data may suggest that specific ranges of maternal age are correlated to a higher likelihood of having an offspring with a specific chromosome abnormality, hence the variable of maternal age may be weighed differently verses being weighed the same as other variables.

In certain embodiments, several algorithms may be chosen to be tested. These algorithms can be trained with raw data. For each new raw data sample, the trained algorithms will assign a classification to that sample (i.e. trisomy or normal). Based on the classifications of the new raw data samples, the trained algorithms' performance may be assessed based on sensitivity and specificity. Finally, an algorithm with the highest sensitivity and/or specificity or combination thereof may be identified.

DETAILED DESCRIPTION

Introduction

The presence of fetal nucleic acid in maternal plasma was first reported in 1997 and offers the possibility for non-invasive prenatal diagnosis simply through the analysis of a maternal blood sample (Lo et al., Lancet 350:485-487, 1997). To date, numerous potential clinical applications have been developed. In particular, quantitative abnormalities of fetal nucleic acid, for example DNA, concentrations in maternal plasma have been found to be associated with a number of pregnancy-associated disorders, including preeclampsia, preterm labor, antepartum hemorrhage, invasive placentation, fetal Down syndrome, and other fetal chromosomal aneuploidies. Hence, fetal nucleic acid analysis in maternal plasma represents a powerful mechanism for the monitoring of fetomaternal well-being.

However, fetal DNA co-exists with background maternal DNA in maternal plasma. Hence, most reported applications have relied on the detection of Y-chromosome sequences as these are most conveniently distinguishable from maternal DNA. Such an approach limits the applicability of the existing assays to only 50% of all pregnancies, namely those with male fetuses. Thus, there is much need for the development of sex-independent compositions and methods for enriching and analyzing fetal nucleic acid from a maternal sample. Also, methods that rely on polymorphic markers to quantify fetal nucleic acid may be susceptible to varying heterozygosity rates across different ethnicities thereby limiting their applicability (e.g., by increasing the number of markers that are needed).

It was previously demonstrated that fetal and maternal DNA can be distinguished by their differences in methylation status (U.S. Pat. No. 6,927,028, which is hereby incorporated by reference). Methylation is an epigenetic phenomenon, which refers to processes that alter a phenotype without involving changes in the DNA sequence. By exploiting the difference in the DNA methylation status between mother and fetus, one can successfully detect and analyze fetal nucleic acid in a background of maternal nucleic acid.

The present inventors provides novel genomic polynucleotides that are differentially methylated between the fetal DNA from the fetus (e.g., from the placenta) and the maternal DNA from the mother, for example from peripheral blood cells. This discovery thus provides a new approach for distinguishing fetal and maternal genomic DNA and new methods for accurately quantifying fetal nucleic which may be used for non-invasive prenatal diagnosis.

Methodology

Practicing the technology utilizes routine techniques in the field of molecular biology. Basic texts disclosing the general methods of use in the technology include Sambrook and Russell, Molecular Cloning, A Laboratory Manual (3rd ed. 2001); Kriegler, Gene Transfer and Expression: A Laboratory Manual (1990); and Current Protocols in Molecular Biology (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Protein sizes are estimated from gel electrophoresis, from sequenced proteins, from derived amino acid sequences, or from published protein sequences.

Oligonucleotides that are not commercially available can be chemically synthesized, e.g., according to the solid phase phosphoramidite triester method first described by Beaucage & Caruthers, Tetrahedron Lett. 22: 1859-1862 (1981), using an automated synthesizer, as described in Van Devanter et. al., Nucleic Acids Res. 12: 6159-6168 (1984). Purification of oligonucleotides is performed using any art-recognized strategy, e.g., native acrylamide gel electrophoresis or anion-exchange high performance liquid chromatography (HPLC) as described in Pearson & Reanier, J. Chrom. 255: 137-149 (1983).

Acquisition of Blood Samples and Extraction of DNA

The present technology relates to separating, enriching and analyzing fetal DNA found in maternal blood as a non-invasive means to detect the presence and/or to monitor the progress of a pregnancy-associated condition or disorder. Thus, the first steps of practicing the technology are to obtain a blood sample from a pregnant woman and extract DNA from the sample.

A. Acquisition of Blood Samples

A blood sample is obtained from a pregnant woman at a gestational age suitable for testing using a method of the present technology. The suitable gestational age may vary depending on the disorder tested, as discussed below. Collection of blood from a woman is performed in accordance with the standard protocol hospitals or clinics generally follow. An appropriate amount of peripheral blood, e.g., typically between 5-50 ml, is collected and may be stored according to standard procedure prior to further preparation. Blood samples may be collected, stored or transported in a manner known to the person of ordinary skill in the art to minimize degradation or the quality of nucleic acid present in the sample.

B. Preparation of Blood Samples

The analysis of fetal DNA found in maternal blood according to the present technology may be performed using, e.g., the whole blood, serum, or plasma. The methods for preparing serum or plasma from maternal blood are well known among those of skill in the art. For example, a pregnant woman's blood can be placed in a tube containing EDTA or a specialized commercial product such as Vacutainer SST (Becton Dickinson, Franklin Lakes, N.J.) to prevent blood clotting, and plasma can then be obtained from whole blood through centrifugation. On the other hand, serum may be obtained with or without centrifugation-following blood clotting. If centrifugation is used then it is typically, though not exclusively, conducted at an appropriate speed, e.g., 1,500-3,000 times g. Plasma or serum may be subjected to additional centrifugation steps before being transferred to a fresh tube for DNA extraction.

In addition to the acellular portion of the whole blood, DNA may also be recovered from the cellular fraction, enriched in the buffy coat portion, which can be obtained following centrifugation of a whole blood sample from the woman and removal of the plasma.

C. Extraction of DNA

There are numerous known methods for extracting DNA from a biological sample including blood. The general methods of DNA preparation (e.g., described by Sambrook and Russell, Molecular Cloning: A Laboratory Manual 3d ed., 2001) can be followed; various commercially available reagents or kits, such as Qiagen's QIAamp Circulating Nucleic Acid Kit, QiaAmp DNA Mini Kit or QiaAmp DNA Blood Mini Kit (Qiagen, Hilden, Germany), GenomicPrep™ Blood DNA Isolation Kit (Promega, Madison, Wis.), and GFX™ Genomic Blood DNA Purification Kit (Amersham, Piscataway, N.J.), may also be used to obtain DNA from a blood sample from a pregnant woman. Combinations of more than one of these methods may also be used.

In some embodiments, the sample may first be enriched or relatively enriched for fetal nucleic acid by one or more methods. For example, the discrimination of fetal and maternal DNA can be performed using the compositions and processes of the present technology alone or in combination with other discriminating factors. Examples of these factors include, but are not limited to, single nucleotide differences between chromosome X and Y, chromosome Y-specific sequences, polymorphisms located elsewhere in the genome, size differences between fetal and maternal DNA and differences in methylation pattern between maternal and fetal tissues.

Other methods for enriching a sample for a particular species of nucleic acid are described in PCT Patent Application Number PCT/US07/69991, filed May 30, 2007, PCT Patent Application Number PCT/US2007/071232, filed Jun. 15, 2007, U.S. Provisional Application Nos. 60/968,876 and 60/968,878 (assigned to the Applicant), (PCT Patent Application Number PCT/EP05/012707, filed Nov. 28, 2005) which are all hereby incorporated by reference. In certain embodiments, maternal nucleic acid is selectively removed (either partially, substantially, almost completely or completely) from the sample.

Methylation Specific Separation of Nucleic Acid

The methods provided herein offer an alternative approach for the enrichment of fetal DNA based on the methylation-specific separation of differentially methylated DNA. It has recently been discovered that many genes involved in developmental regulation are controlled through epigenetics in embryonic stem cells. Consequently, multiple genes can be expected to show differential DNA methylation between nucleic acid of fetal origin and maternal origin. Once these regions are identified, a technique to capture methylated DNA can be used to specifically enrich fetal DNA. For identification of differentially methylated regions, a novel approach was used to capture methylated DNA. This approach uses a protein, in which the methyl binding domain of MBD2 is fused to the Fc fragment of an antibody (MBD-FC) (Gebhard C, Schwarzfischer L, Pham T H, Schilling E, Klug M, Andreesen R, Rehli M (2006) Genom-ewide profiling of CpG methylation identifies novel targets of aberrant hypermethylation in myeloid leukemia. Cancer Res 66:6118-6128). This fusion protein has several advantages over conventional methylation specific antibodies. The MBD-FC has a higher affinity to methylated DNA and it binds double stranded DNA. Most importantly the two proteins differ in the way they bind DNA. Methylation specific antibodies bind DNA stochastically, which means that only a binary answer can be obtained. The methyl binding domain of MBD-FC on the other hand binds DNA molecules regardless of their methylation status. The strength of this protein-DNA interaction is defined by the level of DNA methylation. After binding genomic DNA, eluate solutions of increasing salt concentrations can be used to fractionate non-methylated and methylated DNA allowing for a more controlled separation (Gebhard C, Schwarzfischer L, Pham T H, Andreesen R, Mackensen A, Rehli M (2006) Rapid and sensitive detection of CpG-methylation using methyl-binding (MB)-PCR. Nucleic Acids Res 34:e82). Consequently this method, called Methyl-CpG immunoprecipitation (MCIP), cannot only enrich, but also fractionate genomic DNA according to methylation level, which is particularly helpful when the unmethylated DNA fraction should be investigated as well.

Methylation Sensitive Restriction Enzyme Digestion

The technology also provides compositions and processes for determining the amount of fetal nucleic acid from a maternal sample. The technology allows for the enrichment of fetal nucleic acid regions in a maternal sample by selectively digesting nucleic acid from said maternal sample with an enzyme that selectively and completely or substantially digests the maternal nucleic acid to enrich the sample for at least one fetal nucleic acid region. Preferably, the digestion efficiency is greater than about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%. Following enrichment, the amount of fetal nucleic acid can be determined by quantitative methods that do not require polymorphic sequences or bisulfite treatment, thereby, offering a solution that works equally well for female fetuses and across different ethnicities and preserves the low copy number fetal nucleic acid present in the sample.

For example, there are methyl-sensitive enzymes that preferentially or substantially cleave or digest at their DNA recognition sequence if it is non-methylated. Thus, an unmethylated DNA sample will be cut into smaller fragments than a methylated DNA sample. Similarly, a hypermethylated DNA sample will not be cleaved. In contrast, there are methyl-sensitive enzymes that cleave at their DNA recognition sequence only if it is methylated.

Methyl-sensitive enzymes that digest unmethylated DNA suitable for use in methods of the technology include, but are not limited to, HpaII, HhaI, MaeII, BstUI and AciI. An enzyme that can be used is HpaII that cuts only the unmethylated sequence CCGG. Another enzyme that can be used is HhaI that cuts only the unmethylated sequence GCGC. Both enzymes are available from New England BioLabs®, Inc. Combinations of two or more methyl-sensitive enzymes that digest only unmethylated DNA can also be used. Suitable enzymes that digest only methylated DNA include, but are not limited to, DpnI, which cuts at a recognition sequence GATC, and McrBC, which belongs to the family of AAA.sup.+ proteins and cuts DNA containing modified cytosines and cuts at recognition site 5' . . . Pu.sup.mC (N.sub.40-3000) Pu.sup.mC . . . 3' (New England BioLabs, Inc., Beverly, Mass.).

Cleavage methods and procedures for selected restriction enzymes for cutting DNA at specific sites are well known to the skilled artisan. For example, many suppliers of restriction enzymes provide information on conditions and types of DNA sequences cut by specific restriction enzymes, including New England BioLabs, Pro-Mega Biochems, Boehringer-Mannheim, and the like. Sambrook et al. (See Sambrook et al., Molecular Biology: A laboratory Approach, Cold Spring Harbor, N.Y. 1989) provide a general description of methods for using restriction enzymes and other enzymes. In methods of the present technology enzymes often are used under conditions that will enable cleavage of the maternal DNA with about 95%-100% efficiency, preferably with about 98%-100% efficiency.

Other Methods for Methylation Analysis

Various methylation analysis procedures are known in the art, and can be used in conjunction with the present technology. These assays allow for determination of the methylation state of one or a plurality of CpG islands within a DNA sequence. In addition, the methods maybe used to quantify methylated nucleic acid. Such assays involve, among other techniques, DNA sequencing of bisulfite-treated DNA, PCR (for sequence-specific amplification), Southern blot analysis, and use of methylation-sensitive restriction enzymes.

Genomic sequencing is a technique that has been simplified for analysis of DNA methylation patterns and 5-methylcytosine distribution by using bisulfite treatment (Frommer et al., Proc. Natl. Acad. Sci. USA 89:1827-1831, 1992). Additionally, restriction enzyme digestion of PCR products amplified from bisulfite-converted DNA may be used, e.g., the method described by Sadri & Hornsby (Nucl. Acids Res. 24:5058-5059, 1996), or COBRA (Combined Bisulfite Restriction Analysis) (Xiong & Laird, Nucleic Acids Res. 25:2532-2534, 1997).

COBRA analysis is a quantitative methylation assay useful for determining DNA methylation levels at specific gene loci in small amounts of genomic DNA (Xiong & Laird, Nucleic Acids Res. 25:2532-2534, 1997). Briefly, restriction enzyme digestion is used to reveal methylation-dependent sequence differences in PCR products of sodium bisulfite-treated DNA. Methylation-dependent sequence differences are first introduced into the genomic DNA by standard bisulfite treatment according to the procedure described by Frommer et al. (Proc. Natl. Acad. Sci. USA 89:1827-1831, 1992). PCR amplification of the bisulfite converted DNA is then performed using primers specific for the interested CpG islands, followed by restriction endonuclease digestion, gel electrophoresis, and detection using specific, labeled hybridization probes. Methylation levels in the original DNA sample are represented by the relative amounts of digested and undigested PCR product in a linearly quantitative fashion across a wide spectrum of DNA methylation levels. In addition, this technique can be reliably applied to DNA obtained from microdissected paraffin-embedded tissue samples. Typical reagents (e.g., as might be found in a typical COBRA-based kit) for COBRA analysis may include, but are not limited to: PCR primers for specific gene (or methylation-altered DNA sequence or CpG island); restriction enzyme and appropriate buffer; gene-hybridization oligo; control hybridization oligo; kinase labeling kit for oligo probe; and radioactive nucleotides. Additionally, bisulfite conversion reagents may include: DNA denaturation buffer; sulfonation buffer; DNA recovery reagents or kits (e.g., precipitation, ultrafiltration, affinity column); desulfonation buffer; and DNA recovery components.

The MethyLight™ assay is a high-throughput quantitative methylation assay that utilizes fluorescence-based real-time PCR (TaqMan®) technology that requires no further manipulations after the PCR step (Eads et al., Cancer Res.

59:2302-2306, 1999). Briefly, the MethyLight™ process begins with a mixed sample of genomic DNA that is converted, in a sodium bisulfite reaction, to a mixed pool of methylation-dependent sequence differences according to standard procedures (the bisulfite process converts unmethylated cytosine residues to uracil). Fluorescence-based PCR is then performed either in an "unbiased" (with primers that do not overlap known CpG methylation sites) PCR reaction, or in a "biased" (with PCR primers that overlap known CpG dinucleotides) reaction. Sequence discrimination can occur either at the level of the amplification process or at the level of the fluorescence detection process, or both.

The MethyLight assay may be used as a quantitative test for methylation patterns in the genomic DNA sample, wherein sequence discrimination occurs at the level of probe hybridization. In this quantitative version, the PCR reaction provides for unbiased amplification in the presence of a fluorescent probe that overlaps a particular putative methylation site. An unbiased control for the amount of input DNA is provided by a reaction in which neither the primers, nor the probe overlie any CpG dinucleotides. Alternatively, a qualitative test for genomic methylation is achieved by probing of the biased PCR pool with either control oligonucleotides that do not "cover" known methylation sites (a fluorescence-based version of the "MSP" technique), or with oligonucleotides covering potential methylation sites.

The MethyLight process can by used with a "TaqMan" probe in the amplification process. For example, doublestranded genomic DNA is treated with sodium bisulfite and subjected to one of two sets of PCR reactions using TaqMan® probes; e.g., with either biased primers and TaqMan® probe, or unbiased primers and TaqMan® probe. The TaqMan® probe is dual-labeled with fluorescent "reporter" and "quencher" molecules, and is designed to be specific for a relatively high GC content region so that it melts out at about 10.degree. C. higher temperature in the PCR cycle than the forward or reverse primers. This allows the TaqMan® probe to remain fully hybridized during the PCR annealing/extension step. As the Taq polymerase enzymatically synthesizes a new strand during PCR, it will eventually reach the annealed TaqMan® probe. The Taq polymerase 5' to 3' endonuclease activity will then displace the TaqMan® probe by digesting it to release the fluorescent reporter molecule for quantitative detection of its now unquenched signal using a real-time fluorescent detection system.

Typical reagents (e.g., as might be found in a typical MethyLight™-based kit) for MethyLight™ analysis may include, but are not limited to: PCR primers for specific gene (or methylation-altered DNA sequence or CpG island); TaqMan® probes; optimized PCR buffers and deoxynucleotides; and Taq polymerase.

The Ms-SNuPE technique is a quantitative method for assessing methylation differences at specific CpG sites based on bisulfite treatment of DNA, followed by single-nucleotide primer extension (Gonzalgo & Jones, Nucleic Acids Res. 25:2529-2531, 1997).

Briefly, genomic DNA is reacted with sodium bisulfite to convert unmethylated cytosine to uracil while leaving 5-methylcytosine unchanged. Amplification of the desired target sequence is then performed using PCR primers specific for bisulfite-converted DNA, and the resulting product is isolated and used as a template for methylation analysis at the CpG site(s) of interest.

Small amounts of DNA can be analyzed (e.g., microdissected pathology sections), and it avoids utilization of restriction enzymes for determining the methylation status at CpG sites.

Typical reagents (e.g., as might be found in a typical Ms-SNuPE-based kit) for Ms-SNuPE analysis may include, but are not limited to: PCR primers for specific gene (or methylation-altered DNA sequence or CpG island); optimized PCR buffers and deoxynucleotides; gel extraction kit; positive control primers; Ms-SNuPE primers for specific gene; reaction buffer (for the Ms-SNuPE reaction); and radioactive nucleotides. Additionally, bisulfite conversion reagents may include: DNA denaturation buffer; sulfonation buffer; DNA recovery regents or kit (e.g., precipitation, ultrafiltration, affinity column); desulfonation buffer; and DNA recovery components.

MSP (methylation-specific PCR) allows for assessing the methylation status of virtually any group of CpG sites within a CpG island, independent of the use of methylation-sensitive restriction enzymes (Herman et al. Proc. Nat. Acad. Sci. USA 93:9821-9826, 1996; U.S. Pat. No. 5,786,146). Briefly, DNA is modified by sodium bisulfite converting unmethylated, but not methylated cytosines to uracil, and subsequently amplified with primers specific for methylated versus ummethylated DNA. MSP requires only small quantities of DNA, is sensitive to 0.1% methylated alleles of a given CpG island locus, and can be performed on DNA extracted from paraffin-embedded samples. Typical reagents (e.g., as might be found in a typical MSP-based kit) for MSP analysis may include, but are not limited to: methylated and unmethylated PCR primers for specific gene (or methylation-altered DNA sequence or CpG island), optimized PCR buffers and deoxynucleotides, and specific probes.

The MCA technique is a method that can be used to screen for altered methylation patterns in genomic DNA, and to isolate specific sequences associated with these changes (Toyota et al., Cancer Res. 59:2307-12, 1999). Briefly, restriction enzymes with different sensitivities to cytosine methylation in their recognition sites are used to digest genomic DNAs from primary tumors, cell lines, and normal tissues prior to arbitrarily primed PCR amplification. Fragments that show differential methylation are cloned and sequenced after resolving the PCR products on high-resolution polyacrylamide gels. The cloned fragments are then used as probes for Southern analysis to confirm differential methylation of these regions. Typical reagents (e.g., as might be found in a typical MCA-based kit) for MCA analysis may include, but are not limited to: PCR primers for arbitrary priming Genomic DNA; PCR buffers and nucleotides, restriction enzymes and appropriate buffers; gene-hybridization oligos or probes; control hybridization oligos or probes.

Another method for analyzing methylation sites is a primer extension assay, including an optimized PCR amplification reaction that produces amplified targets for subsequent primer extension genotyping analysis using mass spectrometry. The assay can also be done in multiplex. This method (particularly as it relates to genotyping single nucleotide polymorphisms) is described in detail in PCT publication WO05012578A1 and US publication US20050079521A1. For methylation analysis, the assay can be adopted to detect bisulfite introduced methylation dependent C to T sequence changes. These methods are particularly useful for performing multiplexed amplification reactions and multiplexed primer extension reactions (e.g., multiplexed homogeneous primer mass extension (hME) assays) in a single well to further increase the throughput and reduce the cost per reaction for primer extension reactions.

Four additional methods for DNA methylation analysis include restriction landmark genomic scanning (RLGS, Costello et al., 2000), methylation-sensitive-representational difference analysis (MS-RDA), methylation-specific AP-PCR (MS-AP-PCR) and methyl-CpG binding domain column/segregation of partly melted molecules (MBD/SPM).

Additional methylation analysis methods that may be used in conjunction with the present technology are described in the following papers: Laird, P. W. Nature Reviews Cancer 3, 253-266 (2003); Biotechniques; Uhlmann, K. et al. Electrophoresis 23:4072-4079 (2002)—PyroMeth; Colella et al. Biotechniques. 2003 July; 35(1): 146-50; Dupont J M, Tost J, Jammes H, and Gut I G. Anal Biochem, October 2004; 333(1): 119-27; and Tooke N and Pettersson M. IVDT. November 2004; 41.

Polynucleotide Sequence Amplification and Determination

Following separation of nucleic acid in a methylation-differential manner, the nucleic acid may be subjected to sequence-based analysis. Furthermore, once it is determined that one particular genomic sequence of fetal origin is hypermethylated or hypomethylated compared to the maternal counterpart, the amount of this fetal genomic sequence can be determined. Subsequently, this amount can be compared to a standard control value and serve as an indication for the potential of certain pregnancy-associated disorder.

A. Amplification of Nucleotide Sequences

In many instances, it is desirable to amplify a nucleic acid sequence of the technology using any of several nucleic acid amplification procedures which are well known in the art (listed above and described in greater detail below). Specifically, nucleic acid amplification is the enzymatic synthesis of nucleic acid amplicons (copies) which contain a sequence that is complementary to a nucleic acid sequence being amplified. Nucleic acid amplification is especially beneficial when the amount of target sequence present in a sample is very low. By amplifying the target sequences and detecting the amplicon synthesized, the sensitivity of an assay can be vastly improved, since fewer target sequences are needed at the beginning of the assay to better ensure detection of nucleic acid in the sample belonging to the organism or virus of interest.

A variety of polynucleotide amplification methods are well established and frequently used in research. For instance, the general methods of polymerase chain reaction (PCR) for polynucleotide sequence amplification are well known in the art and are thus not described in detail herein. For a review of PCR methods, protocols, and principles in designing primers, see, e.g., Innis, et al., PCR Protocols: A Guide to Methods and Applications, Academic Press, Inc. N.Y., 1990. PCR reagents and protocols are also available from commercial vendors, such as Roche Molecular Systems.

PCR is most usually carried out as an automated process with a thermostable enzyme. In this process, the temperature of the reaction mixture is cycled through a denaturing region, a primer annealing region, and an extension reaction region automatically. Machines specifically adapted for this purpose are commercially available.

Although PCR amplification of a polynucleotide sequence is typically used in practicing the present technology, one of skill in the art will recognize that the amplification of a genomic sequence found in a maternal blood sample may be accomplished by any known method, such as ligase chain reaction (LCR), transcription-mediated amplification, and self-sustained sequence replication or nucleic acid sequence-based amplification (NASBA), each of which provides sufficient amplification. More recently developed branched-DNA technology may also be used to qualitatively demonstrate the presence of a particular genomic sequence of the technology, which represents a particular methylation pattern, or to quantitatively determine the amount of this particular genomic sequence in the maternal blood. For a review of branched-DNA signal amplification for direct quantitation of nucleic acid sequences in clinical samples, see Nolte, Adv. Clin. Chem. 33:201-235, 1998.

The compositions and processes of the technology are also particularly useful when practiced with digital PCR. Digital PCR was first developed by Kalinina and colleagues (Kalinina et al., "Nanoliter scale PCR with TaqMan detection." Nucleic Acids Research. 25; 1999-2004, (1997)) and further developed by Vogelstein and Kinzler (Digital PCR. Proc Natl Acad Sci USA. 96; 9236-41, (1999)). The application of digital PCR for use with fetal diagnostics was first described by Cantor et al. (PCT Patent Publication No. WO05023091A2) and subsequently described by Quake et al. (US Patent Publication No. US 20070202525), which are both hereby incorporated by reference. Digital PCR takes advantage of nucleic acid (DNA, cDNA or RNA) amplification on a single molecule level, and offers a highly sensitive method for quantifying low copy number nucleic acid. Fluidigm® Corporation offers systems for the digital analysis of nucleic acids.

B. Determination of Polynucleotide Sequences

Techniques for polynucleotide sequence determination are also well established and widely practiced in the relevant research field. For instance, the basic principles and general techniques for polynucleotide sequencing are described in various research reports and treatises on molecular biology and recombinant genetics, such as Wallace et al., supra; Sambrook and Russell, supra, and Ausubel et al., supra. DNA sequencing methods routinely practiced in research laboratories, either manual or automated, can be used for practicing the present technology. Additional means suitable for detecting changes in a polynucleotide sequence for practicing the methods of the present technology include but are not limited to mass spectrometry, primer extension, polynucleotide hybridization, real-time PCR, and electrophoresis.

Use of a primer extension reaction also can be applied in methods of the technology. A primer extension reaction operates, for example, by discriminating the SNP alleles by the incorporation of deoxynucleotides and/or dideoxynucleotides to a primer extension primer which hybridizes to a region adjacent to the SNP site. The primer is extended with a polymerase. The primer extended SNP can be detected physically by mass spectrometry or by a tagging moiety such as biotin. As the SNP site is only extended by a complementary deoxynucleotide or dideoxynucleotide that is either tagged by a specific label or generates a primer extension product with a specific mass, the SNP alleles can be discriminated and quantified.

Reverse transcribed and amplified nucleic acids may be modified nucleic acids. Modified nucleic acids can include nucleotide analogs, and in certain embodiments include a detectable label and/or a capture agent. Examples of detectable labels include without limitation fluorophores, radioisotopes, colormetric agents, light emitting agents, chemiluminescent agents, light scattering agents, enzymes and the like. Examples of capture agents include without limitation an agent from a binding pair selected from antibody/antigen, antibody/antibody, antibody/antibody fragment, antibody/antibody receptor, antibody/protein A or protein G, hapten/anti-hapten, biotin/avidin, biotin/streptavidin, folic acid/folate binding protein, vitamin B12/intrinsic factor, chemical reactive group/complementary chemical reactive group (e.g., sulfhydryl/maleimide, sulfhydryl/haloacetyl derivative, amine/isotriocyanate, amine/succinimidyl ester, and amine/sulfonyl halides) pairs, and the like. Modified nucleic acids having a capture agent can be immobilized to a solid support in certain embodiments Mass spectrometry is a particularly effective method for the detection of a polynucleotide of the technology, for example a PCR amplicon, a primer extension product or a detector probe that is cleaved from a target nucleic acid. The presence of the polynucleotide sequence is verified by comparing the mass of the detected signal with the expected mass of the polynucleotide of interest. The relative signal strength, e.g., mass peak on a spectra, for a particular polynucleotide sequence indicates the relative population of a specific allele, thus enabling calculation of the allele ratio directly from the data. For a review of genotyping methods using Sequenom® standard iPLEX™ assay and MassARRAY® technology, see Jurinke, C., Oeth, P., van den Boom, D., "MALDI-TOF mass spectrometry: a versatile tool for high-performance DNA analysis." Mol. Biotechnol. 26, 147-164 (2004); and Oeth, P. et al., "iPLEX™ Assay: Increased Plexing Efficiency and Flexibility for MassARRAY® System through single base primer extension with mass-modified Terminators." SEQUENOM Application Note (2005), both of which are hereby incorporated by reference. For a review of detecting and quantifying target nucleic using cleavable detector probes that are cleaved during the amplification process and detected by mass spectrometry, see U.S. patent application Ser. No. 11/950,395, which was filed Dec. 4, 2007, and is hereby incorporated by reference.

Sequencing technologies are improving in terms of throughput and cost. Sequencing technologies, such as that achievable on the 454 platform (Roche) (Margulies, M. et al. 2005 Nature 437, 376-380), Illumina Genome Analyzer (or Solexa platform) or SOLiD System (Applied Biosystems) or the Helicos True Single Molecule DNA sequencing technology (Harris T D et al. 2008 Science, 320, 106-109), the single molecule, real-time (SMRT™) technology of Pacific Biosciences, and nanopore sequencing (Soni G V and Meller A. 2007 Clin Chem 53: 1996-2001), allow the sequencing of many nucleic acid molecules isolated from a specimen at high orders of multiplexing in a parallel fashion (Dear Brief Funct Genomic Proteomic 2003; 1: 397-416).

Each of these platforms allow sequencing of clonally expanded or non-amplified single molecules of nucleic acid fragments. Certain platforms involve, for example, (i) sequencing by ligation of dye-modified probes (including cyclic ligation and cleavage), (ii) pyrosequencing, and (iii) single-molecule sequencing. Nucleotide sequence species, amplification nucleic acid species and detectable products generated there from can be considered a "study nucleic acid" for purposes of analyzing a nucleotide sequence by such sequence analysis platforms.

Sequencing by ligation is a nucleic acid sequencing method that relies on the sensitivity of DNA ligase to base-pairing mismatch. DNA ligase joins together ends of DNA that are correctly base paired. Combining the ability of DNA ligase to join together only correctly base paired DNA ends, with mixed pools of fluorescently labeled oligonucleotides or primers, enables sequence determination by fluorescence detection. Longer sequence reads may be obtained by including primers containing cleavable linkages that can be cleaved after label identification. Cleavage at the linker removes the label and regenerates the 5' phosphate on the end of the ligated primer, preparing the primer for another round of ligation. In some embodiments primers may be labeled with more than one fluorescent label (e.g., 1 fluorescent label, 2, 3, or 4 fluorescent labels).

An example of a system that can be used by a person of ordinary skill based on sequencing by ligation generally involves the following steps. Clonal bead populations can be prepared in emulsion microreactors containing study nucleic acid ("template"), amplification reaction components, beads and primers. After amplification, templates are denatured and bead enrichment is performed to separate beads with extended templates from undesired beads (e.g., beads with no extended templates). The template on the selected beads undergoes a 3' modification to allow covalent bonding to the slide, and modified beads can be deposited onto a glass slide. Deposition chambers offer the ability to segment a slide into one, four or eight chambers during the bead loading process. For sequence analysis, primers hybridize to the adapter sequence. A set of four color dye-labeled probes competes for ligation to the sequencing primer. Specificity of probe ligation is achieved by interrogating every 4th and 5th base during the ligation series. Five to seven rounds of ligation, detection and cleavage record the color at every 5th position with the number of rounds determined by the type of library used. Following each round of ligation, a new complimentary primer offset by one base in the 5' direction is laid down for another series of ligations. Primer reset and ligation rounds (5-7 ligation cycles per round) are repeated sequentially five times to generate 25-35 base pairs of sequence for a single tag. With mate-paired sequencing, this process is repeated for a second tag. Such a system can be used to exponentially amplify amplification products generated by a process described herein, e.g., by ligating a heterologous nucleic acid to the first amplification product generated by a process described herein and performing emulsion amplification using the same or a different solid support originally used to generate the first amplification product. Such a system also may be used to analyze amplification products directly generated by a process described herein by bypassing an exponential amplification process and directly sorting the solid supports described herein on the glass slide.

Pyrosequencing is a nucleic acid sequencing method based on sequencing by synthesis, which relies on detection of a pyrophosphate released on nucleotide incorporation. Generally, sequencing by synthesis involves synthesizing, one nucleotide at a time, a DNA strand complimentary to the strand whose sequence is being sought. Study nucleic acids may be immobilized to a solid support, hybridized with a sequencing primer, incubated with DNA polymerase, ATP sulfurylase, luciferase, apyrase, adenosine 5' phosphsulfate and luciferin. Nucleotide solutions are sequentially added and removed. Correct incorporation of a nucleotide releases a pyrophosphate, which interacts with ATP sulfurylase and produces ATP in the presence of adenosine 5' phosphsulfate, fueling the luciferin reaction, which produces a chemiluminescent signal allowing sequence determination.

An example of a system that can be used by a person of ordinary skill based on pyrosequencing generally involves the following steps: ligating an adaptor nucleic acid to a study nucleic acid and hybridizing the study nucleic acid to a bead; amplifying a nucleotide sequence in the study nucleic acid in an emulsion; sorting beads using a picoliter multiwell solid support; and sequencing amplified nucleotide sequences by pyrosequencing methodology (e.g., Nakano et al., "Single-molecule PCR using water-in-oil emulsion;" Journal of Biotechnology 102: 117-124 (2003)). Such a system can be used to exponentially amplify amplification products generated by a process described herein, e.g., by ligating a heterologous nucleic acid to the first amplification product generated by a process described herein.

Certain single-molecule sequencing embodiments are based on the principal of sequencing by synthesis, and utilize single-pair Fluorescence Resonance Energy Transfer (single pair FRET) as a mechanism by which photons are emitted as a result of successful nucleotide incorporation. The emitted photons often are detected using intensified or high sensitivity cooled charge-couple-devices in conjunction with total internal reflection microscopy (TIRM). Photons are only emitted when the introduced reaction solution contains the correct nucleotide for incorporation into the growing nucleic acid chain that is synthesized as a result of the sequencing process. In FRET based single-molecule sequencing, energy is transferred between two fluorescent dyes, sometimes polymethine cyanine dyes Cy3 and Cy5, through long-range dipole interactions. The donor is excited at its specific excitation wavelength and the excited state energy is transferred, non-radiatively to the acceptor dye, which in turn becomes excited. The acceptor dye eventually returns to the ground state by radiative emission of a photon. The two dyes used in the energy transfer process represent the "single pair", in single pair FRET. Cy3 often is used as the donor fluorophore and often is incorporated as the first labeled nucleotide. Cy5 often is used as the acceptor fluorophore and is used as the nucleotide label for successive nucleotide additions after incorporation of a first Cy3 labeled nucleotide. The fluorophores generally are within 10 nanometers of each for energy transfer to occur successfully.

An example of a system that can be used based on single-molecule sequencing generally involves hybridizing a primer to a study nucleic acid to generate a complex; associating the complex with a solid phase; iteratively extending the primer by a nucleotide tagged with a fluorescent molecule; and capturing an image of fluorescence resonance energy transfer signals after each iteration (e.g., U.S. Pat. No. 7,169,314; Braslaysky et al., PNAS 100(7): 3960-3964 (2003)). Such a system can be used to directly sequence amplification products generated by processes described herein. In some embodiments the released linear amplification product can be hybridized to a primer that contains sequences complementary to immobilized capture sequences present on a solid support, a bead or glass slide for example. Hybridization of the primer-released linear amplification product complexes with the immobilized capture sequences, immobilizes released linear amplification products to solid supports for single pair FRET based sequencing by synthesis. The primer often is fluorescent, so that an initial reference image of the surface of the slide with immobilized nucleic acids can be generated. The initial reference image is useful for determining locations at which true nucleotide incorporation is occurring. Fluorescence signals detected in array locations not initially identified in the "primer only" reference image are discarded as non-specific fluorescence. Following immobilization of the primer-released linear amplification product complexes, the bound nucleic acids often are sequenced in parallel by the iterative steps of, a) polymerase extension in the presence of one fluorescently labeled nucleotide, b) detection of fluorescence using appropriate microscopy, TIRM for example, c) removal of fluorescent nucleotide, and d) return to step a with a different fluorescently labeled nucleotide.

In some embodiments, nucleotide sequencing may be by solid phase single nucleotide sequencing methods and processes. Solid phase single nucleotide sequencing methods involve contacting sample nucleic acid and solid support under conditions in which a single molecule of sample nucleic acid hybridizes to a single molecule of a solid support. Such conditions can include providing the solid support molecules and a single molecule of sample nucleic acid in a "microreactor." Such conditions also can include providing a mixture in which the sample nucleic acid molecule can hybridize to solid phase nucleic acid on the solid support. Single nucleotide sequencing methods useful in the embodiments described herein are described in U.S. Provisional Patent Application Ser. No. 61/021,871 filed Jan. 17, 2008.

In certain embodiments, nanopore sequencing detection methods include (a) contacting a nucleic acid for sequencing ("base nucleic acid," e.g., linked probe molecule) with sequence-specific detectors, under conditions in which the detectors specifically hybridize to substantially complementary subsequences of the base nucleic acid; (b) detecting signals from the detectors and (c) determining the sequence of the base nucleic acid according to the signals detected. In certain embodiments, the detectors hybridized to the base nucleic acid are disassociated from the base nucleic acid (e.g., sequentially dissociated) when the detectors interfere with a nanopore structure as the base nucleic acid passes through a pore, and the detectors disassociated from the base sequence are detected. In some embodiments, a detector disassociated from a base nucleic acid emits a detectable signal, and the detector hybridized to the base nucleic acid emits a different detectable signal or no detectable signal. In certain embodiments, nucleotides in a nucleic acid (e.g., linked probe molecule) are substituted with specific nucleotide sequences corresponding to specific nucleotides ("nucleotide representatives"), thereby giving rise to an expanded nucleic acid (e.g., U.S. Pat. No. 6,723,513), and the detectors hybridize to the nucleotide representatives in the expanded nucleic acid, which serves as a base nucleic acid. In such embodiments, nucleotide representatives may be arranged in a binary or higher order arrangement (e.g., Soni and Meller, Clinical Chemistry 53(11): 1996-2001 (2007)). In some embodiments, a nucleic acid is not expanded, does not give rise to an expanded nucleic acid, and directly serves a base nucleic acid (e.g., a linked probe molecule serves as a non-expanded base nucleic acid), and detectors are directly contacted with the base nucleic acid. For example, a first detector may hybridize to a first subsequence and a second detector may hybridize to a second subsequence, where the first detector and second detector each have detectable labels that can be distinguished from one another, and where the signals from the first detector and second detector can be distinguished from one another when the detectors are disassociated from the base nucleic acid. In certain embodiments, detectors include a region that hybridizes to the base nucleic acid (e.g., two regions), which can be about 3 to about 100 nucleotides in length (e.g., about 4, 5, 6, 7, 8, 9, 10, 11, 12, 13, 14, 15, 16, 17, 18, 19, 20, 25, 30, 35, 40, 50, 55, 60, 65, 70, 75, 80, 85, 90, or 95 nucleotides in length). A detector also may include one or more regions of nucleotides that do not hybridize to the base nucleic acid. In some embodiments, a detector is a molecular beacon. A detector often comprises one or more detectable labels independently selected from those described herein. Each detectable label can be detected by any convenient detection process capable of detecting a signal generated by each label (e.g., magnetic, electric, chemical, optical and the like). For example, a CD camera can be used to detect signals from one or more distinguishable quantum dots linked to a detector.

In certain sequence analysis embodiments, reads may be used to construct a larger nucleotide sequence, which can be facilitated by identifying overlapping sequences in different reads and by using identification sequences in the reads. Such sequence analysis methods and software for constructing larger sequences from reads are known to the person of ordinary skill (e.g., Venter et al., Science 291: 1304-1351 (2001)). Specific reads, partial nucleotide sequence constructs, and full nucleotide sequence constructs may be compared between nucleotide sequences within a sample nucleic acid (i.e., internal comparison) or may be compared with a reference sequence (i.e., reference comparison) in certain sequence analysis embodiments. Internal comparisons sometimes are performed in situations where a sample nucleic acid is prepared from multiple samples or from a single sample source that contains sequence variations. Reference comparisons sometimes are performed when a reference nucleotide sequence is known and an objective is to determine whether a sample nucleic acid contains a nucleotide sequence that is substantially similar or the same, or different, than a reference nucleotide sequence. Sequence analysis is facilitated by sequence analysis apparatus and components known to the person of ordinary skill in the art.

Methods provided herein allow for high-throughput detection of nucleic acid species in a plurality of nucleic acids (e.g., nucleotide sequence species, amplified nucleic acid species and detectable products generated from the foregoing). Multiplexing refers to the simultaneous detection of more than one nucleic acid species. General methods for performing multiplexed reactions in conjunction with mass spectrometry, are known (see, e.g., U.S. Pat. Nos. 6,043,031, 5,547,835 and International PCT application No. WO 97/37041). Multiplexing provides an advantage that a plurality of nucleic acid species (e.g., some having different sequence variations) can be identified in as few as a single mass spectrum, as compared to having to perform a separate mass spectrometry analysis for each individual target nucleic acid species. Methods provided herein lend themselves to high-throughput, highly-automated processes for analyzing sequence variations with high speed and accuracy, in some embodiments. In some embodiments, methods herein may be multiplexed at high levels in a single reaction.

In certain embodiments, the number of nucleic acid species multiplexed include, without limitation, about 1 to about 500 (e.g., about 1-3, 3-5, 5-7, 7-9, 9-11, 11-13, 13-15, 15-17, 17-19, 19-21, 21-23, 23-25, 25-27, 27-29, 29-31, 31-33, 33-35, 35-37, 37-39, 39-41, 41-43, 43-45, 45-47, 47-49, 49-51, 51-53, 53-55, 55-57, 57-59, 59-61, 61-63, 63-65, 65-67, 67-69, 69-71, 71-73, 73-75, 75-77, 77-79, 79-81, 81-83, 83-85, 85-87, 87-89, 89-91, 91-93, 93-95, 95-97, 97-101, 101-103, 103-105, 105-107, 107-109, 109-111, 111-113, 113-115, 115-117, 117-119, 121-123, 123-125, 125-127, 127-129, 129-131, 131-133, 133-135, 135-137, 137-139, 139-141, 141-143, 143-145, 145-147, 147-149, 149-151, 151-153, 153-155, 155-157, 157-159, 159-161, 161-163, 163-165, 165-167, 167-169, 169-171, 171-173, 173-175, 175-177, 177-179, 179-181, 181-183, 183-185, 185-187, 187-189, 189-191, 191-193, 193-195, 195-197, 197-199, 199-201, 201-203, 203-205, 205-207, 207-209, 209-211, 211-213, 213-215, 215-217, 217-219, 219-221, 221-223, 223-225, 225-227, 227-229, 229-231, 231-233, 233-235, 235-237, 237-239, 239-241, 241-243, 243-245, 245-247, 247-249, 249-251, 251-253, 253-255, 255-257, 257-259, 259-261, 261-263, 263-265, 265-267, 267-269, 269-271, 271-273, 273-275, 275-277, 277-279, 279-281, 281-283, 283-285, 285-287, 287-289, 289-291, 291-293, 293-295, 295-297, 297-299, 299-301, 301-303, 303-305, 305-307, 307-309, 309-311, 311-313, 313-315, 315-317, 317-319, 319-321, 321-323, 323-325, 325-327, 327-329, 329-331, 331-333, 333-335, 335-337, 337-339, 339-341, 341-343, 343-345, 345-347, 347-349, 349-351, 351-353, 353-355, 355-357, 357-359, 359-361, 361-363, 363-365, 365-367, 367-369, 369-371, 371-373, 373-375, 375-377, 377-379, 379-381, 381-383, 383-385, 385-387, 387-389, 389-391, 391-393, 393-395, 395-397, 397-401, 401-403, 403-405, 405-407, 407-409, 409-411, 411-413, 413-415, 415-417, 417-419, 419-421, 421-423, 423-425, 425-427, 427-429, 429-431, 431-433, 433-435, 435-437, 437-439, 439-441, 441-443, 443-445, 445-447, 447-449, 449-451, 451-453, 453-455, 455-457, 457-459, 459-461, 461-463, 463-465, 465-467, 467-469, 469-471, 471-473, 473-475, 475-477, 477-479, 479-481, 481-483, 483-485, 485-487, 487-489, 489-491, 491-493, 493-495, 495-497, 497-501).

Design methods for achieving resolved mass spectra with multiplexed assays can include primer and oligonucleotide design methods and reaction design methods. See, for example, the multiplex schemes provided in Tables X and Y. For primer and oligonucleotide design in multiplexed assays, the same general guidelines for primer design applies for uniplexed reactions, such as avoiding false priming and primer dimers, only more primers are involved for multiplex reactions. For mass spectrometry applications, analyte peaks in the mass spectra for one assay are sufficiently resolved from a product of any assay with which that assay is multiplexed, including pausing peaks and any other by-product peaks. Also, analyte peaks optimally fall within a user-specified mass window, for example, within a range of 5,000-8,500 Da. In some embodiments multiplex analysis may be adapted to mass spectrometric detection of chromosome abnormalities, for example. In certain embodiments multiplex analysis may be adapted to various single nucleotide or nanopore based sequencing methods described herein. Commercially produced micro-reaction chambers or devices or arrays or chips may be used to facilitate multiplex analysis, and are commercially available.

Detection of Fetal Aneuploidy

For the detection of fetal aneuploidies, some methods rely on measuring the ratio between maternally and paternally inherited alleles. However, the ability to quantify chromosomal changes is impaired by the maternal contribution of cell free nucleic acids, which makes it necessary to deplete the sample from maternal DNA prior to measurement. Promising approaches take advantage of the different size distribution of fetal and maternal DNA or measure RNA that is exclusively expressed by the fetus (see for example, U.S. patent application Ser. No. 11/384,128, which published as US20060252071 and is hereby incorporated by reference). Assuming fetal DNA makes up only about 5% of all cell free DNA in the maternal plasma, there is a decrease of the ratio difference from 1.6% to only about 1.2% between a trisomy sample and a healthy control. Consequently, reliable detection of allele ratio changes requires enriching the fetal fraction of cell free DNA, for example, using the compositions and methods of the present technology.

Some methods rely on measuring the ratio of maternal to paternally inherited alleles to detect fetal chromosomal aneuploidies from maternal plasma. A diploid set yields a 1:1 ratio while trisomies can be detected as a 2:1 ratio. Detection of this difference is impaired by statistical sampling due to the low abundance of fetal DNA, presence of excess maternal DNA in the plasma sample and variability of the measurement technique. The latter is addressed by using methods with high measurement precision, like digital PCR or mass spectrometry. Enriching the fetal fraction of cell free DNA in a sample is currently achieved by either depleting maternal DNA through size exclusion or focusing on fetal-specific nucleic acids, like fetal-expressed RNA. Another differentiating feature of fetal DNA is its DNA methylation pattern. Thus, provided herein are novel compositions and methods for accurately quantifying fetal nucleic acid based on differential methylation between a fetus and mother. The methods rely on sensitive absolute copy number analysis to quantify the fetal nucleic acid portion of a maternal sample, thereby allowing for the prenatal detection of fetal traits. The methods of the technology have identified approximately 3000 CpG rich regions in the genome that are differentially methylated between maternal and fetal DNA. The selected regions showed highly conserved differential methylation across all measured samples. In addition the set of regions is enriched for genes important in developmental regulation, indicating that epigenetic regulation of these areas is a biologically relevant and consistent process (see Table 3). Enrichment of fetal DNA can now be achieved by using our MBD-FC protein to capture cell free DNA (e.g., substantially all cell free DNA) and then elute the highly methylated DNA fraction with high salt concentrations. Using the low salt eluate fractions, the MBD-FC is equally capable of enriching non-methylated fetal DNA.

The present technology provides 63 confirmed genomic regions on chromosomes 13, 18 and 21 with low maternal and high fetal methylation levels. After capturing these regions, SNPs can be used to determine the aforementioned allele ratios. When high frequency SNPs are used around 10 markers have to be measured to achieve a high confidence of finding at least one SNP where the parents have opposite homozygote genotypes and the child has a heterozygote genotype.

In another embodiment, a method for chromosomal abnormality detection is provided that utilizes absolute copy number quantification. A diploid chromosome set will show the same number of copies for differentially methylated regions across all chromosomes, but, for example, a trisomy 21 sample would show 1.5 times more copies for differentially methylated regions on chromosome 21. Normalization of the genomic DNA amounts for a diploid chromosome set can be achieved by using unaltered autosomes as reference (also provided herein—see Table 1). Comparable to other approaches, a single marker is less likely to be sufficient for detection of this difference, because the overall copy numbers are low. Typically there are approximately 100 to 200 copies of fetal DNA from 1 ml of maternal plasma at 10 to 12 weeks of gestation. However, the methods of the present technology offer a redundancy of detectable markers that enables highly reliable discrimination of diploid versus aneuploid chromosome sets.

Data Processing and Identifying Presence or Absence of a Chromosome Abnormality

The term "detection" of a chromosome abnormality as used herein refers to identification of an imbalance of chromosomes by processing data arising from detecting sets of amplified nucleic acid species, nucleotide sequence species, or a detectable product generated from the foregoing (collectively "detectable product"). Any suitable detection device and method can be used to distinguish one or more sets of detectable products, as addressed herein. An outcome pertaining to the presence or absence of a chromosome abnormality can be expressed in any suitable form, including, without limitation, probability (e.g., odds ratio, p-value), likelihood, percentage, value over a threshold, or risk factor, associated with the presence of a chromosome abnormality for a subject or sample. An outcome may be provided with one or more of sensitivity, specificity, standard deviation, coefficient of variation (CV) and/or confidence level, or combinations of the foregoing, in certain embodiments.

Detection of a chromosome abnormality based on one or more sets of detectable products may be identified based on one or more calculated variables, including, but not limited to, sensitivity, specificity, standard deviation, coefficient of variation (CV), a threshold, confidence level, score, probability and/or a combination thereof. In some embodiments, (i) the number of sets selected for a diagnostic method, and/or (ii) the particular nucleotide sequence species of each set selected for a diagnostic method, is determined in part or in full according to one or more of such calculated variables.

In certain embodiments, one or more of sensitivity, specificity and/or confidence level are expressed as a percentage. In some embodiments, the percentage, independently for each variable, is greater than about 90% (e.g., about 90, 91, 92, 93, 94, 95, 96, 97, 98 or 99%, or greater than 99% (e.g., about 99.5%, or greater, about 99.9% or greater, about 99.95% or greater, about 99.99% or greater)). Coefficient of variation (CV) in some embodiments is expressed as a percentage, and sometimes the percentage is about 10% or less (e.g., about 10, 9, 8, 7, 6, 5, 4, 3, 2 or 1%, or less than 1% (e.g., about 0.5% or less, about 0.1% or less, about 0.05% or less, about 0.01% or less)). A probability (e.g., that a particular outcome determined by an algorithm is not due to chance) in certain embodiments is expressed as a p-value, and sometimes the p-value is about 0.05 or less (e.g., about 0.05, 0.04, 0.03, 0.02 or 0.01, or less than 0.01 (e.g., about 0.001 or less, about 0.0001 or less, about 0.00001 or less, about 0.000001 or less)).

For example, scoring or a score may refer to calculating the probability that a particular chromosome abnormality is actually present or absent in a subject/sample. The value of a score may be used to determine for example the variation, difference, or ratio of amplified nucleic detectable product that may correspond to the actual chromosome abnormality. For example, calculating a positive score from detectable products can lead to an identification of a chromosome abnormality, which is particularly relevant to analysis of single samples.

In certain embodiments, simulated (or simulation) data can aid data processing for example by training an algorithm or testing an algorithm. Simulated data may for instance involve hypothetical various samples of different concentrations of fetal and maternal nucleic acid in serum, plasma and the like. Simulated data may be based on what might be expected from a real population or may be skewed to test an algorithm and/or to assign a correct classification based on a simulated data set. Simulated data also is referred to herein as "virtual" data. Fetal/maternal contributions within a sample can be simulated as a table or array of numbers (for example, as a list of peaks corresponding to the mass signals of cleavage products of a reference biomolecule or amplified nucleic acid sequence), as a mass spectrum, as a pattern of bands on a gel, or as a representation of any technique that measures mass distribution. Simulations can be performed in most instances by a computer program. One possible step in using a simulated data set is to evaluate the confidence of the identified results, i.e. how well the selected positives/negatives match the sample and whether there are additional variations. A common approach is to calculate the probability value (p-value) which estimates the probability of a random sample having better score than the selected one. As p-value calculations can be prohibitive in certain circumstances, an empirical model may be assessed, in which it is assumed that at least one sample matches a reference sample (with or without resolved variations). Alternatively other distributions such as Poisson distribution can be used to describe the probability distribution.

In certain embodiments, an algorithm can assign a confidence value to the true positives, true negatives, false positives and false negatives calculated. The assignment of a likelihood of the occurrence of a chromosome abnormality can also be based on a certain probability model.

Simulated data often is generated in an in silico process. As used herein, the term "in silico" refers to research and experiments performed using a computer. In silico methods include, but are not limited to, molecular modeling studies, karyotyping, genetic calculations, biomolecular docking experiments, and virtual representations of molecular structures and/or processes, such as molecular interactions.

As used herein, a "data processing routine" refers to a process, that can be embodied in software, that determines the biological significance of acquired data (i.e., the ultimate results of an assay). For example, a data processing routine can determine the amount of each nucleotide sequence species based upon the data collected. A data processing routine also may control an instrument and/or a data collection routine based upon results determined. A data processing routine and a data collection routine often are integrated and provide feedback to operate data acquisition by the instrument, and hence provide assay-based judging methods provided herein.

As used herein, software refers to computer readable program instructions that, when executed by a computer, perform computer operations. Typically, software is provided on a program product containing program instructions recorded on a computer readable medium, including, but not limited to, magnetic media including floppy disks, hard disks, and magnetic tape; and optical media including CD-ROM discs, DVD discs, magneto-optical discs, and other such media on which the program instructions can be recorded.

Different methods of predicting abnormality or normality can produce different types of results. For any given prediction, there are four possible types of outcomes: true positive, true negative, false positive, or false negative. The term "true positive" as used herein refers to a subject correctly diagnosed as having a chromosome abnormality. The term "false positive" as used herein refers to a subject wrongly identified as having a chromosome abnormality. The term "true negative" as used herein refers to a subject correctly identified as not having a chromosome abnormality. The term "false negative" as used herein refers to a subject wrongly identified as not having a chromosome abnormality. Two measures of performance for any given method can be calculated based on the ratios of these occurrences: (i) a sensitivity value, the fraction of predicted positives that are correctly identified as being positives (e.g., the fraction of nucleotide sequence sets correctly identified by level comparison detection/determination as indicative of chromosome abnormality, relative to all nucleotide sequence sets identified as such, correctly or incorrectly), thereby reflecting the accuracy of the results in detecting the chromosome abnormality; and (ii) a specificity value, the fraction of predicted negatives correctly identified as being negative (the fraction of nucleotide sequence sets correctly identified by level comparison detection/determination as indicative of chromosomal normality, relative to all nucleotide sequence sets identified as such, correctly or incorrectly), thereby reflecting accuracy of the results in detecting the chromosome abnormality.

EXAMPLES

The following examples are provided by way of illustration only and not by way of limitation. Those of skill in the art will readily recognize a variety of non-critical parameters that could be changed or modified to yield essentially the same or similar results.

In Example 1 below, the Applicants used a new fusion protein that captures methylated DNA in combination with CpG Island array to identify genomic regions that are differentially methylated between fetal placenta tissue and maternal blood. A stringent statistical approach was used to only select regions which show little variation between the samples, and hence suggest an underlying biological mechanism. Eighty-five differentially methylated genomic regions predominantly located on chromosomes 13, 18 and 21 were validated. For this validation, a quantitative mass spectrometry based approach was used that interrogated 261 PCR amplicons covering these 85 regions. The results are in very good concordance (95% confirmation), proving the feasibility of the approach.

Next, the Applicants provide an innovative approach for aneuploidy testing, which relies on the measurement of absolute copy numbers rather than allele ratios.

Example 1

Figure 3:
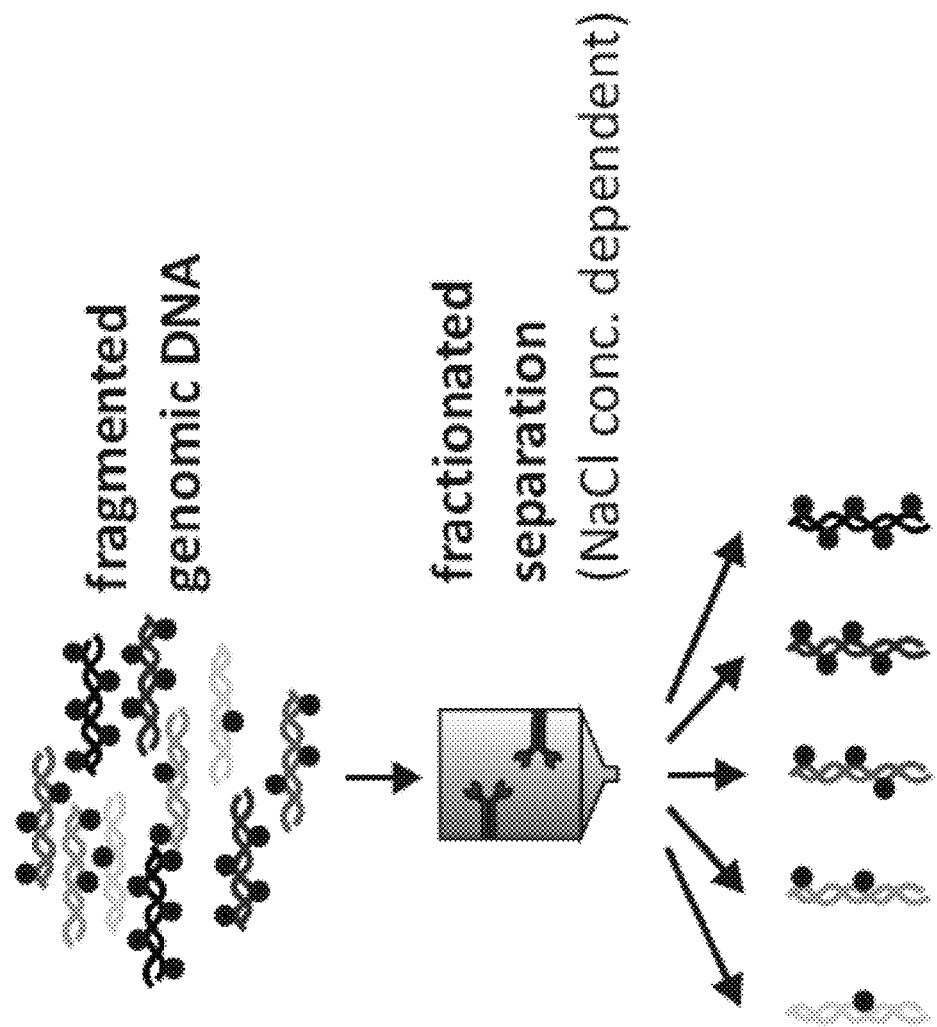
FIG. 3: Shows the methyl binding domain of MBD-FC binds DNA molecules regardless of their methylation status. The strength of this protein/DNA interaction is defined by the level of DNA methylation. After binding genomic DNA, eluate solutions of increasing salt concentrations can be used to fractionate non-methylated and methylated DNA allowing for a controlled separation.
Figure 4:
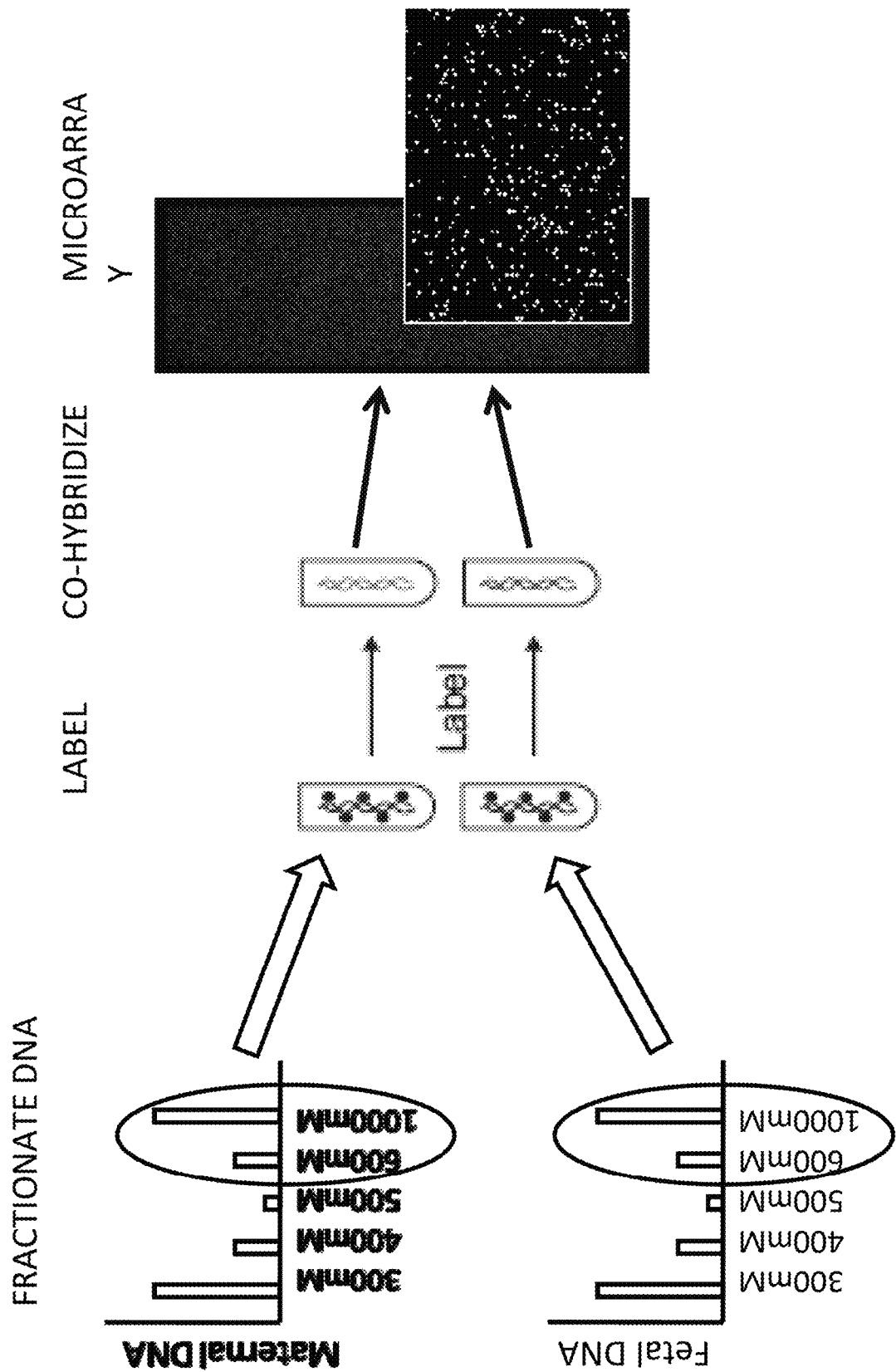
FIG. 4: Shows the experiment used to identify differentially methylated DNA from a fetus and mother using the recombinant MBD-Fc protein and a microarray.
Figure 5:
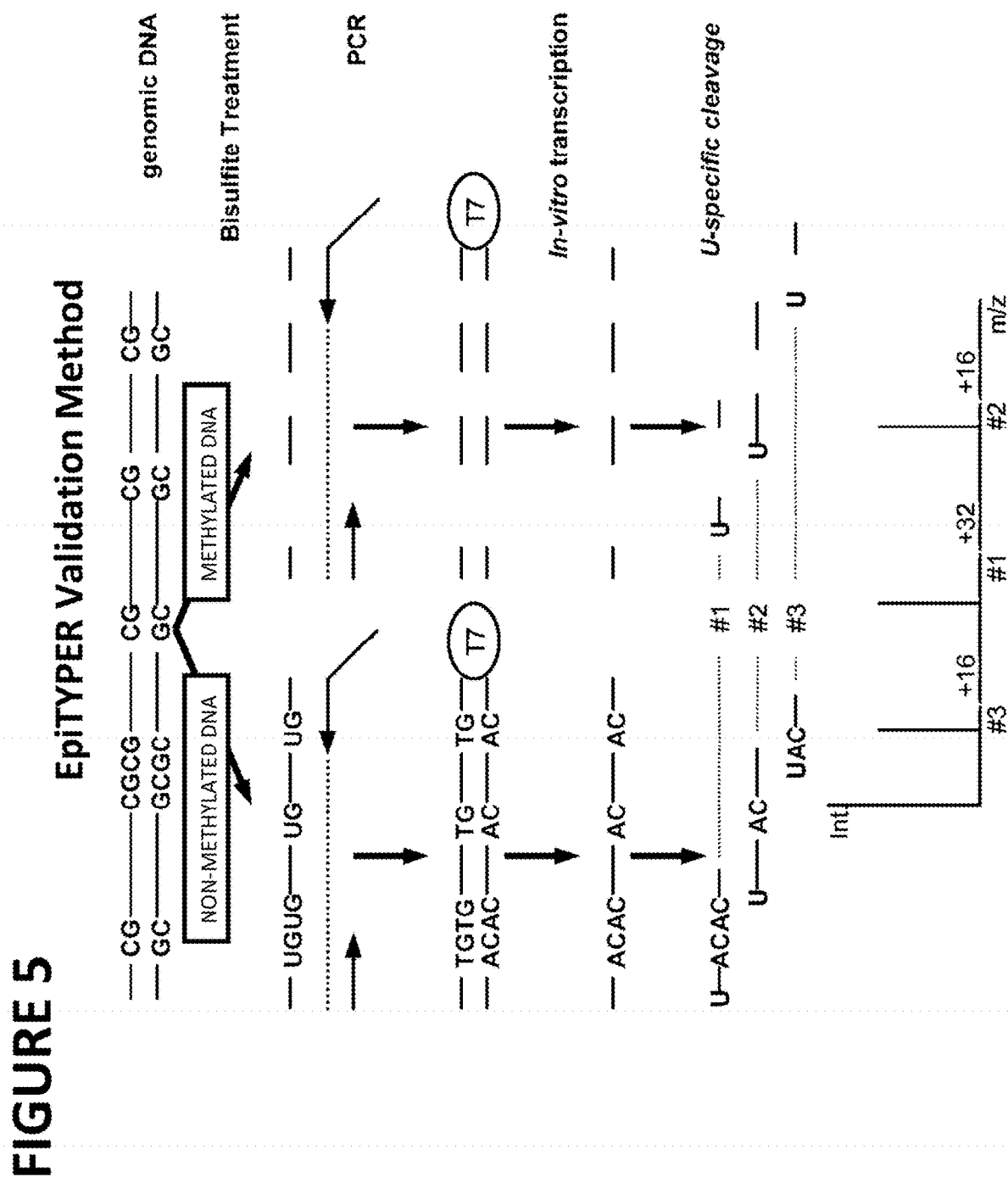
FIG. 5: Shows typical results generated by Sequenom® EpiTYPER™ method, which was used to validate the results generated from the experiment illustrated in FIG. 4.
Figure 6:
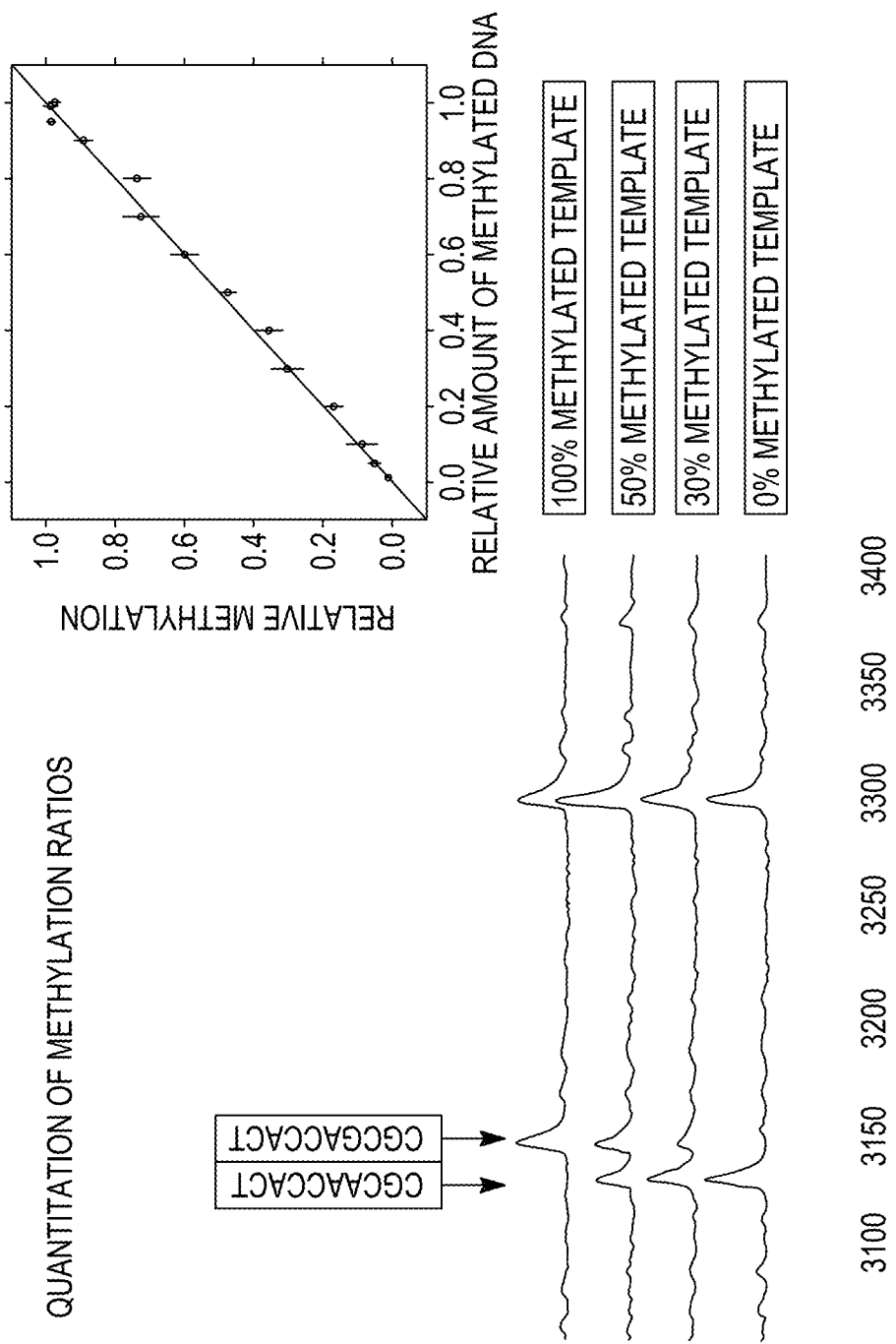
FIG. 6: Shows the correlation between the log ratios derived from microarray analysis (x axis) and methylation differences obtained by EpiTYPER analysis (y axis). Each data point represents the average for one region across all measured samples. The microarray analysis is comparative in nature because the highly methylated fraction of the maternal DNA is hybridized together with the highly methylated fraction of placenta DNA. Positive values indicate higher methylation of the placenta samples. In mass spectrometry each samples is measured individually. We first calculated difference in methylation by subtracting the maternal methylation values from the placenta methylation value. To compare the results with the microarray data we calculated the average of the differences for all maternal/placenta DNA pairs.

In the below Example, ten paired maternal and placental DNA samples were used to identify differentially methylated regions. These results were validated using a mass spectrometry-based quantitative methylation assay. First, genomic DNA from maternal buffy coat and corresponding placental tissue was first extracted. Next the MBD-FC was used to capture the methylated fraction of each DNA sample. See FIGS. 1-3. The two tissue fractions were labeled with different fluorescent dyes and hybridized to an Agilent® CpG Island microarray. See FIG. 4. This was done to identify differentially methylated regions that could be utilized for prenatal diagnoses. Therefore, two criteria were employed to select genomic regions as potential enrichment markers: the observed methylation difference had to be present in all tested sample pairs, and the region had to be more than 200 bp in length.

DNA Preparation and Fragmentation

Genomic DNA (gDNA) from maternal buffy coat and placental tissue was prepared using the QIAamp DNA Mini Kit™ and QIAamp DNA Blood Mini Kit™, respectively, from Qiagen® (Hilden, Germany). For MCIp, gDNA was quantified using the NanoDrop ND 1000™ spectrophotometer (Thermo Fisher®, Waltham, Mass., USA). Ultrasonication of 2.5 µg DNA in 500 µl TE buffer to a mean fragment size of 300-500 bp was carried out with the Branson Digital Sonifer 450™ (Danbury, Conn., USA) using the following settings: amplitude 20%, sonication time 110 seconds, pulse on/pulse off time 1.4/0.6 seconds. Fragment range was monitored using gel electrophoresis.

Methyl-CpG Immunoprecipitation

Per sample, 56 µg purified MBD-Fc protein and 150 µl of Protein A Sepharose 4 Fast Flow beads (Amersham Biosciences®, Piscataway, N.J., USA) were rotated in 15 ml TBS overnight at 4° C. Then, the MBD-Fc beads (150 µl/assay) were transferred and dispersed in to 2 ml Ultrafree-CL centrifugal filter devices (Millipore®, Billerica, Mass., USA) and spin-washed three times with Buffer A (20 mM Tris-HCl, pH8.0, 2 mM MgCl2, 0.5 mM EDTA 300 mM NaCl, 0.1% NP-40). Sonicated DNA (2 µg) was added to the washed MBD-Fc beads in 2 ml Buffer A and rotated for 3 hours at 4° C. Beads were centrifuged to recover unbound DNA fragments (300 mM fraction) and subsequently washed twice with 600 µl of buffers containing increasing NaCl concentrations (400, 500, 550, 600, and 1000 mM). The flow through of each wash step was collected in separate tubes and desalted using a MinElute PCR Purification Kit™ (Qiagen®). In parallel, 200 ng sonicated input DNA was processed as a control using the MinElute PCR Purification Kit™ (Qiagen®).

Microarray Handling and Analysis

To generate fluorescently labeled DNA for microarray hybridization, the 600 mM and 1M NaCl fractions (enriched methylated DNA) for each sample were combined and labeled with either Alexa Fluor 555-aha-dCTP (maternal) or Alexa Fluor 647-aha-dCTP (placental) using the BioPrime Total Genomic Labeling System™ (Invitrogen®, Carlsbad, Calif., USA). The labeling reaction was carried out according to the manufacturer's manual. The differently labeled genomic DNA fragments of matched maternal/placental pairs were combined to a final volume of 80 µl, supplemented with 50 µg Cot-1 DNA (Invitrogen®), 52 µl of Agilent 10x blocking reagent (Agilent Technologies®, Santa Clara, Calif., USA), 78 µl of deionized formamide, and 260 µl Agilent 2x hybridization buffer. The samples were heated to 95° C. for 3 min, mixed, and subsequently incubated at 37° C. for 30 min. Hybridization on Agilent CpG Island Microarray Kit™ was then carried out at 67° C. for 40 hours using an Agilent SureHyb™ chamber and an Agilent hybridization oven. Slides were washed in Wash I (6×SSPE, 0.005% N-lauroylsarcosine) at room temperature for 5 min and in Wash II (0.06×SSPE) at 37° C. for an additional 5 min. Next, the slides were submerged in acetonitrile and Agilent Ozone Protection Solution™, respectively, for 30 seconds. Images were scanned immediately and analyzed using an Agilent DNA Microarray Scanner™. Microarray images were processed using Feature Extraction Software v9.5 and the standard CGH protocol.

Bisulfite Treatment

Genomic DNA sodium bisulfite conversion was performed using EZ-96 DNA Methylation Kit™ (ZymoResearch, Orange County, Calif.). The manufacturer's protocol was followed using 1 ug of genomic DNA and the alternative conversion protocol (a two temperature DNA denaturation).

Quantitative Methylation Analysis

Sequenom's MassARRAY® System was used to perform quantitative methylation analysis. This system utilizes matrix-assisted laser desorption ionization time-of-flight (MALDI-TOF) mass spectrometry in combination with RNA base specific cleavage (Sequenom® MassCLEAVE™). A detectable pattern is then analyzed for methylation status. PCR primers were designed using Sequenom® EpiDESIGNER™ (www.epidesigner.com). A total of 261 amplicons, covering 85 target regions, were used for validation (median amplification length=367 bp, min=108, max=500; median number of CpG's per amplicon=23, min=4, max=65). For each reverse primer, an additional T7 promoter tag for in-vivo transcription was added, as well as a 10mer tag on the forward primer to adjust for melting temperature differences. The MassCLEAVE™ biochemistry was performed as previously described (Ehrich M, et al. (2005) Quantitative high-throughput analysis of DNA methylation patterns by base specific cleavage and mass spectrometry. *Proc Natl Acad Sci USA* 102:15785-15790). Mass spectra were acquired using a MassARRAY™ Compact MALDI-TOF (Sequenom®, San Diego) and methylation ratios were generated by the EpiTYPER™ software v1.0 (Sequenom®, San Diego).

Statistical Analysis

All statistical calculations were performed using the R statistical software package (www.r-project.org). First, the array probes were grouped based on their genomic location. Subsequent probes that were less than 1000 bp apart were grouped together. To identify differentially methylated regions, a control sample was used as reference. In the control sample, the methylated fraction of a blood derived control DNA was hybridized against itself. Ideally this sample should show log ratios of the two color channels around 0. However because of the variability in hybridization behavior, the probes show a mean log ratio of 0.02 and a standard deviation of 0.18. Next the log ratios observed in our samples were compared to the control sample. A two way, paired t-test was used to test the NULL hypothesis that the groups are identical. Groups that contained less than 4 probes were excluded from the analysis. For groups including four or five probes, all probes were used in a paired t-test. For Groups with six or more probes, a sliding window test consisting of five probes at a time was used, whereby the window was moved by one probe increments. Each test sample was compared to the control sample and the p-values were recorded. Genomic regions were selected as being differentially methylated if eight out of ten samples showed a p value<0.01, or if six out of ten samples showed a p value<0.001. The genomic regions were classified as being not differentially methylated when the group showed less than eight samples with a p value<0.01 and less than six samples with a p value<0.001. Samples that didn't fall in either category were excluded from the analysis. For a subset of genomic regions that have been identified as differentially methylated, the results were confirmed using quantitative methylation analysis.

The Go analysis was performed using the online GOstat tool (http://gostat.wehi.edu.au/cgibin/-goStat.pl). P values were calculated using Fisher's exact test.

Microarray-Based Marker Discovery Results

To identify differentially methylated regions a standard sample was used, in which the methylated DNA fraction of monocytes was hybridized against itself. This standard provided a reference for the variability of fluorescent measurements in a genomic region. Differentially methylated regions were then identified by comparing the log ratios of each of the ten placental/maternal samples against this standard. Because the goal of this study was to identify markers that allow the reliable separation of maternal and fetal DNA, the target selection was limited to genes that showed a stable, consistent methylation difference over a contiguous stretch of genomic DNA. This focused the analysis on genomic regions where multiple probes indicated differential methylation. The selection was also limited to target regions where all samples showed differential methylation, excluding those with strong inter-individual differences. Two of the samples showed generally lower log ratios in the microarray analysis. Because a paired test was used for target selection, this did not negatively impact the results.

Based on these selection criteria, 3043 genomic regions were identified that were differentially methylated between maternal and fetal DNA. 21778 regions did not show a methylation difference. No inter-chromosomal bias in the distribution of differentially methylated regions was observed. The differentially methylated regions were located next to or within 2159 known genes. The majority of differentially methylated regions are located in the promoter area (18%) and inside the coding region (68%), while only few regions are located downstream of the gene (7%) or at the transition from promoter to coding region (7%). Regions that showed no differential methylation showed a similar distribution for promoter (13%) and downstream (5%) locations, but the fraction of regions located in the transition of promoter to coding region was higher (39%) and the fraction inside the coding region was lower (43%).

It has been shown in embryonic stem cells (ES) that genes targeted by the polycomb repressive complex2 (PRC2) are enriched for genes regulating development (Lee T I, et al. (2006) Control of developmental regulators by Polycomb in human embryonic stem cells. *Cell* 125:301-313). It has also been shown that differentially methylated genes are enriched for genes targeted by PRC2 in many cancer types (Ehrich M, et al. (2008) Cytosine methylation profiling of cancer cell lines. *Proc Natl Acad Sci USA* 105:4844-48). The set of genes identified as differentially methylated in this study is also enriched for genes targeted by PRC2 (p-value<0.001, odds ratio=3.6, 95% CI for odds ratio=3.1-4.2). A GO analysis of the set of differentially methylated genes reveals that this set is significantly enriched for functions important during development. Six out of the ten most enriched functions include developmental or morphogenic processes [anatomical structure morphogenesis (GO:0009653, p value=0), developmental process (GO:0032502, p value=0), multicellular organismal development (GO:0007275, p value=0), developmental of an organ (GO:0048513, p value=0), system development (GO:0048731, p value=0) and development of an anatomical structure (GO:0048856, p value=0)].

Validation Using Sequenom® EpiTYPER™

Figure 7:
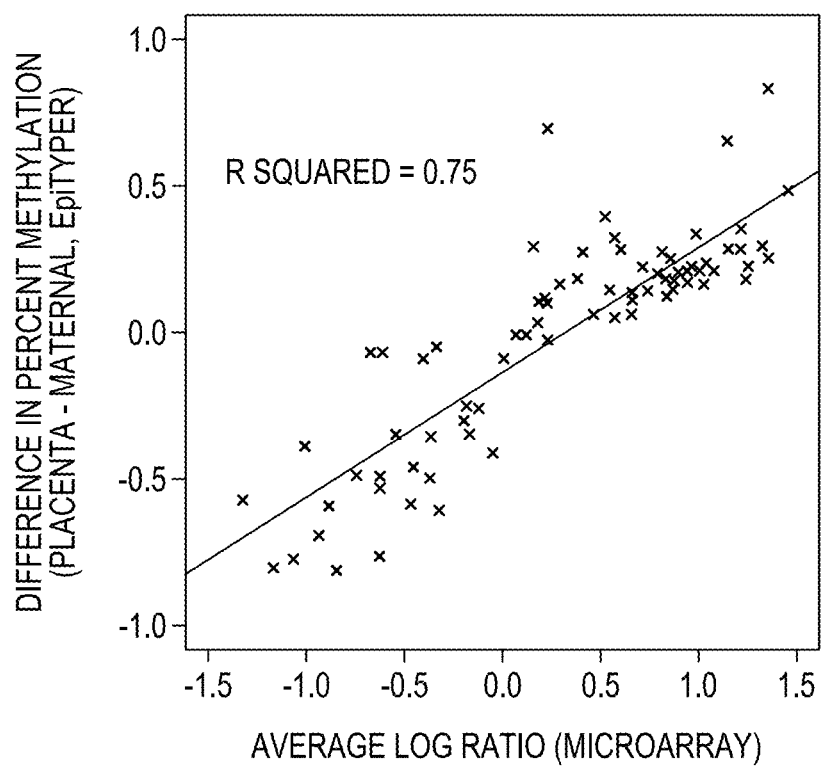
FIG. 7: Shows a correlation between microarray and EpiTYPER™ results.

To validate the microarray findings, 63 regions from chromosomes 13, 18 and 21 and an additional 26 regions from other autosomes were selected for confirmation by a different technology. Sequenom EpiTYPER™ technology was used to quantitatively measure DNA methylation in maternal and placental samples. For an explanation of the EpiTYPER™ methods, see Ehrich M, Nelson M R, Stanssens P, Zabeau M, Liloglou T, Xinarianos G, Cantor C R, Field J K, van den Boom D (2005) Quantitative high-throughput analysis of DNA methylation patterns by base specific cleavage and mass spectrometry. Proc Natl Acad Sci USA 102:15785-15790). For each individual CpG site in a target region the average methylation value across all maternal DNA samples and across all placenta samples was calculated. The difference between average maternal and placenta methylation was then compared to the microarray results. The results from the two technologies were in good concordance (see FIG. 7). For 85 target regions the quantitative results confirm the microarray results (95% confirmation rate). For 4 target regions, all located on chromosome 18, the results could not be confirmed. The reason for this discrepancy is currently unclear.

In contrast to microarrays, which focus on identification of methylation differences, the quantitative measurement of DNA methylation allowed analysis of absolute methylation values. In the validation set of 85 confirmed differentially methylated regions, a subset of 26 regions is more methylated in the maternal DNA sample and 59 regions are more methylated in the placental sample (see Table 1). Interestingly, genes that are hypomethylated in the placental samples tend to show larger methylation differences than genes that are hypermethylated in the placental sample (median methylation difference for hypomethylated genes=39%, for hypermethylated genes=20%).

Example 2

Example 2 describes a non-invasive approach for detecting the amount of fetal nucleic acid present in a maternal sample (herein referred to as the "Fetal Quantifier Method"), which may be used to detect or confirm fetal traits (e.g., fetal sex of RhD compatibility), or diagnose chromosomal abnormalities such as Trisomy 21 (both of which are herein referred to as the "Methylation-Based Fetal Diagnostic Method"). FIG. 10 shows one embodiment of the Fetal Quantifier Method, and FIG. 11 shows one embodiment of the Methylation-Based Fetal Diagnostic Method. Both processes use fetal DNA obtained from a maternal sample. The sample comprises maternal and fetal nucleic acid that is differentially methylated. For example, the sample may be maternal plasma or serum. Fetal DNA comprises approximately 2-30% of the total DNA in maternal plasma. The actual amount of fetal contribution to the total nucleic acid present in a sample varies from pregnancy to pregnancy and can change based on a number of factors, including, but not limited to, gestational age, the mother's health and the fetus' health.

As described herein, the technical challenge posed by analysis of fetal DNA in maternal plasma lies in the need to be able to discriminate the fetal DNA from the co-existing background maternal DNA. The methods of the present technology exploit such differences, for example, the differential methylation that is observed between fetal and maternal DNA, as a means to enrich for the relatively small percentage of fetal DNA present in a sample from the mother. The non-invasive nature of the approach provides a major advantage over conventional methods of prenatal diagnosis such as, amniocentesis, chronic villus sampling and cordocentesis, which are associated with a small but finite risk of fetal loss. Also, because the method is not dependent on fetal cells being in any particular cell phase, the method provides a rapid detection means to determine the presence and also the nature of the chromosomal abnormality. Further, the approach is sex-independent (i.e., does not require the presence of a Y-chromosome) and polymorphic-independent (i.e., an allelic ratio is not determined). Thus, the compositions and methods of the technology represent improved universal, noninvasive approaches for accurately determining the amount of fetal nucleic acid present in a maternal sample.

Assay Design and Advantages

There is a need for accurate detection and quantification of fetal DNA isolated noninvasively from a maternal sample. The present technology takes advantage of the presence of circulating, cell free fetal nucleic acid (ccfDNA) in maternal plasma or serum. In order to be commercially and clinically practical, the methods of the technology should only consume a small portion of the limited available fetal DNA. For example, less than 50%, 40%, 30%, 25%, 20%, 15%, 10%, 5% or less of the sample. Further, the approach should preferably be developed in a multiplex assay format in which one or more (preferably all) of the following assays are included:

Assays for the detection of total amount of genomic equivalents present in the sample, i.e., assays recognizing both maternal and fetal DNA species;

Assays for the detection of fetal DNA isolated from a male pregnancy, i.e., sequences specific for chromosome Y;

Assays specific for regions identified as differentially methylated between the fetus and mother; or Assays specific for regions known to be hypomethylated in all tissues to be investigated, which can serve as a control for restriction efficiency.

Other features of the assay may include one or more of the following:

For each assay, a target-specific, competitor oligonucleotide that is identical, or substantially identical, to the target sequence apart from a distinguishable feature of the competitor, such as a difference in one or more nucleotides relative to the target sequence. This oligonucleotide when added into the PCR reaction will be co-amplified with the target and a ratio obtained between these two PCR amplicons will indicate the number of target specific DNA sequences (e.g., fetal DNA from a specific locus) present in the maternal sample.

The amplicon lengths should preferably be of similar length in order not to skew the amplification towards the shorter fragments. However, as long as the amplification efficiency is about equal, different lengths may be used.

Differentially methylated targets can be selected from Table 1 or from any other targets known to be differentially methylated between mother and fetus. These targets can be hypomethylated in DNA isolated from non-pregnant women and hypermethylated in samples obtained from fetal samples. These assays will serve as controls for the restriction efficiency.

The results obtained from the different assays can be used to quantify one or more of the following:

Total number of amplifiable genomes present in the sample (total amount of genomic equivalents);

The fetal fraction of the amplifiable genomes (fetal concentration or percentage); or Differences in copy number between fetally-derived DNA sequences (for example, between fetal chromosome 21 and a reference chromosome such as chromosome 3).

Examples of Assays Used in the Test

Below is an outline of the reaction steps used to perform a method of the technology, for example, as provided in FIG. 10. This outline is not intended to limit the scope of the technology. Rather it provides one embodiment of the technology using the Sequenom® MassARRAY® technology.

1) DNA isolation from plasma samples.
2) Digestion of the DNA targets using methylation sensitive restriction enzymes (for example, HhaI and HpaII).

For each reaction the available DNA was mixed with water to a final volume of 25 ul.

10 ul of a reaction mix consisting of 10 units HhaI, 10 units HpaII and a reaction buffer were added. The sample was incubated at an optimal temperature for the restriction enzymes. HhaI and HpaII digest non-methylated DNA (and will not digest hemi- or completely methylated DNA). Following digestion, the enzymes were denatured using a heating step.

3) Genomic Amplification—PCR was performed in a total volume of 50 ul by adding PCR reagents (Buffer, dNTPs, primers and polymerase). Exemplary PCR and extend primers are provided below. In addition, synthetic competitor oligonucleotide was added at known concentrations.

4) Replicates (optional)—Following PCR the 50 ul reaction was split into 5 ul parallel reactions (replicates) in order to minimize variation introduced during the post PCR steps of the test. Post PCR steps include SAP, primer extension (MassEXTEND® technology), resin treatment, dispensing of spectrochip and MassARRAY.

5) Quantification of the Amplifiable Genomes—Sequenom MassARRAY® technology was used to determine the amount of amplification product for each assay. Following PCR, a single base extension assay was used to interrogate the amplified regions (including the competitor oligonucleotides introduced in step 3). Specific extend primers designed to hybridize directly adjacent to the site of interest were introduced. See extend primers provided below. These DNA oligonucleotides are referred to as iPLEX® MassEXTEND® primers. In the extension reaction, the iPLEX primers were hybridized to the complementary DNA templates and extended with a DNA polymerase. Special termination mixtures that contain different combinations of deoxy- and dideoxynucleotide triphosphates along with enzyme and buffer, directed limited extension of the iPLEX primers. Primer extension occurs until a complementary dideoxynucleotide is incorporated.

The extension reaction generated primer products of varying length, each with a unique molecular weight. As a result, the primer extension products can be simultaneously separated and detected using Matrix Assisted Laser Desorption/Ionization, Time-Of-Flight (MALDI-TOF) mass spectrometry on the MassARRAY® Analyzer Compact. Following this separation and detection, SEQUENOM's proprietary software automatically analyzes the data.

Figure 18:
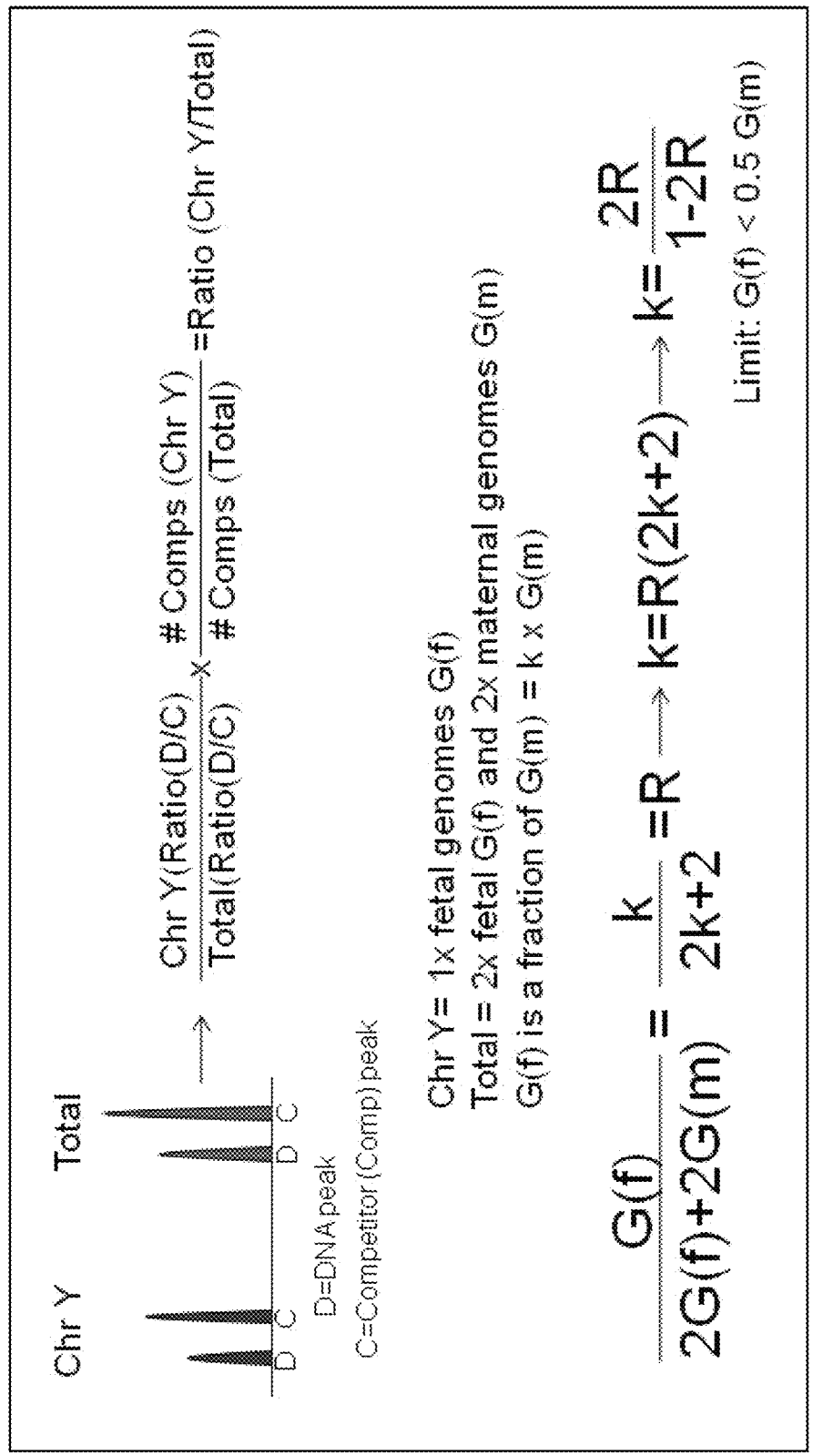
FIG. 18: Provides a specific method for calculating fetal DNA fraction (or concentration) in a sample using the Y-chromosome-specific markers for male pregnancies and the mean of the methylated fraction for all pregnancies (regardless of fetal sex).

6) Calculating the amount and concentration of fetal nucleic acid—Methods for calculating the total amount of genomic equivalents present in the sample, the amount (and concentration) of fetal nucleic acid isolated from a male pregnancy, and the amount (and concentration) of fetal nucleic based on differentially methylated targets are provided below and in FIGS. 18 and 19.

The above protocol can be used to perform one or more of the assays described below. In addition to the sequences provided immediately below, a multiplex scheme that interrogates multiple is provided in Table X below.

1) Assay for the Quantification of the Total Number of Amplifiable Genomic Equivalents in the Sample.

Targets were selected in housekeeping genes not located on the chromosomes 13, 18, 21, X or Y. The targets should be in a single copy gene and not contain any recognition sites for the methylation sensitive restriction enzymes.

Underlined sequences are PCR primer sites, italic is the site for the single base extend primer and bold letter (C) is the nucleotide extended on human DNA ApoE Chromosome 19:45409835-45409922 DNA target sequence with interrogated nucleotide C in bold. All of the chromosome positions provided in this section are from the February 2009 UCSC Genome Build.

```
                                          (SEQ ID NO: 90)
GATTGACAGTTTCTCCTTCCCCAGACTGGCCAATCACAGGCAGG

AAGATGAAGGTTCTGTGGGCTGCGTTGCTGGTCACATTCCTGGC

ApoE Forward Primer:
                                          (SEQ ID NO: 91)
5'-ACGTTGGATG-TTGACAGTTTCTCCTTCCCC
(Primer contains a 5' 10 bp MassTag separated
by a dash)
```

-continued

ApoE Reverse Primer:
                                        (SEQ ID NO: 92)
5'-ACGTTGGATG-GAATGTGACCAGCAACGCAG
(Primer contains a 5' 10 bp MassTag separated
by a dash)

ApoE Extension Primer:
                                        (SEQ ID NO: 93)
5'-GCAGGAAGATGAAGGTT[C/T]
Primer extends C on human DNA targets and T
on synthetic DNA targets ApoE synthetic competitor oligonucleotide:
                                        (SEQ ID NO: 94)
5'-GATTGACAGTTTCTCCTTCCCCAGACTGGCCAATCACAGGC

AGGAAGATGAAGGTTTTGTGGGCTGCGTTGCTGGTCACATTCCT

GGC
(Bold T at position 57 is different from human
DNA)

2) Assay for the Quantification of the Total Number of Chromosome Y Sequences in the Sample.

Targets specific for the Y-chromosome were selected, with no similar or paralog sequences elsewhere in the genome. The targets should preferably be in a single copy gene and not contain any recognition sites for the methylation sensitive restriction enzyme(s).

Underlined sequences are PCR primer sites, and italic nucleotide(s) is the site for the single-base extend primer and bold letter (C) is the nucleotide extended on human DNA.

SRY on chrY: 2655628-2655717 (reverse
complement)
                                        (SEQ ID NO: 95)
GAGTTTT<u>TGGATAGTAAAATAAGTTTCGAACTCTGGCACC</u>*TTTCAAT*

*TTTGTCGCACT*C*TCCTT*<u>GTTTTTGACAATGCAATCATATGCTTC</u>

SRY Forward Primer:
                                        (SEQ ID NO: 96)
5'-ACG-TGGATAGTAAAATAAGTTTCGAACTCTG
(Primer contains a 5' 3 bp MassTag separated
by a dash)

SRY Reverse Primer:
                                        (SEQ ID NO: 97)
5'-GAAGCATATGATTGCATTGTCAAAAAC SRY Extension Primer:
                                        (SEQ ID NO: 98)
5'-aTTTCAATTTTGTCGCACT[C/T]
Primer extends C on human DNA targets and T
on synthetic DNA targets. 5' Lower case "a"
is a non-complementary nucleotide SRY synthetic competitor oligonucleotide:
                                        (SEQ ID NO: 99)
5'-GAGTTTTGGATAGTAAAATAAGTTTCGAACTCTGGCACCTTTCAAT

TTTGTCGCACTTTCCTTGTTTTTGACAATGCAATCATATGCTTC

3) Assay for the Quantification of Fetal Methylated DNA Sequences Present in the Sample.

Targets were selected in regions known to be differentially methylated between maternal and fetal DNA. Sequences were selected to contain several restriction sites for methylation sensitive enzymes. For this study the HhaI (GCGC) and HpaII (CCGG) enzymes were used.

Underlined sequences are PCR primer sites, italic is the site for the single base extend primer and bold letter (C) is the nucleotide extended on human DNA, lower case letter are recognition sites for the methylation sensitive restriction enzymes.

TBX3 on chr12: 115124905-115125001
                                        (SEQ ID NO: 100)
GAACTCC<u>TCTTTGTCTCTGCGTGC</u>ccggcgcgc*CCCCCTCccgg*TGGGT

*GATAAA*CCCACTCTGgcgccggCCATgcgcTGGGTGATTAA<u>TTTGCGA</u>

-continued

TBX3 Forward Primer:
                                        (SEQ ID NO: 101)
5'-ACGTTGGATG-TCTTTGTCTCTGCGTGCCC
(Primer contains a 5' 10 bp MassTag separated
by a dash)

TBX3 Reverse Primer:
                                        (SEQ ID NO: 102)
5'-ACGTTGGATG-TTAATCACCCAGCGCATGCC
(Primer contains a 5' 10 bp MassTag separated
by a dash)

TBX3 Extension Primer:
                                        (SEQ ID NO: 103)
5'-CCCCTCCCGGTGGGTGATAAA[C/T]
Primer extends C on human DNA targets and T on
synthetic DNA targets. 5' Lower case "a" is a
non-complementary nucleotide TBX3 synthetic competitor oligonucleotide:
                                        (SEQ ID NO: 104)
5'-GAACTCCTCTTTGTCTCTGCGTGCCCGGCGCGCCCCCCTCCCGGTG

GGTGATAAATCCACTCTGGCGCCGGCCATGCGCTGGGTGATTAATTTGC

GA

4) Control Assay for the Enzyme Restriction Efficiency.

Targets were selected in regions known not to be methylated in any tissue to be investigated. Sequences were selected to contain no more than one site for each restriction enzyme to be used.

Underlined sequences are PCR primer sites, italic nucleotide(s) represent the site for the single-base extend primer and bold letter (G) is the reverse nucleotide extended on human DNA, lower case letter are recognition sites for the methylation sensitive restriction enzymes.

CACNA1G chr17: 48637892-48637977 (reverse
complement)
                                        (SEQ ID NO: 105)
<u>CCATTGGCCGTCCGCCGTGGCAGTGCGGGCGGGA</u>gcgcAGGGAGAGAAC

*CACAGCTGGAATCCGA*<u>TTCCCACCCCAAAACCCAGGA</u>

HhaI Forward Primer:
                                        (SEQ ID NO: 106)
5'-ACGTTGGATG-CCATTGGCCGTCCGCCGTG
(Primer contains a 5' 10 bp MassTag separated
by a dash)

HhaI Reverse Primer:
                                        (SEQ ID NO: 107)
5'-ACGTTGGATG-TCCTGGGTTTTGGGGTGGGAA
(Primer contains a 5' 10 bp MassTag separated
by a dash)

HhaI Extension Primer:
                                        (SEQ ID NO: 108)
5'-TTCCAGCTGTGGTTCTCTC HhaI synthetic competitor oligonucleotide:
                                        (SEQ ID NO: 109)
5'-<u>CCATTGGCCGTCCGCCGTGGCAGTGCGGGCGGG</u>AGCGCAGA*GAGAG*

*AA*CCACAGCTGGAATCCGA<u>TTCCCACCCCAAAACCCAGGA</u>

Validation Experiments

The sensitivity and accuracy of the present technology was measured using both a model system and clinical samples. In the different samples, a multiplex assay was run that contains 2 assays for total copy number quantification, 3 assays for methylation quantification, 1 assay specific for chromosome Y and 1 digestion control assay. See Tables X1 and X2. Another multiplex scheme with additional assays is provided in Tables Y1 and Y2.

TABLE X1

PCR Primers and Extend Primers
Table X1 discloses SEQ ID NOS 110-130,
respectively, in order of appearance.

| Gene ID | * | First Primer | Second Primer | Extend Primer |
|---|---|---|---|---|
| SOX14 | M | ACGTTGGATGACATGGT CGGCCCCACGGAAT | ACGTTGGATGCTCCTTC CTAGTGTGAGAACCG | CAGGTTCCGGGGC TTGGG |
| HhaI_CTRL | D | ACGTTGGATGACCCATT GGCCGTCCGCCGT | ACGTTGGATGTTTTGGG GTGGGAATCGGATT | CGCAGGGAGAGAA CCACAG |
| TBX3 | M | ACGTTGGATGGAACTCC TCTTTGTCTCTGCG | ACGTTGGATGTGGCATG GCCGGCGCCAGA | CCCCTCCCGGTGG GTGATAAA |
| SRY | Y | ACGTTGGATGCGCAGCA ACGGGACCGCTACA | ACGTTGGCATCTAGGTA GGTCTTTGTAGCCAA | AAAGCTGTAGGAC AATCGGGT |
| ALB | T | ACGTTGCGTAGCAACCT GTTACATATTAA | ACGTTGGATCTGAGCAA AGGCAATCAACACCC | CATTTTTCTACAT CCTTTGTTT |
| EDG6 | M | ACGTTGGATGCATAGAG GCCCATGATGGTGG | ACGTTGGATGACCTTCT GCCCCTCTACTCCAA | agAAGATCACCAG GCAGAAGAGG |
| RNaseP | T | ACGTTGGATGGTGTGGT CAGCTCTTCCCTTCAT | ACGTTGGCCCACATGTA ATGTGTTGAAAAGCA | ACTTGGAGAACAA AGGACACCGTTA |

TABLE X2

Competitor Oligonucleotide Sequence
Table X2 discloses SEQ ID NOS 131-137,
respectively, in order of appearance.

| Gene ID | * | Competitor Oligonucleotide Sequence |
|---|---|---|
| SOX14 | M | GGTCGGCCCCACGGAATCCCGGCTCTGTGTGC GCCCAGGTTCCGGGGCTTGGGTGTTGCCGGTT CTCACACTAGGAAGGAG |
| HhaI_CTRL | D | CCATTGGCCGTCCGCCGTGGCAGTGCGGGCGG GAGCGCAGAGAGAGAACCACAGCTGGAATCCG ATTCCCACCCCAAAA |
| TBX3 | M | GAACTCCTCTTTGTCTCTGCGTGCCCGGCGCG CCCCCCTCCCGGTGGGTGATAAATCCACTCTG GCGCCGGCCATGC |
| SRY | Y | GCAGCAACGGGACCGCTACAGCCACTGGACAA AGCCGTAGGACAATCGGGTAACATTGGCTACA AAGACCTACCTAGATGC |
| ALB | T | GCGTAGCAACCTGTTACATATTAAAGTTTTAT TATACTACATTTTTCTACATCCTTTGTTTCAG AGTGTTGATTGCCTTTGCTCAGTATCTTCAG |
| EDG6 | M | CCTTCTGCCCCTCTACTCCAAGCGCTACACCC TCTTCTGCCTGGTGATCTTTGCCGGCGTCCTG GCCACCATCATGGGCCTCTATG |
| RNaseP | T | GTGTGGTCAGCTCTTCCCTTCATCACATACTT GGAGAACAAAGGACACCGTTATCCATGCTTTT TCAACACATTACATGTGGG |

TABLE Y1

PCR Primers and Extend Primers
Table Y1 discloses SEQ ID NOS 138-167,
respectively, in order of appearance.

| Gene ID | * | First Primer | Second Primer | Extend Primer |
|---|---|---|---|---|
| EDG6 | M | ACGTTGGATGTTCTGC CCCTCTACTCCAAG | ACGTTGGATGCATAGA GGCCCATGATGGTG | TTCTGCCTGGT GATCTT |
| RNAseP | T | ACGTTGGATGTCAGCT CTTCCCTTCATCAC | ACGTTGGATGCCTACC TCCCACATGTAATGT | AACAAAGGACA CCGTTA |
| ApoE | T | ACGTTGGATGTTGACA GTTTCTCCTTCCCC | ACGTTGGATGGAATGT GACCAGCAACGCAG | GCAGGAAGATG AAGGTT |
| SOX14 | M | ACGTTGGATGCGGTCG GCCCCACGGAAT | ACGTTGGATGCTCCTT CCTAGTGTGAGAACCG | aAGGTTCCGGG GCTTGGG |
| SRY no2 | Y | ACGTGGATAGTAAAAT AAGTTTCGAACTCTG | GAAGCATATGATTGCA TTGTCAAAAAC | aTTTCAATTTT GTCGCACT |

TABLE Y1-continued

PCR Primers and Extend Primers
Table Y1 discloses SEQ ID NOS 138-167,
respectively, in order of appearance.

| Gene ID | * | First Primer | Second Primer | Extend Primer |
|---|---|---|---|---|
| SRY no1 | Y | ACGTTGGATGCACAGC TCACCGCAGCAACG | ACGTTGGATGCTAGGT AGGTCTTTGTAGCCAA | AGCTGTAGGAC AATCGGGT |
| TBX3 | M | ACGTTGGATGTCTTTG TCTCTGCGTGCCC | ACGTTGGATGTTAATC ACCCAGCGCATGGC | CCCTCCCGGTG GGTGATAAA |
| CACNA1G dig CTRL 1 | D | ACGTTGGATGGACTGA GCCCCAGAACTCG | ACGTTGGATGGTGGGT TTGTGCTTTCCACG | AGGGCCGGGGT CTGCGCGTG |
| DAPK1 dig CTRL 2 | D | ACGTTGGATGAAGCCA AGTTTCCCTCCGC | ACGTTGGATGCTTTTG CTTTCCCAGCCAGG | GAGGCACTGCC CGGACAAACC |
| ALB | T | ACGTTAGCGTAGCAAC CTGTTACATATTAA | ACGTTGGATGCTGAGC AAAGGCAATCAACA | CATTTTTCTAC ATCCTTTGTTT |

TABLE Y2

Competitor Oligonucleotide Sequence
Table Y2 discloses SEQ ID NOS 168-177,
respectively, in order of appearance.

| Gene ID | * | Competitor |
|---|---|---|
| EDG6 | M | CCTTCTGCCCCTCTACTCCAAGCGCTACACC CTCTTCTGCCTGGTGATCTTTGCCGGCGTCC TGGCCACCATCATGGGCCTCTATG |
| RNAseP | T | GTGTGGTCAGCTCTTCCCTTCATCACATACT TGGAGAACAAAGGACACCGTTATCCATGCTT TTTCAACACATTACATGTGGGAGGTAGG |
| ApoE | T | GATTGACAGTTTCTCCTTCCCCAGACTGGCC AATCACAGGCAGGAAGATGAAGGTTTTGTGG GCTGCGTTGCTGGTCACATTCCTGGC |
| SOX14 | M | AAAACCAGAGATTCGCGGTCGGCCCCACGGA ATCCCGGCTCTGTGTGCGCCCAGGTTCCGGG GCTTGGGTGTTGCCGGTTCTCACACTAGGAA GGAGC |
| SRY no2 | Y | GAGTTTTGGATAGTAAAATAAGTTTCGAACT CTGGCACCTTTCAATTTTGTCGCACTTTCCT TGTTTTTGACAATGCAATCATATGCTTC |
| SRY no1 | Y | GCAGCCAGCTCACCGCAGCAACGGGACCGCT ACAGCCACTGGACAAAGCTGTAGGACAATCG GGTGACATTGGCTACAAAGACCTACCTAGAT GC |
| TBX3 | M | GAACTCCTCTTTGTCTCTGCGTGCCCGGCGC GCCCCCTCCCGGTGGGTGATAAATCCACTC TGGCGCCGGCCATGCGCTGGGTGATTAATTT GCGA |
| CACNA1G dig CTRL 1 | D | GTGGGTTTGTGCTTTCCACGCGTGCACACAC ACGCGCAGACCCCGGCCCTTGCCCCGCCTAC CTCCCCGAGTTCTGGGGCTCAGTC |
| DAPK1 dig CTRL 2 | D | GCGCCAGCTTTTGCTTTCCCAGCCAGGGCGC GGTGAGGTTTGTCCGGGCAGTGCCTCGAGCA ACTGGGAAGGCCAAGGCGGAGGGAAAC |
| ALB | T | GCGTAGCAACCTGTTACATATTAAAGTTTTA TTATACTACATTTTTCTACATCCTTTGTTTT AGGGTGTTGATTGCCTTTGCTCAGTATCTTC AGC |

Figure 12:
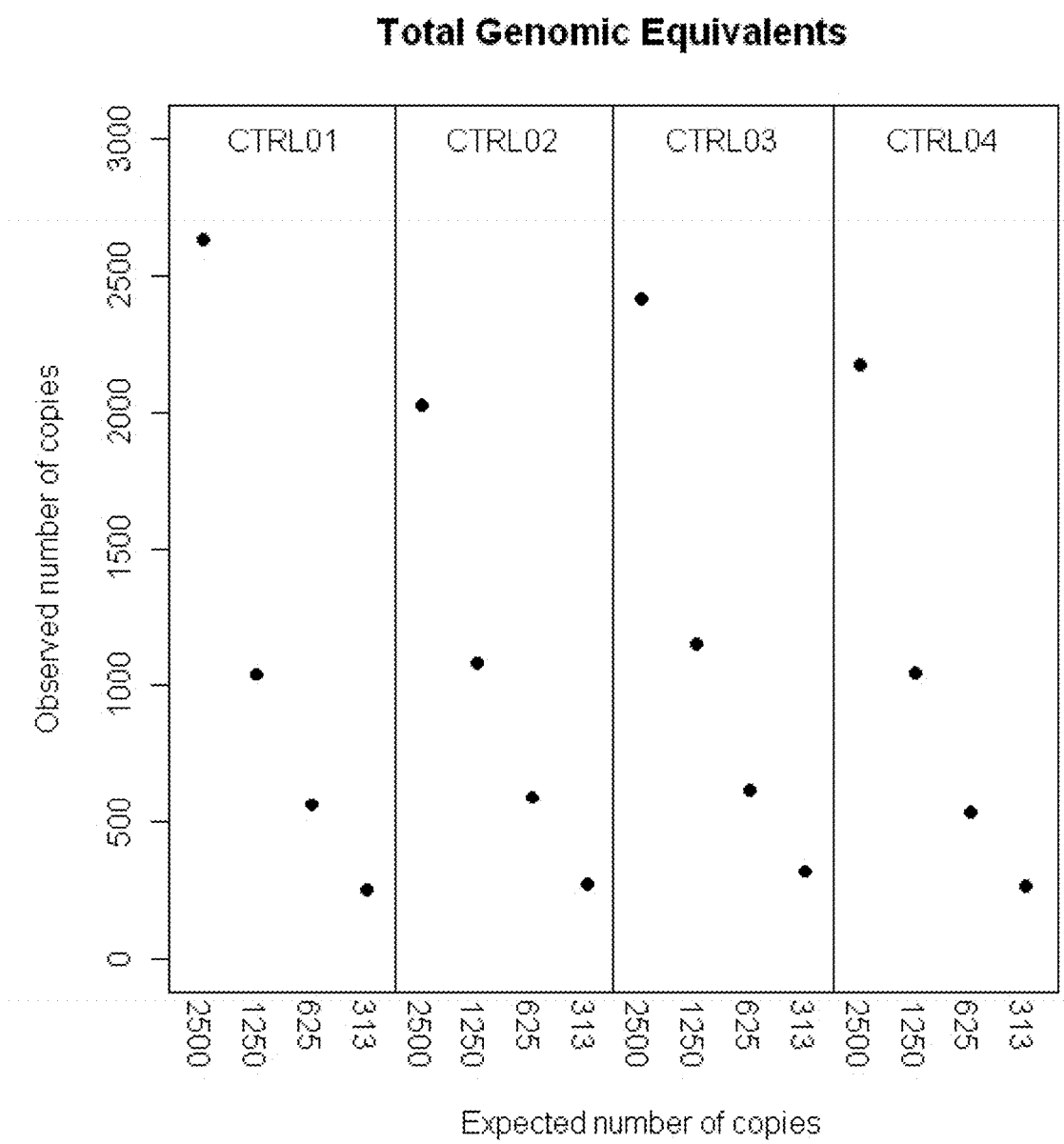
FIG. 12: Shows the total number of amplifiable genomic copies from four different DNA samples isolated from the blood of non-pregnant women. Each sample was diluted to contain approximately 2500, 1250, 625 or 313 copies per reaction. Each measurement was obtained by taking the mean DNA/competitor ratio obtained from two total copy number assays (ALB and RNAseP in Table X). As FIG. 12 shows, the total copy number is accurate and stable across the different samples, thus validating the usefulness of the competitor-based approach.

T = Assay for Total Amount;
M = Assay for Methylation quantification;
Y = Y-Chromosome Specific Assay;
D = Digestion control Model System Using Genomic DNA In order to determine the sensitivity and accuracy of the method when determining the total number of amplifiable genomic copies in a sample, a subset of different DNA samples isolated from the blood of non-pregnant women was tested. Each sample was diluted to contain approximately 2500, 1250, 625 or 313 copies per reaction. The total number of amplifiable genomic copies was obtained by taking the mean DNA/competitor ratio obtained from the three total copy number assays. The results from the four different samples are shown in FIG. 12.

Figure 13A:
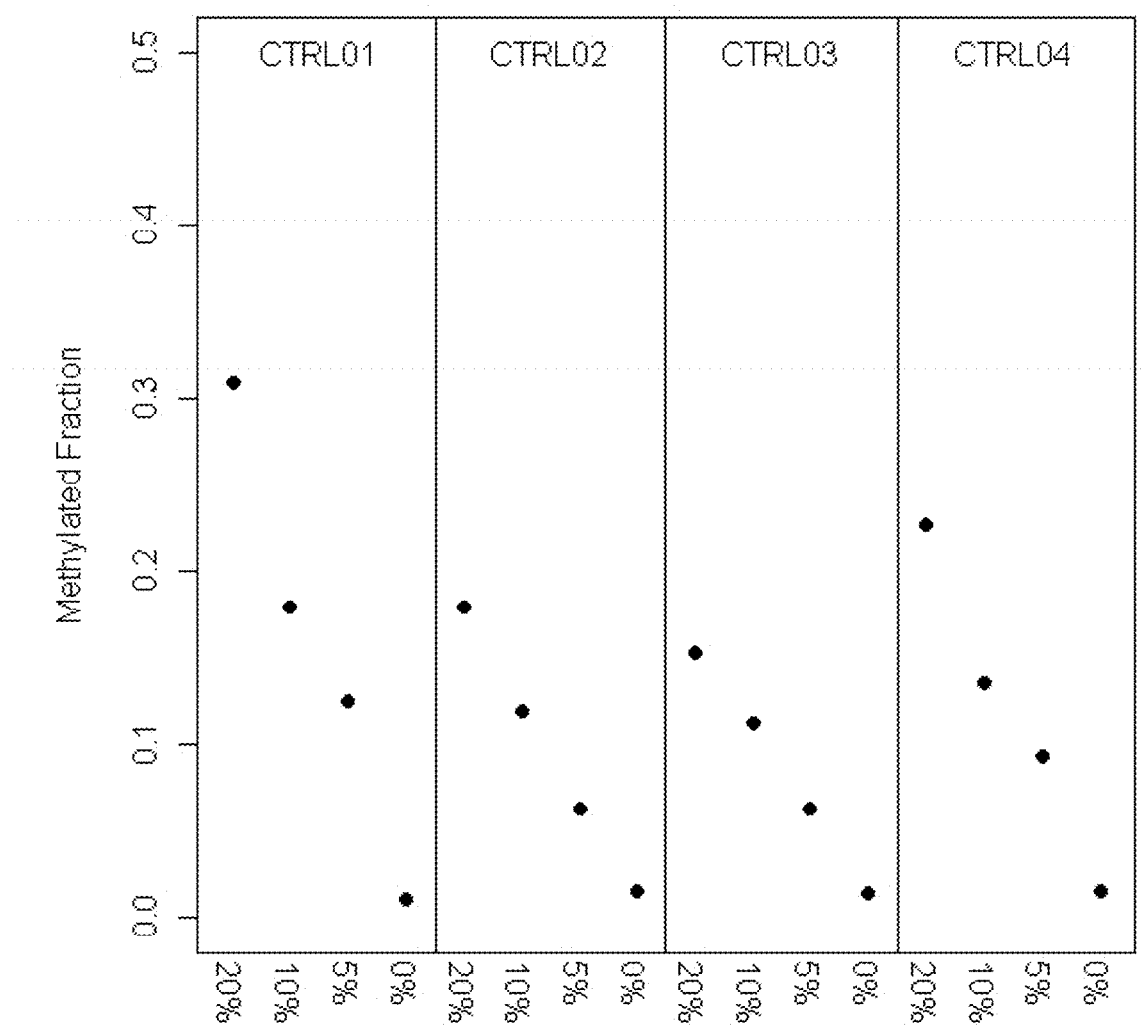
FIGS. 13A and B: A model system was created that contained a constant number of maternal non-methylated DNA with varying amounts of male placental methylated DNA spiked-in. The samples were spiked with male placental amounts ranging from approximately 0 to 25% relative to the maternal non-methylated DNA. The fraction of placental DNA was calculated using the ratios obtained from the methylation assays (FIG. 13A) and the Y-chromosome marker (FIG. 13B) as compared to the total copy number assay. The methylation and Y-chromosome markers are provided in Table X.
Figure 13B:
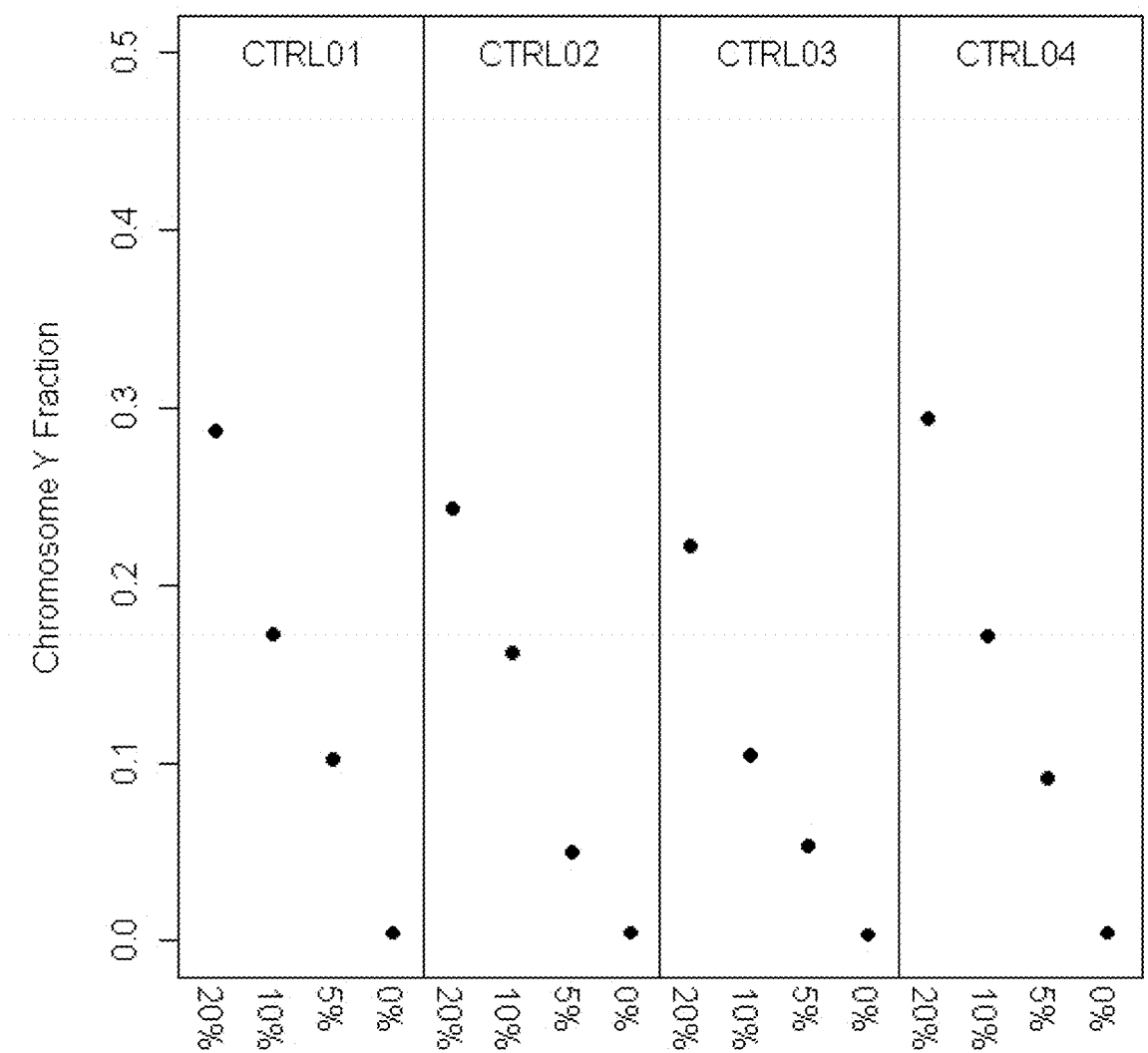

To optimize the reaction, a model system was developed to simulate DNA samples isolated from plasma. These samples contained a constant number of maternal non-methylated DNA and were spiked with different amounts of male placental methylated DNA. The samples were spiked with amounts ranging from approximately 0 to 25% relative to the maternal non-methylated DNA. The results are shown in FIGS. 13A and B. The fraction of placental DNA was calculated using the ratios obtained from the methylation assays (FIG. 13A), the SRY markers (FIG. 13B) and the total copy number assays. The primer sequences for the methylation assays (TBX), Y-chromosome assays (SRY) and total copy number (APOE) are provided above. The model system demonstrated that the methylation-based method performed equal to the Y-chromosome method (SRY markers), thus validating the methylation-based method as a sex-independent fetal quantifier.

Plasma Samples

To investigate the sensitivity and accuracy of the methods in clinical samples, 33 plasma samples obtained from women pregnant with a male fetus were investigated using the multiplex scheme from Table X. For each reaction, a quarter of the DNA obtained from a 4 ml extraction was used in order to meet the important requirement that only a portion of the total sample is used.

Total Copy Number Quantification

Figures 14A, 14B:
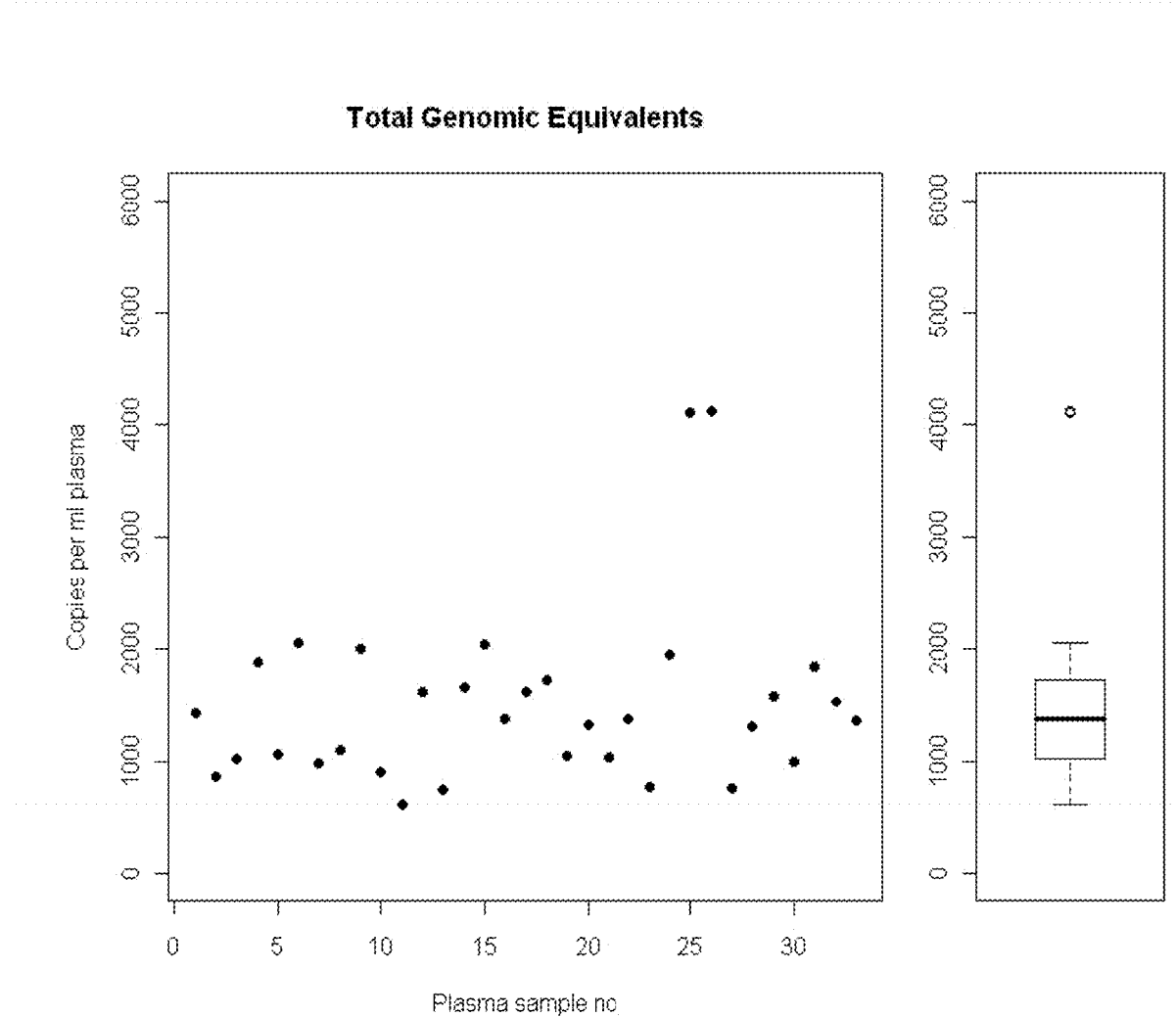
In FIG. 14A, the copy number for each sample is shown. Two samples (no 25 and 26) have a significantly higher total copy number than all the other samples. A mean of approximately 1300 amplifiable copies/ml plasma was obtained (range 766-2055).
FIG. 14B shows a box-and-whisker plot of the given values, summarizing the results.

The results from the total copy number quantification can be seen in FIGS. 14A and B. In FIG. 14A, the copy number for each sample is shown. Two samples (nos. 25 and 26) have a significantly higher total copy number than all the other samples. In general, a mean of approximately 1300 amplifiable copies/ml plasma was obtained (range 766-2055). FIG. 14B shows a box-and-whisker plot of the given values, summarizing the results.

Figures 15A, 15B:
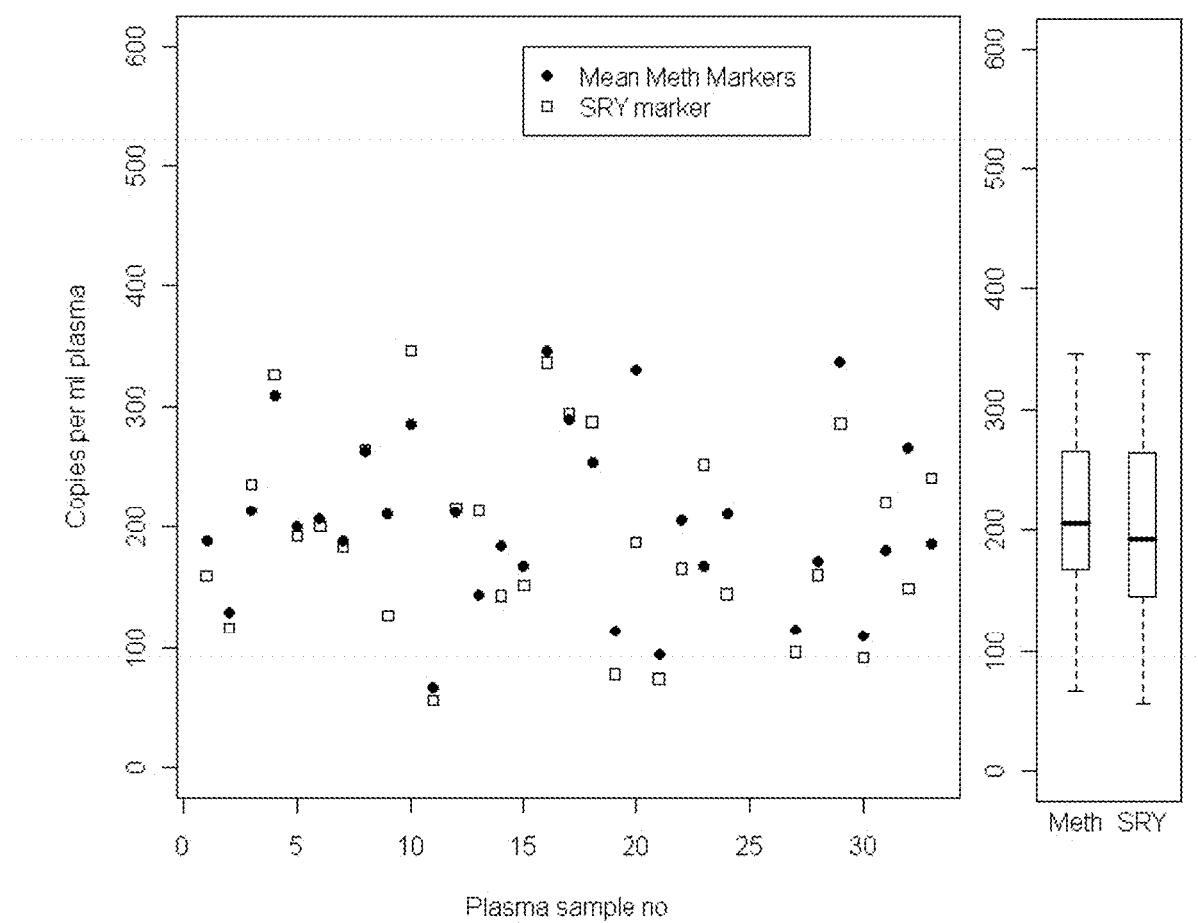
FIGS. 15A and B: The amount (or copy numbers) of fetal nucleic acid from 33 different plasma samples taken from pregnant women with male fetuses are plotted. The copy numbers obtained were calculated using the methylation markers and the Y-chromosome-specific markers using the assays provided in Table X. As can be seen in FIG. 15B, the box-and-whisker plot of the given values indicated minimal difference between the two different measurements, thus validating the accuracy and stability of the method.

Correlation Between Results Obtained from the Methylation Markers and the Y-Chromosome Marker In FIGS. 15A and B, the numbers of fetal copies for each sample are plotted. As all samples were from male pregnancies. The copy numbers obtained can be calculated using either the methylation or the Y-chromosome-specific markers. As can be seen in FIG. 15B, the box-and-whisker plot of the given values indicated minimal difference between the two different measurements.

Figure 16:
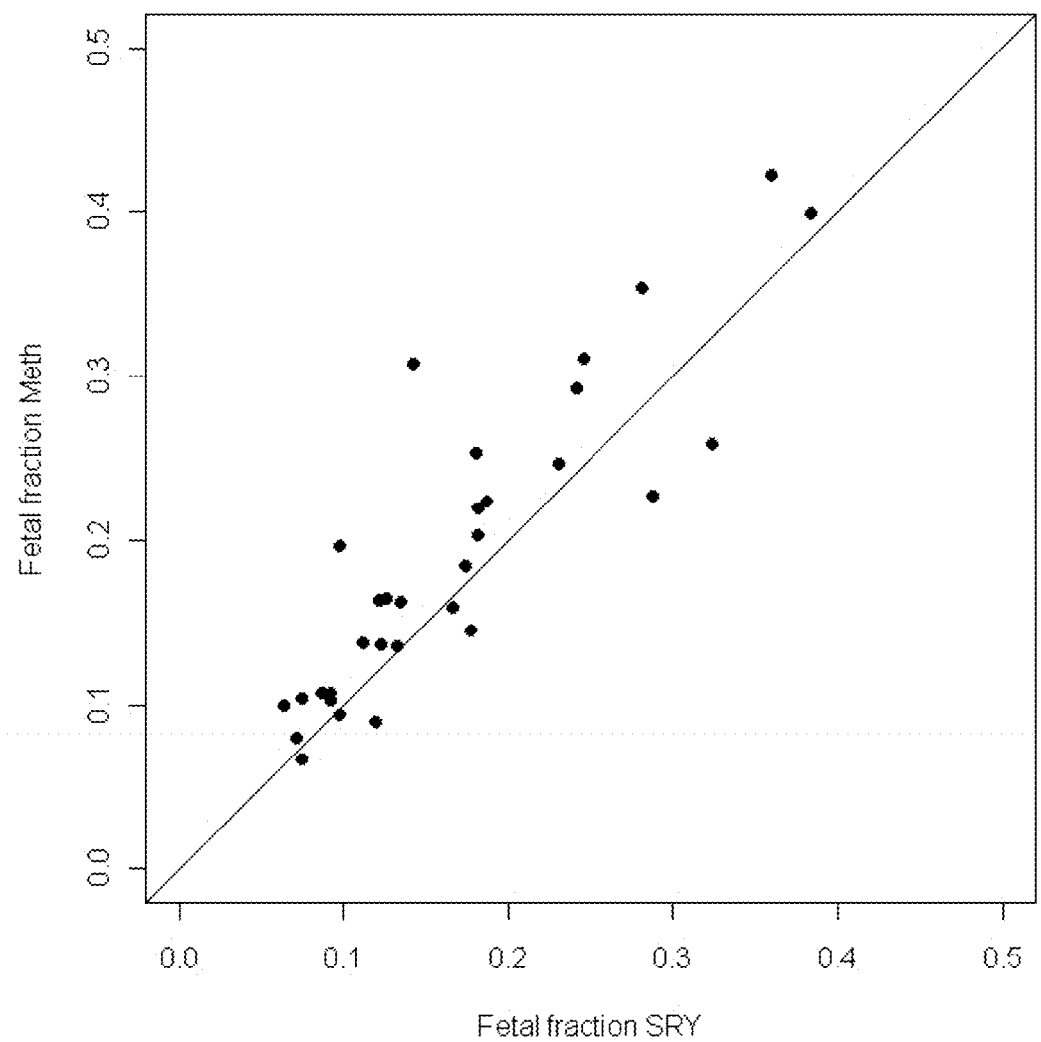
FIG. 16: Shows a paired correlation between the results obtained using the methylation markers versus the Y-chromosome marker from FIG. 15A.

The results showing the correlation between results obtained from the methylation markers and the Y-chromosome marker (SRY) is shown in FIG. 16. Again, the methylation-based method performed equal to the Y-chromosome method (SRY markers), further validating the methylation-based method as a sex-independent and polymorphism-independent fetal quantifier. The multiplexed assays disclosed in Table X were used to determine the amount fetal nucleic.

Figure 17:
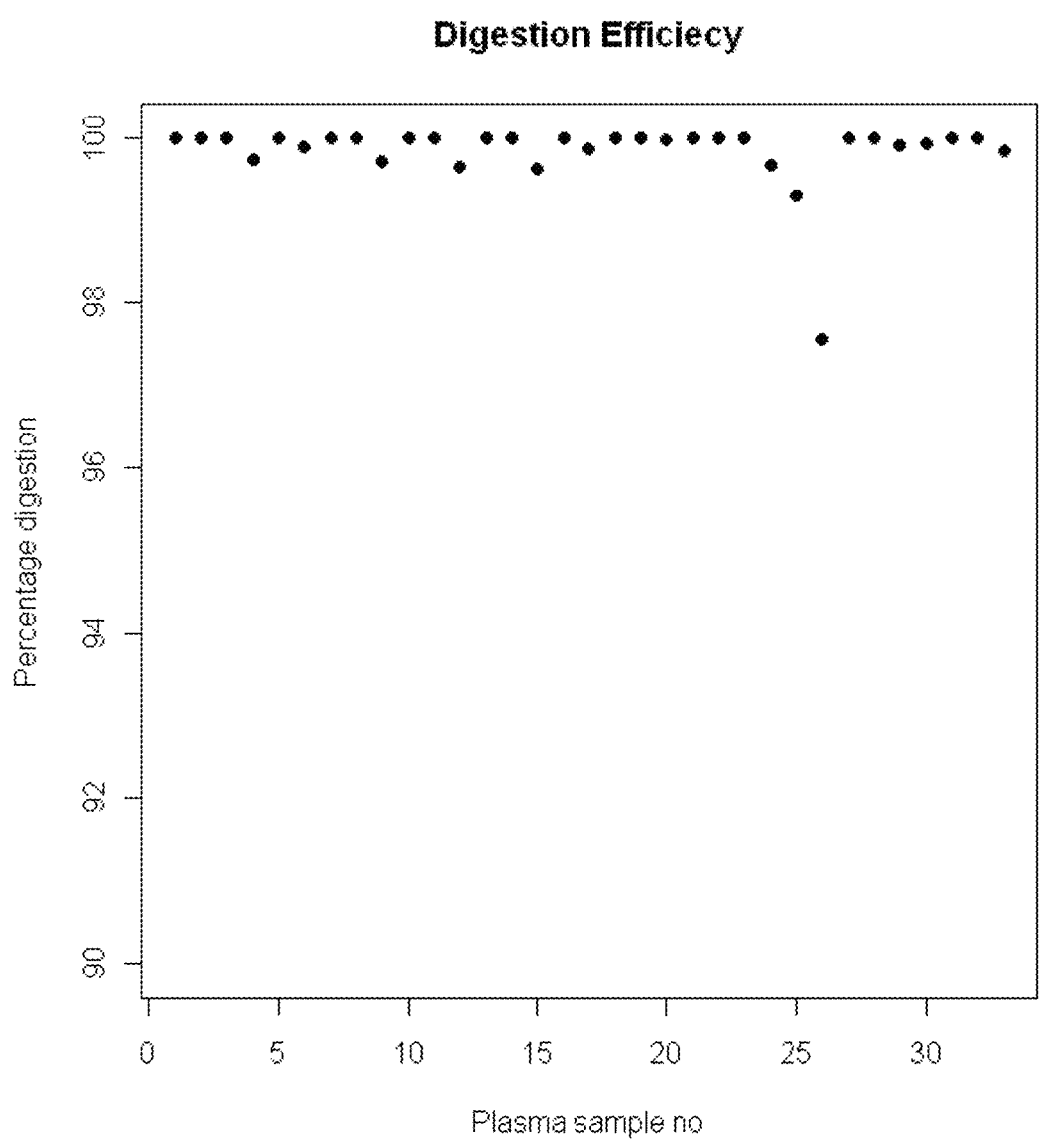
FIG. 17: Shows the digestion efficiency of the restriction enzymes using the ratio of digestion for the control versus the competitor and comparing this value to the mean total copy number assays. Apart from sample 26 all reactions indicate the efficiency to be above about 99%.

Finally, the digestion efficiency was determined by using the ratio of digestion for the control versus the competitor and comparing this value to the mean total copy number assays. See FIG. 17. Apart from sample 26 all reactions indicate the efficiency to be above 99%.

Data Analysis

Mass spectra analysis was done using Typer 4 (a Sequenom software product). The peak height (signal over noise) for each individual DNA analyte and competitor assay was determined and exported for further analysis.

The total number of molecules present for each amplicon was calculated by dividing the DNA specific peak by the competitor specific peak to give a ratio. (The "DNA" Peak in FIGS. 18 and 19 can be thought of as the analyte peak for a given assay). Since the number of competitor molecules added into the reaction is known, the total number of DNA molecules can be determined by multiplying the ratio by the number of added competitor molecules.

The fetal DNA fraction (or concentration) in each sample was calculated using the Y-chromosome-specific markers for male pregnancies and the mean of the methylated fraction for all pregnancies. In brief, for chromosome Y, the ratio was obtained by dividing the analyte (DNA) peak by the competitor peak and multiplying this ratio by the number of competitor molecules added into the reaction. This value was divided by a similar ratio obtained from the total number of amplifiable genome equivalents determination (using the Assay(s) for Total Amount). See FIG. 18. Since the total amount of nucleic acid present in a sample is a sum of maternal and fetal nucleic acid, the fetal contribution can be considered to be a fraction of the larger, background maternal contribution. Therefore, translating this into the equation shown in FIG. 18, the fetal fraction (k) of the total nucleic acid present in the sample is equal to the equation: $k=2\times R/(1-2R)$, where R is the ratio between the Y-chromosome amount and the total amount. Since the Y-chromosome is haploid and Assays for the Total Amount are determined using diploid targets, this calculation is limited to a fetal fraction smaller than 50% of the maternal fraction.

Figure 19:
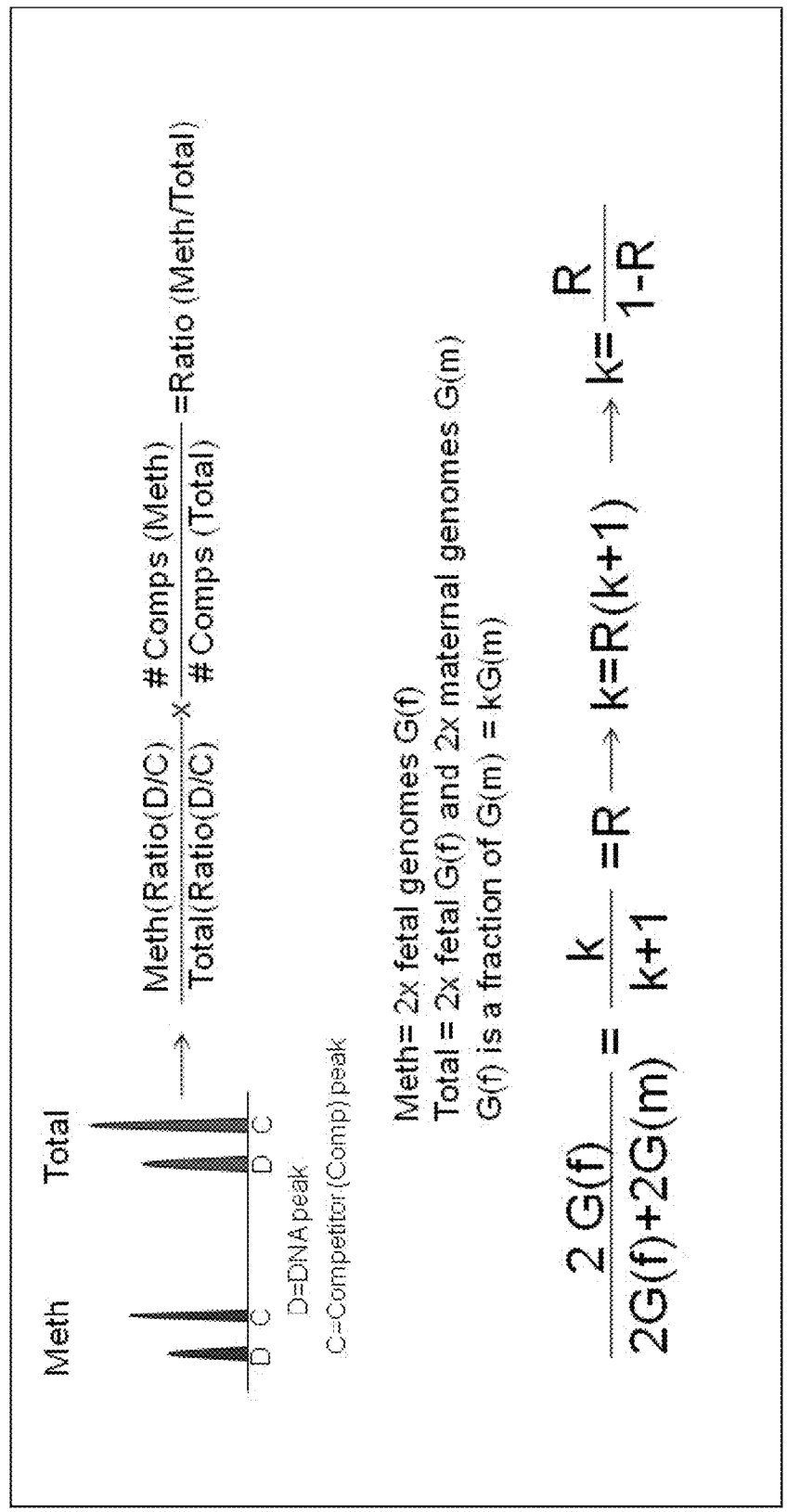
FIG. 19: Provides a specific method for calculating fetal DNA fraction (or concentration) in a sample without the Y-chromosome-specific markers. Instead, only the Assays for Methylation Quantification were used to determine the concentration of fetal DNA.

In FIG. 19, a similar calculation for the fetal concentration is shown by using the methylation specific markers (see Assays for Methylation Quantification). In contrast to Y-chromosome specific markers, these markers are from diploid targets, therefore, the limitations stated for the Y-Chromosome Specific Assay can be omitted. Thus, the fetal fraction (k) can be determined using the equation: $k=R(1-R)$, where R is the ratio between the methylation assay and the total assay.

Simulation

Figure 8:
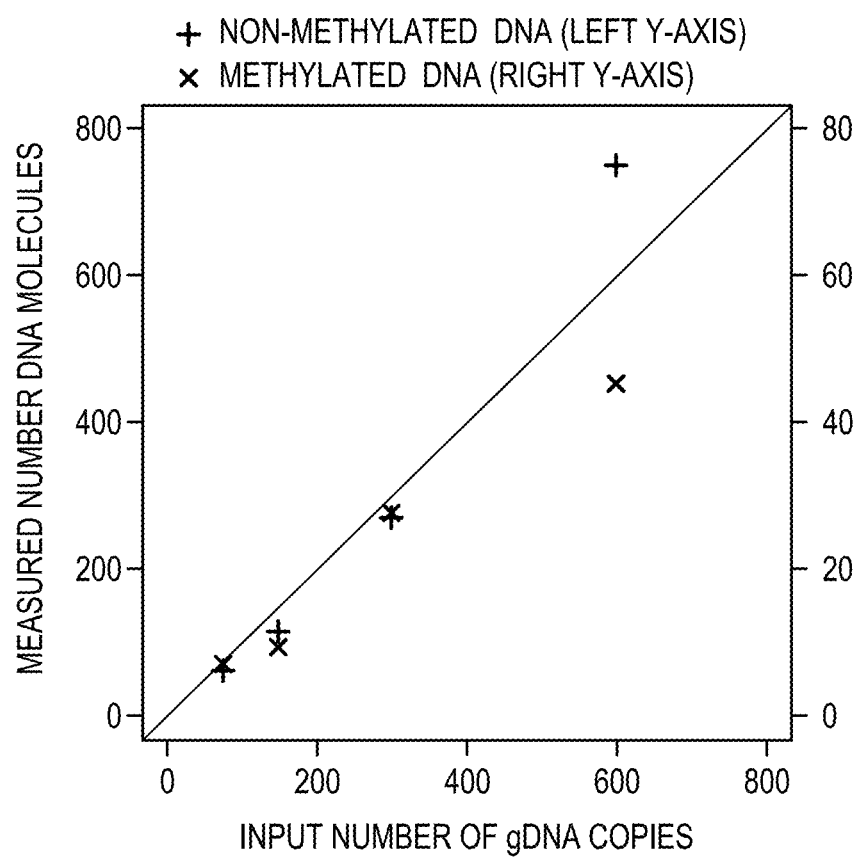
FIG. 8: Shown is the correlation between the number of gDNA molecules that were expected and the number of molecules measured by competitive PCR in combination with mass spectrometry analysis. In this experiment we used DNA derived from whole blood (black plus signs) and commercially available fully methylated DNA (red crosses) in a 90 to 10 ratio. We used the MBD-FC fusion protein to separate the non-methylated and the methylated fraction of DNA. Each fraction was subject to competitive PCR analysis with mass spectrometry readout. The method has been described earlier for the analysis of copy number variations and is commercially available for gene expression analysis. The approach allows absolute quantification of DNA molecules with the help of a synthetic oligonucleotides of know concentration. In this experiment we targeted the MGMT locus, which was not methylated in the whole blood sample used here. Using an input of 300 total gDNA copies we expect to see 270 copies of non-methylated DNA and 30 copies of methylated DNA. The measured copy numbers are largely in agreement with the expected values. The data point at 600 copies of input DNA indicates a bias in the reaction and shows that this initial proof of concept experiment needs to be followed up with more development work, before the assay can be used. However, this initial data indicates the feasibility of the approach for capturing and quantifying of a few copies of methylated DNA in the presence of an excess of unmethylated DNA species.
Figure 9A:
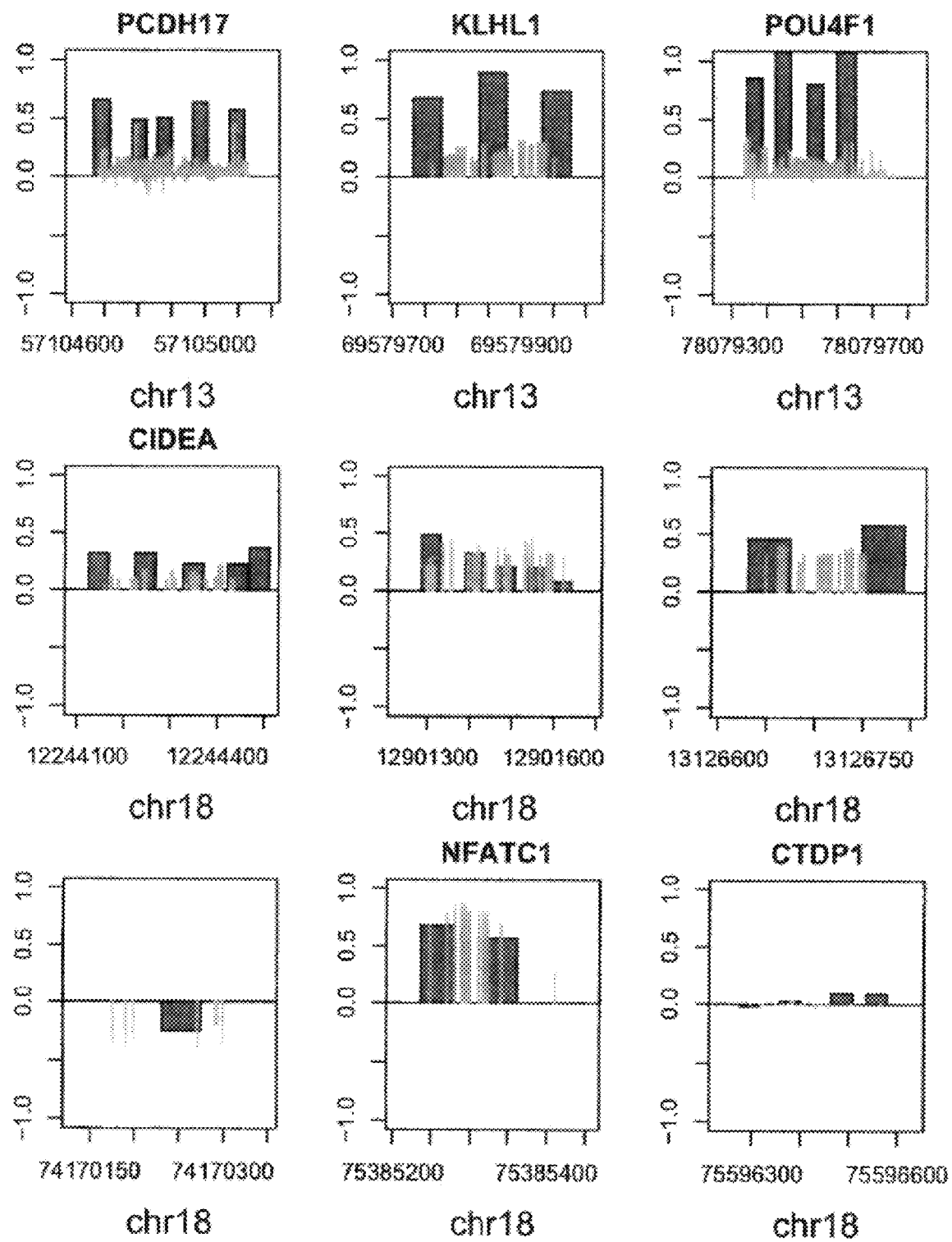
FIG. 9A-9L: Shown are bar graph plots of the methylation differences obtained from the microarray analysis (dark bars) and the mass spectrometry analysis (light grey bars) with respect to their genomic location. For each of the 85 region that were identified to be differentially methylated by microarray an individual plot is provided. The x axis for each plot shows the chromosomal position of the region. The y axis depicts the log ration (in case of the microarrays) and the methylation differences (in case of the mass spectrometry results). For the microarrays each hybridization probe in the area is shown as a single black (or dark grey) bar. For the mass spectrometry results each CpG site, is shown as a light grey bar. Bars showing values greater than zero indicate higher DNA methylation in the placenta samples compared to the maternal DNA. For some genes the differences are small (i.e. RB1 or DSCR6) but still statistically significant. Those regions would be less suitable for a fetal DNA enrichment strategy.
Figure 9B:
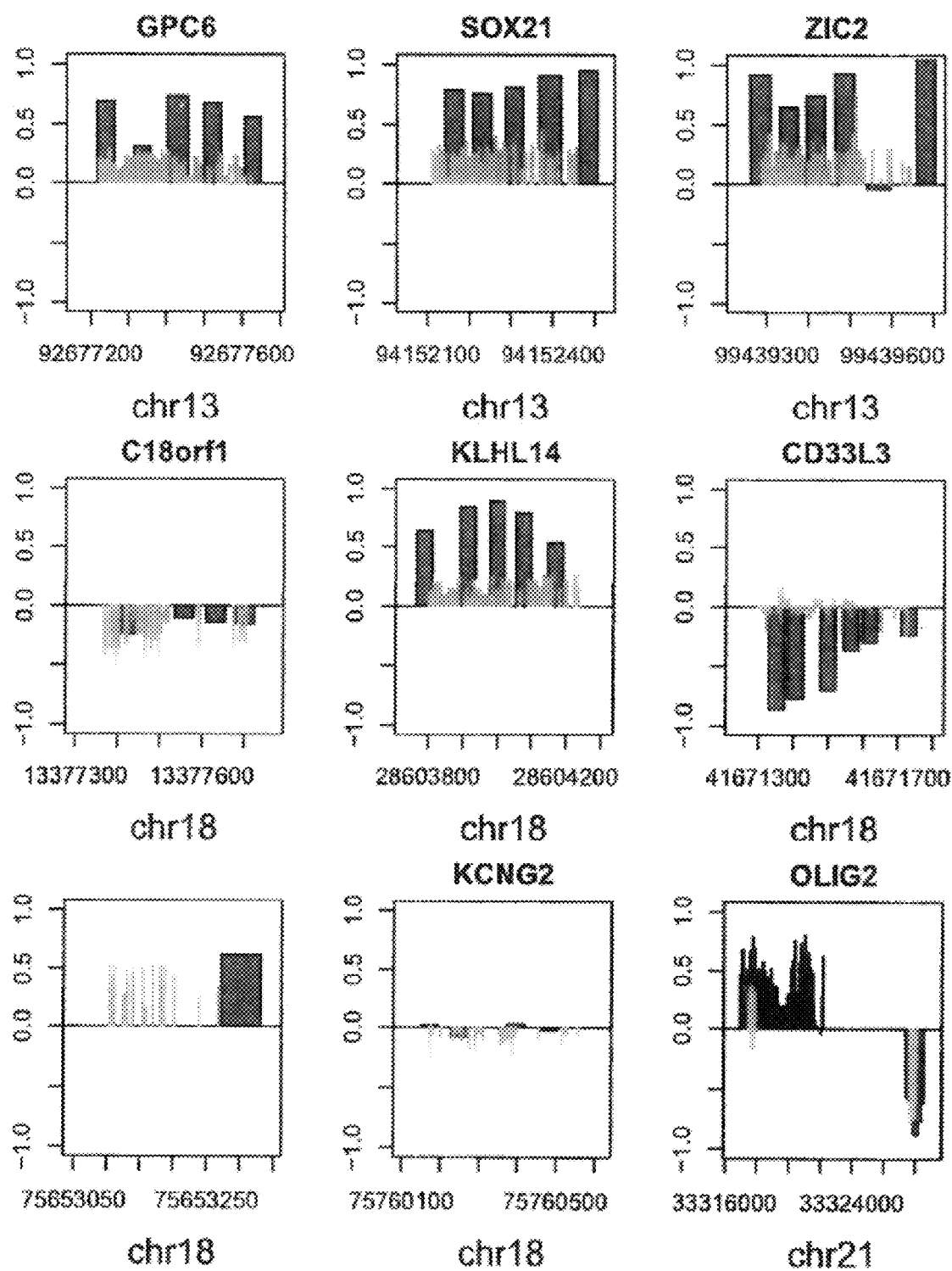
Figure 9C:
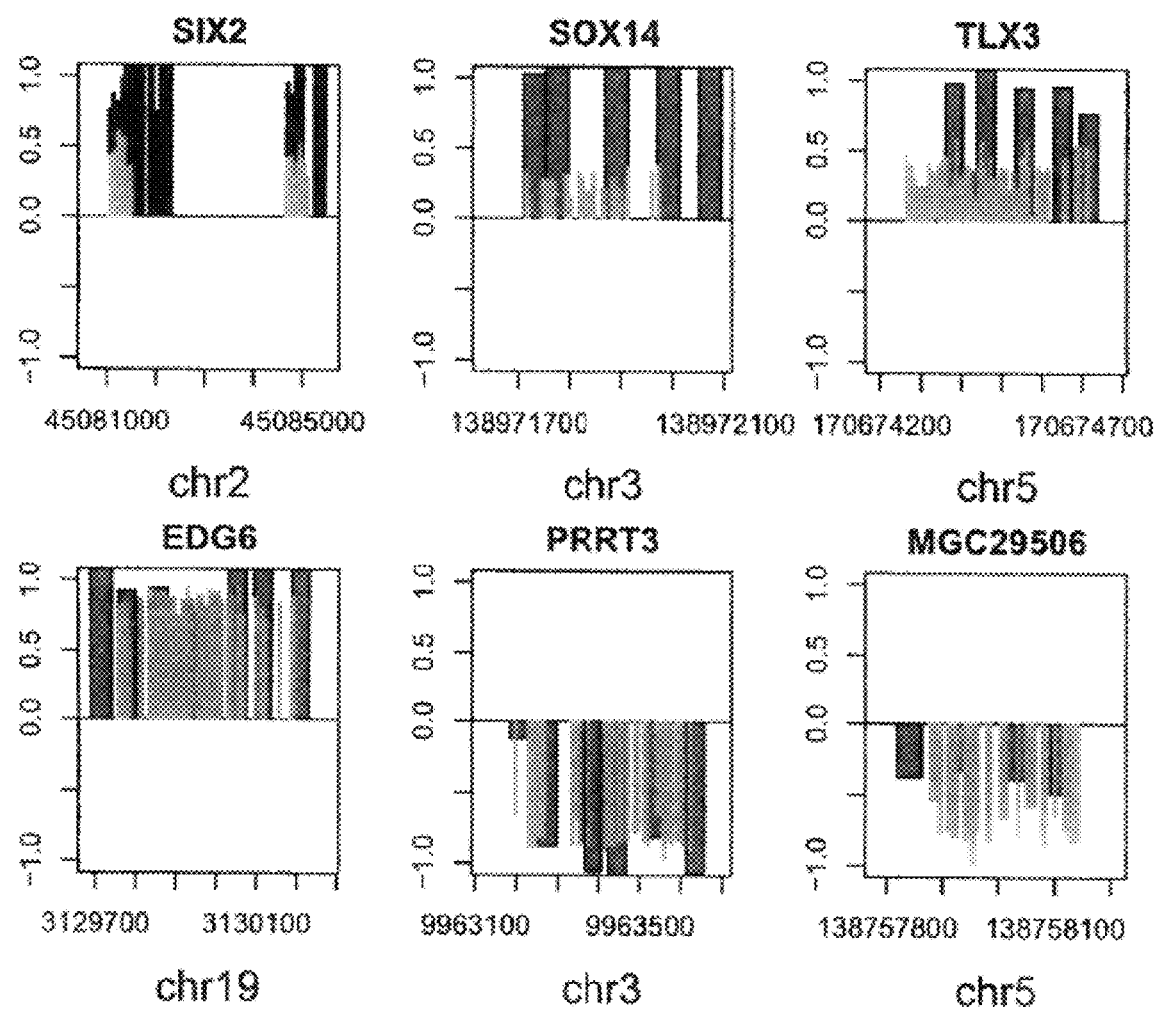
Figure 9D:
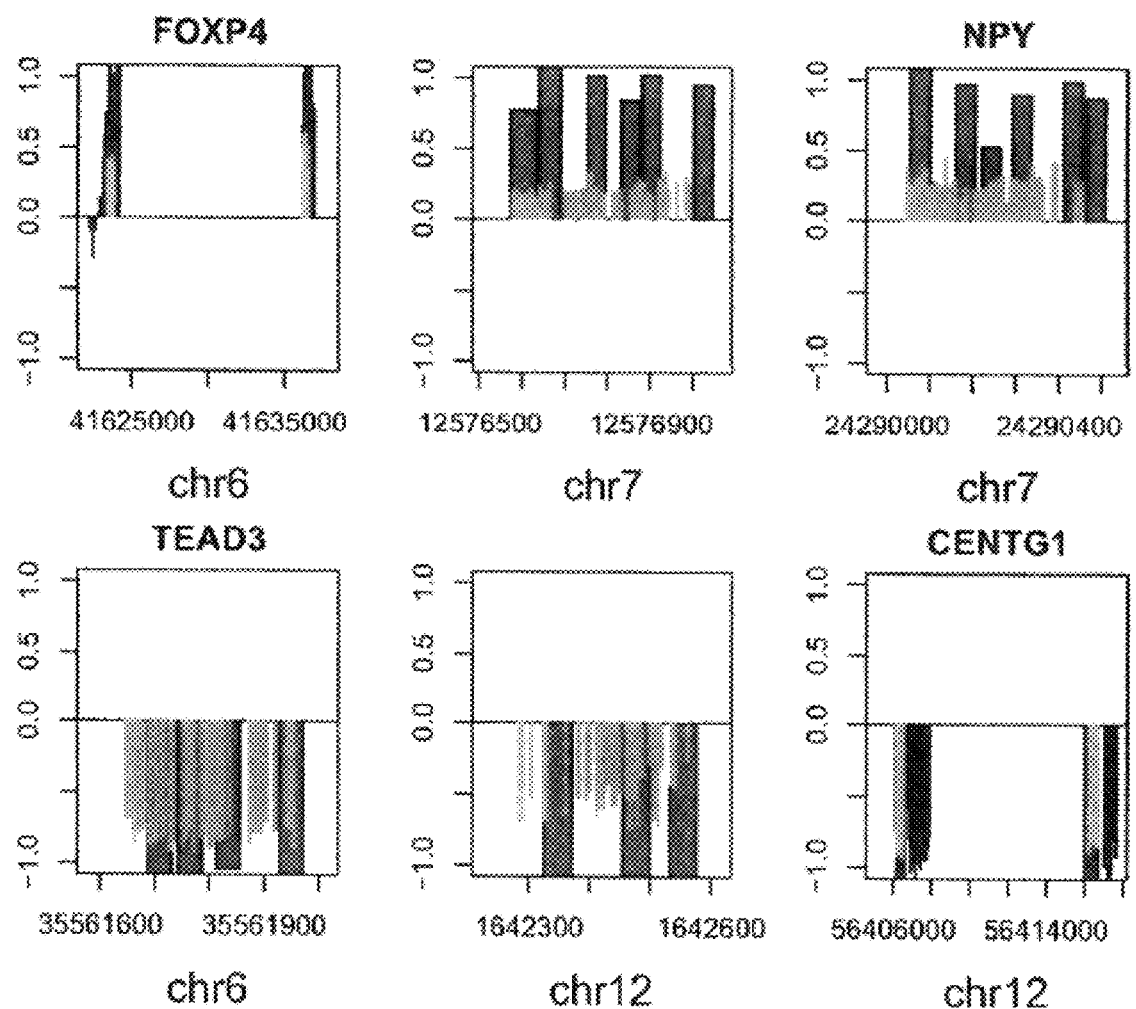
Figure 9E:
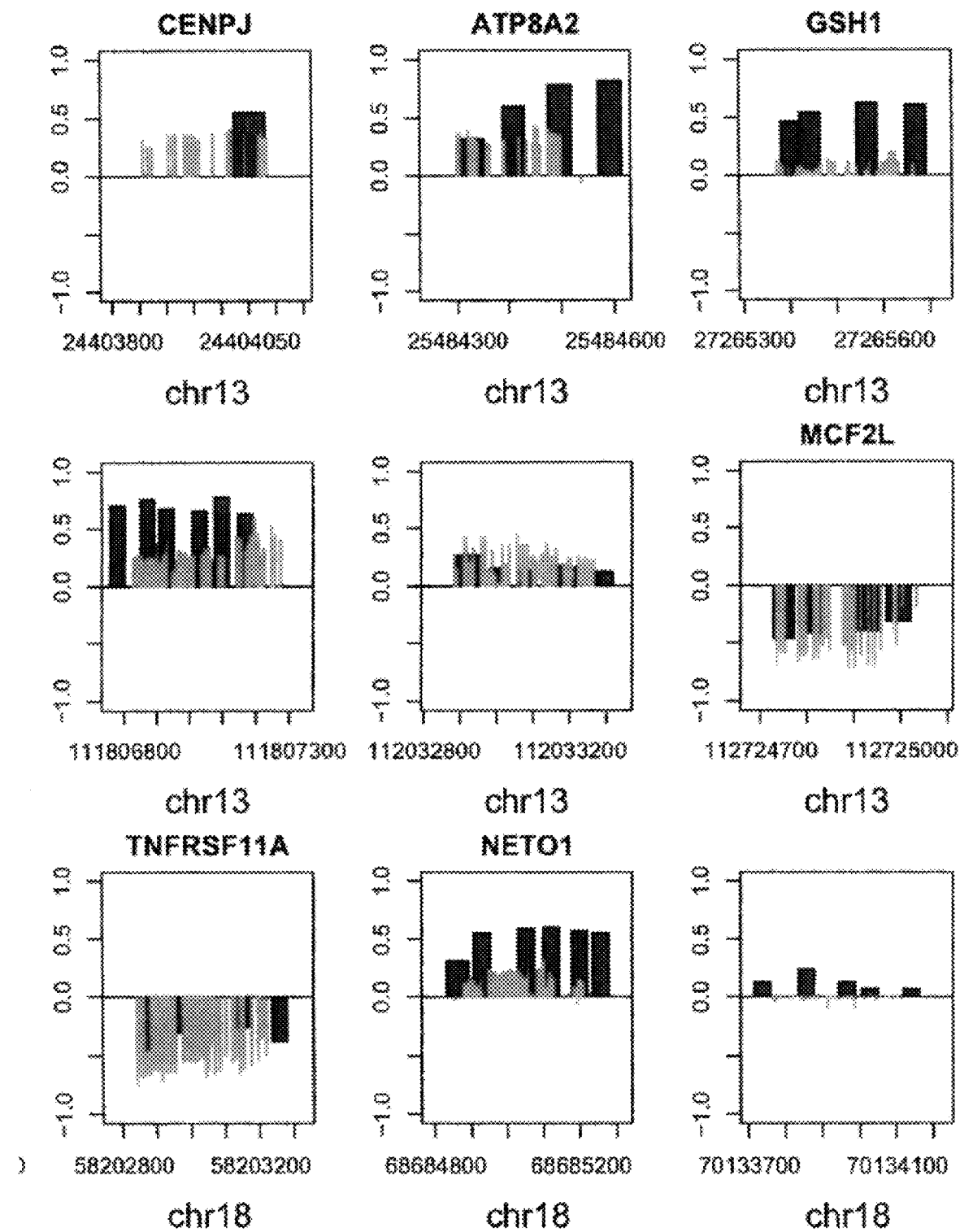
Figure 9F:
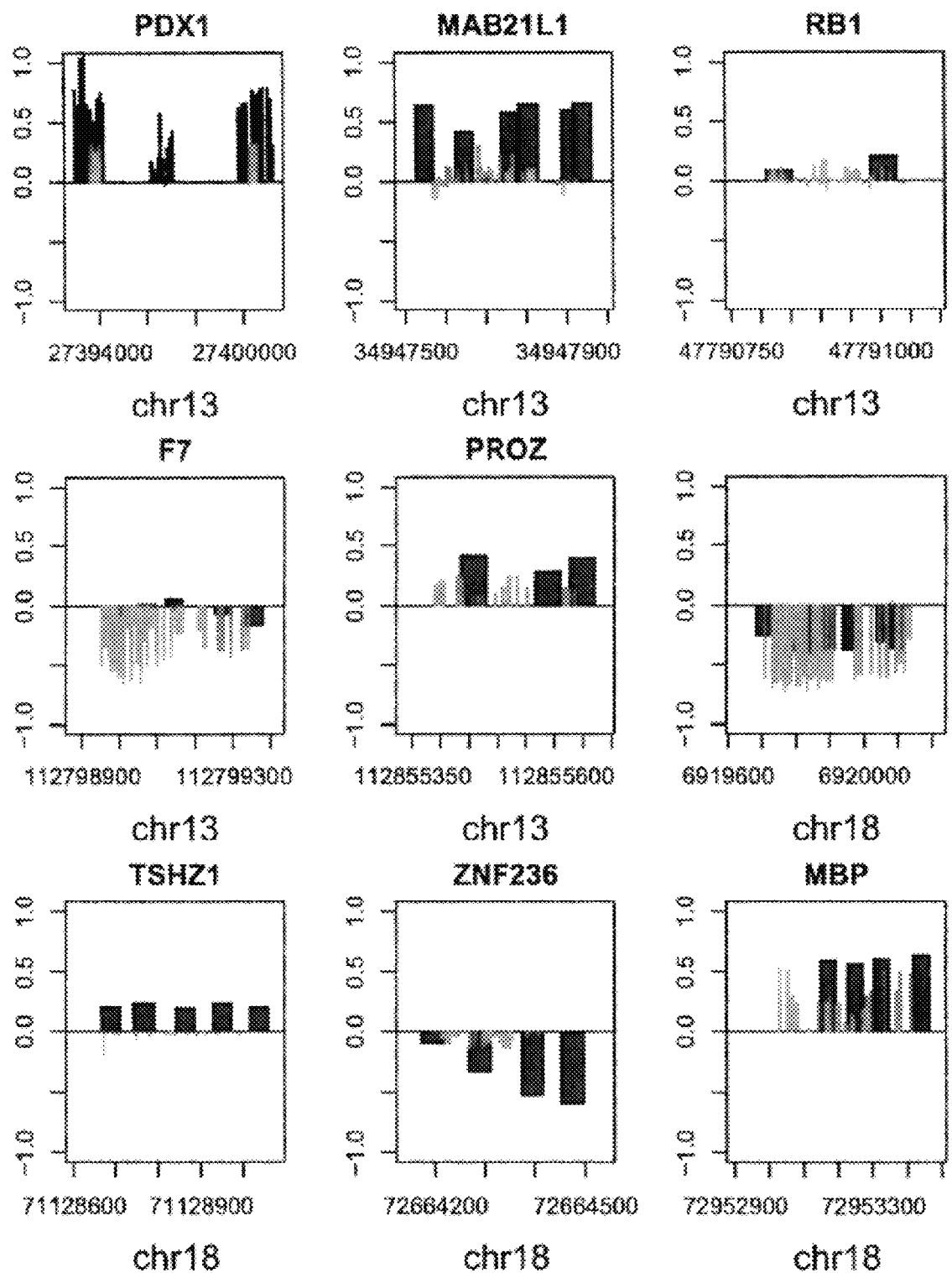
Figure 9G:
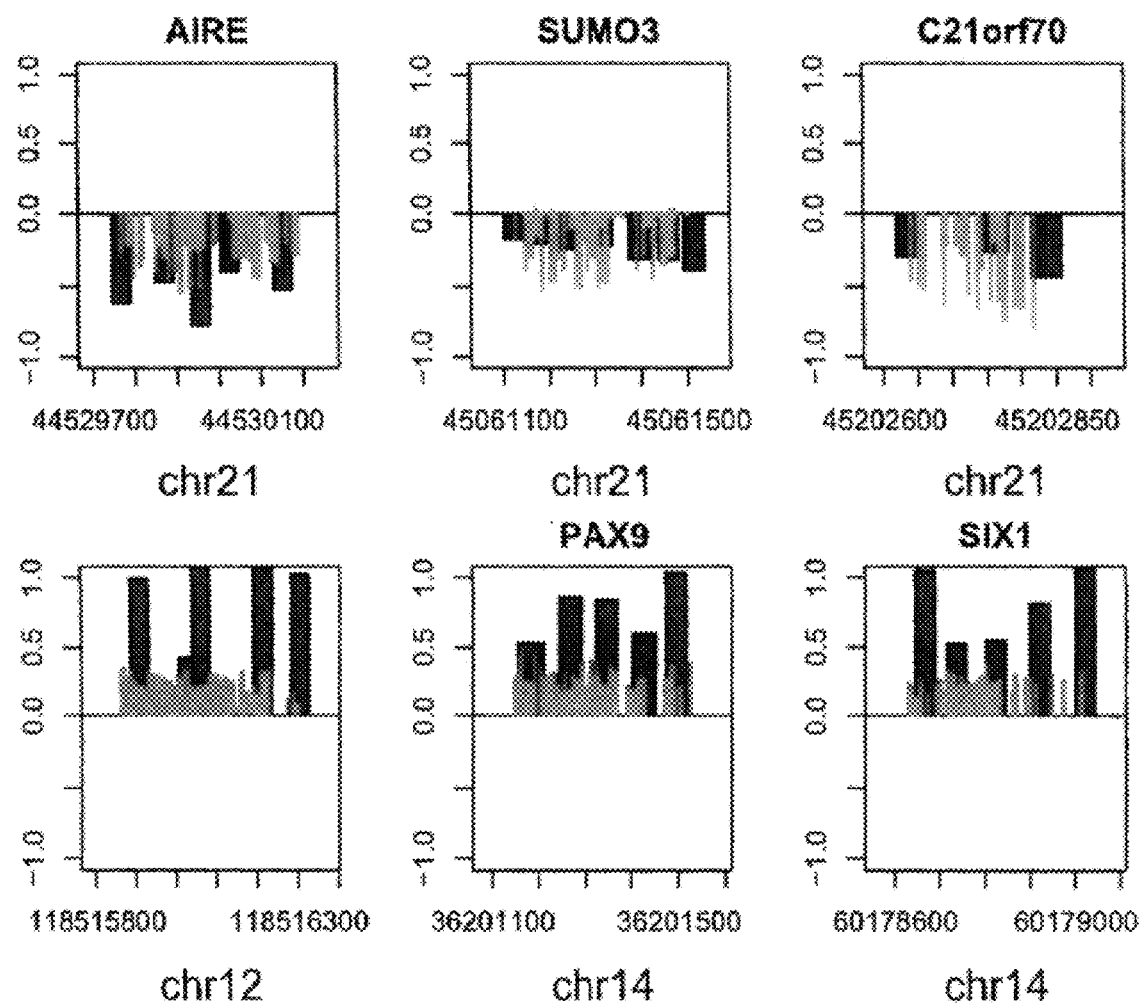
Figure 9H:
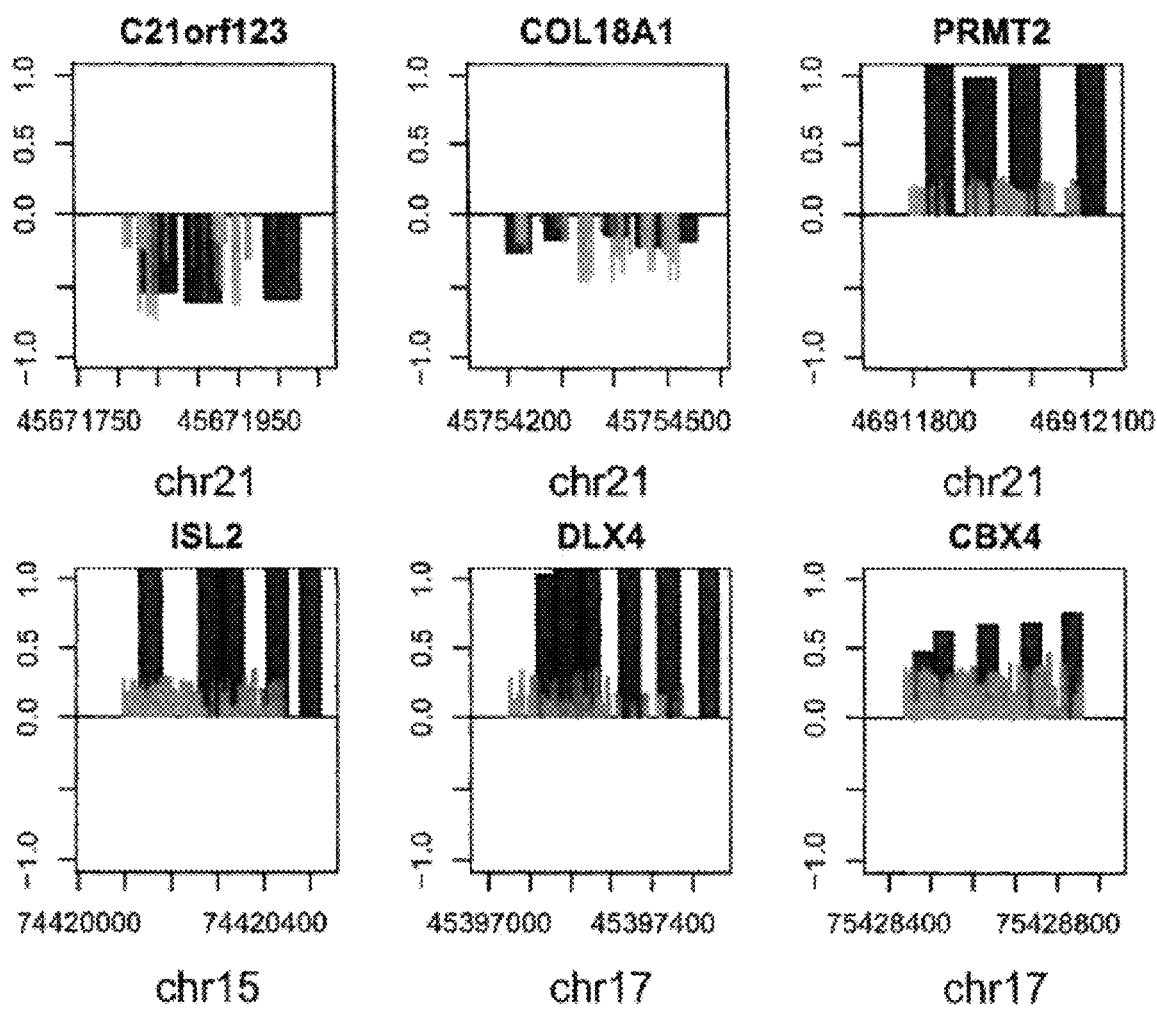
Figure 9I:
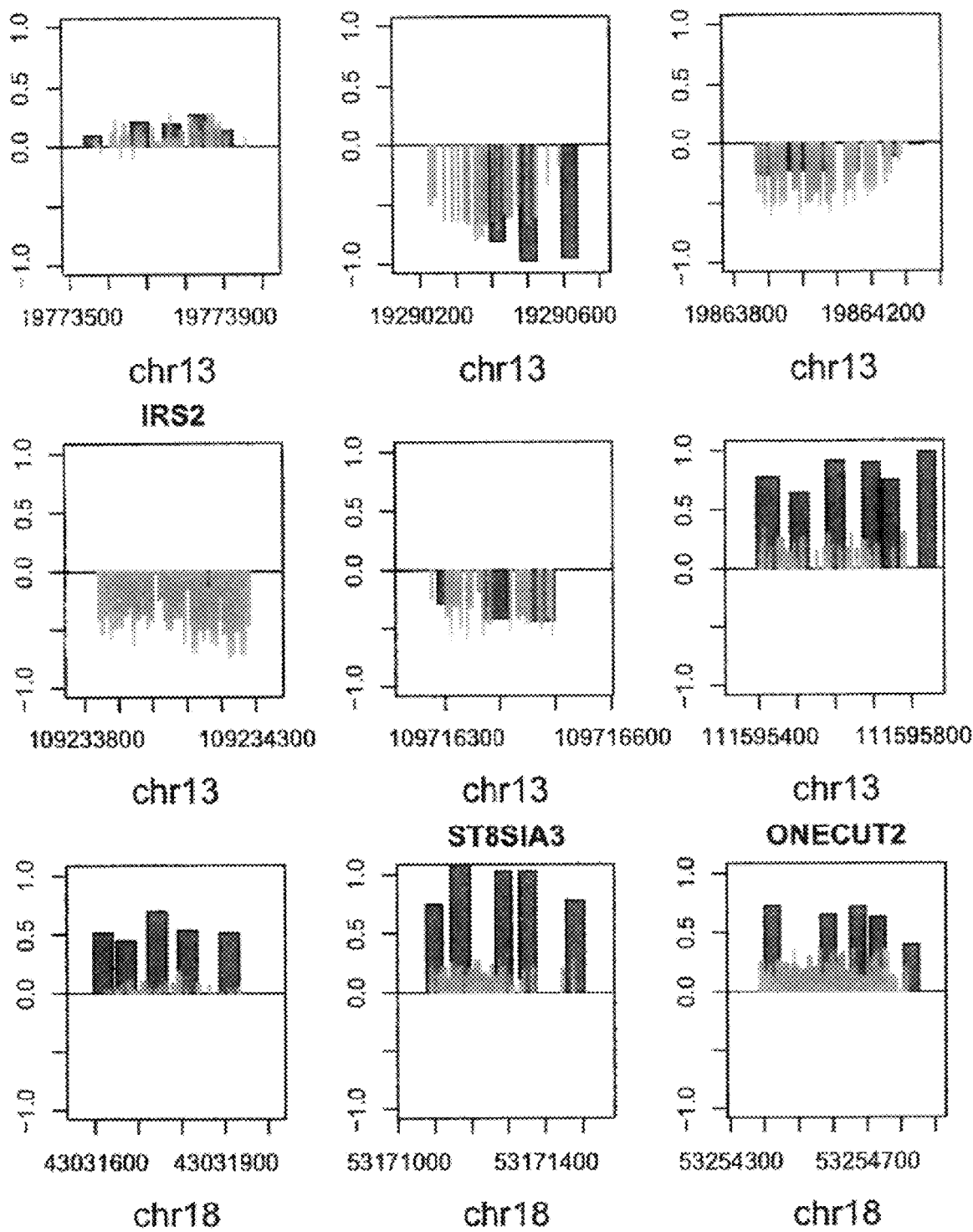
Figure 9J:
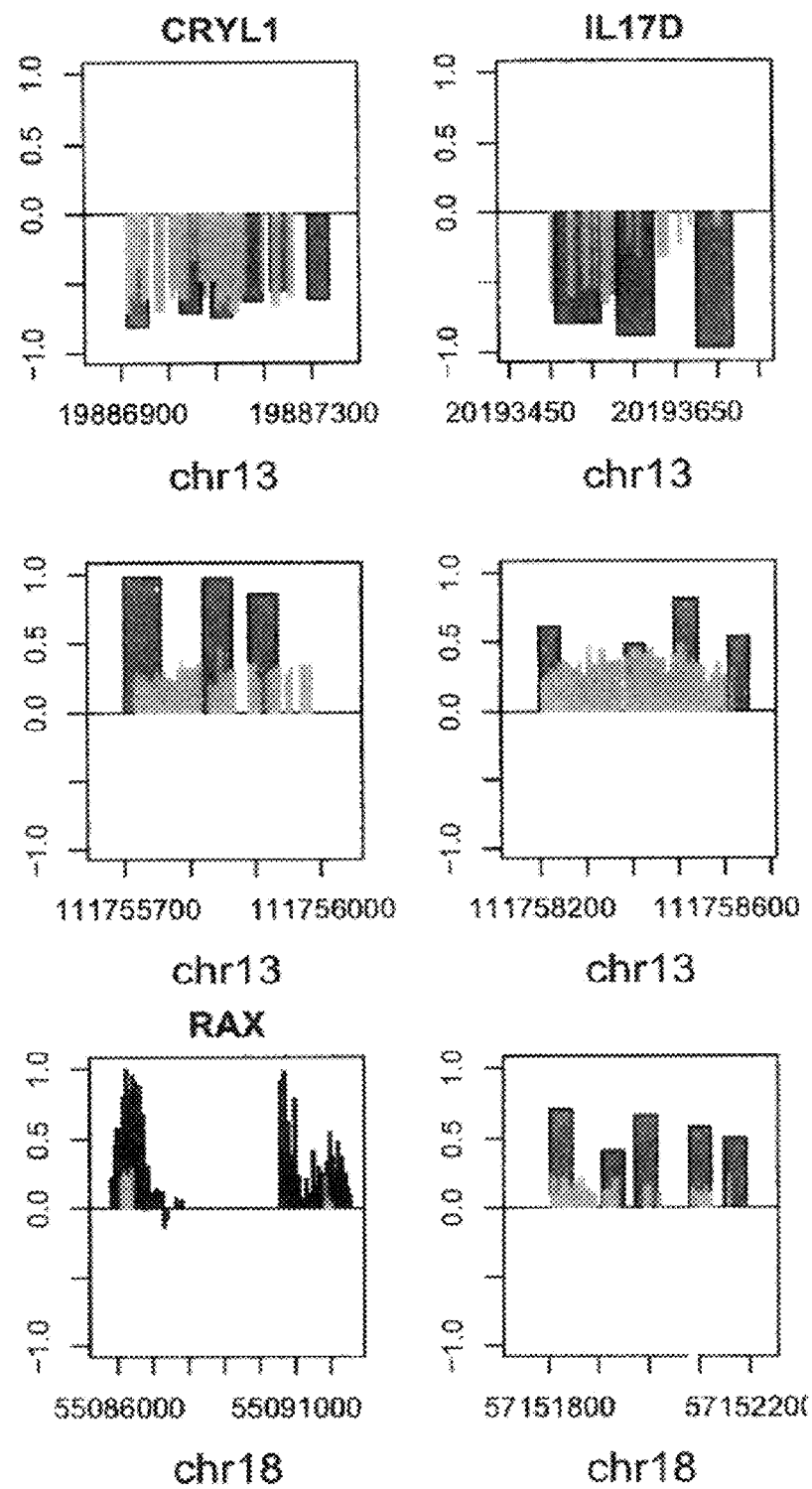
Figure 9K:
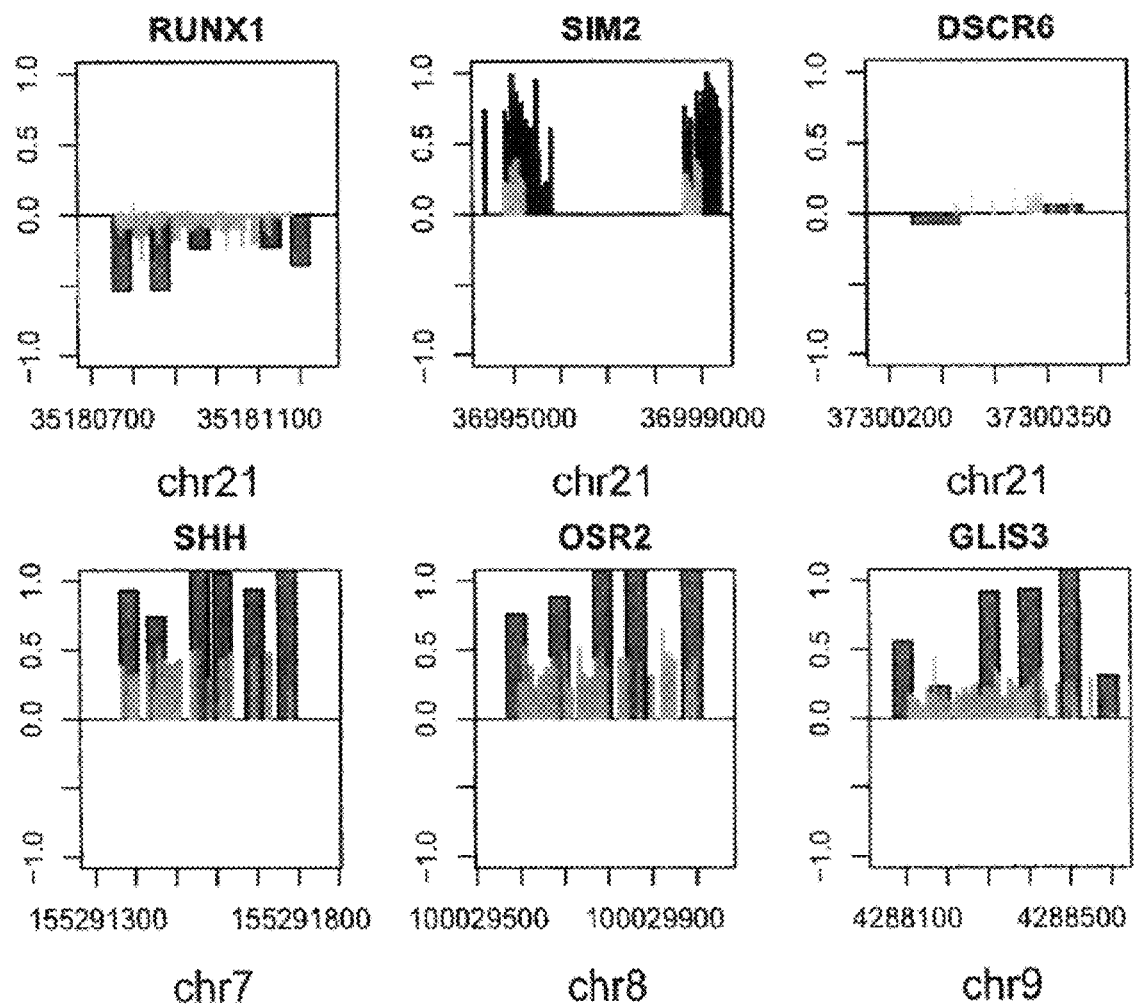
Figure 9L:
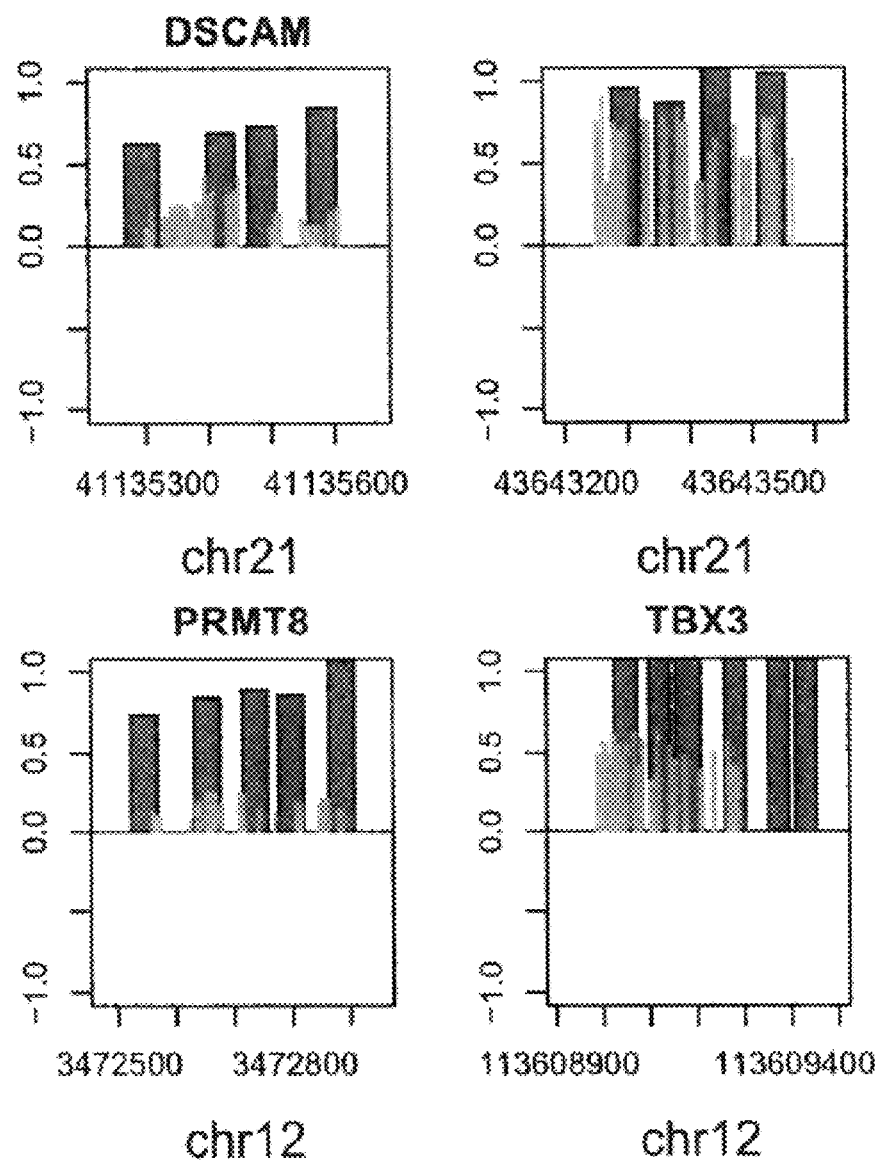

A first simple power calculation was performed that assumes a measurement system that uses 20 markers from chromosome 21, and 20 markers from one or more other autosomes. Starting with 100 copies of fetal DNA, a measurement standard deviation of 25 copies and the probability for a type I error to be lower than 0.001, it was found that the methods of the technology will be able to differentiate a diploid from a triploid chromosome set in 99.5% of all cases. The practical implementation of such an approach could for example be achieved using mass spectrometry, a system that uses a competitive PCR approach for absolute copy number measurements. The method can run 20 assays in a single reaction and has been shown to have a standard deviation in repeated measurements of around 3 to 5%. This method was used in combination with known methods for differentiating methylated and non-methylated nucleic acid, for example, using methyl-binding agents to separate nucleic acid or using methylation-sensitive enzymes to digest maternal nucleic acid. FIG. 8 shows the effectiveness of MBD-FC protein (a methyl-binding agent) for capturing and thereby separating methylated DNA in the presence of an excess of unmethylated DNA (see FIG. 8).

A second statistical power analysis was performed to assess the predictive power of an embodiment of the Methylation-Based Fetal Diagnostic Method described herein. The simulation was designed to demonstrate the likelihood of differentiating a group of trisomic chromosome 21 specific markers from a group of reference markers (for example, autosomes excluding chromosome 21). Many parameters influence the ability to discriminate the two populations of markers reliably. For the present simulation, values were chosen for each parameter that have been shown to be the most likely to occur based on experimentation. The following parameters and respective values were used:

Copy Numbers
  Maternal copy numbers=2000
  Fetal copy numbers for chromosomes other than 21, X and Y=200
  Fetal copy numbers for chromosome 21 in case of euploid fetus=200
  Fetal copy numbers for chromosome 21 in case of aneuploid T21 fetus=300
  Percent fetal DNA (before methylation-based enrichment) =10% (see above)
Methylation Frequency
  Average methylation percentage in a target region for maternal DNA=10%
  Average methylation percentage in a target region for fetal DNA=80%
  Average percentage of non-methylated and non-digested maternal DNA (i.e., a function of restriction efficiency (among other things)=5%
  Number of assays targeting chromosome 21=10
  Number of assays targeting chromosomes other than 21, X and Y=10

Figure 20:
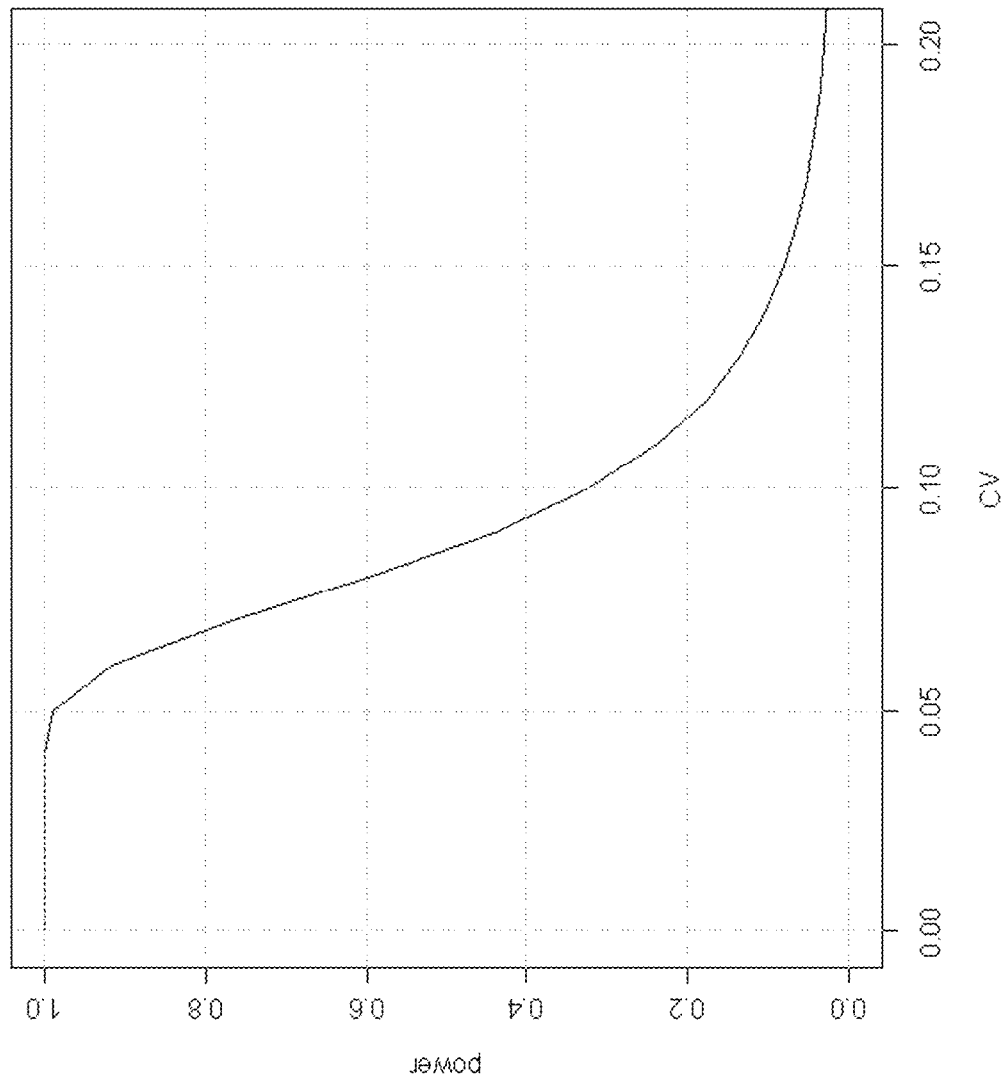
FIG. 20: Shows a power calculation t-test for a simulated trisomy 21 diagnosis using the methods of the technology. The Figure shows the relationship between the coefficient of variation (CV) on the x-axis and the power to discriminate the assay populations using a simple t-test (y-axis). The data indicates that in 99% of all cases, one can discriminate the two population (euploid vs. aneuploid) on a significance level of 0.001 provided a CV of 5% or less.

The results are displayed in FIG. 20. Shown is the relationship between the coefficient of variation (CV) on the x-axis and the power to discriminate the assay populations using a simple t-test (y-axis). The data indicates that in 99% of all cases, one can discriminate the two population (euploid vs. aneuploid) on a significance level of 0.001 provided a CV of 5% or less. Based on this simulation, the method represents a powerful noninvasive diagnostic method for the prenatal detection of fetal aneuploidy that is sex-independent and will work in all ethnicities (i.e., no allelic bias).

TABLE 1

| GENE NAME | CHROM | START | END | CpG ISLAND | MEAN LOG RATIO MICRO-ARRAY | MEAN MATERNAL METHYL-ATION EPITYPER | MEAN PLACENTA METHYL-ATION EPITYPER | METHY-LATION DIFFERENCE PLACENTA-MATERNAL | RELATIVE METHYLATION PLACENTA TO MATERNAL |
|---|---|---|---|---|---|---|---|---|---|
| chr13 group00016 | chr13 | 19773745 | 19774050 | chr13:19773518-19774214 | 0.19 | 0.22 | 0.32 | 0.1 | HYPER-METHYLATION |
| chr13 group00005 | chr13 | 19290394 | 19290768 | :- | −0.89 | 0.94 | 0.35 | −0.59 | HYPO-METHYLATION |
| CRYL1 | chr13 | 19887090 | 19887336 | chr13:19887007-19887836 | −0.63 | 0.74 | 0.21 | −0.53 | HYPO-METHYLATION |
| IL17D | chr13 | 20193675 | 20193897 | chr13:20193611-20194438 | −1.01 | 0.53 | 0.13 | −0.39 | HYPO-METHYLATION |
| CENPJ | chr13 | 24404023 | 24404359 | :- | 0.57 | 0.17 | 0.49 | 0.32 | HYPER-METHYLATION |
| ATP8A2 | chr13 | 25484475 | 25484614 | chr13:25484287-25484761 | 0.81 | 0.16 | 0.43 | 0.27 | HYPER-METHYLATION |
| GSH1 | chr13 | 27265542 | 27265834 | chr13:27264549-27266505 | 0.57 | 0.13 | 0.19 | 0.05 | HYPER-METHYLATION |
| PDX1 | chr13 | 27393789 | 27393979 | chr13:27392001-27394099 | 0.55 | 0.06 | 0.2 | 0.14 | HYPER-METHYLATION |
| PDX1 | chr13 | 27400459 | 27401165 | chr13:27400362-27400744; chr13:27401057-27401374 | 0.73 | 0.12 | 0.26 | 0.14 | HYPER-METHYLATION |
| MAB21L1 | chr13 | 34947737 | 34948062 | chr13:34947570-34948159 | 0.66 | 0.11 | 0.17 | 0.06 | HYPER-METHYLATION |
| RB1 | chr13 | 47790983 | 47791646 | chr13:47790636-47791858 | 0.18 | 0.45 | 0.48 | 0.03 | HYPER-METHYLATION |
| PCDH17 | chr13 | 57104856 | 57106841 | chr13:57104527-57106931 | 0.46 | 0.15 | 0.21 | 0.06 | HYPER-METHYLATION |
| KLHL1 | chr13 | 69579933 | 69580146 | chr13:69579733-69580220 | 0.79 | 0.09 | 0.28 | 0.2 | HYPER-METHYLATION |
| POU4F1 | chr13 | 78079515 | 78081073 | chr13:78079328-78079615; chr13:78080860-78081881 | 0.66 | 0.12 | 0.23 | 0.11 | HYPER-METHYLATION |
| GPC6 | chr13 | 92677402 | 92678666 | chr13:92677246-92678878 | 0.66 | 0.06 | 0.19 | 0.13 | HYPER-METHYLATION |
| SOX21 | chr13 | 94152286 | 94153047 | chr13:94152190-94153185 | 0.94 | 0.16 | 0.4 | 0.25 | HYPER-METHYLATION |
| ZIC2 | chr13 | 99439660 | 99440858 | chr13:99439335-99440189; chr13:99440775-99441095 | 0.89 | 0.13 | 0.35 | 0.22 | HYPER-METHYLATION |
| IRS2 | chr13 | 109232856 | 109235065 | chr13:109232467-109238181 | −0.17 | 0.73 | 0.38 | −0.35 | HYPO-METHYLATION |
| chr13 group00350 | chr13 | 109716455 | 109716604 | chr13:109716325-109716726 | −0.37 | 0.77 | 0.41 | −0.36 | HYPO-METHYLATION |
| chr13 group00385 | chr13 | 111595578 | 111595955 | chr13:111595459-111596131 | 0.87 | 0.06 | 0.2 | 0.14 | HYPER-METHYLATION |
| chr13 group00390 | chr13 | 111756337 | 111756593 | chr13:111755805-111756697 | 0.71 | 0.12 | 0.34 | 0.22 | HYPER-METHYLATION |
| chr13 group00391 | chr13 | 111759856 | 111760045 | chr13:111757885-111760666 | 0.86 | 0.11 | 0.36 | 0.25 | HYPER-METHYLATION |
| chr13 group00395 | chr13 | 111808255 | 111808962 | chr13:111806599-111808492; chr13:111808866-111809114 | 0.96 | 0.13 | 0.35 | 0.22 | HYPER-METHYLATION |
| chr13 group00399 | chr13 | 112033503 | 112033685 | chr13:112032967-112033734 | 0.38 | 0.26 | 0.43 | 0.18 | HYPER-METHYLATION |
| MCF2L | chr13 | 112724910 | 112725742 | chr13:112724782-112725121; chr13:112725628-112725837 | −0.47 | 0.91 | 0.33 | −0.58 | HYPO-METHYLATION |
| F7 | chr13 | 112799123 | 112799379 | chr13:112798487-112799566 | −0.05 | 0.97 | 0.55 | −0.41 | HYPO-METHYLATION |
| PROZ | chr13 | 112855566 | 112855745 | chr13:112855289-112855866 | 0.29 | 0.15 | 0.3 | 0.16 | HYPER-METHYLATION |
| chr18 group00039 | chr18 | 6919797 | 6919981 | chr18:6919450-6920088 | −0.38 | 0.88 | 0.39 | −0.49 | HYPO-METHYLATION |
| CIDEA | chr18 | 12244327 | 12244696 | chr18:12244147-12245089 | 0.23 | 0.14 | 0.23 | 0.1 | HYPER-METHYLATION |
| chr18 group00091 | chr18 | 12901467 | 12901643 | chr18:12901024-12902704 | 0.16 | 0.15 | 0.43 | 0.29 | HYPER-METHYLATION |
| chr18 group00094 | chr18 | 13126819 | 13126986 | chr18:13126596-13127564 | 0.41 | 0.07 | 0.34 | 0.27 | HYPER-METHYLATION |
| C18orf1 | chr18 | 13377536 | 13377654 | chr18:13377385-13377686 | −0.12 | 0.95 | 0.69 | −0.26 | HYPO-METHYLATION |

TABLE 1-continued

| GENE NAME | CHROM | START | END | CpG ISLAND | MEAN LOG RATIO MICRO-ARRAY | MEAN MATERNAL METHYL-ATION EPITYPER | MEAN PLACENTA METHYL-ATION EPITYPER | METHY-LATION DIFFERENCE PLACENTA-MATERNAL | RELATIVE METHYLATION PLACENTA TO MATERNAL |
|---|---|---|---|---|---|---|---|---|---|
| KLHL14 | chr18 | 28603978 | 28605183 | chr18:28603688-28606300 | 0.83 | 0.07 | 0.19 | 0.12 | HYPER-METHYLATION |
| CD33L3 | chr18 | 41671477 | 41673011 | chr18:41671386-41673101 | −0.34 | 0.49 | 0.44 | −0.05 | HYPO-METHYLATION |
| ST8SIA3 | chr18 | 53171265 | 53171309 | chr18:53170705-53172603 | 1.02 | 0.09 | 0.25 | 0.16 | HYPER-METHYLATION |
| ONECUT2 | chr18 | 53254808 | 53259810 | chr18:53254152-53259851 | 0.74 | 0.09 | 0.23 | 0.14 | HYPER-METHYLATION |
| RAX | chr18 | 55086286 | 55086436 | chr18:55085813-55087807 | 0.88 | 0.11 | 0.26 | 0.16 | HYPER-METHYLATION |
| chr18 group00277 | chr18 | 57151972 | 57152311 | chr18:57151663-57152672 | 0.58 | 0.08 | 0.21 | 0.13 | HYPER-METHYLATION |
| TNFRSF11A | chr18 | 58203013 | 58203282 | chr18:58202849-58203367 | −0.33 | 0.88 | 0.28 | −0.6 | HYPO-METHYLATION |
| NETO1 | chr18 | 68685099 | 68687060 | chr18:68684945-68687851 | 0.65 | 0.09 | 0.22 | 0.13 | HYPER-METHYLATION |
| chr18 group00304 | chr18 | 70133945 | 70134397 | chr18:70133732-70134724 | 0.12 | 0.93 | 0.92 | −0.01 | NOT CONFIRMED |
| TSHZ1 | chr18 | 71128742 | 71128974 | chr18:71128638-71129076 | 0.23 | 0.95 | 0.92 | −0.03 | NOT CONFIRMED |
| ZNF236 | chr18 | 72664454 | 72664736 | chr18:72662797-72664893 | −0.62 | 0.17 | 0.1 | −0.07 | HYPO-METHYLATION |
| MBP | chr18 | 72953150 | 72953464 | chr18:72953137-72953402 | 0.6 | 0.44 | 0.72 | 0.28 | HYPER-METHYLATION |
| chr18 group00342 | chr18 | 74170347 | 74170489 | chr18:74170210-74170687 | −0.2 | 0.78 | 0.48 | −0.3 | HYPO-METHYLATION |
| NFATC1 | chr18 | 75385424 | 75386008 | chr18:75385279-75386532 | 0.23 | 0.14 | 0.84 | 0.7 | HYPER-METHYLATION |
| CTDP1 | chr18 | 75596358 | 75596579 | chr18:75596009-75596899 | 0.07 | 0.97 | 0.96 | −0.01 | NOT CONFIRMED |
| chr18 group00430 | chr18 | 75653272 | 75653621 | :- | 0.52 | 0.24 | 0.62 | 0.39 | HYPER-METHYLATION |
| KCNG2 | chr18 | 75760343 | 75760820 | chr18:75759900-75760988 | 0.01 | 0.84 | 0.75 | −0.09 | NOT CONFIRMED |
| OLIG2 | chr21 | 33317673 | 33321183 | chr21:33316998-33322115 | 0.66 | 0.11 | 0.2 | 0.09 | HYPER-METHYLATION |
| OLIG2 | chr21 | 33327593 | 33328334 | chr21:33327447-33328408 | −0.75 | 0.77 | 0.28 | −0.49 | HYPO-METHYLATION |
| RUNX1 | chr21 | 35180938 | 35185436 | chr21:35180822-35181342; chr21:35182320-35185557 | −0.68 | 0.14 | 0.07 | −0.07 | HYPO-METHYLATION |
| SIM2 | chr21 | 36994965 | 36995298 | chr21:36990063-36995761 | 0.83 | 0.08 | 0.26 | 0.18 | HYPER-METHYLATION |
| SIM2 | chr21 | 36999025 | 36999410 | chr21:36998632-36999555 | 0.87 | 0.06 | 0.24 | 0.18 | HYPER-METHYLATION |
| DSCR6 | chr21 | 37300407 | 37300512 | chr21:37299807-37301307 | 0.22 | 0.04 | 0.14 | 0.11 | HYPER-METHYLATION |
| DSCAM | chr21 | 41135559 | 41135706 | chr21:41135380-41135816 | 1.03 | 0.06 | 0.29 | 0.23 | HYPER-METHYLATION |
| chr21 group00165 | chr21 | 43643421 | 43643786 | chr21:43643322-43643874 | 1.14 | 0.16 | 0.81 | 0.65 | HYPER-METHYLATION |
| AIRE | chr21 | 44529935 | 44530388 | chr21:44529856-44530472 | −0.55 | 0.62 | 0.27 | −0.35 | HYPO-METHYLATION |
| SUMO3 | chr21 | 45061293 | 45061853 | chr21:45061154-45063386 | −0.41 | 0.55 | 0.46 | −0.09 | HYPO-METHYLATION |
| C21orf70 | chr21 | 45202815 | 45202972 | chr21:45202706-45203073 | −0.46 | 0.96 | 0.51 | −0.46 | HYPO-METHYLATION |
| C21orf123 | chr21 | 45671984 | 45672098 | chr21:45671933-45672201 | −0.63 | 0.92 | 0.43 | −0.49 | HYPO-METHYLATION |
| COL18A1 | chr21 | 45754383 | 45754487 | chr21:45753653-45754639 | −0.18 | 0.97 | 0.72 | −0.25 | HYPO-METHYLATION |
| PRMT2 | chr21 | 46911967 | 46912385 | chr21:46911628-46912534 | 1.08 | 0.04 | 0.25 | 0.21 | HYPER-METHYLATION |
| SIX2 | chr2 | 45081223 | 45082129 | chr2:45081148-45082287 | 1.15 | 0.08 | 0.36 | 0.28 | HYPER-METHYLATION |
| SIX2 | chr2 | 45084851 | 45085711 | chr2:45084715-45084986; chr2:45085285-45086054 | 1.21 | 0.07 | 0.35 | 0.28 | HYPER-METHYLATION |
| SOX14 | chr3 | 138971870 | 138972322 | chr3:138971738-138972096; chr3:138972281-138973691 | 1.35 | 0.08 | 0.33 | 0.25 | HYPER-METHYLATION |

TABLE 1-continued

| GENE NAME | CHROM | START | END | CpG ISLAND | MEAN LOG RATIO MICRO-ARRAY | MEAN MATERNAL METHYL-ATION EPITYPER | MEAN PLACENTA METHYL-ATION EPITYPER | METHY-LATION DIFFERENCE PLACENTA-MATERNAL | RELATIVE METHYLATION PLACENTA TO MATERNAL |
|---|---|---|---|---|---|---|---|---|---|
| TLX3 | chr5 | 170674439 | 170676431 | chr5:170674208-170675356; chr5:170675783-170676712 | 0.91 | 0.11 | 0.35 | 0.24 | HYPER-METHYLATION |
| FOXP4 | chr6 | 41623666 | 41624114 | chr6:41621630-41624167 | 1.1 | 0.07 | 0.27 | 0.2 | HYPER-METHYLATION |
| FOXP4 | chr6 | 41636384 | 41636779 | chr6:41636244-41636878 | 1.32 | 0.04 | 0.33 | 0.29 | HYPER-METHYLATION |
| chr7 group00267 | chr7 | 12576755 | 12577246 | chr7:12576690-12577359 | 0.94 | 0.08 | 0.26 | 0.17 | HYPER-METHYLATION |
| NPY | chr7 | 24290224 | 24291508 | chr7:24290083-24291605 | 0.93 | 0.09 | 0.3 | 0.21 | HYPER-METHYLATION |
| SHH | chr7 | 155291537 | 155292091 | chr7:155288453-155292175 | 0.98 | 0.19 | 0.52 | 0.33 | HYPER-METHYLATION |
| OSR2 | chr8 | 100029764 | 100030536 | chr8:100029673-100030614 | 1.21 | 0.08 | 0.43 | 0.35 | HYPER-METHYLATION |
| GLIS3 | chr9 | 4288283 | 4289645 | chr9:4287817-4290182 | 1.24 | 0.06 | 0.24 | 0.18 | HYPER-METHYLATION |
| PRMT8 | chr12 | 3472714 | 3473190 | chr12:3470227-3473269 | 0.86 | 0.07 | 0.23 | 0.16 | HYPER-METHYLATION |
| TBX3 | chr12 | 113609153 | 113609453 | chr12:113609112-113609535 | 1.45 | 0.09 | 0.56 | 0.48 | HYPER-METHYLATION |
| chr12 group00801 | chr12 | 118516189 | 118517435 | chr12:118515877-118517595 | 1.1 | 0.06 | 0.25 | 0.19 | HYPER-METHYLATION |
| PAX9 | chr14 | 36201402 | 36202386 | chr14:36200932-36202536 | 0.89 | 0.11 | 0.32 | 0.21 | HYPER-METHYLATION |
| SIX1 | chr14 | 60178801 | 60179346 | chr14:60178707-60179539 | 0.95 | 0.1 | 0.33 | 0.22 | HYPER-METHYLATION |
| ISL2 | chr15 | 74420013 | 74421546 | chr15:74419317-74422570 | 1.08 | 0.08 | 0.27 | 0.19 | HYPER-METHYLATION |
| DLX4 | chr17 | 45397228 | 45397930 | chr17:45396281-45398063 | 1.25 | 0.1 | 0.32 | 0.22 | HYPER-METHYLATION |
| CBX4 | chr17 | 75428613 | 75431793 | chr17:75427586-75433676 | 1 | 0.07 | 0.27 | 0.21 | HYPER-METHYLATION |
| EDG6 | chr19 | 3129836 | 3130874 | chr19:3129741-3130986 | 1.35 | 0.04 | 0.87 | 0.83 | HYPER-METHYLATION |
| PRRT3 | chr3 | 9963364 | 9964023 | chr3:9962895-9964619 | −0.85 | 0.9 | 0.09 | −0.81 | HYPO-METHYLATION |
| MGC29506 | chr5 | 138757911 | 138758724 | chr5:138755609-138758810 | −0.63 | 0.93 | 0.17 | −0.76 | HYPO-METHYLATION |
| TEAD3 | chr6 | 35561812 | 35562252 | chr6:35561754-35562413 | −1.17 | 0.92 | 0.13 | −0.8 | HYPO-METHYLATION |
| chr12 group00022 | chr12 | 1642456 | 1642708 | chr12:1642195-1642774 | −1.33 | 0.66 | 0.09 | −0.57 | HYPO-METHYLATION |
| CENTG1 | chr12 | 56406249 | 56407788 | chr12:56406176-56407818 | −1.07 | 0.95 | 0.19 | −0.77 | HYPO-METHYLATION |
| CENTG1 | chr12 | 56416146 | 56418794 | chr12:56416095-56416628; chr12:56418745-56419001 | −0.94 | 0.85 | 0.16 | −0.69 | HYPO-METHYLATION |

Information based on the March 2006 human reference sequence (NCBI Build 36.1), which was produced by the International Human Genome Sequencing Consortium.

TABLE 2

| GENE NAME | CHROM | START | END | SNPs |
|---|---|---|---|---|
| chr13 group00016 | chr13 | 19773745 | 19774050 | rs7996310; rs12870878 |
| chr13 group00005 | chr13 | 19290394 | 19290768 | rs11304938 |
| CENPJ | chr13 | 24404023 | 24404359 | rs7326661 |
| ATP8A2 | chr13 | 25484475 | 25484614 | rs61947088 |
| PDX1 | chr13 | 27400459 | 27401165 | rs58173592; rs55836809; rs61944011 |
| RB1 | chr13 | 47790983 | 47791646 | rs2804094; rs4151432; rs4151433; rs4151434; rs4151435 |
| PCDH17 | chr13 | 57104856 | 57106841 | rs35287822; rs34642962; rs41292834; rs45500496; rs45571031; rs41292836; rs28374395; rs41292838 |
| KLHL1 | chr13 | 69579933 | 69580146 | rs3751429 |
| POU4F1 | chr13 | 78079515 | 78081073 | rs11620410; rs35794447; rs2765065 |
| GPC6 | chr13 | 92677402 | 92678666 | rs35689696; rs11839555; rs55695812; rs35259892 |
| SOX21 | chr13 | 94152286 | 94153047 | rs41277652; rs41277654; rs35276096; rs5805873; rs35109406 |
| ZIC2 | chr13 | 99439660 | 99440858 | rs9585309; rs35501321; rs9585310; rs7991728; rs1368511 |

TABLE 2-continued

| GENE NAME | CHROM | START | END | SNPs |
|---|---|---|---|---|
| IRS2 | chr13 | 109232856 | 109235065 | rs61747993; rs1805097; rs9583424; rs35927012; rs1056077; rs1056078; rs34889228; rs1056080; rs1056081; rs12853546; rs4773092; rs35223808; rs35894564; rs3742210; rs34412495; rs61962699; rs45545638; rs61743905 |
| chr13 group00395 | chr13 | 111808255 | 111808962 | rs930346 |
| MCF2L | chr13 | 112724910 | 112725742 | rs35661110; rs2993304; rs1320519; rs7320418; rs58416100 |
| F7 | chr13 | 112799123 | 112799379 | rs2480951; rs2476320 |
| CIDEA | chr18 | 12244327 | 12244696 | rs60132277 |
| chr18 group00091 | chr18 | 12901467 | 12901643 | rs34568924; rs8094284; rs8094285 |
| C18orf1 | chr18 | 13377536 | 13377654 | rs9957861 |
| KLHL14 | chr18 | 28603978 | 28605183 | rs61737323; rs61737324; rs12960414 |
| CD33L3 | chr18 | 41671477 | 41673011 | rs62095363; rs2919643 |
| ONECUT2 | chr18 | 53254808 | 53259810 | rs35685953; rs61735644; rs8084084; rs35937482; rs35427632; rs7232930; rs3786486; rs34286480; rs3786485; rs28655657; rs4940717; rs4940719; rs3786484; rs34040569; rs35542747; rs33946478; rs35848049; rs7231349; rs7231354; rs34481218; rs12962172; rs3911641 |
| RAX | chr18 | 55086286 | 55086436 | rs58797899; rs45501496 |
| chr18 group00277 | chr18 | 57151972 | 57152311 | rs17062547 |
| TNFRSF11A | chr18 | 58203013 | 58203282 | rs35114461 |
| NETO1 | chr18 | 68685099 | 68687060 | rs4433898; rs34497518; rs35135773; rs6566677; rs57425572; rs36026929; rs34666288; rs10627137; rs35943684; rs9964226; rs4892054; rs9964397; rs4606820; rs12966677; rs8095606 |
| chr18 group00304 | chr18 | 70133945 | 70134397 | rs8086706; rs8086587; rs8090367; rs999332; rs17806420; rs58811193 |
| TSHZ1 | chr18 | 71128742 | 71128974 | rs61732783; rs3744910; rs1802180 |
| chr18 group00342 | chr18 | 74170347 | 74170489 | rs7226678 |
| NFATC1 | chr18 | 75385424 | 75386008 | rs28446281; rs56384153; rs4531815; rs3894049 |
| chr18 group00430 | chr18 | 75653272 | 75653621 | rs34967079; rs35465647 |
| KCNG2 | chr18 | 75760343 | 75760820 | rs3744887; rs3744886 |
| OLIG2 | chr21 | 33317673 | 33321183 | rs2236618; rs11908971; rs9975039; rs6517135; rs2009130; rs1005573; rs1122807; rs10653491; rs10653077; rs35086972; rs28588289; rs7509766; rs62216114; rs35561747; rs7509885; rs11547332 |
| OLIG2 | chr21 | 33327593 | 33328334 | rs7276788; rs7275842; rs7275962; rs7276232; rs16990069; rs13051692; rs56231743; rs35931056 |
| RUNX1 | chr21 | 35180938 | 35185436 | rs2843956; rs55941652; rs56020428; rs56251824; rs13051109; rs13051111; rs3833348; rs7510136; rs743289; rs5843690; rs33915227; rs11402829; rs2843723; rs8128138; rs8131386; rs2843957; rs57537540; rs13048584; rs7281361; rs2843965; rs2843958 |
| SIM2 | chr21 | 36994965 | 36995298 | rs2252821 |
| SIM2 | chr21 | 36999025 | 36999410 | rs58347144; rs737380 |
| DSCAM | chr21 | 41135559 | 41135706 | rs35298822 |
| AIRE | chr21 | 44529935 | 44530388 | rs35110251; rs751032; rs9978641 |
| SUMO3 | chr21 | 45061293 | 45061853 | rs9979741; rs235337; rs7282882 |
| C21orf70 | chr21 | 45202815 | 45202972 | rs61103857; rs9979028; rs881318; rs881317 |
| COL18A1 | chr21 | 45754383 | 45754487 | rs35102708; rs9980939 |
| PRMT2 | chr21 | 46911967 | 46912385 | rs35481242; rs61743122; rs8131044; rs2839379 |
| SIX2 | chr2 | 45081223 | 45082129 | rs62130902 |
| SIX2 | chr2 | 45084851 | 45085711 | rs35417092; rs57340219 |
| SOX14 | chr3 | 138971870 | 138972322 | rs57343003 |
| TLX3 | chr5 | 170674439 | 170676431 | rs11134682; rs35704956; rs2964533; rs35601828 |
| FOXP4 | chr6 | 41623666 | 41624114 | rs12203107; rs1325690 |
| FOXP4 | chr6 | 41636384 | 41636779 | rs56835416 |
| chr7 group00267 | chr7 | 12576755 | 12577246 | rs56752985; rs17149965; rs6948573; rs2240572 |
| NPY | chr7 | 24290224 | 24291508 | rs2390965; rs2390966; rs2390967; rs2390968; rs3025123; rs16146; rs16145; rs16144; rs13235842; rs13235935; rs13235938; rs13235940; rs13235944; rs36083509; rs3025122; rs16143; rs16478; rs16142; rs16141; rs16140; rs16139; rs2229966; rs1042552; rs5571; rs5572 |
| SHH | chr7 | 155291537 | 155292091 | rs9333622; rs1233554; rs9333620; rs1233555 |
| GLIS3 | chr9 | 4288283 | 4289645 | rs56728573; rs12340657; rs12350099; rs35338539; rs10974444; rs7852293 |
| PRMT8 | chr12 | 3472714 | 3473190 | rs12172776 |
| TBX3 | chr12 | 113609153 | 113609453 | rs60114979 |
| chr12 group00801 | chr12 | 118516189 | 118517435 | rs966246; rs17407022; rs970095; rs2711748 |
| PAX9 | chr14 | 36201402 | 36202386 | rs17104893; rs12883298; rs17104895; rs35510737; rs12882923; rs12883049; rs28933970; rs28933972; rs28933971; rs28933373; rs61734510 |
| SIX1 | chr14 | 60178801 | 60179346 | rs761555 |
| ISL2 | chr15 | 74420013 | 74421546 | rs34173230; rs11854453 |
| DLX4 | chr17 | 45397228 | 45397930 | rs62059964; rs57481357; rs56888011; rs17638215; rs59056690; rs34601685; rs17551082 |
| CBX4 | chr17 | 75428613 | 75431793 | rs12285243; rs35035500; rs12949177; rs3764374; rs62075212; rs62075213; rs3764373; rs3764372; rs55973291 |
| EDG6 | chr19 | 3129836 | 3130874 | rs34728133; rs34573539; rs3826936; rs34914134; rs61731111; rs34205484 |
| MGC29506 | chr5 | 138757911 | 138758724 | rs11748963; rs7447765; rs35262202 |

TABLE 2-continued

| GENE NAME | CHROM | START | END | SNPs |
|---|---|---|---|---|
| CENTG1 | chr12 | 56406249 | 56407788 | rs61935742; rs12318065; rs238519; rs238520; rs238521; rs808930; rs2640595; rs2640596; rs2640597; rs2640598; rs34772922 |
| CENTG1 | chr12 | 56416146 | 56418794 | rs11830475; rs34482618; rs2650057; rs2518686; rs12829991 |

TABLE 3

| GENE NAME | RELATIVE METHYLATION PLACENTA TO MATERNAL | PRC2 TARGET |
|---|---|---|
| CRYL1 | HYPOMETHYLATION | TRUE |
| IL17D | HYPOMETHYLATION | TRUE |
| GSH1 | HYPERMETHYLATION | TRUE |
| MAB21L1 | HYPERMETHYLATION | TRUE |
| PCDH17 | HYPERMETHYLATION | TRUE |
| KLHL1 | HYPERMETHYLATION | TRUE |
| POU4F1 | HYPERMETHYLATION | TRUE |
| SOX21 | HYPERMETHYLATION | TRUE |
| ZIC2 | HYPERMETHYLATION | TRUE |
| CIDEA | HYPERMETHYLATION | TRUE |
| KLHL14 | HYPERMETHYLATION | TRUE |
| ONECUT2 | HYPERMETHYLATION | TRUE |
| RAX | HYPERMETHYLATION | TRUE |
| TNFRSF11A | HYPOMETHYLATION | TRUE |
| OLIG2 | HYPERMETHYLATION | TRUE |
| OLIG2 | HYPOMETHYLATION | TRUE |
| SIM2 | HYPERMETHYLATION | TRUE |
| SIM2 | HYPERMETHYLATION | TRUE |
| SIX2 | HYPERMETHYLATION | TRUE |
| SIX2 | HYPERMETHYLATION | TRUE |
| SOX14 | HYPERMETHYLATION | TRUE |
| TLX3 | HYPERMETHYLATION | TRUE |
| SHH | HYPERMETHYLATION | TRUE |
| OSR2 | HYPERMETHYLATION | TRUE |
| TBX3 | HYPERMETHYLATION | TRUE |
| PAX9 | HYPERMETHYLATION | TRUE |
| SIX1 | HYPERMETHYLATION | TRUE |
| ISL2 | HYPERMETHYLATION | TRUE |
| DLX4 | HYPERMETHYLATION | TRUE |
| CBX4 | HYPERMETHYLATION | TRUE |
| CENTG1 | HYPOMETHYLATION | TRUE |
| CENTG1 | HYPOMETHYLATION | TRUE |

TABLE 4

| SEQ ID NO | GENE NAME | SEQUENCE |
|---|---|---|
| 1 | chr13 group-00016 | CAGCAGGCGCGCTCCCGGCGAATCTGCCTGAATCGCCGTGAATGCGGTGGGGTGCAGGGCAGGGGCTGGTT TTCTCAGCCGGTCTTGGCTTTTCTCTTTCTCTCCTGCTCCACCAGCAGCCCCTCCGCGGGTCCCATGGGCT CCGCGCTCAGAACAGCCCGGAACCAGGCGCCGCTCGCCGCTCGCTGGGGGCCACCCGCCTCTCCCCGGAAC AGCCTCCCGCGGGCCTCTTGGCCTCGCACTGGCGCCCTCACCCACACATCGTCCCTTTATCCGCTCAGACG CTGCAAAGGGCCTTCTGTCTC |
| 2 | CENPJ | GCTTTGGATTTATCCTCATTGGCTAAATCCCTCCTGAAACATGAAACTGAAACAAAGCCCTGAACCCCCTC AGGCTGAAAAGACAAACCCCGCCTGAGGCCGGGTCCCGCTCCCACCTGGAGGGACCCAATTCTGGGCGCC TTCTGGCGACGGTCCCTGCTAGGGAGCTGCGCTCTCCGAGTGCGAGTTTTCGCCAAACTGATAAAGCACG CAGAACCGCAATCCCCAAACTAACACTGAACCCGGACCCGCGATCCCCAAACTGACAAGGGACCCGGAACA GCGACCCCCAAACCGACACGGGACTCGGGAACCGCTATCTCCAAAGGGCAGC |
| 3 | ATP8A2 | TTTCCACAACAGGGAGCCAGCATTGAGGCGCCCAGATGGCATCTGCTGGAAATCACGGGCCGCTGGTGAAG CACCACGCCTTACCCGACGTGGGGAGGTGATCCCCCACCTCATCCCACCCCCTTCTGTCTGTCTCCTT |
| 4 | GSH1 | GCTGGACAAGGAGCGCTCACTGTAGCTCTGCTGTGGATTGTGTTGGGGCGAAGAGATGGGTAAGAGGTCAA AGTCGTAGGATTCTGGCGACCGCCTACCAAGGGATTGGGTCCACAGCACAGAGGTCTGATCGCTTCCTTCT CTGCTCTGCCACCTCCAGACAGCAGCTCTAACCAGCTGCCCAGCAGCAAGAGGATGCGCACGGCTTTCACC AGCACGCAGCTGCTAGAGCTGGAGCGCGAGTTCGCTTCTAATATGTACCTGTCCCGCCTACGTCGCATCGA GATCGCGA |
| 5 | PDX1 | TGCCTGACACTGACCCCAGGCGCAGCCAGGAGGGGCTTTGTGCGGGAGAGGGAGGGGGACCCCAGCTTGCC TGGGGTCCACGGGACTCTCTTTCTTCCTAGTTCACTTTCTTGCTAAGGCGAAGGTCCTGAGGCAGGACGAGG GCTGAACTGCGCTGCAATCGTCCCCACCTCCAGCGAAACCCAGTTGAC |
| 6 | PDX1 | TCGGCGGAGAGACCTCGAGGAGAGTATGGGGAAAGGAATGAATGCTGCGGAGCGCCCCTCTGGGCTCCACC CAAGCCTCGGAGGCGGGACGGTGGGCTCCGTCCCGACCCCTTAGGCAGCTGGACCGATACCTCCTGGATCA GACCCCACAGGAAGACTCGCGTGGGGCCCGATATGTGTACTTCAAACTCTGAGCGGCCACCCTCAGCCAAC TGGCCAGTGGATGCGAATCGTGGGCCCTGAGGGGCGAGGGCGCTCGGAACTGCATGCCTGTGCACGGTGCC GGGCTCTCCAGAGTGAGGGGGCCGTAAGGAGATCTCCAAGGAAGCCGAAAAAAGCAGCCAGTTGGGCTTCG GGAAAGACTTTTCTGCAAAGGAAGTGATCTGGTCCCAGAACTCCAGGGTTGACCCCAGTACCTGACTTCTC CGGGAGCTGTCAGCTCTCCTCTGTTCTTCGGGCTTGGCGCGCTCCTTTCATAATGGACAGACACCAGTGGC CTTCAAAAGGTCTGGGGTGGGGAACGGAGGAAGTGGCCTTGGGTGCAGAGGAAGAGCAGAGCTCCTGCCA AAGCTGAACGCAGTTAGCCCTACCCAAGTGCGCGCTGGCTCGGCATATGCGCTCCAGAGCCGGCAGGACAG CCCGGCCCTGCTCACCCCGAGGAGAAATCCAACAGCGCAGCCTCCTGCACCTCCTTGCCCAGAGAC |
| 7 | MAB21L1 | AGATCCCGGTGCATTTAAAGGCCGGCGTGATCTGCACCACGTACCTATCTCGGATTCTCAGTTTCACTTCG CTGGTGTCTGCCACCATCTTTACCACATCCCGGTAGCTACATTTGTCTACCGCTTGAGCCACCAGCGTCTG AAACCTGGACCGGATTTTGCGCGCCGAGAGGTAGCCGGAGGCGGTAATGAATTCCACCCAGAGGGACATGC TCCTCTTGCGCCCGTCGCTCAACTTCAGCACCGCGCAGCCGGGCAGTGAGCCATCGTCCACGAAGTTGAAC ACCCCCATTTGGTTGAGATAAAGCACCACTTCAAATTCGGT |

TABLE 4-continued

| SEQ ID NO | GENE NAME | SEQUENCE |
|---|---|---|
| 8 | RB1 | ACTATGCCTTGAGGGTCAAAACGTCTGGATTTCCTGATCGATGCTGTCGTCGCTGTCCACGGAGCTACTGT<br>CGCCGTCAGAGCGGGAAGGCACGTTCAGGGAGTAGAAGCGTGGGCTTGCAGAAAGGGACCTGTTGCTGCCT<br>TACATGGGGGCCGGCAGGGTAGTCTTGGAAATGCCCAAGATTGCTTCCGCGCGCGTCAGTTCAGCGGACGT<br>GTCTGCCTGGCACGAGGACCGTTCTACAAACTCGTTCCTGGAAGCCGGGCTCGCTGGAGGCGGACGTTTGG<br>TTTCCTTCGGGAGCTTGTGGGGAATGGTCAGCGTCTAGGCACCCCGGGCAAGGGTCTGTGGCCTTGGTGGC<br>CACTGGCTTCCTCTAGCTGGGTGTTTTCCTGTGGGTCTCGCGCAAGGCACTTTTTTGTGGCGCTGCTTGTG<br>CTGTGTGCGGGGTCAGGCGTCCTCTCTCCTCCCGGCGCTGGGCCCTCTGGGGCAGGTCCCCGTTGGCCTCC<br>TTGCGTGTTTGCCGCAGCTAGTACACCTGGATGCCTCCTCAGTGCCGTCGTTGCTGCTGGAGTCTGACGC<br>CTCGGGCGCCTGCGCCGCCACTTGTGACTTGCTTTCCCCTTCTCAGGGCGCCAGCGCTCCTCTTGACCCCGC<br>TTTTATTCTGTGGTGCTTCTGAAG |
| 9 | PCDH17 | GCAAGTCGGGTAGCTACCGGGTGCTGGAGAACTCCGCACCGCACCTGCTGGACGTGGACGCAGACAGCGGG<br>CTCCTCTACACCAAGCAGCGCATCGACCGCGAGTCCCTGTGCCGCCACAATGCCAAGTGCCAGCTGTCCCT<br>CGAGGTGTTCGCCAACGACAAGGAGATCTGCATGATCAAGGTAGAGATCCAGGACATCAACGACAACGCGC<br>CCTCCTTCTCCTCGGACCAGATCGAAATGGACATCTCGGAGAACGCTGCTCCGGGCACCCGCTTCCCCCTC<br>ACCAGCGCACATGACCCCGACGCCGGCGAGAATGGGCTCCGCACCTACCTGCTCACGCGCGACGATCACGG<br>CCTCTTTGGACTGGACGTTAAGTCCCGGCGACGGCCACCAAGTTCCCAGAACTGGTCATCCAGAAGGCTC<br>TGGACCGCGAGCAACAGAATCACCATACGCTCGTGCTGACTGCCCTGGACGGTGGCGAGCCTCCACGTTCC<br>GCCACCGTACAGATCAACGTGAAGGTGATTGACTCCAACGACAACAGCCGGTCTTCGAGGCGCCATCCTA<br>CTTGGTGGAACTGCCCGAGAACGCTCCGCTGGGTACAGTGGTCATCGATCTGAACGCCACCGACGCCGATG<br>AAGGTCCCAATGGTGAAGTGCTCTACTCTTTCAGCAGCTACGTGCCTGACCGCGTGCGGGAGCTCTTCTCC<br>ATCGACCCCAAGACCGGCCTAATCCGTGTGAAGGGCAATCTGGACTATGAGGAAAACGGGATGCTGGAGAT<br>TGACGTGCAGGCCCGAGACCTGGGGCCTAACCCTATCCCAGCCCACTGCAAAGTCACGGTCAAGCTCATCG<br>ACCGCAACGACAATGCGCCGTCCATCGGTTTCGTCTCCGTGCGCCAGGGGCGCTGAGCGAGGCCGCCCCT<br>CCCGGCACCGTCATCGCCTGGTCGGGTCACTGACCGGACTCTGGCAAGAACGGACAGCTGCAGTGTCG<br>GGTCCTAGGCGGAGGAGGGACGGGCGGCGGCGGGGGCCTGGGCGGGCCCGGGGGGTTCCGTCCCCTTCAAGC<br>TTGAGGAGAACTACGACAACTTCTACACGGTGGTGACTGACCGCCCGCTGGACCGCGAGACACAAGACGAG<br>TACAACGTGACCATCGTGGCGCGGGACGGGGGCTCTCCTCCCCTCAACTCCACCAAGTCGTTCGCGATCAA<br>GATTCTAGACGAGAACGACAACCCGCCTCGGTTCACCAAAGGGCTCTACGTGCTTCAGGTGCACGAGAACA<br>ACATCCCGGGAGAGTACCTGGGCTCTGTGCTCGCCCAGGACCCGACCTGGGCACGAACGCACCGTATCC<br>TACTCTATCCTGCCCTCGCACATCGGCGACGTGTCTATCACACCTATGTGTCTGTAATCCCACGAACGG<br>GGCCATCTACGCCCTGCGCTCCTTTAACTTCGAGCAGACCAAGGCTTTTGAGTTCAAGGTGCTTGCTAAGG<br>ACTCGGGGGCGCCCGCACTTGGAGAGCAACGCCACGGTGAGGGTGACAGTGCTAGACGTGAATGACAAC<br>GCGCCAGTGATCGTGCTCCCCACGCTGCAGAACGACACCGCGGAGCTGCAGGTGCCGCGCAACGCTGGCCT<br>GGGCTATCTGGTGAGCACTGTGCGCGCCCTAGACAGCGACTTCGGCGAGAGCGGGCGTCTCACCTACGAGA<br>TCGTGGACGGCAACGACGACCACCTGTTTGAGATCGACCCGTCCAGCGGCGAGATCCGCACGCTGCACCCT<br>TTCTGGGAGGACGTGACGCCCGTGGTGGAGCTGGTGGTGAAGGTGACCGACCACGGCAAGCCTACCCTGTC<br>CGCAGTGGCCAAGCTCATCATCCGCTCGGTGAGCGGATCCCTTCCCGAGGGGGTACCACGGGTGAATGGCG<br>AGCAGCACCACTGGGACATGTCGCTGCCGCTCATCGTGACTCTGAGCACTATCTCCATCATCCTCCTA |
| 10 | KLHL1 | ATGCGCCCTCTGCACCCCTAGAGCCAGAAGACGCTAGGTGGGCTGCGCGCTCTGCCAGGCGAAGGCTGGAG<br>CGCAGACGGCAAAGCCGCGCGTTTCAGCCGTGGTCGGGTCCGCAGGACCTGGGCGTGGGAGCACACCAGG<br>CAGGAGCAGAGGCAGGACTGGGACGCCAAAAGCTGAGAATCCTCGATGCCCGCGCGAGAGCCCCGTGTTAT |
| 11 | POU4F1 | TTCTGGAAACCGGGCCCCACTTGCAGGCCCGGCCACCTTGGGTTCTGGTGGCCGAAGCCGGAGCTGTGTTT<br>CTCGCAGACTCGGGGAGCTACATTGTCGCGTAGGCAATTTGTTTAGTTTGAAAGGAGGCACATTCACCACGC<br>AGCCAGCGCCCTGCATGCAGGAGAAGCCCCCAGGGCCCAGGGTCGGCTGGCTTTAGAGGCCACTTAGGTTG<br>TTTTAAGCACATGTGAAAGGGCAGACAGCAGGGGAGCAGGATATGGGTAAGATCTTCGGGTCTCAGAACAG<br>GGGCTGCCCTTGGGCTGTCCCGGCGCCCTGGGCTCTGACACTGAAGGGTGGAATGGAGGAAGGAATGGAGA<br>AAGGACGGTGGAACTTTCGCTTCCCCTCTGGGCCGCTTCCCAGGGTCATGCCTGAGCTGCTTTGATCCCA<br>GTGTCGCGCATCTTGGTCCGCTACCTCCCAGGCGATAGCTACTGGGCTCCTCGCTGGCCTCACTGGGGGCC<br>ATCCCGGGCAGTGGCCTGCCCTCCGAGGCCCGCGGGACCCAGCCCAGAGCTGAGGTTGGAGTTCTCCGGGC<br>CACGTTCCGGGTCGCTTAGGCTCGGAGATTTCCCGGAGACCGTCGTCCTCCCTTTCTGCTTGGCACTGCGG<br>AGCTCCCTCGGCCTCTCTCCTCCTCTGGTCCCTAAGGGCCCAGGAGTGGTTGCGGTGCTGTGGGGCCCGTCGTC<br>ATCTCTGCTTCTAAGGCATTCAGACTGGGCTCCAGCTGGGACCGGCAGAGGAGGTTCTCAAGGAAACTGGT<br>GGGAAATATAGTTTTCTTTCGTCTGGTCGTTTAATTTAAATGCAACTTCCCTTGGGGACATTTTCCTGGAC<br>GTTAACCAGACCACCTTGAGATGTCGTTGATGACCTAGAGACCCAGATGATGCGTCCCAGGAAAGTTCACT<br>GCTGACTATTGTCACTCTTGGCGTTATATCTATAGATATAGACCTATGTACATATCTCCACCCTGATCTCT<br>CCGTGGACATGAAAACCCACCTACCTTGTGAAAGCCCTACGGGTGACACATGACTACTACGTCTCTGTCCA<br>ACAGGGGCTGGGCCTCCCCTGCCTAATAGTTGCCAGGAGTTTCGCAGCCCAAGTGAATAATGTCTTATGGC<br>TGAACGTGGCCAAGGACTCCTGTGATTTAGGTCCCAGGAGGAGCAGAGACGTCCCCGCCCCGCCTGGGCCC<br>TGCCGCATTCAAAGCTGGAAGAAGGCGCTGATCAGAGAAGGGGCTTCCAGGTCCTGGGTTAGAACAACAAC<br>AAACAAACGAAACTCCACAACAGACACGCCTGCCCATGACCCCAAGGACATAGGAAGTTCTGTCGCC<br>TTCCTGCTCCGCGGATAGCCGCCTGCCGTCTGCTGCCACCAGAACGCACGGACGCTCGGGGTGGAGGTAGT<br>CAATGGGCAGCAGGGGACCCCAGCCCCACAAGCGCGGCTCCGAGGACCTGGAAGCGGGTGCCTGTCGCT<br>CTCCGCAGGCTCCGCTCTGCCTCCAGGAGCAAGATCCCCAAAAGGGTCTGGAAGCTGTGGAGAAAAC |
| 12 | GPC6 | TTTTTTAAACACTTCTTTTCCTTCTCTTCCTCGTTTTGATTGCACCGTTTCCATCTGGGGCTAGAGGAGC<br>AAGGCAGCAGCCTTCCCAGCCAGCCCTTGTTGGCTTGCCATCGTCCATCTGGCTTATAAAGTTTGCTGAG<br>CGCAGTCCAGAGGGCTGCGCTGCTCGTCCCCTCGGCTGGCAGAAGGGGGTGACGCTGGGCAGCGGCGAGGA<br>GCGCGCCTGCTCTGGCGGGCTTTCGGCTTGAGGGGCAAGGTGAAGAGCGCACCGCCGTGGAGTGTTTAC<br>CGAGCTGGATTTGTATGTTGCACCATGCCTTCTTGGATCGGGGCTGTGATTCTTCCCCTCTTGGGGCTGCT<br>GCTCTCCCTCCCCGCCGGGGCGGATGTGAAGGCTCGGAGCTGCGGAGAGGTCCGCCAGGCGTACGGTGCCA<br>AGGGATTCAGCCTGGCGGACATCCCCTACCAGGAGATCGCAGGTAAGCGCGGGCGCGCTGCAGGGGCAGGC<br>TGCAGCCCTCGGCTGCCGCACGTCCCACTGGCCGCCCGGCGTCCCCTTCCTCCCCCTGTTGCTGAGTTGG<br>TGCTCACTTTCTGCCACCGCTATGGGACTCCGCGTCTCCGTGTTGGGCGGCGGATGCTCCTGCGGCTTCTT |

TABLE 4-continued

| SEQ ID NO | GENE NAME | SEQUENCE |
|---|---|---|
| | | CGGCGGGGAAGGTGTGCGTCTCCGCCGCCTCATTGTGTGCACACGCGGGAGCACCCTGGCTCCCGCCTCC<br>CGCTGCTCTCGCGCCCTTCTACCCCTTAGTTGATGGCTCAGGCCCGGCTGGCCAGGGAGCCCGGGTCACTC<br>CGGGGCGGCTGCAAGGCGCAGACGGAGAGCCGAGCCGGGCGCTCACTCCGCGTTCTGGTTCGGGCAAACTT<br>GGAAGAACTGCGACCGCAGTTTGCCCAGCGCCACAGTCTGAGTGGCGCCTTCTCCACTCCCGCCCTTGCGC<br>CGGCAGGGGCGGTGGAGAGACGCGGAGGGCTCCCCCAGCCCCTCTCTCCCCTATCCGTCCTTCGGGCGACA<br>GAGCGCCCGGCGCTCGGGCCGGGGCGGGCAAGGCTGGGAGGGACCCTCGCCGGGGACCTGGCCTCTGGAC<br>GCCGGCGTTTCAAGGCTGGTTTGGGGACTTCACGGGCTGCCTGTTTCAGATGTGGGCGGGCTTTCCCGTT<br>AGGGTTCCTCAGTGCTTCCCCAGTTGCTGTTGGCACTCAGGGCCCGGGGACACCCTGCCACCCGGTCTGG<br>AGCCGGCCTCGTCGCCAGCGAACAGCCAACTTTAGCGGGTGGCTCAGCTGGGGATT |
| 13 | SOX21 | CACTCAGTGTGTGCATATGAGAGCGGAGAGACAGCGACCTGGAGGCCATGGGTGGGGCGGGTGGTGAAGC<br>TGCCGAAGCCTACACATACACTTAGCTTTGACACTTCTCGTAGGTTCCAAAGACGAAGACACGGTGGCTTC<br>AGGGAGACAAGTCGCAAGGGCGACTTTTCCAAGCGGGAGATGGTGAAGTCTTTGGACGTGTAGTGGGTAGG<br>TGATGATCCCCGCAGCCGCCTGTAGGCCCGCAGACTTCAGAAAACAAGGGCCTTCTGTGAGCGCTGTGTCC<br>TCCCCGGAATCCGCGGCTTAACACATTCTTTCCAGCTGCGGGGCCAGGATCTCCACCCCGCGCATCCGTGG<br>ACACACTTAGGGTCGCCTTTGTTTTGCGCAGTGATTCAAGTTGGGTAACCCTTGCTCAACACTTGGGAAAT<br>GGGGAGAATCTCCCCCACCCGCACTTCCCGCACCCCAGGTTCCCAAAATCTGAATCTGTATCCTAGAGTG<br>GAGGCAGCGTCTAGAAAGCAAAGAAACGGTGTCCAAAGACCCCGGAGAGTTGAGTGAGCGCAGATCCGTGA<br>CGCCTGCGGTACGCTAGGGCATCCAGGCTAGGGTGTGTGTGCGGGTCGGGGGGCGCACAGAGACCGCGC<br>TGGTTTAGGTGGACCCGCAGTCCCGCCCGCATCTGGAACGAGCTGCTTCGCAGTTCCGGCTCCCGGCGCCC<br>CAGAGAAGTTCGGGGAGCGGTGAGCCTAGCCGCCGCGCGCTCATGTTTATT |
| 14 | ZIC2 | AGTCACTCCAGGATCAGAGGCCGCGTCGGTTCTGCTTGGGGCATGGGCAGAGGGAGGCTGCTGGGGCCAAG<br>CCCCGGCTGGACGCGAGGGAAGAAACTCGTCCCAGGACCCGCACGCCCATACCTGGCTGTCCCAGAGCTCT<br>TCCCTAGGCCGGCACCTTCGCTCTTCCTCTTCCCCACCCCCTAGCCCTTTTGTCTCTTTTTCAGACGGATG<br>TTTTCAGTCTCAAGTGGTTTTATTTTCCGCACAAAACCCTGAGATCAAGGGCAGATCACGACTGTACCGG<br>AGGCTCGGGTTTCCCTGGACTCTGTGCTGTTCTGCGTCCCAGGGTTGGCTAGGAAGGAAGGCCTGGGCCGG<br>CGAGGTGACGGGTCTCCCGCCCAGGTCGGCAGGACGGGGGGAGGTGTGTCCCGGTAGGTCCCTGGTGAGCT<br>CACCCGTGGCATCGGGGACCCGCGGGAACCCACCGGGCGCCCACTAGAGACTCGGGTCCTACCCTCCCCCA<br>CACTACTCCACCGAAATGATCGGAAGGGCGCGCTAGGCCTGCTTCCAAGGGCTCAGTGATAAAGGCCTCAA<br>AATCACACTCCATCAAGACTTGGTTGAAGCTTTGGGTAGGTTTGTTGTTGTTGTTGTTGTTGTTTGTTTGT<br>TTGTTTTAGCAGACACGTCCTGGAAAGAGGTCCTCAGAACCCAAAGGTTCAATAATGATTTGTGGATGGAT<br>TGATTATAGTCTGATATCGCTCTGGTTCCACAGAAACCCGGAGCTCCTTGGCCCACTGTTACCCCAGCAGA<br>CCTAAATGGACGGTTTCTGTTTTTCACTGGCAGCTCAGAACTGGGACCGGAAGAAGTTCCCCTCCACTTCC<br>CCCTCCCGACACCAGATCATTGCTGGGTTTTTATTTTCGGGGAAAAACAACAACAACAACAACAAAAAA<br>ACACTAGGTCCTTCCAGACTGGATCAGGTGATCGGGCAAAAACCCTCAGGCTAGTCCGGCTGGGTGCCCGA<br>GCATGAAAAGGCCTCCGTGGCCGTTTGAACAGGGTGTTGCAAATGAGAACTTTTGTAAGCCATAACCAGGG<br>CATCCTGAGGGTCTGAGTTCACGGTCAAGGCTGTGGGCTACTAGGTCCAGCGAGTCCAGGCCTCGCCCCGC<br>CCCCGAGCTGCCACAGCCAAGATCTTCGGCAGGGAATTCGAGACCAGGGTCCTCCCACTCCT |
| 15 | chr13 group-00385 | TTTCGTGCCGCTGTTTTCAATGCGCTAACGAGGCACGTTATTCTTAGCCGCGTCCGGGAGGGGATCACATT<br>CCTGCGCAGTTGCGCTGCTGGCGGAAGTGACTTGTTTTCTAACGACCCTCGTGACAGCCAGAGAATGTCCG<br>TTTCTCGGAGCGCAGCACAGCCTGTCCCATCGAGAAGCTCGGGTGAGGGGCCCGGTGGGCGCCCGGAGGC<br>CGCTGGAGGGCTGTGGGAGGGACGGTGGCTCCCACTCCCGTGGCGAAGGGCAGGCAAACCAGAAGCCTCT<br>TTTGAGAGCCGTTTGGGATTGAGACGAGTAAGCCACAGCGAGTGGTTAGAAGTAGGTTAGGAAGAAGGGGA<br>GGTAAGAAAGCCGAGTAGGGTT |
| 16 | chr13 group-00390 | GTTCGGTGGACAAGGGGGCAGCGCCCACAGCAAGCCGGAAAGAGGGAGGCGCGGGGCCGCGCTTGGGGCCT<br>GCCGCTGCACGCCAGCCTGGGCAAAGAGCTGCCACCTTCTGCGGGCGAAGCGGGTCGGGACGCAGGACGGC<br>AGCGGGGCTGGAGGCAGCTACGTGGGTCCACACCCCATGCCCTGCAAGGCTCCTTGGCCCTGCTTCTCCT<br>CTGTCTCGGCGGGAGAGGAGCAGCCTCGGTTTTACAGAATTTC |
| 17 | chr13 group-00391 | TGTGCCATTTAGTGAGAGGTGTTTTGGGCAAAGAATCAATTTAACTGTGACTGACCGACGGGCTTGACTGT<br>ATTAATTCTGCTACCGAAAAAAAAAAAAAAAAAAAGCAATGAGCCGCAAGCCTTGGACTCGCAGAGCTGC<br>CGGTGCCCGTCCGAGAGCCCCACCAGCGCGGCTCACGCCTCAGTCTC |
| 18 | chr13 group-00395 | AGAGTCCCAGTTCTGCAGGCCGCTCCAGGGCTAGGGGTAGAGATGGTGGCAGGTGGTGCGTCAACTCTCTA<br>GGGAAGAGGAACTTGCATTACAAAGACTTGTCTTTCTGAGCTGAAGTCAAAACGGGGGCGTCAAGCGCGCT<br>CCGTTTGGCGGCGGTGGAGGGGCGCGCGCCCCGCGCTGTCCCAGCCGGACGCTGCCCTGGCTGGTGATTGA<br>GGTTTAACGTCCGGAATTCAGGCGCTTCTGCAGCTCAGATTTGCCGGCCAAGGGGCCTCAGTTGCAACTTT<br>TCAAAATGGTGTTTCTGGAAAATAACAAATTCAGACTCAACTGGTGACAGCTTTTGGCTATAGAGAATGAA<br>ACTGCTTCCCTTTGGCGGTGGAACTCTTAAACTTCGAAGAGTGAAAGAATACAATGAAATAAAATGCCATA<br>AGATCACTGGATTTTTCAGAAAAAGGAAGACCCCAAATTACTCCCAAAATGAAGGCTTTGTAAATTCTTGTT<br>AAAAATCTTTAAATCTCGAATTTCCCCCTACAACATCTGATGAGTGCTTTAAGAGCAAACGAGCAAATCCC<br>ACCTCGAGAATCAACAAACCCAAGCTCTGGCCAAGGCTCTCCCCGCGTTTTCTTCTCGTGACCTGGGGAAT<br>GTCCCGCCCCATCGCTCACCTGGCTCTTGTCATCTCGCTCATCTTGAAGTGACCCGTGGACAATGCTG |
| 19 | chr13 group-00399 | AGCTGCCCTCTGTGGCCATGAGCGGGTGTCCAGCCCCTTCCAAGGCTGCACCGGGGAGACGCTGGTTTTCT<br>GCTCGCTGTGACCGAACAAAGCCCCTAAGAGTCAGTGCGCGGAACAGAAGAGCCGGACCCCGACGGGCCGA<br>GTCCCAACGTGAGGCACCCGGCAGAGAAAACACGTTCACG |
| 20 | PROZ | CCTCGGCAGCACCGGCATGGCTGGAGGCCAGTACGGCCAGGTGTGGCGGGAGGGAGCGCCGTCTGGCTTGG<br>GTCGTCCATCCTGACAGGACGCTGCAAGGGCAGGAGCCCCGCGCCCCGTGTCCTGCGCCCCCGCTCGAGGA<br>CAAGCCCCAGCCGCCGGTCTCCGCTGGGTTCCGACAG |

TABLE 4-continued

| SEQ ID NO | GENE NAME | SEQUENCE |
|---|---|---|
| 21 | CIDEA | CTTTAAGAGGCTGTGCAGGCAGACAGACCTCCAGGCCCGCTAGGGGATCCGCGCCATGGAGGCCGCCCGG<br>ACTATGCAGGAGCCCTCATCAGGCGAGTGCCCCGCGTCCCCTGATTGCCGTGCGCTTCCAATCGCCTTGC<br>GTTCGGTGGCCTCATATTCCCCTGTGCGCCTCTAGTACCGTACCCCGCTCCCTTCAGCCCCCTGCTCCCCG<br>CATTCTCTTGCGCTCCGCGACCCCGCGCACACACCCATCCGCCCCACTGGTGCCCAAGCCGTCCAGCCGCG<br>CCCGCGGGCAGAGCCCAATCCCGTCCCGCGCCTCCTCACCCTCTTGCAGCTGGGCACAGGTACCAGGTGTG<br>GCTCTTGCGAGGTG |
| 22 | chr18 group- 00091 | AGACTTGCAGAACTCGGGCCCCCTGGAGGAGACCTAACCGCCACGGTCTTGGGGAGGTTCCGGAGGGCCTC<br>GGTTGTCTGCACTCCCAACACCAAGAAACCCCTGAGACGCGAAGCTGCCAGCGTGCTGCCCTCAGAGCAGG<br>GCGACGCAAAGCCAGCGGACCCCGGGGTGGCGGG |
| 23 | chr18 group- 00094 | TGCTCGGCTGGGGGGCTCGCTCCGCACTTTCGGTGCCAGAAAATGCCCAGAGGAGCGGGGCGGCCCCAGAG<br>CCTCCTTTCGGGGCGCGAGGCCCGGCGCGTGTGTACGGAGTCCAGTCCCCCAGGGAGTGGGGTGCCCGCA<br>CCTTCCCCTCCGCGCTCGGAGCCAC |
| 24 | KLHL14 | TCTTGCACACCTGCTTGTAGTTCTGCACCGAGATCTGGTCGTTGAGGAACTGCACGCAGAGCTTGGTGACC<br>TGGGGGATGTGCAGGATCTTGCTGACCGACACCTCCTCCACCGTGTCCAGGGACAGGGTCACGTTGGC<br>CGTGTAGAGGTACTCGAGCACCAGGCGCAGCCCGATGGACGAGCAGCCCTGCAGCACCAGGTTGTTGATGG<br>CCCCGGGGGCTGGTCAGCAGCTTGTCGTCGGGGAGGAAGAAGGAGTCCCGGGCTCCTCCTGCGGCGGCGGC<br>TGCTGCTGCTGTGACGGCTGCTGCTGCGGCGGCTGCTGCTGGTCCTTGGGGGCCCCCAGGCCGTCCTGGCC<br>GCCGACCCCTCCCCCGAGAGGGGGGTGGCTGGAGAAGGAGGCGATCGGAAGTACTGCGAGCAGGAGGCCAGCA<br>CGGCCTTGTGGCAATGGAACTGCTGGCCCTGGGCCGTCAGGGTCACGTCGCAAAACAGCTGCTTCCTCCAC<br>AGCAGGTTGAGGCCGTGCAGCAGGTTGTCGCTGTGGCTGGGGTCGAAGGTGGAGGTCCTGTCCCCGGATCT<br>GGACATGGCGAGCTGACTCGGTGCACCTGGCTTTAAACCCTCCTCCAACCTGGCAGACAGGGGTGGGGGAT<br>GGGAGGGAGGGGAGCAGGGTGGTGGAGCGGGTGGGGTGTGGTCGGGGTGGGAAGGGTGTGGAGGGGAGGG<br>GAGGGCGAAGAACAAGAATCAAGGCTCAGCTTGACTCCCTCCTGGCGCGCTCCGGACCCCGACCCTAGGAG<br>GAAAGTCCGAAGACGCTGGATCCGTGAGCGCCACCAGAAGGGCCCTGTCTGGGGTCCCGGCGCCGGTTCTG<br>CGCCCTGCGGCTCCTCTCGCCACCTCCCACACACTTCGTCCCTCACTTTCCTAAAACCAACCACCTCAGCT<br>CGGCTGTTGGCAGCAACAGCAGTGGCAGCAGCGCAGCAAAGTGGCGGCTGAGGCCGAGGCACCTCGTGGG<br>CTCGTGTCCATGCCGGGCCAGATGAAGGGAAAGGCCGGGAAGTGGGGAGCCGGGGGTGCCCTGAAAGCTCA<br>GAGGCGACCGACGGCGAAGGTTCCAGGTCAACTTGTGCCCGAAGCTTTGCTTTTCGCAGTTGGCCCAGTTT<br>GGGGGAGGGGGTAGGAACAGGGGCCCGACCAGCGTGCGGGGTGTGCGAATCTTAGCTCTCCAAAAGCTG |
| 25 | ST8SIA3 | CCTCTGTGTTAGTGCCCTCGGGAATTTGGTTGATGGGGTGTTTG |
| 26 | ONECUT2 | TGATGTCGCACCTGAACGGCCTGCACCACCCGGGCCACACTCAGTCTCACGGGCCGGTGCTGGCACCCAGT<br>CGCGAGCGGCCACCCTCGTCCTCATCGGGCTCGCAGGTGGCCACGTCGGGCCAGCTGGAAGAAATCAACAC<br>CAAAGAGGTGGCCCAGCGCATCACAGCGGAGCTGAAGCGCTACAGTATCCCCCAGGCGATCTTTGCGCAGA<br>GGGTGCTGTGCCGGTCTCAGGGGACTCTCTCCGACCTGCTCCGGAATCCAAAACCGTGGAGTAAACTCAAA<br>TCTGGCAGGGAGACCTTCCGCAGGATGTGGAAGTGGCTTCAGGAGCCCGAGTTCCAGCGCATGTCCGCCTT<br>ACGCCTGGCAGGTAAGGCCGGGGCTAGCCAGGGGCCAGGCTGCTGGGAAGAGGGCTCCGGGTCCGGTGCTT<br>GTGGCCCAAGTCTGCGCGCCGAGTCACTTCTCTTGATTCTTTCCTTCTCTTTCCTATACACGTCCTCTTTC<br>TTCTCGTTTTTATTTCTTCTTCCATTTTCTCTTTCTCTTCCGCTCTTCCCCTACTTTCCCTTCTCCCTTTT<br>CTTTTTCTTTCTTACTCTCCTTGTCCCTGAGCTTTCATTGACCGACCCCCCCCATTTCATTCGCCCTC<br>CCCTCAATGTGCCAACCTTTGCCCTATTTCCGATCTTCCCAGGTACTGGGAGGCGGGATGGGGGTGTGCGT<br>TTTCCTCTAGGAGCCCTGTCTTTCCAAGACCCACAGAAACCAGGACCTGCCCTTATTCAAAACCCCATGCA<br>CTTCAAGTCTCTTTTAGACAACACATTTCAATTTTCCGGGCTGACTAGTCTCCCTGTGCAGAGGCAGTTGA<br>GAGGCTTTGCTCTGCAGAGGGAAAGAGCTCTCTACTCTCCCACCCACCATATAGGCAAACTTATTTGGTC<br>ATTGGCTGAAGGCACAGCCTTGCCCCCGCGGGGAACCGGCGGCCAGGATACAACAGCGCTCCTGGAGCCCA<br>TCTCTGGCCTTGGCGTTGGCGCAGGGACTTTCTGACCGGGCTTGAGGGGCTCGGGCCAGCTCCAATGTCAC<br>TACCTACAGCGAGGGCAGGGTGTAAGGTTGAGAAGGTCACATTCACCGCTTTGGGAGGACGTGGGAGAAGA<br>GACTGAGGTGGAAAGCGCTTTGCCTTGCTCACCGGCCGTCCTTGCCCCGGTCCCAGCGTTTGCTGGGATTT<br>GCCAGGATTTGCCGGGGCTCCGGGAGACCCTGAGCACTCGCAGGAAGAGGTGCTGAGAAATTAAAAATTCA<br>GGTTAGTTAATGCATCCCTGCCGCCGGCTGCAGGCTCCGCCTTTGCATTAAGCGGGCGCTGATTGTGCGCG<br>CCTGGCGACCGCGGGGAGGACTGGCGGCCCGCGGGAGGGGACGGGTAGAGGCGCGGGTTACATTGTTCTGG<br>AGCCGGCTCGGCTCTTTGTGCCTCCTCTAGCGGCCAAGCTGCGAGGTACAGCCCTCTATTGTTCTAGGAGC<br>ACAGAAACCTCCTGTGTGGGCGGCGGGTGCGCGAGCTAGAGGGAAAGATGCAGTAGTTACTGCGACTGGCA<br>CGCAGTTGCGCGCTTTTGTGCGCACGGACCCCGCGCGGTGTGCGTGGCGACTGCGCTGCCCCTAGGAGCAA<br>GCCACGGGCCCAGAGGGGCAAAATGTCCAGGTCCCCCGCTGGGAAGGACACACTATACCCTATGGCAAGCC<br>AGGGTGGGCGACTTCCCATGGATCGGGTGGAGGGGGGTATCTTTCAGGATCGGCGGGCGGTCTAGGGGAAC<br>AATTCGTGGTGGCGATGATTTGCATAGCGCGGGTCTTGGGATGCGCGCGGTTCCGAGCCAGCCTCGCACAG<br>CTCGCTTCCGGAGCTGCGAGCTCAGGTTTCCACCCCCGATCCCCCGGGCTTTCCTCGCACCGCTGAGCCCA<br>GCTTGTGGGGTGCACTCGACCAACGCCCGACAGGGTGGGGAATGTGACAGGCAGCAGGTTCACCCGGGCT<br>TGGGGAGGGGGAGTTTCCGCTTTGACAGCATTTTCCTTTGCCGTCTGCTGGTGGATTCCTATTCCCAGTCG<br>GTAATCGCCCCGCAGTGTTGATCTAAGAAGGTAAAGAAAACTAGGTTTCCCTGCAAAGAGCCTCCCCCAAA<br>TCGGCGGACTCCGGATACTTTGAGTGGATTTAGAAATTTATGTAATCTTTCTCCTTTAGTTTATTTTTCAT<br>CCTCTCTACAGTTTTCTCTGATTTGCTGTTGGTTCGGGGCAAGATAAAGCAGCCAGTAGAGACGGATAAT<br>AATAGCGGCGGGAAATGAACTGGAGACTGGCTGACAGTTCTTAACATTTTGTCATAGATCCCCCCGAATGT<br>CCCAGGCTGTCTCTGGTGGGTTTTAGTACCCGCCGGCTTCTTGGGCACCGGGGACCAGAAGGAACTTGGCA<br>GCTGGTCTTAGGGGTACAGTTAAAGGCAGGATGACAGCTATTCTCCTGCTCATCTCAGAGCGCTGCCGCCC<br>CCTCACTCCGGTCCGTCGCGCAAAGAACACAGCTTTTAAAAAACACGTGCCTTCTGCCCATATAGGTCTGAAAGT<br>GATGAGGAAAGTAATGCTTCGCCTATTAGCGAGTTTCAGCTTTTAAAATGATCCCAAGCGTTGCTGAGATG<br>AGAAAGCGTGGCATCCCGGGGTCCTCAGCCCCACCCGCGCCCATGGTGCAAGTCTGCAGGGACAGGCCCG<br>GGACAGCACTGCCCACGCTGCTAGATTTTCCGCAGAGGATCGCTGAAGCTGCCTTCGTGGGAGACAGAATG<br>CCTCCTCCAGCGAGTGGAAAAGGCCTGCTGAGGACCCCGCTTTGCTCGAGCATTCAAATGTGTGTCTGTTT<br>TATTACCCTGGGTTGAAAAGGGACAAGAGCTTTAGCCTTTTTATCTGGCCATTTTATCAGCAACTACAAGT |

TABLE 4-continued

| SEQ ID NO | GENE NAME | SEQUENCE |
|---|---|---|
| | | GTGTTGAGTGGTTATTATTACATAGGAGGCTTTTCAGTTTGGGGTCAGTAGATCAGTCTCTTCAGACACTG ATGCAGAAGCTGGGACTGGTAAGTAGGTATTATGTGCTCGGAGCGCTAGGGGACAGGAGCAAATGGAGAAG AAAAGCGGAGGCTTTCTCCGCCCGGAGTATCGATCGGAATCCCCGCCGGTACGCCGCAGAGGGCCCTCGCC GTTGGGCCCCGGGGGTTTAACAAGCCCAGCCGCTCCGCAGGCGGCTCGGCCGGACTCTCAGACCGGTGCCT GGAAGACACCGTCCCTGCCCCCCTCCCGCCAAACCTGCCTCTTCTCTTTCTCTCATAGGTTATAGGTTCCC TTTCTCTCTCATTTTGGCCCCGCCCCCGGGTCCTGCCAAACAGCCAAGCAGGCCGGGGTTTAGGGGGCTCA GAATGAAGAGGTCTGATTTGGCCAGCGCCGGCAAAGCTCACCCTTAGGCGAGGTCACAACAGAGGCAGGTC CTTCCTGCCCAGCCTGCCGGTGTAGTCACAGCCAAGGGTGGCACTTGAAAGGAAAAGGGAGAAAACTTCGG AGAAATTTAGATTGCCCCAACGTTAGATTTCAGAGAAATTGACTCCAAATGCACGGATTCGTTCGGAAAGG GCGGCTAAGTGGCAGGTGGTTGCAACCCCGCCCGGTCGGGCCTTCGCAGAGGTTCCCCAAGACCAGCCCTT GCAGGGCGGTTTTCAGCAACCTGACAAGAGGCGGCCAAGACAAATTTCTGCGGGTTCGAGCACACACTCTC GGGCGTTGGGCCCCAGAGACCTCTAAACCAAGCACAAACAAGAAGGGAGTGAGAGAACCCAGGCTAGAACT TGCACGGGCATCCCACTGAGGAAAAGCGAGGCCTCGGTGGCAGGCATGTTTTCTTCCGACGCCCGAAAATC GAGCCGAGCGCCCGACTACATTTACTGCAGAGGTTTCCGCCTCCAGTGAGCCCGGATCCCCAGCGGCCTG CCCGGAGCTGGTCTCCAGTCCCCGCCGTAGTCCGACGCACGGCCCTCTCCTGGCAGCAAGCTCCCAGCGGC CAGTCTGAAGCCAATTCTGTTCAGGCGGCCGAGGGCCCTTAGCCAACCCACCATGATGTCGCCTGGGCCAC CTGATGCCCGCAGCGGCGGGACACGGCCCGGGCAGTGCGCAGGTGGCTCCTGCTAGGGGCACCGCGTGCGTG CTTGTCTCCCGCTGCGCCGGGGACGTCCTTGGGTGACACGGGCCGCTGGGCACCTCCCAAGCCGAGGAAAC GGACCCCCTTCGCAGAGTCTCGCGCCCACCCCCAACCTCCCACCTCGTTTCTCGCTGCTAGGGCTCCCGA CTCAGCCCACCTCTCCTGGCGGTTTAGTTAGGGATCAGAGCTGGAGAGGCTGAACGCAACCCGTGCCAGTA CGGAACAGACGATATGTTTGCCTGCTAGCTGCTTGGATGAATAATTGAAAAGTTCGCTGCAGTCTGTGCTT CGTCAAGTCCCGGGTGCCGGGAGAACACCTTCCCAACACGCATCAGGGTGGGCGGGAGCGGGCAGAGGAGG CGGGACCCGAGGGAGGAGAGTGAACCCGAGCAGGAGAAGCAGCCCAGGCAGCCAGGCGCCCTCGATGCGAG AGGCTGGGCATTTATTTTTATTCCAGGCTTTCCACTGTGTGGTTATGTCACTTTCTCAAACAAATGTGTAT ATGGAGGGAGATCGATGCTGATAATGTTTAGAAGATTAAAAGAGCATTAATGCTGGCAACATAACGTAAA CGTGTGGACCCAGATTTCATTGATCTGGAACTTGATCCGGCGCGTTTCCAGTAAGCCCGACGGCGCGCTCT TCCCAGCAGAGCGCTCACCAGCGCCACGGCCCCGCGGTTTTCCAGCGGTGCCGCTTCGCCAGCTCTGCGCG GGTTCTCCCGTCTGACCGCAGCTCCTCCCCCGCGAGGCCCCAGCCCGCCTTACTTCCCGAGGTTTTCTCC TCCTCTCGCGGGGCTCTCTGCCCTCTGCACCCCTCCCCCGACCTCTGCACCACCCGCCCCTGTGCGCACA CACCGCTACTTGCGCTTCCGGCGATCCGCCTG |
| 27 | RAX | AACCGGAGATCTGCTTGGTGAACTGAGAGGAGTCCTTAGGAGAGCGGGGACGCCAGGGGCCGGGGACACT TCGCTCTCGCCCTAGGGAAGGTGGTCTTGACGCTTTCTATTGAAGTCAAACTTGAAAATATCAGCTGCCGC TGGACTAT |
| 28 | chr18 group-00277 | CGTGAGCAGAACGCCCGCCCTGGAGCAGTTAGGACCGAAGGTCTCCGGAGAGTCGCCGGCGGTGCCAGGTA ACGCAGAGGGCTCGGGTCGGGCCCCGCTTCTGGGGCTTGGGACTCCGGGCGCGCGGAGCCAGCCCTCTGGG GCGAAATCCCCGGGCGGCGTGCGCGGTCCCTCTCCGGGTCGACTTCGACTTCCTCGGACTTAGTGGGAGAAGGGGTTGGAAATGGGCTGCCG GGACTGGGGGAGCTGCTCTCTGGAAGCAGGGAAGCTGGGGCGCACCGGGGCAGGT |
| 29 | NETO1 | TAGAAGAGGAAGACTCCTCTGGCCCCACTAGGTATCATCCGCGCTCTCCCGCTTTCCACCTGCGCCCTCGC TTGGGCCAATCTCTGCCGCACGTGTCCATCCCTGAACTGCACGCTATCCTCCACCCCGGGGGGTTCCTGC GCACTGAAAGACCGTTCTCCGGCAGGTTTTGGGATCCGGCGACGGCTGACCGCGCGCCGCCCCACGCCCG GTTCCACGATGCTGCAATACAGAAAGTTTACGTCGGCCCCGACCCGCGCGGGACTGCAGGGTCCGCCGGAG CGCGGCGCAGAGGCTTTTCCTGCGCGTTCGGCCCCGGGAAAGGGGCGGGAGGGCTGGCTCCGGGAGCGCAC GGGCGCGGCGGGGAGGGTACTCACTGTGAAGCACGCTGCGCCCATGGATCATGTCTGTGCGTTACACCAGA GGCTCCGGGCTCCACTAATTCCATTTAGAGACGGGAAGACTTCCAGTGGCGGGGGGAGGACAGGGTCGAGA GGTGTTAAAGACGCAAAGCAAGAAGGAAATAAAGGGGGGCCGAGAGGGAGACCGAGAGGAAGGGGGAGCTC CGAGCCCACGCTGCAGCCAGATCCGGATGAGTCCGTCCTCCGCCCCGGGCGGGCTCTGCTCTCGCTGGCC CTCAGCGCCGCGCAGCCAGCAGCATCCCCACCGTGACGCTCGCATCACACCCGGGCGCCGGCCGCCACCAT CCGCGCCGCCGCCGTCAGGACCCTCCTCCCGGGCATCGTCGCCGCCGCGGGTCGGAGGACGCGGCGCGC GGGAGGCGGCGGTCGCAGGGCGAGCCCCGGGACGCCCCGAGCCGGGGCGGGGCCGGGGAGAGGGCGCAGC GAGGTGGGGGCCAGTCCAGACCGACGGCAGCGACGGAGCGGGCGGCGGCGGCGCGCGGCCGCCGCGGGGG TGGCTCAGTCCCCAGTCTCAGACGCGCCGCGCAGCAGGTCGGAGCAGCCTCCCCGGGAGGATGTCCAGCGG CAGCGCTCCTCGCTCCAGCCCTTGGGGATCTTCCGCTGAGGCATTGAAGGCAGGAAGAAGGGTCCGTCAT CGGCTCGCCGGGCTGCGCGCCACCTCTGCTATCTTGCGGAAAGAGGAGCGGGTGGGTGGCGTCTGGGAGG CGGGCTGGAGGGCGGTGCAGGGGAGCGGGCGGCCGGGGGGGGCCGGGGGCGGGAAGGGAGGGAGGA GAAAGGAGCCGGAAGAGGGCAGAGTTACCAAATGGGCTCCTTAGTCATGGCTTGGGGCTCCACGACCCTCC TGGAAGCCCGGAGCCTGGGTGGGATAGCGAGGCTGCGCGCGGCCGGCGCCCCGGGGCTGGTGCGCGGCAGA ATGGGGCCGCGGCGGCGGCAGCAAGGACATCCCAGCCGCGCGGATCTGGGGAGGGGCGGGAGGGGGTGA GGACCCGGCTGGGATCCGCGGCTCGGCCCGCAGGGCGCAGAGAGGATGCAGCCGCAAATCCCGAGCCG GATCCTCGTGCCGACGGAAGGCGTGGAAGCGGGAGGGGCCTTCGTGTGAAAATCCCTTGTGGGGTTTGGT GTTTCACTTTTTAAAGGTTAGACCTTGCGGGCTCTCTGCCTCCCACCCCTTCTTTTCCATCCGCGTAAAGG AACTGGGCGCCCCCTCTCCCTCCCTCCCTGGGGCGCAGGTTTCGCCGCGGACTCCGCGCTCAGCTTGGGAG ACACGGCAGGGGCGCGCCCAGGGAAAGGCGGCCGTAAAAGTTTCGCGGTTGAGCACTGGGCCTGATGTCC AGTCCCCCCACCAAATTACTCCTGCAAAGACGCGGGCTTCTTGCAATTGAGCCCCCCACCTCGAGGTATTT AAAACCACCCCAAGGCACACACGGACCCCCGTTCCCCGCGCCACTTCCTCCTACAGGCTCGCGCGGCGCG TTAAAGTCTGGGAGACACGAGTTGCGGGAAACAGCACCGGAAG |
| 30 | MBP | AAGAAACAGCTCATTTCGGAGCTGAGGACAAGGCGTGGGAAGAAGACGCGTTTGGTTTCACCCAGGCGGGT GGCGGCAAAGCTGTGGGATGCGCGCTGCACACTCCTTCCGTCATCCCGTTCCCACCTTCCACACACACCTG CGGGAGGTCGGACATGTCCTGATTGCGTGTTCATCACGATGGCAAACCGAACATGAGGAGAACGCCACTGA CGCTGGGTGCGCCGGCTTTCCCAGCCCTCGTGCATAACGGGGAGGGAGATGCAGAAGTTTTTTCCAACATC GGTGCAAAGGGGAAGCTGAGGTTTTCCTAT |

TABLE 4-continued

| SEQ ID NO | GENE NAME | SEQUENCE |
|---|---|---|
| 31 | NFATC1 | TCTGTCAGCTGCTGCCATGGGGCAGCGGGAAGGCCCTGGAGGGTGCCTGGGCTGTGTCTGGTCCCGGCCAC<br>GCGTCCCTGCAGCGTCTGAGACCTTGTGAACACACTTGACCCGGCGCTGGGACGGGGTCGGCCCACACGC<br>ACCGCCAGCCCGCAGGAGTGAGGTGCAGGCTGCCGCTGGCTCCTTAGGCCTCGACAGCTCTCTTGAGGTCG<br>GCCCTCCTCCCCTCCCGAGAGCTCAGCAGCCGCAGACCCAGGCAGAGAGAGCAAAGGAGGCTGTGGTGGCC<br>CCCGACGGGAACCTGGGTGGCCGGGGGACACACCGAGGAACTTTCCGCCCCCCGACGGGCTCTCCCACCGA<br>GGCTCAGGTGCTCGTGGGCAGCAAGGGGAAGCCCCATGGCCATGCCGCTTCCCTTTCACCCTCAGCGACGC<br>GCCCTCCTGTGCCCGCGGGGAACAAGACGGCTCTCGGCGGCCATGCAGGCGGCCTGTCCCACGAACACGAT<br>GGAGACCTCAGACGCCGTCCCCACCCTGTCACTGTCACCATCACCCATCCTGTCCCCTCACGCCTCCCCAC<br>ATCCCATCATTACTAC |
| 32 | chr18 group-00430 | GAAGTAGAATCACAGTAAATGAGGAGTTAGGGAATTTAGGGTAGAGATTAAAGTAATGAACAGAGGAGGAG<br>GCCTGAGACAGCTGCAGAGAGACCCTGTGTTCCCTGTGAGGTGAAGCGTCTGCTGTCAAAGCCGGTTGGCG<br>CTGAGAAGAGGTACCGGGGGCAGCACCCGCTCCTGGGAGGAGGGATGGGCCTGCGGGCACCTGGGGGAACC<br>GCACGGACACAGACGACACTATAAACGCGGGCGAGACATCAGGGACCGGGAAACAGAAGGACGCGCGTTTC<br>GAGCAGCTGCCCAGTGGGCCACAAGCCCCGCCACGCCACAGCCTCTTCCCCTCAGCACGCAGAGA |
| 33 | OLIG2 | TACTCCGGCGACGGGAGGATGTTGAGGGAAGCCTGCCAGGTGAAGAAGGGGCCAGCAGCAGCACAGAGCTT<br>CCGACTTTGCCTTCCAGGCTCTAGACTCGCGCCATGCCAAGACGGGCCCCTCGACTTTCACCCCTGACTCC<br>CAACTCCAGCCACTGGACCGAGCGCGCAAAGAACCTGAGACCGCTTGCTCTCACCGCCGCAAGTCGGTCGC<br>AGGACAGACACCAGTGGGCAGCAACAAAAAAGAAACCGGGTTCCGGGACACGTGCCGGCGGCTGGACTAA<br>CCTCAGCGGCTGCAACCAAGGAGCGCACGTTGCGCCTGCTGGTGTTTATTAGCTACACTGGCAGGCGCA<br>CAACTCCGCGCCCCGACTGGTGGCCCCACAGCGCGCACCACACATGGCCTCGCTGCTGTTGGCGGGGTAGG<br>CCCGAAGGAGGCATCTACAAATGCCCGAGCCCTTTCTGATCCCCACCCCCCGCTCCCTGCGTCGTCCGAG<br>TGACAGATTCTACTAATTGAACGGTTATGGGTCATCCTTGTAACCGTTGGACGACATAACACCACGCTTCA<br>GTTCTTCATGTTTTAAATACATATTTAACGGATGGCTGCAGAGCCAGCTGGGAAACACGCGGATTGAAAAA<br>TAATGCTCCAGAAGGCACGAGACTGGGGCGAAGGCGAGAGCGGGCTGGGCTTCTAGCGGAGACCGCAGAGG<br>GAGACATATCTCAGAACTAGGGGCAATAACGTGGGTTTCTCTTTGTATTTGTTTATTTTGTAACTTTGCTA<br>CTTGAAGACCAATTATTTACTATGCTAATTTGTTTGCTTGTTTTTAAAACCGTACTTGCACAGTAAAAGTT<br>CCCCAACAACGGAAGTAACCCGACGTTCCTCACACTCCCTAGGAGACTGTGTGCGTGTGTGCCCGCGCGTG<br>CGCTCACAGTGTCAAGTGCTAGCATCCGAGATCTGCAGAAACAAATGTCTGAATTCGAAATGTATGGGTGT<br>GAGAAATTCAGCTCGGGGAAGAGATTAGGGACTGGGGGAGACAGGTGGCTGCCTGTACTATAAGGAACCGC<br>CAACGCCAGCATCTGTAGTCCAAGCAGGGCTGCTCTGTAAAGGCTTAGCAATTTTTTCTGTAGGCTTGCTG<br>CACACGGTCTCTGGCTTTTCCCATCTGTAAAATGGGTGAATGCATCCGTACCTCAGCTACCTCCGTGAGGT<br>GCTTCTCCAGTTCGGGCTTAATTCCTCATCGTCAAGAGTTTTCAGGTTTCAGAGCCAGCCTGCAATCGGTA<br>AAACATGTCCCAACGCGGTCGCGAGTGGTTCCATCTCGCTGTCTGGCCCACAGCGTGGAGAAGCCTTGCCC<br>AGGCCTGAAACTTCTCTTTGCAGTTCCAGAAAGCAGGCGACTGGGACGGAAGGCTCTTTGCTAACCTTTTA<br>CAGCGGAGCCCTGCTTGGACTACAGATGCCAGCGTTGCCCCTGCCCCAAGGCGTGTGGTGATCACAAAGAC<br>GACACTGAAAATACTTACTATCATCCGGCTCCCTGCTAATAAATGGAGGGGTGTTTAACTACAGGCACGA<br>CCCTGCCCTTGTGCTAGCGCGGTTACCGTGCGGAAATAACTCGTCCCTGTACCCACACCATCCTCAACCTA<br>AAGGAGAGTTGTGAATTCTTTCAAAACACTCTTCTGGAGTCCGTCCCCTCCCTCTTGCCCGCCCTCTACC<br>CCTCAAGTCCCTGCCCCCAGCTGGGGGCGCTACCGGCTGCCGTCGGAGCTGCAGCCACGGCCATCTCCTAG<br>ACGCGCGAGTAGAGCACCAAGATAGTGGGGACATTTGTGCCTGGGCATCGTTTACATTTGGGGCGCCAAATG<br>CCCACGTGTTGATGAAACCAGTGAGATGGGAACAGGCGGCGGGAAACCAGACAGAGGAAGAGCTAGGGAGG<br>AGACCCCAGCCCCGGATCCTGGGTCGCCAGGGTTTTCCGCGCGCATCCCAAAAGGTGCGGCTGCGTGGGGC<br>ATCAGGTTAGTTTGTTAGACTCTGCAGAGTCTCCAAACCATCCCATCCCCCAACCTGACTCTGTGGTGGCC<br>GTATTTTTACAGAAATTTGACCACGTTCCCTTTCTCCCTTGGTCCCAAGCGCGCTCAGCCCTCCCTCCAT<br>CCCCCCTTGAGCCGCCCTTCTCCTCCCCCTCGCCTCCTCGGGTCCTCCTCCAGTCCCTCCCCAAGAATCTC<br>CCGGCCACGGGCGCCCATTGGTTGTGCGCAGGGAGGAGGCGTGTGCCCGGCCTGCCGAGTTTCATTGAGCG<br>GAATTAGCCCGGATGACATCAGCTTCCCAGCCCCCGGCGGGCCCAGCTCATTGGCGAGGCAGCCCCTCCA<br>GGACACACATTGTTCCCCGCCCCGCCCCCGCCACCGCTGCCGCCGTCGCCGCTGCCACCGGGCTATAA<br>AAACCGGCCGAGCCCCTAAAGGTGCGGATGCTTATTATAGATCGACGCGACACCAGCGCCCGGTGCCAGGT<br>TCTCCCCTGAGGCTTTTCGGAGCGAGCTCCTCCAAATCGCATCCAGAGTAAGTGTCCCCGCCCCACAGCAGC<br>CGCAGCCTAGATCCCAGGGACAGACTCTCCTCAACTCGGCTGTGACCCAGAATGCTCCGATACAGGGGGTC<br>TGGATCCCTACTCTGCGGGCCATTTCTCCAGAGCGACTTTGCTCTTCTGTCCTCCCCACACTCACCGCTGC<br>ATCTCCCTCACCAAAAGCGAGAAGTCGGAGCGACAACAGCTCTTTCTGCCCAAGCCCCAGTCAGCTGGTGA<br>GCTCCCCGTGGTCTCCAGATGCAGCACATGGACTCTGGGCCCCGCGCCGGCTCTGGGTGCATGTGCGTGTG<br>CGTGTGTTTGCTGCGTGGTGTCGATGGAGATAAGGTGGATCCGTTTGAGGAACCAAATCATTAGTTCTCTA<br>TCTAGATCTCCATTCTCCCCAAAGAAAGGCCCTCACTTCCCACTCGTTTATTCCAGCCCGGGGCTCAGTT<br>TTCCCACACCTAACTGAAAGCCCGAAGCCTCTAGAATGCCACCCGCACCCCCGAGGGTCACCAACGCTCCCT<br>GAAATAACCTGTTGCATGAGAGCAGAGGGGAGATAGAGAGAGCTTAATTATAGGTACCCGCGTGCAGCTAA<br>AAGGAGGGCCAGAGATAGTAGCGAGGGGGACGAGGAGCCACGGGCCACCTGTGCCGGGACCCCGCGCTGTG<br>GTACTGCGGTGCAGGCGGGAGCAGCTTTTCTGTCTCTCACTGACTCACTCTCTCTCTCTCCCTCTCTCT<br>CTCTCATTCTCTCTCTTTTCTCCTCCTCCTGGAAGTTTTCGGGTCCGAGGGAAGGAGGACCCTGCGA<br>AAGCTGCGACGACTATCTTCCCCTGGGGCCATGACTCGGACGCCAGCCTGGTGTCCAGCCGCCCGTCGTC<br>GCCAGAGCCCGATGACCTTTTTCTGCCGGCCCGGAGTAAGGGCAGCAGCGGCAGCGCCTTCACTGGGGGCA<br>CCGTGTCCTCGTCACCCCGAGTGACTGCCC |
| 34 | SIM2 | TTAATTCGAAAATGGCAGACAGAGCTGAGCGCTGCCGTTCTTTTCAGGATTGAAAATGTGCCAGTGGGCCA<br>GGGGCGCTGGGACCCGCGGTGCGAAGACTCGGAACAGGAAGAAATAGTGGCGCGCTGGGTGGGCTGCCCC<br>GCCGCCCACGCCGGTTGCCGCTGGTGACAGTGGCTGCCCGGCCAGGCACCTCCGAGCAGCAGGTCTGAGCG<br>TTTTTGGCGTCCCAAGCGTTCGGGCCGCGTCTTCCAGAGCCTCTGCTCCCAGCGGGTCGCTGCGGCCTG<br>GCCCGAAGGATTTGACTCTTTGCTGGGAGGCGCGCTGCTCAGGGTTCTG |
| 35 | SIM2 | CCGGTCCCCAGTTTGGAAAAAGGCGCAAGAAGCGGGCTTTTCAGGGACCCCGGGGAGAACACGAGGGCTCC<br>GACGCGGGAGAAGGATTGAAGCGTGCAGAGGCGCCCCAAATTGCGACAATTTACTGGGATCCTTTTGTGGG<br>GAAAGGAGGCTTAGAGGCTCAAGCTATAGGCTGTCCTAGAGCAACTAGGCGAGAACCTGGCCCCAAACTCC |

TABLE 4-continued

| SEQ ID NO | GENE NAME | SEQUENCE |
|---|---|---|
| | | CTCCTTACGCCCTGGCACAGGTTCCCGGCGACTGGTGTTCCCAAGGGAGCCCCCTGAGCCTACCGCCCTTG<br>CAGGGGGTCGTGCTGCGGCTTCTGGGTCATAAACGCCGAGGTCGGGGGTGGCGGAGCTGTAGAGGCTGCCC<br>GCGCAGAAAGCTCCAGGATCCCAATATGTG |
| 36 | DSCR6 | GCGCAGGTCCCCCAGTCCCGAGGGAGTGCGCCCGACGGAAACGCCCCTAGCCCGCGGGCCTCGCTTTCC<br>TCTCCCGGGTTCCTGGGTCACTTCCCGCTGTCTC |
| 37 | DSCAM | TTCCCTCGCGGCTTTGGAAAGGGGGTGCAAATGCACCCTTCTGCGGGCCCGCTACCCGCTGCAACACCTGT<br>GTTTCCTTTCTGGGCACCTTCTAGGTTTCTAGATATTGCTGTGAATACGGTCCTCCGCTGTACAGTTGAAA<br>ACAAA |
| 38 | chr21<br>group-<br>00165 | TGGGAATTTAGGTCGGGCACTGCCGATATGTCGCCTTCCACAAGGCGGGCCCGGGCCTCTGCTGACCGTGC<br>ACCGGTCCTGGGGCTGGGTAATTCTGCAGCAGCGCAGCCCATGCCGGGGAATTTGCGGGCAGAGGAGA<br>CAGTGAGGCCCGCGTTCTGTGCGGGAACTCCCGAGCTCACAGAGCCCAAGACCACACGGCTGCATCTGCTT<br>GGCTGACTGGGCAGGCCCACGCGTAGTAACCCGGACGTCTCTCTCTCACAGTCCCCTTGCGTCTGGCCAG<br>GGAGCTGCCAGGCTGCACCCCGCGGTGGGGATCGGGAGAGGGGCAGTGTCGCCCATCCCCGGAAGGCTGAG<br>CCTGGTGCAG |
| 39 | PRMT2 | CGGTTTTCTCCTGGAGGACTGTGTTCAGACAGATACTGGTTTCCTTATCCGCAGGTGTGCGCGGCGCTCGC<br>AAGTGGTCAGCATAACGCCGGGCGAATTCGGAAAGCCCGTGCGTCCGTGGACGACCCACTTGGAAGGAGTT<br>GGGAGAAGTCCTTGTTCCCACGCGCGGACGCTTCCCTCCGTGTGCTTCGAGCCACAAAAGCCCAGACC<br>CTAACCCGCTCCTTTCTCCCGCCGCGTCCATGCAGAACTCCGCCGTTCCTGGGAGGGGAAGCCCGCGAGGC<br>GTCGGGAGAGGCACGTCCTCCGTGAGCAAAGAGCTCCTCCGAGCGCGCGGCGGGGACGCTGGGCCGACAGG<br>GGACCGCGGGGGCAGGGCGGAGAGGACCCGCCCTCGAGTCGGCCCAGCCCTAACACTCAGGAC |
| 40 | SIX2 | AGGGAATCGGGCTGACCAGTCCTAAGGTCCCACGCTCCCCTGACCTCAGGGCCCAGAGCCTCGCATTACCC<br>CGAGCAGTGCGTTGGTTACTCTCCCTGGAAAGCCGCCCCGCCGGGGCAAGTGGGAGTTGCTGCACTGCGG<br>TCTTTGGAGGCCTAGGTCGCCCAGAGTAGGCGGAGCCCTGTATCCCTCCTGGAGCCGGCCTGCGGTGAGGT<br>CGGTACCCAGTACTTAGGGAGGGAGGACGCGCTTGGTGCTCAGGGTAGGCTGGGCCGCTGCTAGCTCTTGA<br>TTTAGTCTCATGTCCGCCTTTGTGCCGGCCTCTCCGATTTGTGGGTCCTTCCAAGAAAGAGTCCTCTAGGG<br>CAGCTAGGGTCGTCTCTTGGGTCTGGCGAGGCGGCAGGCCTTCTTCGGACCTATCCCCAGAGGTGTAACGG<br>AGACTTTCTCCACTGCAGGGCGGCCTGGGCGGGCATCTGCCAGGCGAGGGAGCTGCCCTGCCGCCGAGAT<br>TGTGGGGAAACGGCGTGGAAGACACCCCATCGGAGGGCACCCAATCTGCCTCTGCACTCGATTCCATCCTG<br>CAACCCAGGAGAAAACATTTCCGAGTTCCAGCCGCAGAGGCACCCGCGGAGTTGCCAAAAGAGACTCCCGC<br>GAGGTCGCTCGGAACCTTGACCCTGACACCTGGACGCGAGGTCTTTCAGGACCAGTCTCGGCTCGGTAGCC<br>TGGTCCCCGACCACCGCGACCAGGAGTTCCTTCTTCCCTTCCTGCTCACCAGCCGGCCGCCGGCAGCGGCT<br>CCAGGAAGGAGCACCAACCCGCGCTGGGGCGGAGGTTCAGGCGGCAGGAATGGAGAGGCTGATCCTCCTC<br>TAGCCCCGGCGCATTCACTTAGGTGCGGGAGCCCTGAGGTTCAGCCTGACTTTC |
| 41 | SIX2 | CACTACGGATCTGCCTGGACTGGTTCAGATGCGTCGTTTAAAGGGGGGGCTGGCACTCCAGAGAGGAGGG<br>GGCGCTGCAGGTTAATTGATAGCCACGGAAGCACCTAGGCGCCCCATGCGCGGAGCGGGAGCCGCCAGCTC<br>AGTCTGACCCCTGTCTTTTCTCTCCTCTTCCCTCTCCCACCCCTCACTCCGGGAAAGCGAGGGCCGAGGTA<br>GGGGCAGATAGATCACCAGACAGGCGGAGAAGGACAGGAGTACAGATGGAGGGGACCAGGACACAGAATGCA<br>AAAGACTGGCAGGTGAGAAGAAGGGAGAAACAGAGGGAGAGAGAAAGGGAGAAACAGAGCAGAGGCGGCCG<br>CCGGCCCGGCCGCCCTGAGTCCGATTTCCCTCCTTCCCTGACCCTTCAGTTTCACTGCAAATCCACAGAAG<br>CAGGTTTGCGAGCTCGAATACCTTTGCTCCACTGCCACACGCAGCACCGGGACTGGGCGTCTGGAGCTTAA<br>GTCTGGGGGTCTGAGCCTGGGACCGGCAAATCCGCGCAGCGCATCGCGCCCAGTCTCGGAGACTGCAACCA<br>CCGCCAAGGAGTACGCGCGGCAGGAAACTTCTGCGGCCCAATTTCTTCCCCAGCTTTGGCATCTCCGAAGG<br>CACGTACCCGCCCTCGGCACAAGCTCTCTCGTCTTCCACTTCGACCTCGAGGTGGAGAAAGAGGCTGGCAA<br>GGGCTGTGCGCGTCGCTGGTGTGGGGAGGGCAGCAGGCTGCCCCTCCCCGCTTCTGCAGCGAGTTTTCCCA<br>GCCAGGAAAAGGGAGGGAGCTGTTTCAGGAATTTCAGTGCCTTCACCTAGCGACTGACACAAGTCGTGTGT<br>ATAGGAAG |
| 42 | SOX14 | GGAGCCTGAAGTCAGAAAAGATGGGGCCTCGTTACTCACTTTCTAGCCCAGCCCCTGGCCCTGGGTCCCGC<br>AGAGCCGTCATCGCAGGCTCCTGCCCAGCCTCTGGGGTCGGGTGAGCAAGGTGTTCTCTTCGGAAGCGGGA<br>AGGGCTGCGGGTCGGGACGTCCCTTGGCTGCCACCCCTGATTCTGCATCCTTTTCGCTCGAATCCCTGCG<br>CTAGGCATCCTCCCCGATCCCCAAAAGCCCAAGCACTGGGTCTGGGTTGAGGAAGGGAACGGGTGCCCAG<br>GCCGGACAGAGGCTGAAAGGAGGCCTCAAGGTTCCTCTTTGCTACAAAGTGGAGAAGTTGCTCTACTCTGG<br>AGGGCAGTGGCCTTTTCCAAACTTTTTCCACTTAGGTCCGTAAGAAAAGCAATTCATACACGATCAGCGCTT<br>TCGGTGCGAGGATGGAAAGAAACTTC |
| 43 | TLX3 | TTTTCCTGTTACAGAGCTGAGCCCACTCATGTGGTGCCAAGTAGCGACTATCTCTCGGCCACCTCCACCCA<br>GAGCAATGTGGGCGCCCCCAGCGGGTGGGAGCGATTGCCGAGCGGCGCAAGGGCGTTTAAGCCTAACCCC<br>CTCCTCCTGGGTTGCCAAGCCGCTAGGTCGCCGTTTCCAACGTGGCTGCGCGGGACTGAAGTCCGACGCT<br>CCTCGTCCTCAGTAGGAGACACACCTCCCACTGCCCCCAGCCACGCGAGCTATGGGCAGAATCGGGCAAC<br>GGTAATATCTGGATGGGGCAGGCTCCCCTGAGGCTGTGCTTAAGAAAAAAGGAATCTGGAGTAGCCTGAGG<br>GGCCCCACGAGGGGGCCTCCTTTGCGATCGTCTCCCAGCCTTAGGCCAAGGCTACGGAGGCAGGCGGCCGA<br>GTGTTGGCGCCCAGCCCGGCCGAGGACTGGATGGAGGACGAGAAGCAGCCTGCCTCTGGGCAGACAGCTGCG<br>GACGCAGCCTCGCCGCCTCGCCGCCTCAGCCTCGGTCCCAGCGTCTCTAAAGCCGCGCCCATTTTACAGAT<br>GCAGGGCAGGGAGACAAGAGGCATCTCCGGGGGCCGAGTAGAATGATGGCGCGGGTTCTCCCGGCGCCCTG<br>ATTTTCGAGGCTGCGCCGGGGCCCTACATGCAGGCGGGGAGGGCTGGGCCGAAGGCGTCTGCAAGGAGGGG<br>CGAGTCTGCCCGGTCCGGCAGGGAGTGAGGCCACAGTCAGTTCTCCCTAGGAGGCCGCGCAGCGGGTAGG<br>GTATGGGACTGGGGGACGCAACGGGACCTGGCCGAATCAGAGCCCTCAGCAGAGAACGCCGAAACTCTG<br>GGGCCGGCCGCTCGCTTCCCGCTAGTGGGAATGGTTTCCGGTCATCCGTTCCCAGTCCAGCCCCGGGTAGG<br>GAGCTCTGATTTGCAATGCACAGCACTTGCGAGGTTCGAATGCCCCGCAATTTGCAGATGGAAATACTAA<br>GCCTAGGCCGGGCGTGGTGGCTCAAGCCTATCATCTCAGCCCTTTGGGAGGCCAAGCCGGGAGGATTGTTT |

TABLE 4-continued

| SEQ ID NO | GENE NAME | SEQUENCE |
|---|---|---|
| | | GAGCCCAAGAATTCAAAACCAGCCTGAGCAACATAGCGACCCCGTCTCTACAAAATAAAATAAAATAAATT<br>ATCCGGGCGTGGTGGCACGCGCCTGTGGTTCCAGCTACTCCGGAGGCTGAGGTGGGAGGATCGCTTGAGTC<br>CGGGAGGTCGAGGCTACAGTGAGCCGTGATCGCACCACTGCACTCCAGCCTGGGCGACAGAGTGAGACCTT<br>GTCTCAAAAAAGGAAAAAAAGAAAAAGAAAGTAAGCTTCAAAGAAGCTCTGATAATAGTTCTGGGTCGTGC<br>AGCGGTGGCGGCCCCGCGCTCTCGCCCCTAAAGCAAGCGCTCTTTGTACTGGGTGGAGGAGCTTTGAGTAG<br>TGAGGGTGGAGATGCAGCTTCGGGGTGGCGCAGCCACCCTGACACTAGGCCCGGGGTCGCAGTGGGACAGA<br>AGAGTCTGCCGCTCTGACTTGGGCTCTGAGTTCCAAGGGCGCCCGGCACTTCTAGCCTCCCAGGCTTGCGC<br>GCTGGCGCCTTTGCCATCCGTGCCGAAGTGGGGAGACCTAGCCGCGACCACCACGAGCGCAGCGGTGACAC<br>CCAGAGGTCCCACCGGGCCCTGGGCAGGGTAACCTTAGCCTGTCCGCTTCGGCAGCTTTGCGAAGAGTGG<br>CGCGCAGCTAGGGCTGAGGCTCTTGCGGACCTGCGGTCGAAGCAGGCGGCTGAGCCAGTTCGATCGCCAAG<br>GCCTGGGCTGCCGACAGTGGTGCGCGCTCTGTTCCGCCGCGGCCGGGCAGGCGCTCTGGAATAGCGATGG<br>GGGGACACGGCCTCCAACTTTCTGCAGAGACCATCGGGCAGCTCCGGGCCTAAGCAGCGACCTCACCGAAG<br>GTTCCTGGGAACCTTTGCCAAAATCCCAGCCTCTGCCTCGGTCCAGCTAAACCGTGTGTAAACAAGTGCAC<br>CAAG |
| 44 | FOXP4 | ATAAAGGACCGGGTAATTTCGCGGAATGCGGATTTTGAGACAGGCCCAGACGGCGGCGGATTCCCTGTGTC<br>CCCCAACTGGGGCGATCTCGTGAACACACCTGCGTCCCACCCCGATCCTAGGTTGGGGGGAAAGGGTATGG<br>GAACCCTGAGCCCAGAGCGCGCCCCGCTCTTTCCTTTGCTCCCCGGCTTCCCTGGCCAGCCCCCTCCCGGC<br>TGGTTTCCTCGCTCACTCGGCGCCTGGCGTTTCGGGCGTCTGGAGATCACCGCGTGTCTGGCACCCCAACG<br>TCTAGTCTCCCCGCAGGTTGACCGCGGCGCCTGGAGCCGGGAATAGGGGTGGGGAGTCCGGAGAACCAAAC<br>CCGAGCCTGAAGTTGCCATTCGGGTGACTCCCGAGAAAGCCCGGGAGCATTTTGGCCAATGCGGGTTTTTA<br>CCTGAACTTCAGCATCTTCACC |
| 45 | FOXP4 | AATTGGAAAACCCTGGTATTGTGCCTGTTTGGGGGAAGAAAACGTCAATAAAAATTAATTGATGAGTTGGC<br>AGGGCGGGCGGTGCGGGTTCGCGGCGAGGCGCAGGGTGTCATGGCAAATGTTACGGCTCAGATTAAGCGAT<br>TGTTAATTAAAAAGCGACGGTAATTAATACTCGCTACGCCATATGGGCCCGTGAAAAGGCACAAAAGGTTT<br>CTCCGCATGTGGGGTTCCCCTTCTCTTTTCTCCTTCCACAAAAGCACCCCAGCCCGTGGGTCCCCCTTTG<br>GCCCCAAGGTAGGTGGAACTCGTCACTTCCGGCCAGGGAGGGGATGGGGCGGTCTCCGGCGAGTTCCAAGG<br>GCGTCCCTCGTTGCGCACTCGCCCGCCCAGGTTCTTTGAA |
| 46 | chr7 group-00267 | GGGAAGCGATCGTCTCCTCTGTCAACTCGCGCCTGGGCACTTAGCCCCTCCCGTTTCAGGGCGCCGCCTCC<br>CCGGATGGCAAACACTATAAAGTGGCGGCGAATAAGGTTCCTCCTGCTGCTCTCGGTTTAGTCCAAGATCA<br>GCGATATCACGCGTCCCCCGGAGCATCGCGTGCAGGAGCCATGCGCGGGAGCTATACCACGAAGAGTTCG<br>CCCGGCGGGCAAGCAGGCGGGGCTGCAGGTCTGGAGGATTGAGAAGCTGGAGCTGGTGCCCGTGCCCCAG<br>AGCGCTCACGGCGACTTCTACGTCGGGGATGCCTACCTGGTGCTGCACACGGCCAAGACGAGCCGAGGCTT<br>CACCTACCACCTGCACTTCTGGCTCGGTAAGGGACGGCGGGCGGCGGGACCCCGACGCACCAAGGCCGGCG<br>AGGGGAGGGCGTAGGGGTCTGAGATTTGCAGGCGTGGGAGTAAAGGGGACCGCAAACTGAGCTAG |
| 47 | NPY | CTCAGGGGCGGGAAGTGGCGGGTGGGAGTCACCCAAGCGTGACTGCCCGAGGCCCCTCCTGCCGCGGCGAG<br>GAAGCTCCATAAAAGCCCTGTCGCGACCCGCTCTCTGCACCCCATCCGCTGGCTCTCACCCCTCGGAGACG<br>CTCGCCCGACAGCATAGTACTTGCCGCCCAGCCACGCCCGCGCGCCAGCCACCGTGAGTGCTACGACCCGT<br>CTGTCTAGGGGTGGGAGCGAACGGGGCGCCCGCGAACTTGCTAGAGACGCAGCCTCCCGCTCTGTGGAGCC<br>CTGGGGCCCTGGGATGATCGCGCTCCACTCCCCAGCGGACTATGCCGGCTCCGCGCCCCGACGCGGACCAG<br>CCCTCTTGGCGGCTAAATTCCACTTGTTCCTCTGCTCCCCTCTGATTGTCCACGGCCCTTCTCCCGGGCCC<br>TTCCCGCTGGGCGGTTCTTCTGAGTTACCTTTTAGCAGATATGGAGGGAGAACCCGGGACCGCTATCCCAA<br>GGCAGCTGGCGGTCTCCCTGCGGGTCGCCGCCTTGAGGCCCAGGAAGCGGTGCGCGGTAGGAAGGTTTCCC<br>CGGCAGCGCCATCGAGTGAGGAATCCCTGGAGCTCTAGAGCCCCGCGCCTGCCACCTCCCTGGATTCTTG<br>GGCTCCAAATCTCTTTGGAGCAATTCTGGCCCAGGGAGCAATTCTCTTTCCCCTTCCCCACCGCAGTCGTC<br>ACCCCGAGGTGATCTCTGCTGTCAGCGTTGATCCCCTGAAGCTAGGCAGACCAGAAGTAACAGAGAAGAAA<br>CTTTTCTTCCCAGACAAGAGTTTGGGCAAGAAGGGAGAAAAGTGACCCAGCAGGAAGAACTTCCAATTCGG<br>TTTTGAATGCTAAACTGGCGGGGCCCCCACCTTGCACTCTCGCCGCGCGCTTCTTGGTCCCTGAGACTTCG<br>AACGAAGTTGCGCGAAGTTTTCAGGTGGAGCAGAGGGGCAGGTCCCGACCGGACGGCGCCCGGAGCCCGCA<br>AGGTGGTGCTAGCCACTCCTGGGTTCTCTCTGCGGGACTGGGACGAGAGCGGATTGGGGGTCGCGTGTGGT<br>AGCAGGAGGAGGAGCGCGGGGGCAGAGGAGGGAGGTGCTGCGCGTGGGTGCTCTGAATCCCCAAGCCCGT<br>CCGTTGAGCCTTCTGTGCCTGCAGATGCTAGGTAACAAGCGACTGGGGCTGTCCGGACTGACCCTCGCCCT<br>GTCCCTGCTCGTGTGCCTGGGTGCGCTGGCCGAGGCGTACCCCTCCAAGCCGGACAACCCGGGCGAGGACG<br>CACCAG |
| 48 | SHH | TGGAGAACCTTGGGCTCTGTGGCCTCAAAGGTAGGGTGATTTCGAGGGGCCGGCACCTCACAGGGCAGGT<br>TCCACCGCGGAAACGCAGTCATCGCCCAGCGACCCTGCTCCTGGCCCTCAGCCTCCCCCAGGTTTCTTTT<br>TCTCTTGAATCAAGCCGAGGTGCGCCAATGGCCTTCCTTGGGTCGGATCCGGGGGGCCAGGGCCAGCTTAC<br>CTGCTTTCACCGAGCAGTGGATATGTGCCTTGGACTCGTAGTACACCCAGTCGAAGCCGGCCTCCACCGCC<br>AGGCGGGCCAGCATGCCGTACTTGCTGCGGTCGCGGTCAGACGTGGTGATGTCCACTGCGGCGCCCTCGTA<br>GTGCAGAGACTCCTCTGAGTGGTGGCCATCTTCGTCCCAGCCCTCGGTCACCCGCAGTTTCACTCCTGGCC<br>ACTGGTTCATCACCGAGATGGCCAAAGCGTTCAACTTGTCCTTACACCTCTGCGAAGACAAGGGGACCCCC<br>ACCGACGGACACGTTAGCCTGGGCAACCGCCACCCCTCCCGGCCCCTCCATCAGCCT |
| 49 | OSR2 | TCTCACGACCCATCCGTTAACCCACCGTTCCCAGGAGCTCCGAGGCGCAGCGGCGACAGAGGTTCGCCCCG<br>GCCTGCTAGCATTGGCATTGCGGTTGACTGAGCTTCGCCTAACAGGCTTGGGGAGGGTGGGCTGGGCTGGG<br>CTGGGCTGGGCTGGGTGCTGCCCGGCTGTCCGCCTTTCGTTTTCCTGGGACCGAGGAGTCTTCCGCTCCGT<br>ATCTGCCTAGAGTCTGAATCGACTTTCTTTCCTTTGGGCACCGCGCTCGCCAGTGGAGCACTTCTTGTTCT<br>GGCCCCGGGCTGATCTGCACGCGGACTTGAGCAGGTGCCAAGGTGCCACGCAGTCCCCTCACGGCTTTCGG<br>GGGGTCTTGGAGTCGGGTGGGAGGGAGACTTAGGTGTGGTAACCTGCGCAGGTGCCAAAGGGCAGAAGGA<br>GCAGCCTTGGATTATAGTCACGGTCTCTCCCTCTCTTCCCTGCCATTTTTAGGGCTTTCTCTACGTGCTGT<br>TGTCTCACTGGGTTTTTGTCGGAGCCCCACGCCCTCCGGCCTCTGATTCCTGGAAGAAAGGGTTGGTCCCC<br>TCAGCACCCCCAGCATCCCGGAAAATGGGGAGCAAGGCTCTGCCAGCGCCCATCCCGCTCCACCCGTCGCT |

TABLE 4-continued

| SEQ ID NO | GENE NAME | SEQUENCE |
|---|---|---|
| | | GCAGCTCACCAATTACTCCTTCCTGCAGGCCGTGAACACCTTCCCGGCCACGGTGGACCACCTGCAGGGCC<br>TGTACGGTCTCAGCGCGGTACAGACCATGCACATGAACCACTGGAGCGCTGGGGTATCCCAAT |
| 50 | GLIS3 | TGGTTTCCTTTCGCTTCTCGCCTCCCAAACACCTCCAGCAAGTCGGAGGGCGCGAACGCGGAGCCAGAAAC<br>CCTTCCCCAAAGTTTCTCCCGCCAGGTACCTAATTGAATCATCCATAGGATGACAAATCAGCCAGGGCCAA<br>GATTTCCAGACACTTGAGTGACTTCCCGGTCCCCGAGGTGACTTGTCAGCTCCAGTGAGTAACTTGGAACT<br>GTCGCTCGGGGCAAGGTGTGTGTCTAGGAGAGAGCCGGCGGCTCACTCACGCTTTCCAGAGAGCGACCCGG<br>GCCGACTTCAAAATACACACAGGGTCATTTATAGGGACTGGAGCCGCGCGCAGGACAACGTCTCCGAGACT<br>GAGACATTTTCCAAACAGTGCTGACATTTTGTCGGGCCCCATAAAAAATGTAAACGCGAGGTGACGAACCC<br>GGCGGGGAGGGTTCGTGTCTGGCTGTGTCTGCGTCCTGGCGGCGTGGGAGGTTATAGTTCCAGACCTGGCG<br>GCTGCGGATCGCCGGGCCGGTACCCGCGAGGAGTGTAGGTACCCTCAGCCCGACCACCTCCCGCAATCATG<br>GGGACACCGGCTTGGATGAGACACAGGCGTGGAAAACAGCCTTCGTGAAACTCCACAAACACGTGGAACTT<br>GAAAAGACAACTACAGCCCCGCGTGTGCGCGAGAGACCTCACGTCACCCCATCAGTTCCCACTTCGCCAAA<br>GTTTCCCTTCAGTGGGGACTCCAGAGTGGTGCGCCCCATGCCCGTGCGTCCTGTAACGTGCCCTGATTGTG<br>TACCCCTCTGCCCGCTCTACTTGAAATGAAAACACAAAAACTGTTCCGAATTAGCGCAACTTTAAAGCCCC<br>GTTATCTGTCTTCTACACTGGGCGCTCTTAGGCCACTGACAGAAACATGGTTTGAACCCTAATTGTTGCTA<br>TCAGTCTCAGTCAGCGCAGGTCTCTCAGTGACCTGTGACGCCGGGAGTTGAGGTGCGCGTATCCTTAAACC<br>CGCGCGAACGCCACCGGCTCAGCGTAGAAAACTATTTGTAATCCCTAGTTTGCGTCTCTGAGCTTTAACTC<br>CCCCACACTCTCAAGCGCCCGGTTTCTCCTCGTCTCTCGCCTGCGAGCAAAGTTCCTATGGCATCCACTTA<br>CCAGGTAACCGGGATTTCCACAACAAAGCCCGGCGTGCGGGTCCCTTCCCCGGCCGGCCAGCGCGAGTGA<br>CAGCGGGCGGCCGGCGCTGGCGAGGAGTAACTTGGGGCTCCAGCCCTTCAGAGCGCTCCGCGGGCTGTGCC<br>TCCTTCGGAAATGAAAACCCCCATCCAAACGGGGGGACGGAGCGCGAAACCCGGCCCAAGTGCCGTGTGT<br>GCGCGCGCGTCTG |
| 51 | PRMT8 | GAAAGCCATCCTTACCATTCCCCTCACCCTTCCGCCCTCTGATCGCCCACCCGCCGAAAGGGTTTCTAAAAA<br>TAGCCCAGGGCTTCAAGGCCGCGCTTCTGTGAAGTGTGGAGCGAGCGGGCACGTAGCGGTCTCTGCCAGGT<br>GGCTGGAGCCCTGGAAGCGAGAAGGCGCTTCCTCCCTGCATTTCCACCTCACCCCACCCCCGGCTCATTTT<br>TCTAAGAAAAAGTTTTTGCGGTTCCCTTTGCCTCCTACCCCCGCTGCCGCGCGGGGTCTGGGTGCAGACCC<br>CTGCCAGGTTCCGCAGTGTGCAGCGGCGGCTGCTGCGCTCTCCCAGCCTCGGCGAGGGTTAAAGGCGTCCG<br>GAGCAGGCAGAGCGCCGCGCGCCAGTCTATTTTTACTTGCTTCCCCCGCCGCTCCGCGCTCCCCCTTCTCA<br>GCAGTTGCACATGCCAGCTCTGCTGAAGGCATCAATGAAAACAGCAGTAG |
| 52 | TBX3 | ATCGAAAATGTCGACATCTTGCTAATGGTCTGCAAACTTCCGCCAATTATGACTGACCTCCCAGACTCGGC<br>CCCAGGAGGCTCGTATTAGGCAGGGAGGCCGCCGTAATTCTGGGATCAAAAGCGGGAAGGTGCGAACTCCT<br>CTTTGTCTCTGCGTGCCCGGCGCGCCCCCTCCCGGTGGGTGATAAACCCACTCTGGCGCCGGCCATGCGC<br>TGGGTGATTAATTTGCGAACAAACAAAAGCGGCCTGGTGGCCACTGCATTCGGGTTAAACATTGGCCAGCG<br>TGTTCCGAAGGCTTGT |
| 53 | chr12 group-00801 | ATCAACATCGTGGCTTTGGTCTTTTCCATCATGGTGAGTGAATCACGGCCAGAGGCAGCCTGGGAGGAGAG<br>ACCCGGGCGGCTTTGAGCCCTGCAGGGGAGTCCGCGCGCTCTCTGCGGCTCCCTTCCTCACGGCCCGGCC<br>CGCGCTAGGTGTTCTTTGTCCTCGCACCTCCTCCTCACCTTTCTCGGGCTCTCAGAGCTCTCCCCGCAATC<br>ATCAGCACTTCCTCTGCACTCCTCGTGGTACTCAGAGCCCTGATCAAGCTTCCCCCAGGCTAGCTTTCCTC<br>TTCTTTTCCAGCTCCCAGGGTGCGTTTCCTCTCCAACCCGGGGAAGTTCTTCCGTGGACTTTGCTGACTCCT<br>CTGACCTTCCTAGGCACTTGCCCGGGGCTTCTCAACCCTCTTTTCTAGAGCCCCAGTGCGCGCACCCTAG<br>CGAGCGCAGTAAGCTCATACCCCGAGCATGCAGGCTCTACGTTCCTTTCCCTGCCGCTCCGGGGCTCCTG<br>CTCTCCAGCGCCCAGGACTGTCTCTATCTCAGCCTGTGCTCCCTTCTCTCTTTGCTGCGCCCAAGGGCACC<br>GCTTCCGCCACTCTCCGGGGGTCCCCAGGCCGATTCCTGATGCCCCTCCTTGATCCCGTTTCCGCGCTTTT<br>GGCACGGCACGCTCTGTCCAGGCAACAGTTTCCTCTCGCTTCTTCCTACACCCAACTTCCTCTCCTTGCCT<br>CCCTCCGGCGCCCCTTTTTAACGCGCCCGAGGCTGGCTCACACCCACTACCTCTTTAGGCCTTTCTTAGG<br>CTCCCGTGTGCCCCCCTCACCAGCAAAGTGGGTGCGCCTCTCTTACTCTTTCTACCCAGCGCGTCGTAGT<br>TCCTCCCCGTTTGCTGCGCACTGGCCCTAACCTCTCTTCTCTTGGTGTCCCCCAGAGCTCCCAGGCGCCCC<br>TCCACCGCTCTGTCCTGCGCCCGGGGCTCTCCCGGGAATGAACTAGGGGATTCCACGCAACGTGCGGCTCC<br>GCCCGCCCTCTGCGCTCAGACCTCCCGAGCTGCCCGCCTCTCTAGGAGTGGCCGCTGGGGCCTCTAGTCCG<br>CCCTTCCGGAGCTCAGCTCCCTAGCCCTCTTCAACCCTGGTAGGAACACCCGAGCGAACCCCACCAGGAGG<br>GCGACGAGCGCCTGCTAGGCCCTCGCCTTATTGACTGCAGCAGCTGGCCCGGGGTGGCGGCGGGGTGAGG<br>TTCGTACCGGCACTGTCCCGGGACAACCCTTGCAGTTGC |
| 54 | PAX9 | ACAAATAAAACACCCTCTAGCTTCCCCTAGACTTTGTTTAACTGGCGGGTCTCCAGAAGGAACGCTGGGG<br>ATGGGATGGGTGGAGAGAGGGAGCGGCTCAAGGACTTTAGTGAGGAGCAGGCGAGAAGGAGCACGTTCAGG<br>CGTCAAGACCGATTTCTCCCCCTGCTTCGGGAGACTTTTGAACGCTCGGAGAGGCCCGGCATCTCACCACT<br>TTACTTGGCCGTAGGGGCCTCCGGCACGGCAGGAATGAGGGAGGGGGTCCGATTGGACAGTGACGGTTTGG<br>GGCCGTTCGGCTATGTTCAGGGACCATATGGTTTGGGGACAGCCCCAGTAGTTAGTAGGGGACGGGTGCGT<br>TCGCCCAGTCCCCGGATGCGTAGGGAGGCCCAGTGGCAGGCAGCTGTCCCAAGCAGCGGGTGCGCGTCCCT<br>GCGCGCTGTGTGTTCATTTTGCAGAGCCAGCCTTCGGGGAGGTGAACAGCTGGGAGGAGTGTTCGTGAAC<br>GGGAGGCCGCTGCCCAACGCCATCCGGCTTCGCATCGTGGAACTGGCCCAACTGGGCATCGACCGTGTGA<br>CATCAGCCGCCAGCTACGGGTCTCGCACGGCTGCGTCAGCAAGATCCTGGCGCGATACAACGAGACGGGCT<br>CGATCTTGCCAGGAGCCATCGGGGCAGCAAGCCCCGGGTCACTACCCCACCGTGGTGAAACACATCCGG<br>ACCTACAAGCAGAGACCCCGGCATCTTCGCCTGGGACATCCGGGACCGCCTGCTGGCGGACGGCGTGTG<br>CGACAAGTACAATGTGCCCTCCGTGAGCTCCATCAGCCGCATTCTGCGCAACAAGATCGGCAACTTGGCCC<br>AGCAGGGTCATTACGACTCATACAAGCAGCACCAGCCGACGCCGCAGCCAGCGCTGCCCTACAACCACATC<br>TACTCGTACCCCAGCCCTATCACGGCGGCGGCCGCCAAGGTGCCCACGCCACCCGGGTGC |
| 55 | SIX1 | AGGAGGCGCAACGCGCTGCCAGGGCGGCTTTATCCTGCCGCCACAGGGCGGGGACCAGCCCGGCAGCCGGG<br>TGTCCAGCGCCGCTCACGTGCCTCGCCTGGAGCTTAGCTCTCAGACTCCGAAGAGGGCGACTGAGACTTGG<br>GCCTGGGAGTTGGCTTCGGGGTACCCAAGGCGACGACAGCTGAGTTGTACCACGAAGCTCAGGCCGAGGCC<br>TCCTCCCCTTGTCTGGCCTTCGAATCCATACTGGCAGCCTCTCCTCTCAGGCACTCCGCGGGCCGGGCCACT |

TABLE 4-continued

| SEQ ID NO | GENE NAME | SEQUENCE |
|---|---|---|
| | | AGGCCCCCTGCTCCTGGAGCTGCGCTATGATCCGGGTCTTGAGATGCGCGCGATTCTCTCTGAACCGGTGG<br>AGAGGAGGCTCTGCCCCGCGCGGAGCGAGGACAGCGGCGCCCGAGCTTCCCGCGCCTCTCCAGGGCCCAAT<br>GGCAAGAACAGCCTCCGAAGTGCGCGGATGACAGGAAAAGATCTTCAGTTCTTCTGCCGCTAGAGAAGTGC<br>GGGATACAAGCCTCTATTGGATCCACAACCTGGAGTCCTGCCTTCGGA |
| 56 | ISL2 | ATCTGCGTGCCCTTTTCTGGGCGAGCCCTGGGAGATCCAGGGAGAACTGGGCGCTCCAGATGGTGTATGTC<br>TGTACCTTCACAGCAAGGCTTCCCTTGGATTTGAGGCTTCCTATTTTGTCTGGGATCGGGGTTTCTCCTTG<br>TCCCAGTGGCAGCCCCGCGTTGCGGGTTCCGGGCGCTGCGCGGAGCCCAAGGCTGCATGGCAGTGTGCAGC<br>GCCCGCCAGTCGGGCTGGTGGGTTGTGCACTCCGTCGGCAGCTGCAGAAAGGTGGGAGTGCAGGTCTTGCC<br>TTTCCTCACCGGGCGGTTGGCTTCCAGCACCGAGGCTGACCTATCGTGGCAAGTTTGCGGCCCCCGCAGAT<br>CCCCAGTGGAGAAAGAGGGCTCTTCCGATGCGATCGAGTGTGCGCCTCCCCGCAAAGCAATGCAGACCCTA<br>AATCACTCAAGGCCTGGAGCTCCAGTCTCAAAGGTGGCAGAAAAGGCCAGACCTAACTCGAGCACCTACTG<br>CCTTCTGCTTGCCCCGCAGAGCCTTCAGGGACTGACTGGGACGCCCTGGTGGCGGGCAGTCCCATCCGCC<br>ATGAGAACGCCGTGCAGGGCAGCGCAGTGGAGGTGCAGACGTACCAGCCGCCGTGGAAGGCGCTCAGCGAG<br>TTTGCCCTCCAGAGCGACCTGGACCAACCCGCCTTCCAACAGCTGGTGAGGCCCTGCCCTACCCGCCCGA<br>CCTCGGGACTCTGCGGGTTGGGGATTTAGCCACTTAGCCTGGCAGAGAGGGGAGGGGGTGGCCTTGGGCTG<br>AGGGGCTGGGTACAGCCCTAGGCGGTGGGGAGGGGGAACAGTGGCGGGCTCTGAAACCTCACCTCGGCCC<br>ATTACGCGCCCTAAACCAGGTCTCCCTGGATTAAAGTGCTCACAAGAGAGGTCGCAGGATTAACCAACCCG<br>CTCCCCCGCCCTAATCCCCCCTCGTGCGCCTGGGGACCTGGCCTCCTTCTCCGCAGGGCTTGCTCTCAGC<br>TGGCGGCCGGTCCCCAAGGGACACTTTCCGACTCGGAGCACGCGGCCCTGGAGCACCAGCTCGCGTGCCTC<br>TTCACCTGCCTCTTCCCGGTGTTTCCGCCGCCCCAGGTCTCCTTCTCCGAGTCCGGCTCCCTAGGCAACTC<br>CTCCGGCAGCGACGTGACCTCCCTGTCCTCGCAGCTCCCGGACACCCCCAACAGTATGGTGCCGAGTCCCG<br>TGGAGACGTGAGGGGGACCCCTCCCTGCCAGCCCGCGGACCTCGCATGCTCCTGCATGAGACTCACCCAT<br>GCTCAGGCCATTCCAGTTCCGAAAGCTCTCTCGCCTTCGTAATTATTCTATTGTTATTTATGAGAGAGTAC<br>CGAGAGACACGGTCTGGACAGCCCAAGGCGCCAGGATGCAACCTGCTTTCACCAGACTGCAGACCCCTGCT<br>CCGAGGACTCTTAGTTTTTCAAAACCAGAATCTGGGACTTACCAGGGTTAGCTCTGCCCTCTCCTCCTC<br>TCTACGTGGCCGCCGCTCTGTCTCTCCACGCCCCACCTGTGT |
| 57 | DLX4 | AGGTCTCTTCAGACTGCCCATTCTCCGGGCCTCGCTGAATGCGGGGGCTCTATCCACAGCGCGCGGGGCCG<br>AGCTCAGGCAGGCTGGGGCGAAGATCTGATTCTTTCCTTCCCGCCGCCAAACCGAATTAATCAGTTTCTTC<br>AACCTGAGTTACTAAGAAAGAAAGGTCCTTCCAAATAAAACTGAAAATCACTGCGAATGACAATACTATAC<br>TACAAGTTCGTTTTGGGGCCGGTGGGTGGGATGGAGGAGAAAGGGCACGGATAATCCCGGAGGGCCGCGGA<br>GTGAGGAGGACTATGGTCGCGGTGGAATCTCTGTTCCGCTGGCACATCCGCGCAGGTGCGGCTCTGAGTGC<br>TGGCTCGGGGTTACAGACCTCGGCATCCGGCTGCAGGGGCAGACAGAGACCTCCTCTGCTAGGGCGTGCGG<br>TAGGCATCGTATGGAGCCCAGAGACTGCCGAGAGCACTGCGCACTCACCAAGTGTTAGGGGTGCCCGTGAT<br>AGACCGCCAGGGAAGGGCTGGTTCGGAGGGAATTCCCGCTACCGGGAAGGTCGGAACTCGGGGTGATCAA<br>ACAAGGAATGCATCTCACCTCCGTGGGTGCTTGTGCTGCGCAAGGAATTATTACCGGAGCGGTTGCGATGG<br>CCTTTGCCCGGCGACCCAAGAAGAGTAAGCAAACTACCGTCCACCCAGCGGATCAGGTCCAAT |
| 58 | CBX4 | GATGTCCTGTTTCTAGCAGCCTCCAGAGCCAAGCTAGGCGAGAGGCGTAGGAGGCAGAGAGAGCGGGCGCG<br>GGAGGCCAGGGTCCGCCTGGGGGCCTGAGGGGACTTCGTGGGGTCCCGGGAGTGGCCTAGAAACAGGGAGC<br>TGGGAGGGCCGGGAAGAGCTTGAGGCTGAGCGGGGGACGAACGGGCAGCGCAAAGGGGAGATGAACGGAAT<br>GGCCGAGGAGCCACGCATTCGCCTTGTGTCCGCGGACCCTTGTTCCCGACAGGCGACCAAGCCAAGGCCCT<br>CCGGACTGACGCGGCCTGAGCAGCAGCGAGTGTGAAGTTTGGCACCTCCGGCGGCGAGACGGCGCGTTCTG<br>GCGCGCGGCTCCTGCGTCCGGCTGGTGGAGCTGCTGCGCCCTATGCGGCCTGCCGAGGGCGCCGCCGAGGG<br>CCCGCGAGCTCCGTGGGGTCGGGGTGGGGGGCCCGGGAGCGGACAGCGCGGCCCGAGGGGCAGGGGCAGG<br>GGCGCGCCTGGCCTGGGGTGTGTCTGGGCCCCGGCTCCGGGCTCTTGAAGGACCGCGAGCAGGAGGCTTGC<br>GCAATCCCTTGGCTGAGCGTCCACGGAGAAAGAAAAAGAGCAAAAGCAGAGCGAGAGTGGAGCGAGGGATG<br>GGGGCGGGCAAAGAGCCATCCGGGTCTCCACCACCGCCCTGACACGCGACCCGGCTGTCTGTTGGGGACCG<br>CACGGGGGCTCGGGCGAGCAGGGGAGGGAGGAGCCTGCGCGGGGCTCGTGTTCGCCCAGGAATCCCGGAGA<br>AGCTCGAAGACGGTCTGGTGTTGAACGCACACGTGGACTCCATTTCATTACCACCTTGCAGCTCTTGCGCC<br>ACGGAGGCTGCTGCTGCCCGGCGGCTGCTACCCACCGAGACCCACGTGGCCCCTCCCCAGGGGTGTAGGGG<br>TGACGGTTGTCTTCTGGTGACAGCAGAGGTGTTGGGTTTGCGACTGATCTCTAACGAGCTTGAGGCGCAAA<br>CCTAGGATTCCCTGAGTGTTGGGGTGCGGCGGGGGGGCAAGCAAGGTGGGACGACGCCTGCCTGGTTTCCC<br>TGACTAGTTGCGGGGGTGGGGGCCGGCTCTCAGGGGCCACCAGAAGCTGGGTGGGTGTACAGGAAAATAT<br>TTTTCCTGCCGTGTTTGGCTTTTTCCTGGCATTTTTGCCCAGGGCGAAGAACTGTCGCGCGGGGCAGCT<br>CCACCGCGGAGGGAGAGGGGTCGCGAGGCTGGCGCGGGAAGCGCTGTAGGTGGCAGTCATCCGTCCACGCC<br>GCACGCCGTCTGCGCCGTCGGACCATCGGGAGGTCTGCAGCAACTTTGTCCCGGCCAGTCCCCTTGTCC<br>GGGAAGGGCTGAGCTTCCCGACACTCTACCCTCCCCCTCTTGAAAATCCCCTGGAAAATCTGTTTGCAAT<br>GGGTGTTTCCGCGGCGTCCAGGTCTGGGCTGCCGGGGGAGGCCGAGCGGCTGCTGCAGCCTCCCTGCTGCC<br>AGGGGCGTCGGACTCCGCTTCGCTCACTACGCCCAGGCCCCTCAGGGGCCCACGCTCAGGACTTCGGGGCC<br>ACACAGCAGGACCCGGTGCCCCGACGACGAGTTTGCGCAGGACCCGGGCTGGGCCAGCCGCGGAGCTGGGG<br>AGGAAGGGGCGGGGGTCGGTGCAGGCGGATCTTTTCTGTTGCTGCCTGTGCGGCGCAGGAGGCGTCTTGAG<br>GCTCCCCAAGACTACCTGAGGGGCCGCCCAAGCACTTCAGAAGCCAAGGAGCCCCGGCCACCCCCGCTC<br>CTGGCCTTTTTGCCAACGACTTTGAAAGTGAAATGCACAAGCACCAGCAATTGACTTCCCTTCCGTGGTTA<br>TTTATTTTGTCTTTGTGGATGGTGGGCAGATGGGGAGAGAGGCCCCTACCTAACCTCGGTGGCTGGTCCCT<br>AGACCACCCCTGCCAGCCGGTGTGGGGAGGAGCTCAGGTCCGCGGGAGAGCGAATGGGGCGCCAGGAGGTGG<br>GACAGAATCCTGGGAAGGTACAGCGGACGCCCTGGAAGCTCCCCTGATGCCCCAGAGGGCCCTTCCTGGGA<br>AACCTCCCGGGGGGTGCCCCATACCATCCCACCCGGCTGTCTTGGCCCCTCCCAGGGAGCCGCAGGAGAA<br>ACTAGCCCTACACCTGGGATTCCCAGAGCCTTCTGCTGGGGCTCCTGCCCCCGACTTCGGATAACCAGCTC<br>CGCACAGTCCCGAGAAGGGCCGCTGGCCTGCTTATTTGATACTGCCCCCTCCCAGACAGGGGCTGGTCG<br>AGCCCCTGGTTCTGCTGCCAGACTGAAGCCTTCAGACGCCACCTCGGTTTGGGCCCCAGGGCCCTCAGG<br>GGCCCCAGGAGAGGAGAGCTGCTATCTAGCTCAGCCACAGGCTCGCTCCTGGTGGGGGCCAGGCTGAAGGA<br>GTGGACCCTGGAGAGGTCGGGAACCTTTTAACAGCCGTGGGCTGGAGGGTGGCTACTAAGTGTTCGGTCTG<br>GGAAGAGGCATGACCCGCACCATCCCGGGAAATAAACGACTTCTTAAGGGAATCTTCTCGCTGAGCGGGT<br>GCTCTGGGCCAGGAGATTGCCACCGCCAGCCCACGGAACCCAGATTTGGGCTCTGCCTTGAGCGGGCCGCC |

TABLE 4-continued

| SEQ ID NO | GENE NAME | SEQUENCE |
|---|---|---|
| | | TGTGGCTTCCCGGGTCGCTCCCCCGACTCAGAAAGCTCTCAAGTTGGTATCGTTTTCCCGGCCCTCGGAGG
TGGATTGCAGATCACCGAGAGGGGATTTACCAGTAACCACTACAGAATCTACCCGGGCTTTAACAAGCGCT
CATTTCTCTCCCTTGTCCTTAGAAAAACTTCGCGCTGGCGTTGATCATATCGTACTTGTAGCGGCAGCTTA
GGGGCAGCGGAACTGGTGGGGTTGTGCGTGCAGGGGGAGGCTGTGAGGGGAGCCCTGCACTCCGCCCCTCCA
CCCTTCTGGAGGAGTGGCTTTGTTTCTAAGGGTGCCCCCCAACCCCCGGGTCCCCACTTCAATGTTTCTG
CTCTTTGTCCCACCGCCCGTGAAAGCTCGGCTTTCATTTGGTCGGCGAAGCCTCCGACGCCCCGAGTCCC
ACCCTAGCGGGCCGCGCGGCACTGCAGCCGGGGGTTCCTGCGGACTGGCCCGACAGGGTGCGCGGACGGGG
ACGCGGGCCCCGAGCACCGCGACGCCAGGGTCCTTTGGCAGGGCCCAAGCACCCCT |
| 59 | EDG6 | TGGCGGCCGGCGGGCACAGCCGGCTCATTGTTCTGCACTACAACCACTCGGGCCGGCTGGCCGGGCGCGGG
GGGCCGGAGGATGGCGGCCTGGGGGCCCTGCGGGGGCTGTCGGTGGCCGCCAGCTGCCTGGTGGTGCTGGA
GAACTTGCTGGTGCTGGCCGGCCATCACCAGCCACATGCGGTCGCGACGCTGGGTCTACTATTGCCTGGTGA
ACATCGCTGAGTGACCTGCTCACGGGCGCGGCCTACCTGGCCAACGTGCTGCTGTCGGGGGCCCGCACC
TTCCGTCTGGCGCCCGCCCAGTGGTTCCTACGGGAGGGCCTGCTCTTCACCGCCCTGGCCGCCTCCACCTT
CAGCCTGCTCTTCACTGCAGGGGAGCGCTTTGCCACCATGGTCGGCCGGTGGCCGAGAGCGGGGCCACCA
AGACCAGCCGCGTCTACGGCTTCATCGGCCTCTGCTGGCTGCTGGCCGCGCTGCTGGGGATGCTGCCTTTG
CTGGGCTGGAACTGCCTGTGCGCCTTTGACCGCTGCTCCAGCCTTCTGCCCCTCTACTCCAAGCGCTACAT
CCTCTTCTGCCTGGTGATCTTCGCCGGCGTCCTGGCCACCATCATGGGCCTCTATGGGGCCATCTTCCGCC
TGGTGCAGGCCAGCGGGCAGAAGGCCCCACGCCCAGCGGCCCGCCGCAAGCCCGCCGCTGCTGAAGACG
GTGCTGATGATCCTGCTGGCCTTCCTGGTGTGCTGGGGCCCACTCTTCGGGCTGCTGCTGGCCGACGTCTT
TGGCTCCAACCTCTGGGCCCAGGAGTACCTGCGGGGCATGGACTGGATCCTGGCCCTGGCCGTCCTCAACT
CGGCGGTCAACCCCATCATCTACTCCTTCCGCAGCAGGGAGGTGTGCAGAGCCGTGCTCAGCTTCCTCTGC
TGCGGGTGTCTCCGGCTGGGCATGCGAGGGCCCGGGGACTGCCTGGCCCGGGCCGTCGAGGCTCACTCCGG
AGCTTCCACCACCGACAGCTCTCTGAGGCCAAGGGACAGCTTTC |
| 60 | chr13
group-
00005 | TAGTAAGGCACCGAGGGGTGGCTCCTCTCCCTGCAGCGGCTGTCGCTTACCATCCTGTAGACCGTGACCTC
CTCACACAGCGCCAGGACGAGGATCGCGGTGAGCCAGCAGGTGACTGCGATCCTGGAGCTGGTCGCAGCAG
GCCATCCTGCACGCGGTGGAGGCGCCCCCTGCAGGCCGCAGCGCATCCCCAGCTTCTGGACGCACTGTGAG
CGGTTATGCAGCAGCACGCTCATATGAGATGCCCCGCAGGGTGCTATGCAGGCCACGTCCCCACAAAGCC
CATGGCAGGCGCCCGGGTGCCGGAGCACGCACTTGGCCCCATGGATCTCTGTGCCCAGGGCTCAGCCAGGC
ATCTGGCCGCTAAAGGTTT |
| 61 | CRYL1 | TCTCATCTGAGCGCTGTCTTTCACCAGAGCTCTGTAGGACTGAGGCAGTAGCGCTGGCCCGCCTGCGAGAG
CCCGACCGTGGACGATGCGTCGCGCCCTTCCCATCGCGGCCTGGGCGGGCCCGCCTGCCCTCGGCTGAGCC
CGGTTTCCCTACCCCGGGGCACCTCCCCTCGCCCGCACCCGGCCCCAGTCCCTCCCAGGCTTGCGGGTAGA
GCCTGTCTTTGCCCAGAAGGCCGTCTCCAAGCT |
| 62 | IL17D | CAGTCCCCGAGGCCCTCCCCGGTGACTCTAACCAGGAGATTTCAGCGCGCGGCGCGGGGCTGCCCCCAGGCG
TGACCTCACCCGTGCTCTCTCCCTGCAGAATCTCCTACGACCCGGCGAGGTACCCCAGGTACCTGCCTGAA
GCCTACTGCCTGTGCCGGGGCTGCCTGACCGGGCTGTTCGGCGAGGAGGACGTGCGCTTCCGCAGCGCCCC
TGTCTACAT |
| 63 | IRS2 | AGAGAGACATTTTCCACGGAGGCCGAGTTGTGGCGCTTGGGGTTGTGGGCGAAGGACGGGGACACGGGGGT
GACCGTCGTGGTGGAGGAGAAGGTCTCGGAACTGTGGCGGCGGCGGCCCCCCTGCGGGTCTGCGCGGATGA
CCTTGGCGCCGCGGTGGGGGTCCGGGGGCTGGCTGGCCTGCAGGAAGGCCTCGACTCCCGACACCTGCTCC
ATGAGGCTCAGCCTCTTCACGCCCGACGTCGGGCTGGCCACGCGGGCAGCTTCTGGCTTCGGGGGGCCGC
GATAGGTTGCGGCGGGGTGGCGGCCACACCAAAAGCCATCTGGTGTAGTCACCATTGTCCCCGGTGTCCG
AGGACAACGATGAGGCGGCGCCCGGGCCCTGGGCGGTGGCAACGGCCGAGGCGGGGGGCAGGCGGTACAGC
TCCCCCGGGGCCGGCGGCGGTGGCGGCGGCTGCAGAGACGACGACGGGGACGCGGACGGACGCGGGGGCAA
CGGCGGATACGGGGAGGAGGCCTCGGGGGACAGGAGGCCGTCCAAGGAGCCCACGGGGTGGCCGCTCGGGG
CGCCCCGGCTTAGGAGACTTGGGGGAGCTGAAGTCGAGGTTCATGTAGTCGGAGAGCGGAGACCGCTGCCGG
CTGTCGCTGCTGGTGCCCGGGGTGCCTGAGCCCAGCGACGAGGCCGGGCTGCTGGCGGACAAGAGCGAGGA
GGACGAGCCGCCGACGCCAGCAGGGGAGGCGCGGGCGGCGACAGGCGGGCCCGGGCTCGCCAAAGTCGA
TGTTGATGTACTCGCCGGGGCTCTTGGGCTCCGGTGGCAGTGGGTACTCGTGCATGCTGGGCAGGCTGGGC
AGCCCCTCAGGGACAGGCGCGTGGGCCTCACCGCCCGGCCGCGCTGGCCAAGAAGCCCTCCGGGCGGCC
GCCGCTAGGCCGCACGGGCGAAGGCACTACAGGGTGAGGGGCTGCGTGGGCCGGCCCCGAAGGCGCTGG
CCGCCTGGCTGGGCCCTGGCGTGGCCTGAGGCTCCAGACGCTCCTCCTCCAGGATGCGCCCCACGGGGAG
CTCATGAGCACGTACTGGTCGCTGTCCCCGCCACAGGTGTAGGGGGCCTTGTAGGAGCGGGGCAAGGAGCT
GTAGCAGCAGCCGGGAACGCCCCTGAGCGGCTCCCCGCCGGGGCTGCAGGGCTGCGGAGAAGAAGTCGGGCG
GGGTGCCCGTGGTGACCGCGTCGCTGGGGGACACGTTGAGGTAGTCCCCGTTGGGCAGCAGCTTGCCATCT
GCATGCTCCATGGACAGCTTGGAACCGCACCACATGCGCATGTACCCACTGTCCTCGGGGGAGCTCTCGGC
GGGCGAGCTGGCCTTGTAGCCGCCCCGCTCGCCGGGAATGTCCTGCCCGCCGCAGAGGTGGGTGCTGGCC
CCGCAGGCCCCGCAGAAGGCACGGCGGCGGCGGCGGCGGCGCCCTGGGCTGCAAGATCTGCTTGGGG
GCGGACACGCTGGCGGGGCTCATGGGCATGTAGTCGTCGCTCCTGCAGCTGCCGCTCCCACTGCCCGCGAG
GGCCGCGCCGGGCGTCATGGGCATGTAGCCGTCGTCTGCCCCCAGGTTGCTGCTGGAGCTCCTGTGGGAGC
CGATCTCGATGTCTCCGTAGTCCTCTGGGTAGGGTGGTAGGCCACCTTGGGAGAGGACGCGGGGCAGGAC
GGGCAGAGGCGGCCCGCGCTGCCCGAGAAGGTGGCCCGCATCAGGGTGTATTCATCCAGCGAGGCAGAGGA
GGGCTGGGGCACCGGCCGCTGCCGGGCTGGCGTGGTCAGGGAGTAGGTCCTCTTGCGCAGCCCTCGGTCCA
GGTCCTGGGCGCGTCCCCGAGACCCGGCGGTAGGAGCGGCCACAGTGGCTCAGGGGCCTGTCCATGGTC
ATGTACCCGTAGAACTCACCGCCGCCGCCGCGTCTCGGGCCGGGGCGTCTCCGCGATGGACTCGGGCGT
GTTGCTTCGGTGGCTGCAGAAGGCGCGCAGGTCGCCTGGGCTGGAGCCGTACTCGTCCAGGGACATGAAGC
CGGGGTCGCTGGGGGAGCCCGAGGCGGAGGCGCTGCCGCTGGAGGGGCCGCTGGCCGGGGCCGTGGTGCAGC
GGATGCGGCAGAGGCGGGTGCGGGCCGGGCGGCGGCGGGTAGGAGCCCGAGCCGTGGCCGCTGCTGGACGA
CAGGGAGC |

TABLE 4-continued

| SEQ ID NO | GENE NAME | SEQUENCE |
|---|---|---|
| 64 | chr13 group-00350 | TAACCTAAAGAATGAAGTCATGCCCCGGCCTGCACCCGGGAAACTGCACACAGCGAAAGATCGCCACTGAG<br>ATAAAGAGCTGAAAGCTATTCCCCAATTCAGCTGTTTCAGCCGTGCGGTCTCACAATGGGCTCACAGACGG<br>CAGCATC |
| 65 | MCF2L | GTTTCCACAATCCACCTCGTAGCTGGGGCGTGCCGCTTGCCTCGGCTTGTCCCGGCAGAACACTCTTACCT<br>TTAATGGCGACTGAAAAGTTGCCACGAGTTCCTGATCATTGTGGTAGGTGCTGCGTGAAGCTGAGACGTGC<br>GTGAGCCACATCCCAGGGGGCTTTGAGCCCCCACCGCGGCGGCGGCTGAGGGGAGGCTTGTCGTACTCGCA<br>CAGGAGGACACAGGGCTGCAGTGTTCACTCCAGGGCCTCTTATCATTGGGATCTGAGGAATTTTCCGAGAG<br>GAAGTGCGAATTAACAATGATGAAAGGTTTGTGAGTGAGTGACAGGCACGTTCTATTGAGCACTGCATGGG<br>GCATTATGTGCCACCAGAGACGGGGGCAGAGGTCAAGAGCCCTCGAGGGCTGGGAGAGTTCGGAGGATAGA<br>AGTCATCAGAGCACAATGAAGCCAGACCCTGCAGCCGCCTTCCCCTTCGGGGGCTTCCTTAGAATGCAGCA<br>TTGCGGGGACTGAGCTGTCCCAGGTGAAGGGGGGCCGTCACGGTGTGTGGACGCCCCTCGGCTCAGCCCTC<br>TAAGAGACTCGGCAGCCAGGATGGGCTCAAGGCATGAGCCCTCAAAGGAGGTTAGGAAGGGAGCGAGGGAGA<br>AAAGATATGCTTGTGTGACGTCCTGGCCGAAGTGAGAACAATTGTATCAGATAATGAGTCATGTCCCATTG<br>AGGGGTGCCGACAAGGACTCGGGAGGAGGCCACGGAGCCCTGTACTGAGGAGACGCCCACAGGGAGCCTCG<br>GGGGCCCAGCGTCCCGGGATCACTGGATGGTAAAGCCGCCCTGCCTGGCGT |
| 66 | F7 | TCCAGCTGCAGCGAGGGCGGCCAGGCCCCCTTCTCCGACCTGCAGGGGTAGCGCGGCCTCGGCGCCGGAGA<br>CCCGCGCGCTGTCTGGGGCTGCGGTGGCGTGGGAGGGCGCGGCCCCGGACGCCCCGAGGAAGGGGCACC<br>TCACCGCCCCCACCCAGAGCGCCTGGCCGTGCGGGCTGCAGAGGACCCCTCCGGGGCAGAGGCAGGTTCCA<br>CGGAAGACCCCGGCCCGCTGGGGCTTCCCCGGAGACTCCAGAG |
| 67 | chr18 group-00039 | ACTTACTGCTTCCAAAAGCGCTGGGCACAGCCTTATATGACTGACCCCGCCCCGAGTCCCAGGCCGCCCC<br>ATGCAACCGCCCAACCGCCCAACCGCCACTCCAAAGGTCACCAACCACTGCTCCAGGCCACGGGCTGCCTC<br>TCCCCACGGCTCTAGGGCCCTTCCCCTCCACCGCAGGCTGAC |
| 68 | C18orf1 | TGCCACACCCAGGTACCGCCCGCCCGCGCGAGAGCCGGGCAGGTGGGCGCGGATGCTCCCAGAGGCCGGC<br>CCAGCAGAGCGATGGACTTGGACAGGCTAAGATGGAAGTGACCTGAG |
| 69 | CD33L3 | TCGCCAGCGCAGCGCTGGTCCATGCAGGTGCCACCCGAGGTGAGCGCGGAGGCAGGCGACGCGGCAGTGCT<br>GCCCTGCACCTTCACGCACCCGCACCGCCACTACGACGGGCCGCTGACGGCCATCTGGCGCGCGGGCGAGC<br>CCTATGCGGGCCCGCAGGTGTTCCGCTGCGCTGCGGCGCGGGGCAGCGAGCTCTGCCAGACGGCGCTGAGC<br>CTGCACGGCCGCTTCCGGCTGCTGGGCAACCCGCGCCAACGACCTCTGCTGCGCGTCGAGCGCCTCGC<br>CCTGGCTGACGACCGCCGCTACTTCTGCCGCGTCGAGTTCGCCGGCGACGTCCATGACCGCTACGAGAGCC<br>GCCACGGCGTCCGGCTGCACGTGACAGGCGAGGCGGCGTGGGAGCGGGTCCCCGGCCTCCCTTCCCGCCCT<br>CCCGCCTGCCCGCCCAAGGGCTACGTGGGTGCCAGGCGCTGTGCTGAGCCAGGAAGGGCAACGAGACCC<br>AGCCCTCTCCTCTACCCCAGGGATCTCACACCTGGGGGTAGTTTAGGACCACCTGGGAGCTTGACACAAAT<br>GCAGAATCCAGGTCCCAGGAAGGGCTGAGGTGGGCCCGGGAATGAGCATTGCCGTGACTCTCGTAGAGTGA<br>CTGTCCCCAGTGGCTCTCAGACGAAGAGGCGAGAAAGACAAGTGAATGGCAATCCTAAATATGCCAAGAGG<br>TGCAATGTGGTGTGTGCTACCAGCCCGGAAAGACACTCGCAGCCCCTCTACCCAGGGGTGCACAGACAGCC<br>CACCAAGTAGTGCCTAGCACTTTGCCAGACCCTGATATACAAAGATGCCTGAACCAGGGTCCCGTCCCTAG<br>AGCAGTGGCTCTCCACTCTAGCCCCCACCCTGCTCTGCGACAATAATGGCCACTTAGCATTTGCTAGGGAG<br>CCGGGACCTAGTCCAAGCACCCACAAGCATGAATTTGCCAAATCTTTTCAGCAACCTCTTAAGGCAACTGC<br>TATCATGATCCTCACTTTACACATGGAGAAGCAGAAGCAGAGATGATAGAATCTTTCGCCCAAGGCCACAT<br>CTGTATTGGGACGGGGGCAGCCTGGCACCCAAGTGCCCATTCCTCCCTTCTGACCAGCCCCACCCCTCCG<br>GCTCTGGCGTCCAAAGGGCTAAGGGGAGGGGTGCCCTTGTGACAGTCACCCGCCTTCTCCCCTGCACGCGC<br>GCCGCGGATCGTCAACATCTCGGTGCTGCCCAGTCCGGCTCACGCCTTCCGCGCGCTCTGCACTGCCGAAG<br>GGGAGCCGCCGCCCGCCCTCGCCTGGTCCGGCCCGGCCCTGGGCAACAGCTTGGCAGCCGTGCGGAGCCCG<br>CGTGAGGGTCACGGCCACCTAGTGACCGCCGAACTGCCCGCACTGACCCATGACGGCCGCTACACGTGTAC<br>GGCCGCCAACAGCCTGGGCCGCTCCGAGGCCAGCGTCTACCTGTTCCGCTTCCATGGCGCCAGCGGGGCCT<br>CGACGGTCGCCCTCCTGCTCGGCGCTCTCGGCTTCAAGGCGCT |
| 70 | TNFRSF11A | ATGAACTTCAAGGGCGACATCATCGTGGTCTACGTCAGCCAGACCTCGCAGGAGGGCGCGGCGGCGGCTGC<br>GGAGCCCATGGGCCGCCGGTGCAGGAGGAGACCCTGGCGCGCCGAGACTCTTCGCGGGGAACGGCCCGC<br>GCTTCCCGGACCCGTCGGCGGCCCCGAGGGGCTGCGGGAGCCGGAGAAGGCCTCGAGGCCGGTGCAGGAG<br>CAAGGCGGGGCCAAGGCTTGAGCGCCCCCCATGGCTGGGAGCCCGAAGCTCGGAGC |
| 71 | ZNF236 | TCAGTGTTATGTGGGGAGCGCTAGATCGTGCACACAGTAGGCGTCAGGAAGTGTTTTCCCCAGTAATTTAT<br>TCTCGATGGTACTTTGCTAAAGTCATGAAATAACTCAGATTTTGTTTTCCAAGGAAGGAGAAAGGCCCAGA<br>ATTTAAGAGCAGGCAGACACACAACCGGGCACCCCAGACCCTGGCCCTTCCAGCAGTCAGGAATTGACTT<br>GCCTTCCAAAGCCCCAGCCCGGAGCTTGAGGAACGGACTTTCCTGCGCAGGGGGATCGGGGCGCACTCG |
| 72 | chr18 group-00342 | GTGGAAACACAACCTGCCTTCCATTGTCTGCGCCTCCAAAACACACCCCCGCGCATCCGTGAAGCTGTGT<br>GTTTCTGTGTTACTACAGGGGCCGGCTGTGGAAATCCCACGCTCCAGACCGCGTGCCGGGCAGGCCCAGCC |
| 73 | OLIG2 | TCCACACCTCGGGCAGTCACTAGGAAAAGGGTCGCCAACTGAAAGGCCTGCAGGAACCAGGATGATACCTG<br>CGTCAGTCCCGCGGCTGCTGCGAGTGCGCGCTCTCCTGCCAGGGGACCTCAGACCCTCCTTTACAGCACA<br>CCGAGGGCCCTGCAGACACGCGAGCGGGCCTTCAGTTTGCAAACCCTGAAAGCGGGCGCGGTCCACCAGGA<br>CGATCTGGCAGGGTCTGGGTGAGGAGGCCGCGTCTTTATTTGGGGTCCTCGGGCAGCCACGTTGCAGCTC<br>TGGGGGAAGACTGCTTAAGGAACCCGCTCTGAACTGCGCGCTGGTGTCCTCTCCGGCCCTCGCTTCCCCGA<br>CCCCGCACAGGCTAACGGGAGACGCGCAGGCCCACCCCACCGGCTGGAGACCCGGCACGGCCCGCATCCG<br>CCAGGATTGAAGCAGCTGGCTTGGACGCGCGCAGTTTTCCTTTGGCGACATTGCAGCGTCGGTGCGGCCAC<br>AATCCGTCCACTGGTTGTGGGAACGGTTGGAGGTCCCCAAGAAGGAGACACGCAGAGCTCTCCAGAACCG<br>CCTACATGCGCATGGGGCCCAAACAGCCTCCCAAGGAGCACCCAGGTCCATGCACCCGAGCCCAAAATCAC |

TABLE 4-continued

| SEQ ID NO | GENE NAME | SEQUENCE |
|---|---|---|
| | | AGACCCGCTACGGGCTTTTGCACATCAGCTCCAAACACCTGAGTCCACGTGCACAGGCTCTCGCACAGGGG<br>ACTCACGCACCTGAGTTCGCGCTCACAGATC |
| 74 | RUNX1 | CTGCCCTCGCGGATCTCCCCCGGCCTCGCCGGCCTCCGCCTGTCCTCCCACCACCCTCTCCGGGCCAGTAC<br>CTTGAAAGCGATGGGCAGGGTCTTGTTGCAGCGCCAGTGCGTAGGCAGCACGGAGCAGAGGAAGTTGGGGC<br>TGTCGGTGCGCACCAGCTCGCCCGGGTGGTCGGCCAGCACCTCCACCATGCTGCGGTCGCCGCTCCTCAGC<br>TTGCCGGCCAGGGCAGCGCCGGCGTCCGGGGCGCCCAGCGGCAACGCCTCGCTCATCTTGCCTGGGCTCAG<br>CGCGGTGGAAGGCGGCGTGAAGCGGCGGCTCGTGCTGGCATCTACGGGGATACGCATCACAACAAGCCGAT<br>TGAGTTAGGACCCTGCAAACAGCTCCTACCAGACGGCGACAGGGGCGCGGATCTTCAGCAAGCAGCTCCCG<br>GGAGACCAACATACACGTTCAGGGGCCTTTATTACTGCGGGGGGTGGGGGGGGCGGGGGTGGTTAGGGGA<br>GGAGGGAGACTAAGTTACTAACAGTCCAGGAGGGGAAAACGTTCTGGTTCTGCGGATCGGCCTCTGACCCA<br>GGATGGGCTCCTAGCAACCGATTGCTTAGTGCATTAAAAAGTGGAGACTATCTTCCACGAATCTTGCTTGC<br>AGAGGTTAAGTTCTGTCTTTGGCTGTTAGAAAAGTTCCTGAAGGCAAAATTCTCATACACTTCCTAAAATA<br>TTTATGCGAAGAGTAAAACGATCAGCAAACACATTATTTGGAAGTTCCAGTAGTTAATGCCTGTCAGTTTT<br>TTGCAGGTGAGTTTTGTCTAAAGTCCCAACAGAACACAATTATCTCCCGTAACAAGGCACTTTTATCATG<br>CAAAACTGGCTTCAGTCCCGAAAAGCAAGAGCTGAGACTTCCAAAGGTAGTGCTACTAATGTATGTGCACG<br>TATATATAAATATATACATATGCTCTACTTCATAAAATATTTACAATACAATCTGTGGAGAATTTAAACAC<br>AACAGAAATCCATTAATGTACGCTGCAGATTTTTTTAAGTAGCCTTGAAAATCAGCTTCAGTAGTTGGAGC<br>AGTGCTGAGCTAGAAGTACTTGTCATGTTCTCTGTTCTCTCAATGAATTCTGTCAAAACGCTCAGTGCAGA<br>AAATTCAGCGTTTCAGAGATCTTCAGCTAATCTTAAAACAACAATCATAAGAAGGCCCAGTCGATGACACT<br>CAGGGTTCTACAGCTCTCCCACATCTGTGAACTCGGGTTTGGGGATGTTGGTTAAGTTTGTGGCTGGTCCT<br>CTGGTTTGTTGGGAGTTGAGCAGCCGCAGAGTCACACACATGCAAACACGCACTCTTCGGAAGGCAGCCAC<br>TGTCTACATCAGCTGGGTGACTCAGCCCTGACTCGGGCAGCAGCGAGACGATACTCCTCCACCGTCGCCCA<br>GCACCCGCCGGTTAGCTGCTCCGAGGCACGAACACCCACGAGCGCCGCGTAACGCAGCAGGTGGAGCGGG<br>CCTTGAGGGAGGGCTCCGCGGCGCAGATCGAAACAGATCGGGCGGCTCGGGTTACACACGCACGCACATCC<br>TGCCACGCACACTGCCACGCACACGCAACTTCACGGCTCGCCTCGGACCACAGAGCACTTTCTCCCCCTGT<br>TGTAAAAGGAAAACAATTGGGGAAAAGTTCGCAGCCAGGAAAGAAGTTGAAAACATCCAGCCAAGAAGCCA<br>GTTAATTCAAAAGGAAGAAAGGGGAAAAACAAAAAAAAACAACAAAAAAAAGGAAGGTCCAACGCAGGCAA<br>GGAGAAGCAGCAGAGGTTGACTTCCTTCTGGCGTCCCTAGGAGCCCCGGAAAGAAGTGCCTGGCGGCGCAG<br>GGCCGGGCAGCGTGGTGCCCTGGCTGGGTCCGGCCGCGGGGCGCCCGTCCCGCCCGCGCCCGCTGGCTCTA<br>TGAATGAGAGTGCCTGGAAATGAACGTGCTTTTACTGTAAGCCCGGCCGGAGGAATTCCATTCCCTCAGCT<br>CGTTTGCATAGGGGCGGCCGGCGGCCAATCACAGGCCTTTCCGGTATCAGCCAGGGCGCGGCTCGCCGCCG<br>CCGGCTCCTGGAATTGGCCGCGCGCCCCCGCCGCCGCGCCGCGCGCTACTGTACGCAGCCCGGCGGGGA<br>GTCGGAGGCCACCCCCGCGCCCCGCATCCAAGCCTGCATGCTGGCCCGGGGCCCCGCCGCCTGCGGACCC<br>CTTTCCGCAGCCACACGCAGGCTTGTGCGGCTCCGCGAGTGGCCACGGTCCGGAGACCTGGAAAAAGAAAG<br>CAGGCCCCGCCGGCCCGAGGAGGACCCGGCCGGCGCGCCGCACCCGGAGAGGCCCGGCCCCGCGAGCCGCT<br>GCAGGCAGGCGCAGTGGCCGCCACGAGGCTCCCGAACCGGGCTGCAGCCCGCGGACGGCCCCAGATCCTGC<br>GCGGCCGCCCAGGGCCAGGCCTCCGCTTCCAGGGCGGGGGTGCGATTTGGCCGCGGGGCCCGGGGGAGCCA<br>CTCCGCGCTCCTGCACCGTCCGGCTGGCAGCTGCGGCGAAGCGGCGCTGATTCTTGCATGAGGCCGGACG<br>GCGTCCGCGCGTGCCGTTTGCTCTCAGCGTCTTCCCTTGGGTCGGTTTCTGTAATGGGTGTTTTTTACCGC<br>TGCGCCCGGGCCGCGGCTCGATCCCTCCGCGCGTCTCACTTGCTGCGTGCGTCAGCGGCCAGCGAAGAGTT<br>TCCTAGTCAGGAAAAGACCCCAAGAACGCGCGGCTGGAAGGAAAGTTGAAAGCAGCCACGCGGCTTGCTCCC<br>GGGCCTTGTAGCGCCGGCACCCGCAGCAGCCGGACAGCCTGCCCGGGCCCCGCGTCTCCCCTCCGGCTCCC<br>CGGAAGCGGCCCCCGCTCCTCTCCCCGCCCCCGTGCGCTCGAGCGGCCCCAGGTGCGGAACCCACCCCGGC<br>TTCGCGTGCGGGCGGCCGCTTCCCCCTGCGCCGGTCCCCGCGGTGCTGCGGGCATTTTCGCGGAGCTCGGA<br>GGGCCGCCCCGGTCCGGCGTGCGCTGCCAACTCCGACCCCGCCCGGCGGGGCTCCCTCCCAGCGGAGG<br>CTGCTCCCGTCACCATGAGTCCCTCCACGCCCTCCCTGCCGGGCCCTGCACCTCCCGGGGCCTCTCATCCA<br>CCCCGGGGCTGCAACCCAGTCCCCGGATCCCGGCCCCGTTCCACCGCGGGCTGCTTTGTGGTCCCCGCGGA<br>GCCCCTCAATTAAGCTCCCCGGCGCGGGGTCCTCGCCGACCTCACGGGGCCCTGACGCCCGCTCCTCC<br>CTCCCCCAGGGCTAGGGTGCTGTGGCCGCTGCCGCGCAGGGACTGTCCCCGGGCGTTGCCGCGGACCCCGA<br>CGCAGGAGGGGGCCGGGGTTGACTGGCGTGAGGCCTTTCCCGGGCGGGCCCGGACTGCGCGGAGCTGTCG<br>GGACGCGCCGCGGGCTCTGCGGACGCCAGGGGGCAGCAGCCGCCTCCCTGGACGCCGCGCAGTCCCC<br>GGAGCTCCCGGAACGCCCCGACGGCGCGGGGCTGTGCGGCCCGCCTCGTGGCCTTCGGGTCGCCCGGGAA<br>GAACTAGCGTTCGAGGATAAAAGACAGGAAGCCGCCCCAGAGCCCACTTGAGCTGGAACGGCCAAGGCGCG<br>TTTCCGAGGTTCCAATATAGAGTCGCAGCCGGCCAGGTGGGGACTCTCGGACCAGGCCTCCCCGCTGTGCG<br>GCCCGGTCGGGTCTCTTCCCGAAGCCCCTGTTCCTGGGGCTTGACTCGGGCCGCTCTTGGCTATCTGTGC<br>TTCAGGAGCCCGGGCTTCCGGGGGCTAAGGCGGGCGGCCCGCGGCCTCAACCCTCTCCGCCTCCGCTCCC<br>CCTGGGCACTGCCAGCACCCGAGTTCAGTTTTGTTTTAATGGACCTGGGGTCTCGGAAAGAAAACTTACTA<br>CATTTTTCTTTTAAAATGATTTTTTTAAGCCTAATTCCAGTTGTAAATCCCCCCCTCCCCCCGCCCAAACG<br>TCCACTTTCTAACTCTGTCCCTGAGAAGAGTGCATCGCGCGCCCGCCCGCCCGCAGGGGCCGCAGCGCC<br>TTTGCCTGCGGGTTCGGACGCGGCCCGCTCTAGAGGCAAGTTCTGGGCAAGGGAAACCTTTTCGCCTGGTC<br>TCCAATGCATTTCCCCGAGATCCCACCCAGGGCTCCTGGGGCACCCCCACGTGCATCCCCCGGAACCCCC<br>GAGATGCGGGAGGGAGCACGAGGGTGTGGCGGCTCCAAAAGTAGGCTTTTGACTCCAGGGGAAATAGCAGA<br>CTCGGGTGATTTGCCCCTCGGAAAGGTTCCAGGGAGGCTCCTCTGGGTCTCGGGCCGCTTGCCTAAAACCCT<br>AAACCCCGCGACGGGGCTGCGAGTCGGACTCGGGCTGCGGTCTCCCAGGAGGGAGTCAAGTTCCTTTATC<br>GAGTAAGGAAAGTTGGTCCCAGCCTTGCATGCACCGAGTTTAGCCGTCAGAGGCAGCGTCGTGGGAGCTGC<br>TCAGCTAGGAGTTTCAACCGATAAA |
| 75 | AIRE | TTCGGAAGTGAGAGTTCTCTGAGTCCCGCACAGAGCGAGTCTCTGTCCCCAGCCCCAAGGCAGCTGCCCT<br>GGTGGGTGAGTCAGGCCAGGCCCGGAGACTTCCCGAGAGCGAGGGAGGGACAGCAGCGCCTCCATCACAGG<br>GAAGTGTCCCTGCGGGAGGCCCTGGCCCTGATTGGGCGCCGGGGCGGAGCGGCCTTTGCTCTTTGCGTGGT<br>CGCGGGGGTATAACAGCGGCGCGCGTGGCTCGCAGACCGGGGAGACGGGCGGGCGCACAGCCGGCGCGGAG<br>GCCCCACAGCCCCGCCGGGACCCGAGGCCAAGCGAGGGGCTGCCAGTGTCCCGGGACCCACCGCGTCCGCC<br>CCAGCCCCGGGTCCCCGCGCCCACCCCATGGCGACGGACGCGGCGCTACGCCGGCTTCTGAGGCTGCACCG<br>CACGGAGATCGCGGTGGCCGTGGACAG |

TABLE 4-continued

| SEQ ID NO | GENE NAME | SEQUENCE |
|---|---|---|
| 76 | SUMO3 | ACGCACACTGGGGGTGTGATGGAAAGGGGGACGCGATGGATAGGGGTGGGCGCACACTGGGGGACGCGACG<br>GGGAGGGGTGAGCACACACTGGGGGTGTGATGGAGAGGGCGACGCAATAGGGAGGGGTGGGCGCACACCAG<br>GACGCGATGATGGGGACGGGTGGGCGCACACCAGGTGGCATGATGGGGAGGAGTGGGTACACACCATGGG<br>GGGCGTGATGGGGAGGCGTGGGCGTACACCGGGGGGCGCGATGGGGAGGGGTGGGCGCACACCGGGGGACG<br>CGATGGAGGCGGTGGGTGCACACGGGGCGCGATGGGTGGGAGTAGGTGCACACTGAGGGCACGATTGGGGA<br>GACACGAAGGAGAGGGTGGGCGCACACTGGGGGACGCGATGGCCGGGACACGATGCGGAGAAGTGGGTGA<br>ATACCGGGGTCGCGATGGGCGCCCTGGAAGGACGGCAGTGCTGCTCACAGGGGCCAGGCCCCTCAGAGCGC<br>GCCCCTTGGGGGTAACCCCAGACGCTTGTTCCCGAGCCGACTCCGTGCACTCGACACAGGATC |
| 77 | C21orf70 | CCACAGGGTGGGGTGCGCCCACCTGCCCTGTCCATGTGGCCTTGGGCCTGCGGGGAGAGGGAATCAGGAC<br>CCACAGGGCGAGCCCCTCCGTAGCCCGCGGCACCGACTGGATCTCAGTGAACACCCGTCAGCCCATCCAG<br>AGGCTAGAAGGGGGA |
| 78 | C21orf123 | TTGAGGTCTCTGTGCATGCTTGTGCGTACCCTGGACTTTGCCGTGAGGGGTGGCCAGTGCTCTGGGTGCCT<br>TTGCCAGACAACTGGTCTGCCGGGCCGAGCATTCATGCTGGTC |
| 79 | COL18A1 | TGACGCGCCCCTCTCCCCGCAGCTCCACCTGGTTGCGCTCAACAGCCCCCTGTCAGGCGGCATGCGGGGCA<br>TCCGCGGGGCCGACTTCCAGTGCTTCCAGCAGG |
| 80 | PRRT3 | AACACACTGTCTCGCACTAGGTGCTCGCGGAAGAGCGCGGCGTCGATGCTGCGGCTCAGGTTGATGGGCGA<br>TGGCGGCCGCAGATCCAGCTCGCTCAGCGATGGCGCCGGTCCCACACCGTTGCGGGACAGTCCCGGGCCAC<br>CCTGGGGTCCGCGACCCAACGACGCAGCCGAGCCCCAGGCGCCTGAACTGGGCGTGGCCAGCTGCCCACTC<br>TCCGCCGGGTTGCGGATGAGGCTCTTGCTGATGTCCAAGCTGCCTGCACCAACGTTGCTGGGCCCTGCATA<br>GCAGTTATTGGGTCGCTCCGGCACCTCGCTCTTTCCTGACGGCGCCGGGCACGCCAGACGCATCAGCTTAG<br>CCCAGCAAGCGTGCTCCGTGGGCGGCCTGGGTCTCGAGGGCAGCCACCGCGGCCAACGCCAGGGCGAGCGCC<br>CATGTCAGCTCCAGGAGGCGCAGCCAGAAGTGGACACCCCACCAGGCCCACGAGAAGCGGCCCACGCGGCC<br>TGGGCCCGGGTACAGCCAGAGCGCAGCCGCCAGCTGCAAGCCGCTAGCCAGCAGCCCAGCGCGCCCGCCA<br>CAGCCAACAGCCGAGGGCCCGGGCTGGCATCCCAGCCCCGTGGGCCGTCCAGCAGGCGGCGACGGCACAGG<br>CAGAGCGTGCCCAGAGCCAC |
| 81 | MGC29506 | GTCTGCACGAAGCCCGCGGCGGCCTGCAGGGGGCCCAGCGACTCGTCCAGGGAACCGGTGCGCAGGAGCAG<br>CCGGGGGCGCGGCGCGCCGGCCGCCCTTGGGGGACTCTGGGGCGGGGGCGCAGCTCGATCTGACGCTTGG<br>GCACTGTCCGGGGCCTGGCGGGCGCGGCGCCCTCCTCCAGAGCCACCTCCACACACTCGAACTGCGCTGGG<br>GCGGCAGGACTTGGCCCACGGGGCGCCAGCTCTAGGTAGGTGGCCCAGCGGGAGCCACCATCGGGGACCTG<br>GGACTGGCGTGGGACCGCGGCGGGAGACGCTGGCCCCGGCGGCAAGGGGCTGATGAAGGCCGGCTCCGTGA<br>ACTGTTGTTGCGCCTCGCGATCGTCTGCGCCGGAGCAGCCGAACAGGGGTCCGACGCCGAAGATGACTTCC<br>ATCTCCCCCGACGGCAGCGTGCGCAGCTGGGGCTGGGGTGGCCGTGGGCCGGAACCTGGGCCTCGCGGGAA<br>ACCCGAGCCGGGCCCGTGCCGCTGGCGGCTATTCTGGGCGCTGACGGACAGGCGAGGCTGCGCGCCCGCCC<br>CCCGCCCAGGAGCCACCCAGGGCCAATTCGCTGGGCCTTTCGCGTCCGGCCCAACGTCCGGGGGCTCCGGA<br>GAACCTGGAGCCGTGTAGTAGGAGCTGACGAACCGGAGGAGTCCTGGCGCCGCGCGGGGCCGTGGGCAG<br>CTGCCTCGGGATCCCAGGCAGGGCTGGCGGGGCGAGCGCGGTCAGCATGGTGGGGCCGGACGCCGTGCACT<br>ATCTCCCTCGCATTCGCCTCCGCTGGTGGCGC |
| 82 | TEAD3 | CTGGAGAGAACTATACGGGCTGTGGGAGTCACCGGGCGACTATCACCGGGCCTCCTTTCCACATCCTCCTC<br>CGGGAAGGGACCCCGTTCCGGGCCTCGACCGGCGCAGACTGGGCTGACCCACTTTCTTGGGCCCACTGAGT<br>CACCTCGAAACCTCCAGGCCGGTAGCGGGGAGGAGAGGAGGAGCAGGCGGGGGTGCCAAGGTGTGGGCTGC<br>GCCCTGGTTAGGGGGCGAGCCCGGCTTGTTTATGAGGAGGAGCGCGGAGGAGGATCCAGACACACAGGCTT<br>GCGCGCCCAGACTCGCCCGGCCAGCGGCTGGCGCCTCCGACGTCACCAAACCGGTTGGGTGAGAGGGCAG<br>AGAGCAGGGGGAAGGGCCGCAGTCCCGCCCGCGCCCCCCGGCACGCACCGTACATCTTGCCCTCGTCTGAC<br>AGGATGATCTTCCG |
| 83 | chr12 group-00022 | GAGTGCGGAGTGAAGGGGTGCACTGGGCACTCAGCGCGGCCCTTGGGAGGCAGGGCCGCCCCAGCCTGCCC<br>TCCTGTCTGGGAAGGCCGTCCAGAAGCAGGAGCCCCGGGGAAAACAACTGGCTGGACGGGCGGCCTTCAG<br>TGTCTCTCCCAGCCTGAGAGTCGCTTCCCACCACCTGGGCACGAACCTGCTCTGCGATCTCCGGCAAGTTC<br>CTGCGCCTCCTGTCGGTAAAATGCAGATCGTGGCGTCTT |
| 84 | CENTG1 | TCTTCTTTCCGCCCCTAGGGGGCACAAGCGGGCATGTCCAAGCGCCTAGGAGCCCGTACCGCTGGGGACCT<br>CCCCTTCCGCGAACCCCGAGCGGGTAGACCCAGAGCAATCCAGATGTGGAAACAATGGAGAGGGGCGTGT<br>TGAGCTGGGGTCTCCATGCCTCGTTGGGGAGAGGGAGGTGAGTTTGTGTCTTCTGGAAGGCGTGGGGCTG<br>TGCCCTCGTGGGGGTAGGAAGTGCTCCCGTGGGCGGGGTGCGGATCGGAGAGGTGAGTGGGTGCGTCTGT<br>CCAGCGGTCCGCCCGGTGTGGTCGTGCCCGGCCCGCGTGGGGATGGGGGTGTCTCTCCCGCTGGGCAACTA<br>TACCAGCGCAACCGGGCGTCGGCGCGGCCCACGCTAGCGGCGCTGCTCCGGCGGCGGGGCTGGGCGTGG<br>CGGTGATGCTGGGCGTGGTGGCCGCGCTGGGCGTGGTGGCCGCGCTGCCGCCCTCACCCGGGCAGCCGTGC<br>TGGAGAAGGATGTCGGCGCACAGCTGGCTTCCAGCCTGGCGGGCGTAGAACAGCGCCGTGCGGCCCTGGGC<br>GTCACGGGCCGCCACGTCCGCGCCGTACTAGAGGGCGGAAACGGCCGCGTGACCGCGCGTCCCCAGGGCGC<br>CCACACCCGGCGCCGCCTCCCCCACATGGCCAAGCCTACTTCCGGGGTCCCTCTGGGAATTTCGGGCTTTC<br>CCGCGCCAGGCGTTTTCCGAGATGAAGCCTCAAAGACCCCCTTTCCTCCCCCCAGCTCACGTACCCACAGC<br>AGCAGTTGCGTGATGACGACGTGGGCGAGCTCGGCCGCCAGGTGGATGGGGAGCGCAGCTGTGGGTCCTC<br>TACGCTGGTGTCGAGCGGCCCGTGTCGCGCATGGGCCAAAAGCAGGAGAACGGTAGCCACGTCCTGGGCCT<br>GCACGGCGGCCCACAGCTGGCGGCCCAGCGGCTCCTCCGAGGTGCTCAGCGGCGCCAGGAACAGTAGCTGC<br>TCGTACTTGGCGCGAATCCACGACTCGCGCTCCTCCCTGCAAGACCAGGGATCAACGGAAAGGCTCTAGG<br>GACCCCCAGCCAGGACTTCTGCCCCTACCCACGGGACCGTCTCAGGTTCGCACACCCTCAGCAACCCTCCC<br>CCCGCTCTGTTCCCTCACGCTTACCGCGAAGAGTCCCGCGAGGGCTTGGCACGGCCTCGCGTGTCGCTTTC<br>CCACACGCGGTTGGCCGTGTCGTTGCCAATAGCCGTCAGCACCAGGGTCAGCTCCCGTGGCCAGTCGTCCA |

TABLE 4-continued

| SEQ ID NO | GENE NAME | SEQUENCE |
|---|---|---|
| | | AGTCCAGCGAGCGAACGCGGGACAGGTGTGTGCCCAGGTTGCGGTGGATGCCAGAACACTCGATGCAGATG<br>AGGGCGCCCAGGTTCAAGCTGGCCCACGTGGGGTCTGCGGAAGGAGCGTAGAGGTCGGCTCCCAGCCGGGC<br>AGCACAGGCACCCCGGCATTCACTACACTCCCTAGCCCCTCCGCTGCCTCCTGGCACTCACTGGGGGCCCC<br>GCAGTCCACGCAGATTGAATTCCCCTTGGCGTTCCGGATCGCCTGGAT |
| 85 | CENTG1 | AGCCAGGTCCAGCCCCCGCGCCTGACACCGGCCGGACGTTCCCGGGGCGCCGCAGCTGCGGCGGGAACTCT<br>GGGATCCGGAGCCATCTGCTCCCACCCGCTCCGGAGCCAAACCCCGGGGGCCGCCTCCGCTCCCGGACCCG<br>CCTCCTCTCCCGGAGTGTGAGCCGAACCAAGAGTCTCCTGCCTATCTCCTCCAGTAGGAAAATAGTAATA<br>ATAATAGACACCCTGCCCCCGTAAAAAACACTACCTTCCCCGTACCGCCTCCCAAGTCTCCCGGGGTACGG<br>ATTGCCTTTGCAGCAGTTCCGCCCCACCTGACTCACTCCAGGGTCAGCCCCGGGTGGGTTTCAATGCGGCT<br>CTGGGGAGGGGGTGGGCAGTGGGGGAAGTGAGGCTTCCTATCCGCCCCCTCTCACTTCACATTTAAATATT<br>CTGCACGTTCCAGCCCCCGCGGACTCGCGTACCGCCCAATCCGCCTTCACCGCACGAAAAACATCACTAGC<br>CTGCTCTCAGCCCAGGGGACGACTAGTCCCTGGCGAGAAGCTGCCTGCAAGGTCACTGTCATGCCACCTGC<br>CCCAAGTGCTCAGGGGAAACTGAGGCTTCCTCATCCCCTTCACCTTCAACGTCGCTCTAAACACGGCAAAG<br>CCCCGTTTCCATGCTCCCAGAGTTCAGCTGAGGCTGGAAGTGGGGTCCTGGGCTTCTCTGGGAGCAATTTT<br>CTAGTCACTCTGATCAAGGACGTTACTTTCCCAGAAAGCTCTGAGGCTGAGTCCCTCTGAAATCAAGTCCT<br>TTCTCCTGTCGCACAATGTAGCTACTCGCCCCGCTTCAGGACTCCTATTCTTTGCCCCAATCCTTGACAGA<br>GGGGTGAGCTTGGTTCATCCGCCCACCCCAGAGAAAAGCTTCCCTAGTTTCCTGGACCTCGCTCCTCCACC<br>CCAAGCTGAGCATTCCAGGTACCCTTCCCTCCCTGTTCTCAAGCCCTGACTCAACTCACTAGGGGAAGCGC<br>GGAGCTCGGCGCCCAGCAGCTCCCTGGACCCGCTGCCAGAAGACAGGCTGGGGGGTCCGGAAGGGGCCCG<br>GAGCCAGGAGGCCCTCCTGTGCTCTTGGTGAAGATGCCGCTGATAAACTTGAGCATCTTGCGGTCACGAGT<br>GGATGCCTCGGCCCCCCTCCCGGCCCCGTTTCAGCCCCGGAGCTGGAGGCTCCAGAGTGATTGGAGGTGCAG<br>GCCCGGGGGCTGCGCGGAAGCAGCGGTGACAGCAGTGGCTGGACTCGGAGTTGGTGGGAGGGTTAGCGGA<br>GGAGGAGAGCCGGCAGGCGGTCCCGGATGCAAGTCACTGTTGTCCAAGGTCTTACTCTTGCCTTTCCGAGG<br>GGACAACTTCCCTCGGGCTCCAGCCCCAGCCCCGACCCCACCAGAGGTCGAAGCTGTAGAGCCCCCTCCCC<br>CGGCGGCGGCGGCGGTGGCGGCGGCAGAGACCGAAGCTCCAGTCCCGGCGCTGCTCTTTGACCCCTTGACC<br>CTGGGCTTGCCCTCGCTTTCGGGCCATGACAGGCGGCTACCCGCGCCCTTGCCCCCGCCGGCTTTGGCTCC<br>ACTCGTGGTCACGGTCTTGCAAGGCTTGGGAGCCGGCGGAGGAGGCGCCACCTTGAGCCTCCGGCTGCCGG<br>TGCAGGGTGCGGAGAGGATGAGCCAGGGATGCCGCCGCCGCCCGGCCTTCGGGCTCCGGGCGCCCCAG<br>CTCGGGCTGCTGAGCAGGGGCGCCGGGAGGAGGTGGGGGCGCCCCAGGCTTGGGGTCGGGGCTCAGTCC<br>CCCGGAGAGCGGGGGTCCCGGAGGGACGGCCCAGAGGGAGAGGCGGCGGCCGGGAGCGGGGGAGACTGGGC<br>GGGCCGGACTGGCCGGAGCCGGGACAGGGCTGGGGCTCCGCGCCCCCGGTGCCCGCGCTGCTCGTGCTG<br>ATCCACAGCGCATCCTGCCGGTGGAAGAGACGTTCGTGCCGCTTCTTGCCCGGCTCCTCCGCGCCTCGGGG<br>GCTGCCAGGATCCCCAGTCTCGGAGCCTCTGGCACCGGCGGCCGGCCGCGGCCGCAGACGGAGAAGGCG<br>GCGGCGGAGGCACCGACTCGAGCTTAACCAGGGTCAGCGAGATGAGGTAGGTCGTTGTCCGGCGCTGAAGC<br>GCGCCCGCGCCCCGGCTCATGGGGCCCGGAGACCCCCGAGCTGGGGAGGGGAGGGGACTCCCCCGGACTGC<br>CTCAGGGGGCCCGGCCATGGGGCCGCCCTGCTCGCTGCCCCCAGCCCCCGGACCCCGCTGAGCCCCCGGC<br>CCGGCTCCGCTGTCGCGCCGCCTCCGCCGCCTCCGCTTGCGCCCCCTCCCATCACATGGGGCGCCCCCT<br>CCCCATGCTCCCCGCCCTGCCCCCCACCCTCTTGGAGCCCCGGGACCTTGGTGCTGCTCCAGGGAGGCGC<br>GCCGGACCGTCCACCCCGGCCTGGGTGGGGCGCTGAGATGGGTGGGGAGGGCGGGAGGGACAGTAGTGG<br>GGGCAAATGGGGGAGAGAGAGGAAAAGGGAGCAGAAAAGGGGACCGGAGGCTAGGGGAAACGAACCTGTGC<br>GGGGGAGGCAGGGGCGGGGAATTGGGACTCAAGGGACAGGGGCCGCGGATGCGGTCGGAAAGAGGGTCTAG<br>AGGAGGGTGGGAAGCTAGTGG |
| 86 | chr18 group-00304 | AGGAGCGCAAGGCTTGCAGGGCATGCTGGGAGAGCGCAGGGAACGCTGGGAGAGCGCGGGAAATACTGGGA<br>TTTGGCTCCCGAGGGCTGTGAGGAGGGCACGAGGGGACACTCCGATGAAGGCAGGGCACGCGGGGCGAGCCG<br>GGAGCGTCTCCTGAGGGCAGCGAGGAGGGAGCTGAGGCACGCGGGCTCTCAATCGACGCCCACAGAGACC<br>AAGAGGCCTGGCCTTGGGGGGCAGCTGCTTGAAGGAGGCAGAGCGGAAGCGAGGGAGACTGCTGGAGGCCC<br>TGCCGCCCACCCGCCCTTTCCTCCCCCTGAGGAGACGCCTGACGCATCTGCAGTGCAGGAGGCCGTGGGCG<br>TTAGAAGTGTTGCTTTTCCAGTTTGTAAGACCATTTTCCTGATTCTCTTCCCCACGGTTGCGGAGGAGCAG<br>GTCAGGGCCGCCATGAGGGCAGGATC |
| 87 | TSHZ1 | TCGACCGCTACTATTATGAAAACAGCGACCAGCCCATTGACTTAACCAAGTCCAAGAACAAGCCGCTGGTG<br>TCCAGCGTGGCTGATTCGGTGGCATCACCTCTGCGGGAGAGCGCACTCATGGACATCTCCGACATGGTGAA<br>AAACCTCACAGGCCGCCTGACGCCCAAGTCCTCCACGCCCTCCACAGTTTCAGAGAAGTCCGATGCTGATG<br>GCAGCAGCTTTGAGGAGGC |
| 88 | CTDP1 | TGTGCCGTCGCACACAGACGCCCTCAACGTCGGAGAGCTGTGAGCGGGCCGTGCTCTTGGGATGGGAGCC<br>CCCGGGAGAGCTGCCCGCCAACACCACTCCGACGTGATCCATGCTGGACATAAAGTGCTCTTCCCTCCGCT<br>AGTCATCGGCCGAGCGGGCCCCTCGCTCCTGGGTGTAAGTTCTTTCTGTGCGTCCTTCTCCCATCTCCGTG<br>CAGTTCAG |
| 89 | KCNG2 | CCATGCGCCGCTGCGCGCGCGAGTTCGGGCTGCTGCTGCTGTTCCTCTGCGTGGCCATGGCGCTCTTCGCG<br>CCACTGGTGCACCTGGCCGAGCGCGAGCTGGGCGCGCGCCGCGACTTCTCCAGCGTGCCCGCCAGCTATTG<br>GTGGGCCGTCATCTCCATGACCACCGTGGGCTACGGCGACATGGTCCCGCGCAGCCTGCCCGGGCAGGTGG<br>TGGCGCTCAGCAGCATCCTCAGCGGCATCCTGCTCATGGCCTTCCCGGTCACCTCCATCTTCCACACCTTT<br>TCGCGCTCCTACTCCGAGCTCAAGGAGCAGCAGCAGCGCGCGGCCAGCCCCGAGCCGGCCCTGCAGGAGGA<br>CAGCACGCACTCGGCCACAGCCACCGAGGACAGCTCGCAGGGCCCCGACAGCGCGGGCCTGGCCGACGACT<br>CCGCGGATGCGCTGTGGGTGCGGGCAGGGCGCTGACGCCTGCGCCGCCCAC |

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the invention. Although the invention has been described in substantial detail with reference to one or more specific embodiments, those of ordinary skill in the art will recognize that changes may be made to the embodiments specifically disclosed in this application, yet these modifications and improvements are within the scope and spirit of the invention.

The invention illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the invention claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. Further, when a listing of values is described herein (e.g., about 50%, 60%, 70%, 80%, 85% or 86%) the listing includes all intermediate and fractional values thereof (e.g., 54%, 85.4%). Thus, it should be understood that although the present invention has been specifically disclosed by representative embodiments and optional features, modification and variation of the concepts herein disclosed may be resorted to by those skilled in the art, and such modifications and variations are considered within the scope of this invention.

Certain embodiments of the invention are set forth in the claims that follow.

What is claimed is:

1. A method for determining the amount of fetal nucleic acid of a target chromosome comprising:
   a) contacting nucleic acid from a pregnant female, which nucleic acid comprises differentially methylated fetal nucleic acid and maternal nucleic acid, with an agent that specifically binds methylated nucleotides, wherein the agent that binds methylated nucleotides is a methyl-CpG binding protein or fragment thereof, thereby producing bound nucleic acid;
   b) immunoprecipitating the bound nucleic acid of a), thereby enriching for sequences comprising differentially methylated fetal nucleic acid;
   c) amplifying the nucleic acids of b) with primers that specifically amplify SEQ ID NO: 33 or a portion thereof, thereby generating amplification products; and
   d) determining from the products of c) the amount of fetal nucleic acid for SEQ ID NO: 33, wherein determining the amount of fetal nucleic acid comprises the use of RT-PCR or a sequencing method.

2. The method of claim 1, wherein the methyl-CpG binding protein or fragment thereof is fused to an Fc fragment of an antibody.

3. The method of claim 1, wherein the agent that binds methylated nucleotides is a methylation specific antibody.

4. The method of claim 1, wherein step c) further comprises amplifying the nucleic acids of b) with primers that specifically amplify at least one of SEQ ID NOs: 1-32 and 34-59 or a portion thereof; and step d) further comprises determining from the products of c) the amount of fetal nucleic acid for the at least one of SEQ ID NOs: 1-32 and SEQ ID NOs: 34-59.

5. The method of claim 1, further comprising determining the amount of control DNA from a euploid region of a chromosome and comparing the amount of fetal DNA as determined in step d) to the amount of the control nucleic acid to determine the presence or absence of fetal aneuploidy.

6. The method of claim 5, wherein the control nucleic acid is obtained from a female with a normal euploid pregnancy.

7. The method of claim 1, wherein the amount of fetal nucleic acid at 3 or more loci is determined.

8. The method of claim 1, wherein the amount of fetal nucleic acid at 10 or more loci is determined.

9. The method of claim 1, wherein the amount of fetal nucleic acid at 50 or more loci is determined.

* * * * *

SEQUENCE LISTING

```
<160> NUMBER OF SEQ ID NOS: 179

<210> SEQ ID NO 1
<211> LENGTH: 305
<212> TYPE: DNA
<213> ORGANISM: Homo sapiens

<400> SEQUENCE: 1
cagcaggcgc gctcccggcg aatctgcctg aatcgccgtg aatgcggtgg ggtgcagggc      60
aggggctggt tttctcagcc ggtcttggct tttctctttc tctcctgctc caccagcagc     120
ccctccgcgg gtcccatggg ctccgcgctc agaacagccc ggaaccaggc gccgctcgcc     180
gctcgctggg ggccacccgc ctctccccgg aacagcctcc cgcgggcctc ttggcctcgc     240
actggcgccc tcacccacac atcgtccctt tatccgctca gacgctgcaa agggccttct     300
gtctc                                                                 305

<210> SEQ ID NO 2
<211> LENGTH: 336
<212> TYPE: DNA
<213> ORGANISM: Homo sapiens

<400> SEQUENCE: 2
gctttggatt tatcctcatt ggctaaatcc ctcctgaaac atgaaactga aacaaagccc      60
tgaaccccct caggctgaaa agacaaaccc cgcctgaggc cgggtcccgc tccccacctg     120
gagggaccca attctgggcg ccttctggcg acggtccctg ctagggacgc tgcgctctcc     180
gagtgcgagt tttcgccaaa ctgataaagc acgcagaacc gcaatcccca aactaacact     240
gaacccggac ccgcgatccc caaactgaca agggacccgg aacagcgacc cccaaaccga     300
cacgggactc gggaaccgct atctccaaag ggcagc                               336

<210> SEQ ID NO 3
<211> LENGTH: 139
<212> TYPE: DNA
<213> ORGANISM: Homo sapiens
```

<400> SEQUENCE: 3

```
tttccacaac agggagccag cattgaggcg cccagatggc atctgctgga aatcacgggc    60
cgctggtgaa gcaccacgcc ttacccgacg tggggaggtg atccccacc tcatcccacc    120
cccttctgtc tgtctcctt                                                 139
```

<210> SEQ ID NO 4
<211> LENGTH: 292
<212> TYPE: DNA
<213> ORGANISM: Homo sapiens

<400> SEQUENCE: 4

```
gctggacaag gagcgctcac tgtagctctg ctgtggattg tgttggggcg aagagatggg    60
taagaggtca aagtcgtagg attctggcga ccgcctacca agggattggg tccacagcac    120
agaggtctga tcgcttcctt ctctgctctg ccacctccag acagcagctc taaccagctg    180
cccagcagca agaggatgcg cacggctttc accagcacgc agctgctaga gctggagcgc    240
gagttcgctt ctaatatgta cctgtcccgc ctacgtcgca tcgagatcgc ga           292
```

<210> SEQ ID NO 5
<211> LENGTH: 190
<212> TYPE: DNA
<213> ORGANISM: Homo sapiens

<400> SEQUENCE: 5

```
tgcctgacac tgaccccagg cgcagccagg aggggctttg tgcgggagag ggaggggac     60
cccagcttgc ctggggtcca cgggactctc ttcttcctag ttcactttct tgctaaggcg    120
aaggtcctga ggcaggacga gggctgaact gcgctgcaat cgtccccacc tccagcgaaa    180
cccagttgac                                                           190
```

<210> SEQ ID NO 6
<211> LENGTH: 706
<212> TYPE: DNA
<213> ORGANISM: Homo sapiens

<400> SEQUENCE: 6

```
tcggcggaga gacctcgagg agagtatggg gaaaggaatg aatgctgcgg agcgcccctc    60
tgggctccac ccaagcctcg gaggcgggac ggtgggctcc gtcccgaccc cttaggcagc   120
tggaccgata cctcctggat cagaccccac aggaagactc gcgtggggcc cgatatgtgt   180
acttcaaact ctgagcggcc accctcagcc aactggccag tggatgcgaa tcgtgggccc   240
tgaggggcga gggcgctcgg aactgcatgc ctgtgcacgg tgccgggctc tccagagtga   300
gggggccgta aggagatctc caaggaagcc gaaaaaagca gccagttggg cttcgggaaa   360
gacttttctg caaaggaagt gatctggtcc cagaactcca gggttgaccc cagtacctga   420
cttctccggg agctgtcagc tctcctctgt tcttcgggct tggcgcgctc ctttcataat   480
ggacagacac cagtggcctt caaaaggtct ggggtggggg aacggaggaa gtggccttgg   540
gtgcagagga agagcagagc tcctgccaaa gctgaacgca gttagcccta cccaagtgcg   600
cgctggctcg gcatatgcgc tccagagccg gcaggacagc ccggccctgc tcaccccgag   660
gagaaatcca acagcgcagc ctcctgcacc tccttgcccc agagac                  706
```

<210> SEQ ID NO 7
<211> LENGTH: 325
<212> TYPE: DNA
<213> ORGANISM: Homo sapiens

```
<400> SEQUENCE: 7
agatcccggt gcatttaaag gccggcgtga tctgcaccac gtacctatct cggattctca      60
gtttcacttc gctggtgtct gccaccatct ttaccacatc ccggtagcta catttgtcta     120
ccgcttgagc caccagcgtc tgaaacctgg accggatttt gcgcgccgag aggtagccgg     180
aggcggtaat gaattccacc cagagggaca tgctcctctt gcgcccgtcg ctcaacttca     240
gcaccgcgca gccgggcagt gagccatcgt ccacgaagtt gaacaccccc atttggttga     300
gataaagcac cacttcaaat tcggt                                           325

<210> SEQ ID NO 8
<211> LENGTH: 663
<212> TYPE: DNA
<213> ORGANISM: Homo sapiens

<400> SEQUENCE: 8
actatgcctt gagggtcaaa acgtctggat ttcctgatcg atgctgtcgt cgctgtccac      60
ggagctactg tcgccgtcag agcgggaagg cacgttcagg gagtagaagc gtgggcttgc     120
agaaagggac ctgttgctgc cttacatggg ggccggcagg gtagtcttgg aaatgcccaa     180
gattgcttcc gcgcgcgtca gttcagcgga cgtgtctgcc tggcacgagg accgttctac     240
aaactcgttc ctggaagccg ggctcgctgg aggcggagct tggtttcct tcgggagctt     300 gtggggaatg gtcagcgtct aggcaccccg ggcaagggtc tgtggccttg gtggccactg     360
gcttcctcta gctgggtgtt ttcctgtggg tctcgcgcaa ggcactttt tgtggcgctg     420 cttgtgctgt gtgcggggtc aggcgtcctc tctcctcccg gcgctgggcc ctctggggca     480
ggtccccgtt ggcctccttg cgtgtttgcc gcagctagta cacctggatg gcctcctcag     540
tgccgtcgtt gctgctggag tctgacgcct cgggcgcctg cgccgcactt gtgacttgct     600
ttccccttct cagggcgcca gcgctcctct tgaccccgct tttattctgt ggtgcttctg     660
aag                                                                   663

<210> SEQ ID NO 9
<211> LENGTH: 1985
<212> TYPE: DNA
<213> ORGANISM: Homo sapiens

<400> SEQUENCE: 9
gcaagtcggg tagctaccgg gtgctggaga actccgcacc gcacctgctg gacgtggacg      60
cagacagcgg gctcctctac accaagcagc gcatcgaccg cgagtccctg tgccgccaca     120
atgccaagtg ccagctgtcc ctcgaggtgt tcgccaacga caaggagatc tgcatgatca     180
aggtagagat ccaggacatc aacgacaacg cgccctcctt ctcctcggac cagatcgaaa     240
tggacatctc ggagaacgct gctccgggca cccgcttccc cctcaccagc gcacatgacc     300
ccgacgccgg cgagaatggg ctccgcacct acctgctcac gcgcgacgat cacggcctct     360
ttggactgga cgttaagtcc cgcggcgacg gcaccaagtt cccagaactg gtcatccaga     420
aggctctgga ccgcgagcaa cagaatcacc atacgctcgt gctgactgcc ctggacggtg     480
gcgagcctcc acgttccgcc accgtacaga tcaacgtgaa ggtgattgac tccaacgaca     540
acagcccggt cttcgaggcg ccatcctact tggtggaact gcccgagaac gctccgctgg     600
gtacagtggt catcgatctg aacgccaccg acgccgatga aggtcccaat ggtgaagtgc     660
tctactcttt cagcagctac gtgcctgacc gcgtgcggga gctcttctcc atcgacccca     720
agaccggcct aatccgtgtg aagggcaatc tggactatga ggaaaacggg atgctggaga     780
```

| | |
|---|---|
| ttgacgtgca ggcccgagac ctggggccta accctatccc agcccactgc aaagtcacgg | 840 |
| tcaagctcat cgaccgcaac gacaatgcgc cgtccatcgg tttcgtctcc gtgcgccagg | 900 |
| gggcgctgag cgaggccgcc cctcccggca ccgtcatcgc cctggtgcgg gtcactgacc | 960 |
| gggactctgg caagaacgga cagctgcagt gtcgggtcct aggcggagga gggacgggcg | 1020 |
| gcggcgggg cctgggcggg cccggggtt ccgtcccctt caagcttgag gagaactacg | 1080 |
| acaacttcta cacggtggtg actgaccgcc cgctggaccg cgagacacaa gacgagtaca | 1140 |
| acgtgaccat cgtggcgcgg gacggggct ctcctcccct caactccacc aagtcgttcg | 1200 |
| cgatcaagat tctagacgag aacgacaacc cgcctcggtt caccaaaggg ctctacgtgc | 1260 |
| ttcaggtgca cgagaacaac atcccgggag agtacctggg ctctgtgctc gcccaggatc | 1320 |
| ccgacctggg ccagaacggc accgtatcct actctatcct gccctcgcac atcggcgacg | 1380 |
| tgtctatcta cacctatgtg tctgtgaatc ccacgaacgg ggccatctac gccctgcgct | 1440 |
| cctttaactt cgagcagacc aaggcttttg agttcaaggt gcttgctaag gactcggggg | 1500 |
| cgcccgcgca cttggagagc aacgccacgg tgagggtgac agtgctagac gtgaatgaca | 1560 |
| acgcgccagt gatcgtgctc cccacgctgc agaacgacac cgcggagctg caggtgccgc | 1620 |
| gcaacgctgg cctgggctat ctggtgagca ctgtgcgcgc cctagacagc gacttcggcg | 1680 |
| agagcgggcg tctcacctac gagatcgtgg acggcaacga cgaccacctg tttgagatcg | 1740 |
| acccgtccag cggcgagatc cgcacgctgc accctttctg ggaggacgtg acgcccgtgg | 1800 |
| tggagctggt ggtgaaggtg accgaccacg gcaagcctac cctgtccgca gtggccaagc | 1860 |
| tcatcatccg ctcggtgagc ggatccttc ccgaggggt accacgggtg aatggcgagc | 1920 |
| agcaccactg ggacatgtcg ctgccgctca tcgtgactct gagcactatc tccatcatcc | 1980 |
| tccta | 1985 |

<210> SEQ ID NO 10
<211> LENGTH: 213
<212> TYPE: DNA
<213> ORGANISM: Homo sapiens

<400> SEQUENCE: 10

| | |
|---|---|
| atgcgccctc tgcaccccta gagccagaag acgctaggtg ggctgcgcgc tctgccaggc | 60 |
| gaaggctgga gcgcagacgg caaagccgcg cgtttcagcc gtggtcgggt ccgcaggacc | 120 |
| tgggcgtggg gacaccacca ggcaggagca gaggcaggac tgggacgcca aaagctgaga | 180 |
| atcctcgatg cccgcgcgag agccccgtgt tat | 213 |

<210> SEQ ID NO 11
<211> LENGTH: 1558
<212> TYPE: DNA
<213> ORGANISM: Homo sapiens

<400> SEQUENCE: 11

| | |
|---|---|
| ttctggaaaac cgggccccac ttgcaggccc ggccaccttg ggttctggtg gccgaagccg | 60 |
| gagctgtgtt ctcgcagac tcggggagct acattgtgcg taggcaattg tttagtttga | 120 |
| aaggaggcac atttcaccac gcagccacgc ccctgcatgc aggagaagcc cccagggccc | 180 |
| agggtcggct ggctttagag gccacttagg ttgttttaag cacatgtgaa agggcagaca | 240 |
| gcaggggagc aggatatggg taagatcttc gggtctcaga acaggggctg cccttgggct | 300 |
| gtcccggcgc cctgggctct gacactgaag ggtggaatgg aggaaggaat ggagaaagga | 360 |
| cggtggaact ttcgcttccc ctctgggccg ccttcccagg gtcatgcctg agctgctttg | 420 |

```
atcccagtgt cgcgcatctt ggtccgctac ctcccaggcg atagctactg ggctcctcgc    480
tggcctcact gggggccatc ccgggcagtg gcctgccctc cgaggcccgc gggacccagc    540
ccagagctga ggttggagtt ctccgggcca cgttccgggt cgcttaggct cggagatttc    600
ccggagaccg tcgtcctccc tttctgcttg gcactgcgga gctccctcgg cctctctcct    660
cctctggtcc ctaaggcccg gagtggttgg cggtactggg gcccgtcgtc atctctgctt    720
ctaaggcatt cagactgggc tccagctggg accggcagag gaggttctca aggaaactgg    780
tgggaaatat agtttctttt cgtctggtcg tttaatttaa atgcaacttc ccttggggac    840
attttcctgg acgttaacca gaccaccttg agatgtcgtt gatgacctag agacccagat    900
gatgcgtccc aggaaagttc actgctgact attgtcactc ttggcgttat atctatagat    960
atagacctat gtacatatct ccaccctgat ctctccgtgg acatgaaacc cacctacctt   1020
gtgaaagccc tacgggtgac acatgactac tacgtctctg tcccaacagg ggctgggcct   1080
cccctgccta atagttgcca ggagtttcgc agcccaagtg aataatgtct tatggctgaa   1140
cgtggccaag gactcctgtg atttaggtcc caggaggagc agagacgtcc ccgccccgcc   1200
tgggccctgc cgcattcaaa gctggaagaa ggcgctgatc agagaagggg cttccaggtc   1260
ctgggttaga caacaacaa acaaacgaaa ctccacaaca gacacgcctg cccatgaccc   1320
cacgcaagga cataggaagt tctgtcgcct tcctgctccg cggatagccg cctgccgtct   1380
gctgccacca gaacgcacgg acgctcgggg tggaggtagt caatgggcag cagggggaccc   1440 ccagccccca aagcgcggc tccgaggacc tggaagcggg tgcctgtcgc tctccgcagg   1500
ctccgctctg cctccaggag caagatcccc aaaagggtct ggaagctgtg gagaaaac    1558

<210> SEQ ID NO 12
<211> LENGTH: 1264
<212> TYPE: DNA
<213> ORGANISM: Homo sapiens

<400> SEQUENCE: 12 tttttttaaac acttctttc cttctcttcc tcgttttgat tgcaccgttt ccatctgggg     60
gctagaggag caaggcagca gccttcccag ccagcccttg ttggcttgcc atcgtccatc    120
tggcttataa aagtttgctg agcgcagtcc agagggctgc gctgctcgtc ccctcggctg    180
gcagaagggg gtgacgctgg gcagcggcga ggagcgcgcc gctgcctctg gcgggctttc    240
ggcttgaggg gcaaggtgaa gagcgcaccg gccgtggggt ttaccgagct ggatttgtat    300
gttgcaccat gccttcttgg atcggggctg tgattcttcc cctcttgggg ctgctgctct    360
ccctccccgc cggggcggat gtgaaggctc ggagctgcgg agaggtccgc caggcgtacg    420
gtgccaaggg attcagcctg gcggacatcc cctaccagga gatcgcaggt aagcgcgggc    480
gcgctgcagg ggcaggctgc agccctcggc tgccgcacgt cccactggcc gcccggcgtc    540
cccttccttc ccctgttgc tgagttggtg ctcactttct gccaccgcta tgggactccg    600
cgtctccgtg ttgggcggcg gatgctcctg cggcttcttc ggcggggaa ggtgtgcgtc    660 tccgccgcct cattgtgtgc acacgcggga gcaccctggc tcccgcctcc cgctgctctc    720
gcgcccttct accccttagt tgatggctca ggcccggctg gccagggagc ccgggtcact    780
ccggggcggc tgcaaggcgc agacggagag ccgagccggg cgctcactcc gcgttctggt    840
tcgggcaaac ttggaagaac tgcgaccgca gtttgcccag cgccacagtc tgagtggcgc    900
cttctccact cccgcccttg cgccggcagg ggcggtggag agacgcggag ggctccccca    960
gcccctctct cccctatccg tccttcgggc gacagagcgc ccggcgctcg ggccgggggc   1020
```

```
gggcaaggct gggagggacc ctcgccgggg acctggcctc tggacgccgg cgtttcaagg   1080
ctggtttggg gacttcacgg gctgcctgtt tcagatgtgg ggcgggcttt cccgttaggg   1140
ttcctcagtg cttccccagt tgctgttggc cactcagggc ccggggacac cctgccaccc   1200
ggtctggagc cggcctcgtc tgccagcgaa cagccaactt tagcgggtgg ctcagctggg   1260
gatt                                                                1264
```

<210> SEQ ID NO 13
<211> LENGTH: 761
<212> TYPE: DNA
<213> ORGANISM: Homo sapiens

<400> SEQUENCE: 13

```
cactcagtgt gtgcatatga gagcggagag acagcgacct ggaggccatg ggtggggcg     60 ggtggtgaag ctgccgaagc ctacacatac acttagcttt gacacttctc gtaggttcca   120
aagacgaaga cacggtggct tcagggagac aagtcgcaag ggcgactttt ccaagcggga   180
gatggtgaag tctttggacg tgtagtgggt aggtgatgat ccccgcagcc gcctgtaggc   240
ccgcagactt cagaaaacaa gggccttctg tgagcgctgt gtcctccccg gaatccgcgg   300
cttaacacat tcttttccagc tgcggggcca ggatctccac cccgcgcatc cgtggacaca   360
cttagggtcg cctttgtttt gcgcagtgat tcaagttggg taaccccttgc tcaacacttg   420 ggaaatgggg agaatctccc ccacccgcaa cctcccgcac cccaggttcc caaaatctga   480
atctgtatcc tagagtggag gcagcgtcta gaaagcaaag aaacggtgtc caaagacccc   540
ggagagttga gtgagcgcag atccgtgacg cctgcggtac gctagggcat ccaggctagg   600
gtgtgtgtgt gcgggtcggg gggcgcacag agaccgcgct ggtttaggtg gacccgcagt   660
cccgcccgca tctggaacga gctgcttcgc agttccggct cccggcgccc cagagaagtt   720
cggggagcgg tgagcctagc cgccgcgcgc tcatgtttat t                       761
```

<210> SEQ ID NO 14
<211> LENGTH: 1198
<212> TYPE: DNA
<213> ORGANISM: Homo sapiens

<400> SEQUENCE: 14

```
agtcactcca ggatcagagg ccgcgtcggt tctgcttggg gcatgggcag agggaggctg     60
ctggggccaa gccccggctg gacgcgaggg aagaaactcg tcccaggacc cgcacgccca   120
tacctggctg tcccagagct cttccctagg ccggcacctt cgctcttcct cttcccacc    180 ccctagccct tttgtctctt tttcagacgg atgttttcag tctcaagtgg tttttatttc   240
cgcacaaaac cctgagatca agggcagatc acagactgta ccggaggctc gggtttccct   300
ggactctgtg ctgttctgcg tcccagggtt ggctaggaag gaaggcctgg gccggcgagg   360
tgacgggtct cccgcccagg tcggcaggac ggggggaggg gtgtcccggt aggtccctgg   420
tgagctcacc cgtggcatcg ggacccgcg ggaacccacc gggcgccac tagagactcg     480 ggtcctaccc tcccccacac tactccaccg aaatgatcgg aagggcgcgc taggcctgct   540
tccaagggct cagtgataaa ggcctcaaaa tcacactcca tcaagacttg gttgaagctt   600
tgggtaggtt tgttgttgtt gttgttgttg tttgtttgtt tgttttagca gacacgtcct   660
ggaaagaggt cctcagaacc caaaggttca ataatgattt gtggatggat tgattatagt   720
ctgatatcgc tctggttcca cagaaacccg gagctccttg gcccactgtt accccagcag   780
acctaaatgg acggtttctg tttttcactg gcagctcaga actggaccgg aagaagttcc   840
```

```
cctccacttc cccctcccg acaccagatc attgctgggt ttttatttc ggggaaaaa        900
caacaacaac aacaacaaaa aaaacactag gtccttccag actggatcag gtgatcgggc      960
aaaaaccctc aggctagtcc ggctgggtgc ccgagcatga aaaggcctcc gtggccgttt     1020
gaacagggtg ttgcaaatga aacttttgt aagccataac cagggcatcc tgagggtctg      1080
agttcacggt caaggctgtg ggctactagg tccagcgagt ccaggcctcg ccccgccccc     1140
gagctgccac agccaagatc ttcggcaggg aattcgagac cagggtcctc ccactcct       1198

<210> SEQ ID NO 15
<211> LENGTH: 377
<212> TYPE: DNA
<213> ORGANISM: Homo sapiens

<400> SEQUENCE: 15
tttcgtgccg ctgttttcaa tgcgctaacg aggcacgtta ttcttagccg cgtccgggag      60
gggatcacat tcctgcgcag ttgcgctgct ggcggaagtg acttgttttc taacgaccct     120
cgtgacagcc agagaatgtc cgtttctcgg agcgcagcac agcctgtccc atcgagaagc     180
ctcgggtgag gggcccggtg ggcgcccgga ggccgctgga gggctgtggg agggacggtg     240
gctccccact cccgtggcga agggcaggca aaccagaagc tcttttgag agccgtttgg      300
gattgagacg agtaagccac agcgagtggt tagaagtagg ttaggaagaa gggaggtaa      360
gaaagccgag tagggtt                                                   377

<210> SEQ ID NO 16
<211> LENGTH: 256
<212> TYPE: DNA
<213> ORGANISM: Homo sapiens

<400> SEQUENCE: 16
gttcggtgga caagggggca gcgcccacag caagccggaa agagggaggc gcggggccgc      60
gcttggggcc tgccgctgca cgccagcctg ggcaaagagc tgccaccttc tgcgggcgaa     120
gcgggtcggg acgcaggacg gcagcggggc tggaggcagc tacgtgggtc cacaccccca     180
tgccctgcaa ggctccttgg ccctgcttct cctctgtctc ggcgggagag gagcagcctc     240
ggttttacag aatttc                                                    256

<210> SEQ ID NO 17
<211> LENGTH: 189
<212> TYPE: DNA
<213> ORGANISM: Homo sapiens

<400> SEQUENCE: 17
tgtgccattt agtgagaggt gttttgggca aagaatcaat ttaactgtga ctgaccgacg      60
ggcttgactg tattaattct gctaccgaaa aaaaaaaaa aaaaaagca atgagccgca      120
agccttggac tcgcagagct gccggtgccc gtccgagagc cccaccagcg cggctcacgc     180
ctcagtctc                                                            189

<210> SEQ ID NO 18
<211> LENGTH: 707
<212> TYPE: DNA
<213> ORGANISM: Homo sapiens

<400> SEQUENCE: 18
agagtcccag ttctgcaggc cgctccaggg ctaggggtag agatggtggc aggtggtgcg      60
tcaactctct agggaagagg aacttgcatt acaaagactt gtctttctga gctgaagtca     120
```

```
aaacggggc  gtcaagcgcg  ctccgtttgg  cggcggtgga  ggggccgcgc  gcccgcgctg   180
tcccagccgg  agctgccctg  gctggtgatt  ggaggtttaa  cgtccggaat  tcaggcgctt   240
ctgcagctca  gatttgccgg  ccaaggggcc  tcagttgcaa  cttttcaaaa  tggtgtttct   300
ggaaaataac  aaattcagac  tcaactggtg  acagcttttg  gctatagaga  atgaaactgc   360
ttccctttgg  cggtggaact  cttaaacttc  gaagagtgaa  agaatacaat  gaaataaaat   420
gccataagat  cactggattt  ttcagaaaaa  ggaagacccc  aaattactcc  caaaatgagg   480 cttttgtaaat  tcttgttaaa  aatctttaaa  tctcgaattt  cccctacaa   catctgatga   540 gtgctttaag  agcaaacgag  caaatcccac  ctcgagaatc  aacaaaccca  agctctggcc   600
aaggctctcc  ccgcgttttc  ttctcgtgac  ctggggaatg  tcccgcccca  tcgctcacct   660
ggctcttgtc  atctcgctca  tcttgaagtg  accgtggac   aatgctg                 707
```

<210> SEQ ID NO 19
<211> LENGTH: 182
<212> TYPE: DNA
<213> ORGANISM: Homo sapiens

<400> SEQUENCE: 19

```
agctgccctc  tgtggccatg  agcgggtgtc  cagccccttc  caaggctgca  ccggggagac    60
gctggttttc  tgctcgctgt  gaccgaacaa  agcccctaag  agtcagtgcg  cggaacagaa   120
gagccggacc  ccgacgggcc  gagtcccaac  gtgaggcacc  cggcagagaa  aacacgttca   180
cg                                                                      182
```

<210> SEQ ID NO 20
<211> LENGTH: 179
<212> TYPE: DNA
<213> ORGANISM: Homo sapiens

<400> SEQUENCE: 20

```
cctcggcagc  accggcatgg  ctggaggcca  gtacggccag  gtgtggcggg  agggagcgcc    60
gtctggcttg  ggtcgtccat  cctgacagga  cgctgcaagg  gcaggagccc  cgcgccccgt   120
gtcctgcgcc  cccgctcgag  gacaagcccc  agccgccggt  ctccgctggg  ttccgacag    179
```

<210> SEQ ID NO 21
<211> LENGTH: 369
<212> TYPE: DNA
<213> ORGANISM: Homo sapiens

<400> SEQUENCE: 21

```
ctttaagagg  ctgtgcaggc  agacagacct  ccaggcccgc  tagggatcc   gcgccatgga    60 ggccgcccgg  gactatgcag  gagccctcat  caggcgagtg  ccccgcgtcc  ccctgattgc   120
cgtgcgcttc  caatcgcctt  gcgttcggtg  gcctcatatt  cccctgtgcg  cctctagtac   180
cgtaccccgc  tcccttcagc  cccctgctcc  ccgcattctc  ttgcgctccg  cgaccccgcg   240
cacacaccca  tccgccccac  tggtgcccaa  gccgtccagc  cgcgcccgcg  ggcagagccc   300
aatcccgtcc  cgcgcctcct  caccctcttg  cagctgggca  caggtaccag  gtgtggctct   360
tgcgaggtg                                                               369
```

<210> SEQ ID NO 22
<211> LENGTH: 176
<212> TYPE: DNA
<213> ORGANISM: Homo sapiens

<400> SEQUENCE: 22

```
agacttgcag aactcgggcc ccctggagga gacctaaccg ccacggtctt ggggaggttc    60
cggagggcct cggttgtctg cactcccaac accaagaaac ccctgagacg cgaagctgcc   120
agcgtgctgc cctcagagca gggcgacgca aagccagcgg accccggggt ggcggg       176
```

<210> SEQ ID NO 23
<211> LENGTH: 167
<212> TYPE: DNA
<213> ORGANISM: Homo sapiens

<400> SEQUENCE: 23

```
tgctcggctg gggggctcgc tccgcacttt cggtgccaga aaatgcccag aggagcgggg    60
cggccccaga gcctcctttc ggggcgcgag gcccggcgcg tgtgtacgga gtccagtccc   120
cccagggagt ggggtgcccg caccttcccc tccgcgctcg gagccac                 167
```

<210> SEQ ID NO 24
<211> LENGTH: 1205
<212> TYPE: DNA
<213> ORGANISM: Homo sapiens

<400> SEQUENCE: 24

```
tcttgcacac ctgcttgtag ttctgcaccg agatctggtc gttgaggaac tgcacgcaga    60
gcttggtgac ctgggggatg tgcaggatct tgctgaccga cagcacctcc tccaccgtgt   120
ccagggacag ggtcacgttg gccgtgtaga ggtactcgag caccaggcgc agcccgatgg   180
acgagcagcc ctgcagcacc aggttgttga tggcccgggg gctggtcagc agcttgtcgt   240
cgggggagga agaaggagtc ccgggctcct cctgcgcgg cggctgctgc tgctgtgacg    300
gctgctgctg cggcggctgc tgctggtcct tggggccccc caggccgtcc tggccgccga   360
ccctcccccc gagaggggg tggctggaga agagcgatcg gaagtactgc gagcaggagg    420
ccagcacggc cttgtggcaa tggaactgct ggccctgggc cgtcagggtc acgtcgcaaa   480
acagctgctt cctccacagc aggttgaggc cgtgcagcag ttgtcgctg tggctggggt    540
cgaaggtgga ggtcctgtcc ccggatctgg acatggcgag ctgactcggt gcacctggct   600
ttaaaccctc ctccaacctg gcagacaggg gtggggatg ggagggaggg gagcagggtg    660
gtggagcggg tgggtgtgg tcgggtggg aagggtgtg gagggaggg gagggcgaag       720
aacaagaatc aaggctcagc ttgactccct cctggcgcgc tccggacccc gaccctagga   780
ggaaagtccg aagacgctgg atccgtgagc gccaccagaa gggccctgtc tggggtcccg   840
gcgccggttc tgcgccctgc ggctcctctc gccacctccc acacacttcg tccctcactt   900
tcctaaaacc aaccacctca gctcggctgt tggcagcaac agcagtggca gcagcgacgg   960
caaagtggcg gctgaggccg aggcacctcg tgggctcgtg tccatgccgg gccagatgaa  1020
gggaaaggcc gggaagtggg gagccggggg tgccctgaaa gctcagaggc gaccgacggc  1080
gaaggttcca ggtcaacttg tgcccgaagc tttgcttttc gcagttggcc cagtttgggg  1140
gaggggtag gaacaggggc ccgaccagcg tgcgggtgt gcgaatctta gctctccaaa   1200
agctg                                                             1205
```

<210> SEQ ID NO 25
<211> LENGTH: 44
<212> TYPE: DNA
<213> ORGANISM: Homo sapiens

<400> SEQUENCE: 25
cctctgtgtt agtgccctcg ggaatttggt tgatggggtg tttg        44

<210> SEQ ID NO 26
<211> LENGTH: 5002
<212> TYPE: DNA
<213> ORGANISM: Homo sapiens

<400> SEQUENCE: 26
tgatgtcgca cctgaacggc ctgcaccacc cgggccacac tcagtctcac gggccggtgc    60
tggcacccag tcgcgagcgg ccaccctcgt cctcatcggg ctcgcaggtg ccacgtcgg    120
gccagctgga agaaatcaac accaaagagg tggcccagcg catcacagcg agctgaagc    180
gctacagtat cccccaggcg atctttgcgc agagggtgct gtgccggtct caggggactc    240
tctccgacct gctccggaat ccaaaaccgt ggagtaaact caaatctggc agggagacct    300
tccgcaggat gtggaagtgg cttcaggagc ccgagttcca gcgcatgtcc gccttacgcc    360
tggcaggtaa ggccggggct agccaggggc caggctgctg ggaagagggc tccgggtccg    420
gtgcttgtgg cccaagtctg cgcgccgagt cacttctctt gattctttcc ttctcttttcc    480
tatacacgtc ctctttcttc tcgttttat ttcttcttcc attttctctt tctcttccgc    540
tcttccccta ctttcccttc tccttttct ttttctttct tactctctcc ttgtccctga    600
gctttcattg accgaccccc ccccatttca ttcgccctcc cctcaatgtg ccaacctttg    660
ccctattcc gatcttccca ggtactggga ggcgggatgg gggtgtgcgt tttcctctag    720
gagccctgtc tttccaagac ccacagaaac caggacctgc ccttattcaa aaccccatgc    780
acttcaagtc tcttttagac aacacatttc aattttccgg gctgactagt ctccctgtgc    840
agaggcagtt gagaggcttt gctctgcaga gggaaaagag ctctactc tcccacccac    900
catataggca aacttatttg gtcattggct gaaggcacag ccttgcccc gcggggaacc    960
ggcggccagg atacaacagc gctcctggag cccatctctg gccttggcgt tggcgcaggg   1020
actttctgac cgggcttgag gggctcgggc cagctccaat gtcactacct acagcgaggg   1080
cagggtgtaa ggttgagaag gtcacattca ccgctttggg aggacgtggg agaagagact   1140
gaggtggaaa gcgctttgcc ttgctcaccg gccgtccttg cccggtccc agcgtttgct   1200
gggatttgcc aggatttgcc ggggctccgg gagaccctga gcactcgcag gaagaggtgc   1260
tgagaaatta aaaattcagg ttagttaatg catccctgcc gccggctgca ggctccgcct   1320
ttgcattaag cgggcgctga ttgtgcgcgc ctggcgaccg cggggaggac tggcggcccg   1380
cgggagggga cgggtagagg cgcgggttac attgttctgg agccggctcg gctctttgtg   1440
cctcctctag cggccaagct gcgaggtaca gccctctatt gttctaggag cacagaaacc   1500
tcctgtgtgg gcggcgggtg cgcgagctag agggaaagat gcagtagtta ctgcgactgg   1560
cacgcagttg cgcgcttttg tgcgcacgga ccccgcgcgg tgtgcgtggc gactgcgctg   1620
cccctaggag caagccacgg gcccagaggg gcaaaatgtc caggtccccc gctgggaagg   1680
acacactata ccctatggca agccagggtg ggcgacttcc catggatcgg gtggaggggg   1740
gtatctttca ggatcggcgg gcggtctagg ggaacaattc gtggtggcga tgatttgcat   1800
agcgcgggtc ttgggatgcg cgcggttccg agccagcctc gcacagctcg cttccggagc   1860
tgcgagctca ggtttccacc cccgatcccc cgggctttcc tcgcaccgct gagcccagct   1920
tgtgggggtgc actcgaccaa cgcccgacag ggctggggaa tgtgacaggc agcaggttca   1980
cccgggcttg ggaggggga gtttccgctt tgacagcatt ttcctttgcc gtctgctggt   2040

-continued

```
ggattcctat tcccagtcgg taatcgcccc gcagtgttga tctaagaagg taaagaaaac    2100
taggtttccc tgcaaagagc ctcccccaaa tcggcggact ccggatactt tgagtggatt    2160
tagaaattta tgtaatcttt ctcctttagt ttattttca tcctctccta cagttttctc     2220
tgatttgctg ttggttcggg gcaagataaa gcagccagta gagagcgata ataatagcgg    2280
cgggaaatga actggagact ggctgacagt tcttaacatt ttgtcataga tccccccgaa    2340
tgtcccaggc tgtctctggt gggttttagt acccgccggc ttcttgggca ccggggacca    2400
gaaggaactt ggcagctggt cttaggggta cagttaaagg caggatgaca gctattctcc    2460
tgctcatctc agagcgctgc cgccccctca tgccggtcgc gcaaagaaca cagcttttaa    2520
aaaacacgtg ccttctgccc atataggtct gaaagtgatg aggaaagtaa tgcttcgcct    2580
attagcgagt ttcagctttt aaaatgatcc caagcgttgc tgagatgaga aagcgtggca    2640
tcccgggggt cctcagcccc acccgcgccc atggtgcaag tctgcaggga caggcccggg    2700
acagcactgc ccacgctgct agattttccg cagaggatcg ctgaagctgc cttcgtggga    2760
gacagaatgc ctcctccagc gagtggaaaa ggcctgctga ggaccccgct ttgctcgagc    2820
attcaaatgt gtgtctgttt tattaccctg ggttgaaaag ggacaagagc tttagccttt    2880
ttatctggcc attttatcag caactacaag tgtgttgagt ggttattatt acataggagg    2940
cttttcagtt tggggtcagt agatcagtct cttcagacac tgatgcagaa gctgggactg    3000
gtaagtaggt attatgtgct cggagcgcta ggggacagga gcaaatggag aagaaaagcg    3060
gaggctttct ccgcccggag tatcgatcgg aatccccgcc ggtacgccgc agagggccct    3120
cgccgttggg ccccggggt ttaacaagcc cagccgctcc gcaggcggct cggccggact    3180
ctcagaccgg tgcctggaag acaccgtccc tgccccctc ccgccaaacc tgcctcttct    3240 cttctctca taggttatag gttccctttc tctctcattt tggccccgcc ccgggtcct    3300 gccaaacagc caagcaggcc ggggtttagg gggctcagaa tgaagaggtc tgatttggcc    3360
agcgccggca aagctcaccc ttaggcgagg tcacaacaga ggcaggtcct tcctgcccag    3420
cctgccggtg tagtcacagc caagggtggc acttgaaagg aaaagggaga aaacttcgga    3480
gaaatttaga ttgccccaac gttagatttc agagaaattg actccaaatg cacggattcg    3540
ttcggaaagg gcggctaagt ggcaggtggt tgcaaccccg cccggtcggg ccttcgcaga    3600
ggttccccaa gaccagccct tgcagggcgg ttttcagcaa cctgacaaga ggcggccaag    3660
acaaatttct gcgggttcga gcacacactc tcgggcgttg ggccccagag acctctaaac    3720
caagcacaaa caagaaggga gtgagagaac ccaggctaga acttgcacgg gcatcccact    3780
gaggaaaagc gaggcctcgg tggcaggcat gttttcttcc gacgcccgaa aatcgagccg    3840
agcgcccgac tacatttact gcagaggttt ccgcctccag tgagcccgga tcccccagcg    3900
gcctgcccgg agctggtctc cagtcccgc cgtagtccga cgcacggccc tctcctggca    3960
gcaagctccc agcggccagt ctgaagccaa ttctgttcag gcggccgagg gcccttagcc    4020
aacccaccat gatgtcgcct gggccacctg atgcccgcag cggcgggaca cggcccgggc    4080
agtgcgcagt ggctcctgct aggggcaccg cgtgcgtgct tgtctcccgc tgcgccgggg    4140
acgtccttgg gtgacacggg ccgctgggca cctcccaagc cgaggaaacg gaccccccttc   4200 gcagagtctc gcgcccaccc cccaacctcc cacctcgttt ctcgctgcta gggctcccga    4260
ctcagcccac ctctcctggc ggtttagtta gggatcagag ctggagaggc tgaacgcaac    4320
ccgtgccagt acgaacagag cgatatgttt gcctgctagc tgcttggatg aataattgaa    4380
aagttcgctg cagtctgtgc ttcgtcaagt cccgggtgcc gggagaacac cttcccaaca    4440
```

| | |
|---|---|
| cgcatcaggg tgggcgggag cgggcagagg aggcgggacc cgagggagga gagtgaaccc | 4500 |
| gagcaggaga agcagcccag gcagccaggc gccctcgatg cgagaggctg ggcatttatt | 4560 |
| tttattccag gctttccact gtgtggttat gtcactttct caaacaaatg tgtatatgga | 4620 |
| gggagatcga tgctgataat gtttagaaga ttaaaagagc attaatgctg caacaataa | 4680 |
| cgtaaacgtg tggacccaga tttcattgat ctggaacttg atccggcgcg tttccagtaa | 4740 |
| gcccgacggc gcgctcttcc cagcagagcg ctcaccagcg ccacggcccc gcggttttcc | 4800 |
| agcggtgccg cttcgccagc tctgcgcggg ttctcccgtc tgaccgcagc tcctcccccg | 4860 |
| cgaggcccca gcccgcctta cttccccgag gttttctcct cctctcgcgg ggctctctgc | 4920 |
| cctctgcacc ccctcccccg acctctgcac cacccgcccc tgtgcgcaca caccgctact | 4980 |
| tgcgcttccg gcgatccgcc tg | 5002 |

<210> SEQ ID NO 27
<211> LENGTH: 150
<212> TYPE: DNA
<213> ORGANISM: Homo sapiens

<400> SEQUENCE: 27

| | |
|---|---|
| aaccggagat ctgcttggtg aactgagagg agtccttagg agagcgggga cgccaggggc | 60 |
| cgggggacac ttcgctctcg ccctagggaa ggtggtcttg acgctttcta ttgaagtcaa | 120 |
| acttgaaaat atcagctgcc gctggactat | 150 |

<210> SEQ ID NO 28
<211> LENGTH: 339
<212> TYPE: DNA
<213> ORGANISM: Homo sapiens

<400> SEQUENCE: 28

| | |
|---|---|
| cgtgagcaga acgcccgccc tggagcagtt aggaccgaag gtctccggag agtcgccggc | 60 |
| ggtgccaggt aacgcagagg gctcgggtcg ggccccgctt ctggggcttg ggactccggg | 120 |
| cgcgcggagc cagccctctg gggcgaaatc cccgggcggc gtgcgcggtc cctctccgcg | 180 |
| ctgtgctctc ccagcaactc cctgccacct cgacgagcct accggccgct ccagagttcga | 240 |
| cttcctcgga cttagtggga aaggggttg gaaatgggct gccgggactg ggggagctgc | 300 |
| tctctggaag cagggaagct ggggcgcacc ggggcaggt | 339 |

<210> SEQ ID NO 29
<211> LENGTH: 1961
<212> TYPE: DNA
<213> ORGANISM: Homo sapiens

<400> SEQUENCE: 29

| | |
|---|---|
| tagaagagga agactcctct ggccccacta ggtatcatcc gcgctctccc gctttccacc | 60 |
| tgcgccctcg cttgggccaa tctctgccgc acgtgtccat ccctgaactg cacgctatcc | 120 |
| tccaccccg gggggttcct gcgcactgaa agaccgttct ccggcaggtt ttgggatccg | 180 |
| gcgacggctg accgcgcgcc gcccccacgc ccggttccac gatgctgcaa tacagaaagt | 240 |
| ttacgtcggc cccgacccgc gcgggactgc agggtccgcc ggagcgcggc gcagaggctt | 300 |
| ttcctgcgcg ttcggccccg ggaaaggggc gggagggctg gctccgggag cgcacgggcg | 360 |
| cggcggggag ggtactcact gtgaagcacg ctgcgcccat ggatcatgtc tgtgcgttac | 420 |
| accagaggct ccgggctcca ctaattccat ttagagacgg gaagacttcc agtgcgggg | 480 |
| ggaggacagg gtcgagaggt gttaaagacg caaagcaaga aggaaataaa ggggggccga | 540 |

```
gagggagacc gagaggaagg gggagctccg agcccacgct gcagccagat ccggatgagt      600
ccgtcctccg ccccgggcgg gctctcgctc tcgctggccc tcagcgccgc gcagccagca      660
gcatccccac cgtgacgctc gcatcacacc cgggcgccgg ccgccaccat ccgcgccgcc      720
gccgtcagga ccctcctccc gggcatcgtc gccgccgcgg ggtcgggagg acgcggcgcg      780
cgggaggcgg cggtcgcagg gcgagccccg ggacgccccg agccggggcc ggggccgggg      840
agagggcgca gcgaggtggg ggccagtcca gaccgacggc agcgacggag cgggcggcgg      900
cggcggcgcc ggcggcggcg gggtggctca gtccccagtc tcagacgcgc cgcgcagcag      960
gtcggagcag cctccccggg aggatgtcca gcggcagcgc tcctcgctcc agcccttggg     1020
gatcttccgc tgaggcattg aaggcaggaa gaaggggtcc gtcatcggct cgccgggctg     1080
cgcgccacct ctgctatctt gcggaaagag gagcgggtgg gtgggcgtct gggaggcggg     1140
ctggagggcg gtgcagggga gcggggcggc cggggggggg gccgggggc ggggaaggga     1200 gggaggagaa aggagccgga agagggcaga gttaccaaat gggctcctta gtcatggctt     1260
ggggctccac gaccctcctg gaagcccgga gcctgggtgg gatagcgagg ctgcgcgcgg     1320
ccggcgcccc ggggctggtg cgcggcagaa tggggccgcg gcggcggcag caaggacatc     1380
ccagccgcgc ggatctgggg gaggggcggg gaggggtga ggacccggct gggatccgcg     1440
gctcggcccg ccagggcgca gagagaggat gcagccgcaa atcccgagcc ggatcctcgt     1500
gccgacggaa aggcgtggaa gcgggagggg ccttcgtgtg aaaatcccttt gtggggtttg     1560 gtgtttcact ttttaaaggt tagaccttgc gggctctctg cctcccaccc cttcttttcc     1620
atccgcgtaa aggaactggg cgcccctct ccctcccctcc ctggggcgca ggtttcgccg     1680
cggactccgc gctcagcttg ggagacacgg caggggcgcg cccagggaa aggcggccgt     1740 aaaagtttcg cggttgagca ctgggcctga tgtccagtcc ccccaccaaa ttactcctgc     1800
aaagacgcgg gcttcttgca attgagcccc ccacctcgag gtatttaaaa ccaccccaag     1860
gcacacacgg acccccgttc ccccgcgcca cttcctccta caggctcgcg cggcgcgtta     1920
aagtctggga gacacgagtt gcggggaaac agcaccggaa g                        1961

<210> SEQ ID NO 30
<211> LENGTH: 314
<212> TYPE: DNA
<213> ORGANISM: Homo sapiens

<400> SEQUENCE: 30
aagaaacagc tcatttcgga gctgaggaca aggcgtggga agaagacgcg tttggtttca       60
cccaggcggg tggcggcaaa gctgtgggat gcgcgctgca cactccttcc gtcatcccgt      120
tcccaccttc cacacacacc tgcgggaggt cggacatgtc ctgattgcgt gttcatcacg      180
atggcaaacc gaacatgagg agaacgccac tgacgctggg tgcgccggct ttcccagccc      240
tcgtgcataa cggggaggga gatgcagaag ttttttccaa catcggtgca aaggggaagc      300
tgaggttttc ctat                                                       314

<210> SEQ ID NO 31
<211> LENGTH: 584
<212> TYPE: DNA
<213> ORGANISM: Homo sapiens

<400> SEQUENCE: 31
tctgtcagct gctgccatgg ggcagcggga aggccctgga gggtgcctgg gctgtgtctg       60
gtcccggcca cgcgtccctg cagcgtctga gaccttgtgg aacacacttg acccggcgct      120
```

| | |
|---|---|
| gggacggggt cggcccacac gcaccgccag cccgcaggag tgaggtgcag gctgccgctg | 180 |
| gctccttagg cctcgacagc tctcttgagg tcggccctcc tccctcccg agagctcagc | 240 |
| agccgcagac ccaggcagag agagcaaagg aggctgtggt ggcccccgac gggaacctgg | 300 |
| gtggccgggg gacacaccga ggaactttcc gcccccgac gggctctccc accgaggctc | 360 |
| aggtgctcgt gggcagcaag gggaagcccc atggccatgc cgcttccctt tcaccctcag | 420 |
| cgacgcgccc tcctgtgccc gcggggaaca agacggctct cggcggccat gcaggcggcc | 480 |
| tgtcccacga acacgatgga gacctcagac gccgtcccca ccctgtcact gtcaccatca | 540 |
| cccatcctgt cccctcacgc ctccccacat cccatcatta ctac | 584 |

<210> SEQ ID NO 32
<211> LENGTH: 349
<212> TYPE: DNA
<213> ORGANISM: Homo sapiens

<400> SEQUENCE: 32

| | |
|---|---|
| gaagtagaat cacagtaaat gaggagttag ggaatttagg gtagagatta aagtaatgaa | 60 |
| cagaggagga ggcctgagac agctgcagag agaccctgtg ttccctgtga ggtgaagcgt | 120 |
| ctgctgtcaa agccggttgg cgctgagaag aggtaccggg ggcagcaccc gcctcctggg | 180 |
| agagggatgg gcctgcgggc acctggggga accgcacgga cacagacgac actataaacg | 240 |
| cgggcgagac atcagggacc gggaaacaga aggacgcgcg tttcgagcag ctgcccagtg | 300 |
| ggccacaagc cccgccacgc cacagcctct tcccctcagc acgcagaga | 349 |

<210> SEQ ID NO 33
<211> LENGTH: 3510
<212> TYPE: DNA
<213> ORGANISM: Homo sapiens

<400> SEQUENCE: 33

| | |
|---|---|
| tactccggcg acgggaggat gttgagggaa gcctgccagg tgaagaaggg gccagcagca | 60 |
| gcacagagct tccgactttg ccttccaggc tctagactcg cgccatgcca agacgggccc | 120 |
| ctcgactttc acccctgact cccaactcca gccactggac cgagcgcgca agaacctga | 180 |
| gaccgcttgc tctcaccgcc gcaagtcggt cgcaggacag acaccagtgg gcagcaacaa | 240 |
| aaaaagaaac cgggttccgg gacacgtgcc ggcggctgga ctaacctcag cggctgcaac | 300 |
| caaggagcgc gcacgttgcg cctgctggtg tttattagct acactggcag gcgcacaact | 360 |
| ccgcgccccg actggtggcc ccacagcgcg caccacacat ggcctcgctg ctgttggcgg | 420 |
| ggtaggcccg aaggaggcat ctacaaatgc ccgagccctt tctgatcccc accccccgc | 480 |
| tccctgcgtc gtccgagtga cagattctac taattgaacg gttatgggtc atccttgtaa | 540 |
| ccgttggacg acataacacc acgcttcagt tcttcatgtt ttaaatacat atttaacgga | 600 |
| tggctgcaga gccagctggg aaacacgcgg attgaaaaat aatgctccag aaggcacgag | 660 |
| actgggggcga aggcgagagc gggctgggct tctagcggag accgcagagg gagacatatc | 720 |
| tcagaactag gggcaataac gtgggtttct ctttgtattt gtttattttg taactttgct | 780 |
| acttgaagac caattattta ctatgctaat ttgtttgctt gttttaaaa ccgtacttgc | 840 |
| acagtaaaag ttccccaaca acggaagtaa cccgacgttc ctcacactcc ctaggagact | 900 |
| gtgtgcgtgt gtgcccgcgc gtgcgctcac agtgtcaagt gctagcatcc gagatctgca | 960 |
| gaaacaaatg tctgaattcg aaatgtatgg gtgtgagaaa ttcagctcgg ggaagagatt | 1020 |
| agggactggg ggagacaggt ggctgcctgt actataagga accgccaacg ccagcatctg | 1080 |

```
tagtccaagc agggctgctc tgtaaaggct tagcaatttt ttctgtaggc ttgctgcaca   1140
cggtctctgg cttttcccat ctgtaaaatg ggtgaatgca tccgtacctc agctacctcc   1200
gtgaggtgct tctccagttc gggcttaatt cctcatcgtc aagagttttc aggtttcaga   1260
gccagcctgc aatcggtaaa acatgtccca acgcggtcgc gagtggttcc atctcgctgt   1320
ctggcccaca gcgtggagaa gccttgccca ggcctgaaac ttctctttgc agttccagaa   1380
agcaggcgac tgggacggaa ggctctttgc taaccttta cagcggagcc ctgcttggac    1440
tacagatgcc agcgttgccc ctgccccaag gcgtgtggtg atcacaaaga cgacactgaa   1500
aatacttact atcatccggc tccctgcta ataaatggag gggtgtttaa ctacaggcac     1560
gaccctgccc ttgtgctagc gcggttaccg tgcggaaata actcgtccct gtacccacac   1620
catcctcaac ctaaaggaga gttgtgaatt ctttcaaaac actcttctgg agtccgtccc   1680
ctccctcctt gcccgccctc taccctcaa gtccctgccc ccagctgggg gcgctaccgg    1740
ctgccgtcgg agctgcagcc acggccatct cctagacgcg cgagtagagc accaagatag   1800
tggggacttt gtgcctgggc atcgtttaca tttgggcgc caaatgccca cgtgttgatg    1860
aaaccagtga gatgggaaca ggcggcggga aaccagacag aggaagagct agggaggaga   1920
ccccagcccc ggatcctggg tcgccagggt ttccgcgcg catcccaaaa ggtgcggctg    1980
cgtggggcat caggttagtt tgttagactc tgcagagtct ccaaaccatc ccatccccca   2040
acctgactct gtggtggccg tatttttac agaaatttga ccacgttccc tttctccctt    2100
ggtcccaagc gcgctcagcc ctccctccat cccccttgag ccgcccttct cctcccctc     2160 gcctcctcgg gtccctcctc cagtccctcc ccaagaatct cccggccacg ggcgcccatt   2220
ggttgtgcgc agggaggagg cgtgtgcccg gcctggcgag tttcattgag cggaattagc   2280
ccggatgaca tcagcttccc agccccccgg cgggcccagc tcattggcga ggcagcccct   2340
ccaggacacg cacattgttc cccgccccg ccccgccac cgctgccgcc gtcgccgctg      2400
ccaccgggct ataaaaaccg gccgagcccc taaaggtgcg gatgcttatt atagatcgac   2460
gcgacaccag cgcccggtgc caggttctcc cctgaggctt tcggagcga gctcctcaaa    2520 tcgcatccag agtaagtgtc cccgcccac agcagccgca gcctagatcc cagggacaga    2580
ctctcctcaa ctcggctgtg acccagaatg ctccgataca gggggtctgg atccctactc   2640
tgcgggccat ttctccagag cgactttgct cttctgtcct ccccacactc accgctgcat    2700
ctccctcacc aaaagcgaga gtcggagcg acaacagctc tttctgccca gccccagtc     2760 agctggtgag ctccccgtgg tctccagatg cagcacatgg actctgggcc ccgcgccggc   2820
tctgggtgca tgtgcgtgtg cgtgtgtttg ctgcgtggtg tcgatggaga taaggtggat   2880
ccgtttgagg aaccaaatca ttagttctct atctagatct ccattctccc caaagaaagg   2940
ccctcacttc ccactcgttt attccagccc ggggggctcag ttttcccaca cctaactgaa   3000
agcccgaagc ctctagaatg ccacccgcac cccgagggtc accaacgctc cctgaaataa   3060
cctgttgcat gagagcagag gggagataga gagagcttaa ttataggtac ccgcgtgcag   3120
ctaaaaggag ggccagagat agtagcgagg gggacgagga gccacgggcc acctgtgccg   3180
ggaccccgcg ctgtggtact gcggtgcagg cgggagcagc ttttctgtct ctcactgact    3240
cactctctct ctctctccct ctctctctct ctcattctct ctcttttctc ctcctctcct    3300
ggaagttttc gggtccgagg gaaggaggac cctgcgaaag ctgcgacgac tatcttcccc   3360
tggggccatg gactcggacg ccagcctggt gtccagccgc ccgtcgtcgc cagagcccga   3420
```

```
tgaccttttt ctgccggccc ggagtaaggg cagcagcggc agcgccttca ctgggggcac    3480
cgtgtcctcg tccaccccga gtgactgccc                                     3510

<210> SEQ ID NO 34
<211> LENGTH: 333
<212> TYPE: DNA
<213> ORGANISM: Homo sapiens

<400> SEQUENCE: 34
ttaattcgaa aatggcagac agagctgagc gctgccgttc ttttcaggat tgaaaatgtg      60
ccagtgggcc aggggcgctg ggacccgcgg tgcggaagac tcggaacagg aagaaatagt     120
ggcgcgctgg gtgggctgcc ccgccgccca cgccggttgc cgctggtgac agtggctgcc    180
cggccaggca cctccgagca gcaggtctga gcgttttgg cgtcccaagc gttccgggcc      240
gcgtcttcca gagcctctgc tcccagcggg gtcgctgcgg cctggcccga aggatttgac     300
tctttgctgg gaggcgcgct gctcagggtt ctg                                  333

<210> SEQ ID NO 35
<211> LENGTH: 385
<212> TYPE: DNA
<213> ORGANISM: Homo sapiens

<400> SEQUENCE: 35
ccggtcccca gtttggaaaa aggcgcaaga agcgggcttt tcagggaccc cggggagaac      60
acgagggctc cgacgcggga gaaggattga agcgtgcaga ggcgcccaa attgcgacaa      120 tttactggga tccttttgtg gggaaaggag gcttagaggc tcaagctata ggctgtccta     180
gagcaactag gcgagaacct ggccccaaac tccctcctta cgccctggca caggttcccg    240
gcgactggtg ttcccaaggg agcccctga gcctaccgcc cttgcagggg gtcgtgctgc      300
ggcttctggg tcataaacgc cgaggtcggg ggtggcggag ctgtagaggc tgcccgcgca    360
gaaagctcca ggatcccaat atgtg                                           385

<210> SEQ ID NO 36
<211> LENGTH: 105
<212> TYPE: DNA
<213> ORGANISM: Homo sapiens

<400> SEQUENCE: 36
gcgcaggtcc ccccagtccc cgagggagtg cgcccgacgg aaacgcccct agcccgcggg      60
cctcgctttc ctctcccggg ttcctgggtc acttcccgct gtctc                     105

<210> SEQ ID NO 37
<211> LENGTH: 147
<212> TYPE: DNA
<213> ORGANISM: Homo sapiens

<400> SEQUENCE: 37
ttccctcgcg gctttggaaa gggggtgcaa atgcacccct ctgcgggccc gctacccgct      60
gcaacacctg tgtttccttt ctgggcacct tctaggtttc tagatattgc tgtgaatacg     120
gtcctccgct gtacagttga aaacaaa                                         147

<210> SEQ ID NO 38
<211> LENGTH: 365
<212> TYPE: DNA
<213> ORGANISM: Homo sapiens
```

```
<400> SEQUENCE: 38
tgggaattta ggtcgggcac tgccgatatg tcgccttcca caaggcgggc ccgggcctct    60
gctgaccgtg caccggtcct ggggctgggt aattctgcag cagcagcgca gcccatgccg   120
gggaatttgc gggcagagga gacagtgagg cccgcgttct gtgcgggaac tcccgagctc   180
acagagccca agaccacacg gctgcatctg cttggctgac tgggccaggc ccacgcgtag   240
taacccggac gtctctctct cacagtcccc ttgcgtctgg ccaggagct gccaggctgc    300 accccgcggt ggggatcggg agaggggcag tgtcgcccat ccccggaagg ctgagcctgg   360
tgcag                                                               365

<210> SEQ ID NO 39
<211> LENGTH: 418
<212> TYPE: DNA
<213> ORGANISM: Homo sapiens

<400> SEQUENCE: 39
cggttttctc ctggaggact gtgttcagac agatactggt ttccttatcc gcaggtgtgc    60
gcggcgctcg caagtggtca gcataacgcc gggcgaattc ggaaagcccg tgcgtccgtg   120
gacgacccac ttggaaggag ttgggagaag tccttgttcc cacgcgcgga cgcttccctc   180
cgtgtgtcct tcgagccaca aaaagcccag accctaaccc gctccttct cccgccgcgt    240 ccatgcagaa ctccgccgtt cctgggaggg gaagcccgcg aggcgtcggg agaggcacgt   300
cctccgtgag caaagagctc ctccgagcgc gcggcgggga cgctgggccg acggggacc    360 gcggggcag ggcggagagg acccgccctc gagtcggccc agccctaaca ctcaggac     418

<210> SEQ ID NO 40
<211> LENGTH: 906
<212> TYPE: DNA
<213> ORGANISM: Homo sapiens

<400> SEQUENCE: 40
agggaatcgg gctgaccagt cctaaggtcc cacgctcccc tgacctcagg gcccagagcc    60
tcgcattacc ccgagcagtg cgttggttac tctccctgga aagccgcccc cgccggggca   120
agtgggagtt gctgcactgc ggtctttgga ggcctaggtc gcccagagta ggcggagccc   180
tgtatccctc ctggagccgg cctgcggtga ggtcggtacc cagtacttag ggagggagga   240
cgcgcttggt gctcagggta ggctgggccg ctgctagctc ttgatttagt ctcatgtccg   300
cctttgtgcc ggcctctccg atttgtgggt ccttccaaga aagagtcctc tagggcagct   360
agggtcgtct cttgggtctg gcgaggcggc aggccttctt cggacctatc cccagaggtg   420
taacggagac tttctccact gcagggcggc ctggggcggg catctgccag gcgagggagc   480
tgccctgccg ccgagattgt ggggaaacgc cgtggaagac accccatcgg agggcaccca   540
atctgcctct gcactcgatt ccatcctgca acccaggaga aaccatttcc gagttccagc   600
cgcagaggca cccgcggagt tgccaaagga gactcccgcg aggtcgctcg aaccttgac    660 cctgacacct ggacgcgagg tcttttcagga ccagtctcgg ctcggtagcc tggtccccga   720
ccaccgcgac caggagttcc ttcttcccctt cctgctcacc agccggccgc cggcagcggc   780
tccaggaagg agcaccaacc cgcgctgggg gcggaggttc aggcggcagg aatggagagg   840
ctgatcctcc tctagccccg gcgcattcac ttaggtgcgg gagccctgag gttcagcctg   900
actttc                                                              906
```

```
<210> SEQ ID NO 41
<211> LENGTH: 860
<212> TYPE: DNA
<213> ORGANISM: Homo sapiens

<400> SEQUENCE: 41
cactacggat ctgcctggac tggttcagat gcgtcgttta aaggggggggg ctggcactcc      60 agagaggagg gggcgctgca ggttaattga tagccacgga agcacctagg cgccccatgc     120
gcggagccgg agccgccagc tcagtctgac ccctgtcttt tctctcctct tccctctccc     180 accccctcact ccgggaaagc gagggccgag gtaggggcag atagatcacc agacaggcgg    240
agaaggacag gagtacagat ggagggacca ggacacagaa tgcaaaagac tggcaggtga     300
gaagaaggga gaaacagagg gagagagaaa gggagaaaca gagcagaggc ggccgccggc     360
ccggccgccc tgagtccgat ttccctcctt ccctgaccct tcagtttcac tgcaaatcca     420
cagaagcagg tttgcgagct cgaatacctt tgctccactg ccacacgcag caccgggact     480
gggcgtctgg agcttaagtc tggggtctg agcctgggac cggcaaatcc gcgcagcgca      540
tcgcgcccag tctcggagac tgcaaccacc gccaaggagt acgcgcggca ggaaacttct    600
gcggcccaat tcttccccca gctttggcat ctccgaaggc acgtacccgc cctcggcaca    660
agctctctcg tcttccactt cgacctcgag gtggagaaag aggctggcaa gggctgtgcg    720
cgtcgctggt gtggggaggg cagcaggctg cccctcccg cttctgcagc gagttttccc     780
agccaggaaa agggagggag ctgtttcagg aatttcagtg ccttcaccta gcgactgaca   840
caagtcgtgt gtataggaag                                                860

<210> SEQ ID NO 42
<211> LENGTH: 452
<212> TYPE: DNA
<213> ORGANISM: Homo sapiens

<400> SEQUENCE: 42
ggagcctgaa gtcagaaaag atggggcctc gttactcact ttctagccca gcccctggcc     60
ctgggtcccg cagagccgtc atcgcaggct cctgcccagc ctctggggtc gggtgagcaa    120
ggtgttctct tcggaagcgg gaagggctgc gggtcgggga cgtcccttgg ctgccacccc    180
tgattctgca tcctttttcgc tcgaatccct gcgctaggca tcctccccga tcccccaaaa   240
gcccaagcac tgggtctggg ttgaggaagg gaacgggtgc ccaggccgga cagaggctga   300
aaggaggcct caaggttcct ctttgctaca aagtggagaa gttgctctac tctggagggc    360
agtggccttt tccaaacttt tccacttagg tccgtaagaa aagcaattca tacacgatca   420
gcgctttcgg tgcgaggatg gaaagaaact tc                                   452

<210> SEQ ID NO 43
<211> LENGTH: 1992
<212> TYPE: DNA
<213> ORGANISM: Homo sapiens

<400> SEQUENCE: 43
ttttcctgtt acagagctga gcccactcat gtggtgccaa gtagcgacta tctctcggcc     60
acctccaccc agagcaatgt gggcgccccc agcgggtggg agcgattgcc gagcggcgca    120
agggcgttta acgcctaacc ccctcctcct gggttgccaa gccgctaggt cgccgtttcc   180
aacgtggctg cgcggggactg aagtccgacg actcctcgtc ctcagtagga gacacacctc   240
ccactgcccc cagccacgcg agctatgggc agaatcgggg caacggtaat atctggatgg   300
```

| | |
|---|---|
| ggcaggctcc cctgaggctg tgcttaagaa aaaaggaatc tggagtagcc tgaggggccc | 360 |
| cacgagggggg cctcctttgc gatcgtctcc cagccttagg ccaaggctac ggaggcaggc | 420 |
| ggccgagtgt tggcgcccag cccggccgag gactggatgg aggacgagaa gcagcctgcc | 480 |
| tctgggcgac agctgcggac gcagcctcgc cgcctcgccg cctcagcctc ggtcccagcg | 540 |
| tctctaaagc cgcgcccatt ttacagatgc agggcaggga gacaagaggc atctccgggg | 600 |
| gccgagtaga atgatggcgc gggttctccc ggcgccctga tttcgaggct gcgcccgggg | 660 |
| ccctacatgc aggcggggag gcctgggccg aaggcgtctg caaggagggg cgagtctgcc | 720 |
| cggtccgggc agggagtgag gccacagtca gttctcccta ggaggccgcg cagcgggtag | 780 |
| ggtatgggac tggggacgc aacggggacc tggccgaatc agagccctca gcagagaacg | 840 |
| ccgaaaactc tggggccggc cgctcgcttc ccgctagtgg aatggtttc cggtcatccg | 900 |
| ttcccagtcc agccccgggt agggagctct gatttgcaat gcacagcact tgcgaggttc | 960 |
| gaatgccccc gcaatttgca gatggaaata ctaagcctag gccgggcgtg gtggctcaag | 1020 |
| cctatcatct cagcccttg ggaggccaag ccggaggat tgtttgagcc caagaattca | 1080 |
| aaaccagcct gagcaacata gcgaccccgt ctctacaaaa taaataaaa taaattatcc | 1140 |
| gggcgtggtg gcacgcgcct gtggttccag ctactccgga ggctgaggtg gaggatcgc | 1200 |
| ttgagtccgg gaggtcgagg ctacagtgag ccgtgatcgc accactgcac tccagcctgg | 1260 |
| gcgacagagt gagaccttgt ctcaaaaaag gaaaaaaga aaaagaaagt aagcttcaaa | 1320 |
| gaagctctga taatagttct gggtcgtgca gcggtggcgg ccccgcgctc tcgcccctaa | 1380 |
| agcaagcgct ctttgtactg ggtggaggag ctttgagtag tgagggtgga gatgcagctt | 1440 |
| cggggtggcg cagccaccct gacactaggc ccggggtcgc agtgggacag aagagtctgc | 1500 |
| cgctctgact tgggctctga gttccaaggg cgcccggcac ttctagcctc ccaggcttgc | 1560 |
| gcgctggcgc ctttgccatc cgtgccgaag tggggagacc tagccgcgac caccacgagc | 1620 |
| gcagcggtga cacccagagg tcccaccggg ccctgggca gggtaacctt agcctgtccg | 1680 |
| cttcggcagc tttgcgaaga gtggcgcgca gctagggctg aggctcttgc ggacctgcgg | 1740 |
| tcgaagcagg cggctgagcc agttcgatcg ccaaggcctg gctgccgac agtggtgcgc | 1800 |
| gctctgttcc gccgcggccg ggccaggcgc tctggaatag cgatgggggg acacggcctc | 1860 |
| caactttctg cagagaccat cgggcagctc cgggcctaag cagcgacctc accgaaggtt | 1920 |
| cctgggaacc tttgccaaaa tcccagcctc tgcctcggtc cagctaaacc gtgtgtaaac | 1980 |
| aagtgcacca ag | 1992 |

<210> SEQ ID NO 44
<211> LENGTH: 448
<212> TYPE: DNA
<213> ORGANISM: Homo sapiens
<400> SEQUENCE: 44

| | |
|---|---|
| ataaaggacc gggtaatttc gcggaatgcg gattttgaga caggcccaga cggcggcgga | 60 |
| ttccctgtgt cccccaactg gggcgatctc gtgaacacac ctgcgtccca ccccgatcct | 120 |
| aggttggggg gaaagggtat gggaaccctg agcccagagc gcgccccgct ctttcctttg | 180 |
| ctccccggct tccctggcca gcccctccc ggctggtttc ctcgctcact cggcgcctgg | 240 |
| cgtttcgggc gtctggagat caccgcgtgt ctggcacccc aacgtctagt ctccccgcag | 300 |
| gttgaccgcg gcgcctggag ccgggaatag gggtggggag tccggagaac caaacccgag | 360 |

```
cctgaagttg ccattcgggt gactcccgag aaagcccggg agcattttgg ccaatgcggg    420
tttttacctg aacttcagca tcttcacc                                      448

<210> SEQ ID NO 45
<211> LENGTH: 395
<212> TYPE: DNA
<213> ORGANISM: Homo sapiens

<400> SEQUENCE: 45
aattggaaaa ccctggtatt gtgcctgttt gggggaagaa aacgtcaata aaaattaatt    60
gatgagttgg cagggcgggc ggtgcgggtt cgcggcgagg cgcagggtgt catggcaaat   120
gttacggctc agattaagcg attgttaatt aaaaagcgac ggtaattaat actcgctacg   180
ccatatgggc ccgtgaaaag gcacaaaagg tttctccgca tgtggggttc cccttctctt   240
ttctccttcc acaaaagcac cccagcccgt gggtccccccc tttggcccca aggtaggtgg   300
aactcgtcac ttccggccag ggaggggatg gggcggtctc cggcgagttc caagggcgtc   360
cctcgttgcg cactcgcccg cccaggttct ttgaa                              395

<210> SEQ ID NO 46
<211> LENGTH: 491
<212> TYPE: DNA
<213> ORGANISM: Homo sapiens

<400> SEQUENCE: 46
gggaagcgat cgtctcctct gtcaactcgc gcctgggcac ttagcccctc ccgtttcagg    60
gcgccgcctc cccggatggc aaacactata aagtggcggc gaataaggtt cctcctgctg   120
ctctcggttt agtccaagat cagcgatatc acgcgtcccc cggagcatcg cgtgcaggag   180
ccatggcgcg ggagctatac cacgaagagt tcgcccgggc gggcaagcag gcggggctgc   240
aggtctggag gattgagaag ctggagctgg tgcccgtgcc ccagagcgct cacggcgact   300
tctacgtcgg ggatgcctac ctggtgctgc acacggccaa gacgagccga ggcttcacct   360
accacctgca cttctggctc ggtaagggac ggcgggcggc gggaccccga cgcaccaagg   420
ccggcgaggg gagggcgtag gggtctgaga tttgcaggcg tgggagtaaa ggggaccgca   480
aactgagcta g                                                       491

<210> SEQ ID NO 47
<211> LENGTH: 1284
<212> TYPE: DNA
<213> ORGANISM: Homo sapiens

<400> SEQUENCE: 47
ctcaggggcg ggaagtggcg ggtgggagtc acccaagcgt gactgcccga ggcccctcct    60
gccgcggcga ggaagctcca taaaagccct gtcgcgaccc gctctctgca ccccatccgc   120
tggctctcac ccctcggaga cgctcgcccc acagcatagt acttgccgcc cagccacgcc   180
cgcgcgccag ccaccgtgag tgctacgacc cgtctgtcta ggggtgggag cgaacggggc   240
gcccgcgaac ttgctagaga cgcagcctcc cgctctgtgg agccctgggg ccctgggatg   300
atcgcgctcc actccccagc ggactatgcc ggctccgcgc ccgacgcgg accagccctc   360 ttggcggcta aattccactt gttcctctgc tcccctctga ttgtccacgg cccttctccc   420 gggccctttcc cgctgggcgg ttcttctgag ttacctttta gcagatatgg agggagaacc   480
cgggaccgct atcccaaggc agctggcggt ctccctgcgg gtcgccgcct tgaggcccag   540
gaagcggtgc gcggtaggaa ggtttccccg gcagcgccat cgagtgagga atccctggag   600
```

| | |
|---|---|
| ctctagagcc ccgcgccctg ccacctccct ggattcttgg gctccaaatc tctttggagc | 660 |
| aattctggcc cagggagcaa ttctctttcc ccttccccac cgcagtcgtc accccgaggt | 720 |
| gatctctgct gtcagcgttg atcccctgaa gctaggcaga ccagaagtaa cagagaagaa | 780 |
| acttttcttc ccagacaaga gtttgggcaa gaagggagaa aagtgaccca gcaggaagaa | 840 |
| cttccaattc ggttttgaat gctaaactgg cggggccccc accttgcact ctcgccgcgc | 900 |
| gcttcttggt ccctgagact tcgaacgaag ttgcgcgaag ttttcaggtg gagcagaggg | 960 |
| gcaggtcccg accggacggc gcccggagcc cgcaaggtgg tgctagccac tcctgggttc | 1020 |
| tctctgcggg actgggacga gagcggattg ggggtcgcgt gtggtagcag gaggaggagc | 1080 |
| gcgggggggca gaggagggag gtgctgcgcg tgggtgctct gaatcccaa gcccgtccgt | 1140 |
| tgagccttct gtgcctgcag atgctaggta acaagcgact ggggctgtcc ggactgaccc | 1200 |
| tcgccctgtc cctgctcgtg tgcctgggtg cgctggccga ggcgtacccc tccaagccgg | 1260 |
| acaacccggg cgaggacgca ccag | 1284 |

<210> SEQ ID NO 48
<211> LENGTH: 554
<212> TYPE: DNA
<213> ORGANISM: Homo sapiens

<400> SEQUENCE: 48

| | |
|---|---|
| tggagaacct tgggctctgt ggcctcaaag gtaggggtga tttcgagggg ccggcacctc | 60 |
| acagggcagg ttccaccgcg gaaacgcagt catcgcccag cgaccctgct cctggccctc | 120 |
| agcctcccc caggtttctt tttctcttga atcaagccga ggtgcgccaa tggccttcct | 180 |
| tgggtcggat ccggggggcc agggccagct tacctgcttt caccgagcag tggatatgtg | 240 |
| ccttggactc gtagtacacc cagtcgaagc cggcctccac cgccaggcgg gccagcatgc | 300 |
| cgtacttgct gcggtcgcgg tcagacgtgg tgatgtccac tgcgcggccc tcgtagtgca | 360 |
| gagactcctc tgagtggtgg ccatcttcgt cccagccctc ggtcacccgc agtttcactc | 420 |
| ctggccactg gttcatcacc gagatggcca agcgttcaa cttgtcctta cacctctgcg | 480 |
| aagacaaggg gaccccacc gacggacacg ttagcctggg caaccgccac ccctcccggc | 540 |
| ccctccatca gcct | 554 |

<210> SEQ ID NO 49
<211> LENGTH: 772
<212> TYPE: DNA
<213> ORGANISM: Homo sapiens

<400> SEQUENCE: 49

| | |
|---|---|
| tctcacgacc catccgttaa cccaccgttc ccaggagctc cgaggcgcag cggcgacaga | 60 |
| ggttcgcccc ggcctgctag cattggcatt gcggttgact gagcttcgcc taacaggctt | 120 |
| ggggagggtg ggctgggctg ggctgggctg ggctgggtgc tgcccggctg tccgcctttc | 180 |
| gttttcctgg gaccgaggag tcttccgctc cgtatctgcc tagagtctga atccgacttt | 240 |
| ctttcctttg ggcacgcgct cgccagtgga gcacttcttg ttctggcccc gggctgatct | 300 |
| gcacgcggac ttgagcaggt gccaaggtgc cacgcagtcc cctcacgcgct ttcgggggt | 360 |
| cttggagtcg ggtggggagg gagacttagg tgtggtaacc tgcgcaggtg ccaaagggca | 420 |
| gaaggagcag ccttggatta tagtcacggt ctctccctct cttccctgcc attttaggg | 480 |
| cttttctctac gtgctgttgt ctcactgggt ttttgtcgga gccccacgcc ctccggcctc | 540 |
| tgattcctgg aagaaagggt tggtcccctc agcacccca gcatcccgga aaatgggag | 600 |

| | |
|---|---|
| caaggctctg ccagcgccca tcccgctcca cccgtcgctg cagctcacca attactcctt | 660 |
| cctgcaggcc gtgaacacct tcccggccac ggtggaccac ctgcagggcc tgtacggtct | 720 |
| cagcgcggta cagaccatgc acatgaacca ctggacgctg gggtatccca at | 772 |

<210> SEQ ID NO 50
<211> LENGTH: 1362
<212> TYPE: DNA
<213> ORGANISM: Homo sapiens

<400> SEQUENCE: 50

| | |
|---|---|
| tggtttcctt tcgcttctcg cctcccaaac acctccagca agtcggaggg cgcgaacgcg | 60 |
| gagccagaaa cccttcccca aagtttctcc cgccaggtac ctaattgaat catccatagg | 120 |
| atgacaaatc agccagggcc aagatttcca gacacttgag tgacttcccg gtccccgagg | 180 |
| tgacttgtca gctccagtga gtaacttgga actgtcgctc ggggcaaggt gtgtgtctag | 240 |
| gagagagccg gcggctcact cacgctttcc agagagcgac ccgggccgac ttcaaaatac | 300 |
| acacagggtc atttataggg actggagccg cgcgcaggac aacgtctccg agactgagac | 360 |
| attttccaaa cagtgctgac attttgtcgg gccccataaa aaatgtaaac gcgaggtgac | 420 |
| gaacccggcg gggagggttc gtgtctggct gtgtctgcgt cctggcggcg tgggaggtta | 480 |
| tagttccaga cctggcggct gcggatcgcc gggccggtac ccgcgaggag tgtaggtacc | 540 |
| ctcagcccga ccacctcccg caatcatggg gacaccggct tggatgagac acaggcgtgg | 600 |
| aaaacagcct tcgtgaaact ccacaaacac gtggaacttg aaaagacaac tacagccccg | 660 |
| cgtgtgcgcg agagacctca cgtcaccccca tcagttccca cttcgccaaa gtttcccttc | 720 |
| agtggggact ccagagtggt gcgccccatg cccgtgcgtc ctgtaacgtg ccctgattgt | 780 |
| gtaccctct gccgctcta cttgaaatga aaacacaaaa actgttccga attagcgcaa | 840 |
| ctttaaagcc ccgttatctg tcttctacac tgggcgctct taggccactg acagaaacat | 900 |
| ggtttgaacc ctaattgttg ctatcagtct cagtcagcgc aggtctctca gtgacctgtg | 960 |
| acgccgggag ttgaggtgcg cgtatcctta aacccgcgcg aacgccaccg gctcagcgta | 1020 |
| gaaaactatt tgtaatccct agtttgcgtc tctgagcttt aactccccca cactctcaag | 1080 |
| cgcccggttt ctcctcgtct ctcgcctgcg agcaaagttc ctatggcatc cacttaccag | 1140 |
| gtaaccggga tttccacaac aaagcccggc gtgcgggtcc cttcccccgg ccggccagcg | 1200 |
| cgagtgacag cgggcggccg cgcgctggcga ggagtaactt ggggctccag cccttcagag | 1260 |
| cgctccgcgg gctgtgcctc cttcggaaat gaaaaccccc atccaaacgg ggggacggag | 1320 |
| cgcggaaacc cggcccaagt gccgtgtgtg cgcgcgcgtc tg | 1362 |

<210> SEQ ID NO 51
<211> LENGTH: 476
<212> TYPE: DNA
<213> ORGANISM: Homo sapiens

<400> SEQUENCE: 51

| | |
|---|---|
| gaaagccatc cttaccattc ccctcaccct ccgccctctg atcgcccacc cgccgaaagg | 60 |
| gtttctaaaa atagcccagg gcttcaaggc cgcgcttctg tgaagtgtgg agcgagcggg | 120 |
| cacgtagcgg tctctgccag gtggctggag ccctggaagc gagaaggcgc ttcctccctg | 180 |
| catttccacc tcaccccacc cccggctcat ttttctaaga aaaagttttt gcggttccct | 240 |
| ttgcctccta ccccgctgc cgcgcggggt ctgggtgcag accctgcca ggttccgcag | 300 |
| tgtgcagcgg cggctgctgc gctctcccag cctcggcgag ggttaaaggc gtccggagca | 360 |

```
ggcagagcgc cgcgcgccag tctattttta cttgcttccc ccgccgctcc gcgctccccc    420
ttctcagcag ttgcacatgc cagctctgct gaaggcatca atgaaaacag cagtag         476

<210> SEQ ID NO 52
<211> LENGTH: 300
<212> TYPE: DNA
<213> ORGANISM: Homo sapiens

<400> SEQUENCE: 52
atcgaaaatg tcgacatctt gctaatggtc tgcaaacttc cgccaattat gactgacctc     60
ccagactcgg ccccaggagg ctcgtattag gcagggaggc cgccgtaatt ctgggatcaa    120
aagcgggaag gtgcgaactc ctctttgtct ctgcgtgccc ggcgcgcccc cctcccggtg    180
ggtgataaac ccactctggc gccggccatg cgctgggtga ttaatttgcg aacaaacaaa    240
agcggcctgg tggccactgc attcgggtta acattggcc agcgtgttcc gaaggcttgt    300

<210> SEQ ID NO 53
<211> LENGTH: 1246
<212> TYPE: DNA
<213> ORGANISM: Homo sapiens

<400> SEQUENCE: 53
atcaacatcg tggctttggt cttttccatc atggtgagtg aatcacggcc agaggcagcc     60
tgggaggaga gacccgggcg gctttgagcc cctgcagggg agtccgcgcg ctctctgcgg    120
ctcccttcct cacggcccgg cccgcgctag gtgttctttg tcctcgcacc tcctcctcac    180 cttttctcggg ctctcagagc tctccccgca atcatcagca cctcctctgc actcctcgtg    240
gtactcagag ccctgatcaa gcttccccca ggctagcttt cctcttcttt ccagctccca    300
gggtgcgttt cctctccaac ccggggaagt tcttccgtgg actttgctga ctcctctgac    360
cttcctaggc acttgcccgg ggcttctcaa ccctcttttc tagagcccca gtgcgcgcca    420
ccctagcgag cgcagtaagc tcataccccg agcatgcagg ctctacgttc cttccctgc    480 cgctccgggg gctcctgctc tccagcgccc aggactgtct ctatctcagc ctgtgctccc    540
ttctctcttt gctgcgccca agggcaccgc ttccgccact ctccgggggg tcccaggcg    600 attcctgatg ccccctcctt gatcccgttt ccgcgctttg gcacggcacg ctctgtccag    660
gcaacagttt cctctcgctt cttcctacac ccaacttcct ctccttgcct ccctccggcg    720
cccccttttt aacgcgcccg aggctggctc acacccacta cctctttagg cctttcttag    780
gctccccgtg tgcccccctc accagcaaag tgggtgcgcc tctcttactc tttctaccca    840
gcgcgtcgta gttcctcccc gtttgctgcg cactggccct aacctctctt ctcttggtgt    900 ccccagagc tcccaggcgc ccctccaccg ctctgtcctg cgcccggggc tctcccggga    960
atgaactagg ggattccacg caacgtgcgg ctccgcccgc cctctgcgct cagacctccc   1020
gagctgcccg cctctctagg agtggccgct ggggcctcta gtccgcccct ccggagctca   1080
gctccctagc cctcttcaac cctggtagga acacccgagc gaacccacc aggagggcga   1140 cgagcgcctg ctaggccctc gccttattga ctgcagcagc tggcccgggg gtggcggcgg   1200
ggtgaggttc gtaccggcac tgtcccggga caaccctgc agttgc                  1246

<210> SEQ ID NO 54
<211> LENGTH: 984
<212> TYPE: DNA
<213> ORGANISM: Homo sapiens
```

```
<400> SEQUENCE: 54
acaaataaaa cacctctag cttccctag actttgttta actggccggg tctccagaag        60
gaacgctggg gatgggatgg gtggagagag ggagcggctc aaggactta gtgaggagca      120 ggcgagaagg agcacgttca ggcgtcaaga ccgatttctc cccctgcttc gggagacttt     180
tgaacgctcg gagaggcccg gcatctcacc actttacttg gccgtagggg cctccggcac    240
ggcaggaatg agggagggg tccgattgga cagtgacggt ttggggccgt tcggctatgt     300
tcagggacca tatggtttgg ggacagcccc agtagttagt aggggacggg tgcgttcgcc    360
cagtccccgg atgcgtaggg aggcccagtg gcaggcagct gtcccaagca gcgggtgcgc   420
gtccctgcgc gctgtgtgtt cattttgcag agccagcctt cggggaggtg aaccagctgg    480
gaggagtgtt cgtgaacggg aggccgctgc ccaacgccat ccggcttcgc atcgtggaac    540
tggcccaact gggcatccga ccgtgtgaca tcagccgcca gctacgggtc tcgcacggct   600
gcgtcagcaa gatcctggcg cgatacaacg agacgggctc gatcttgcca ggagccatcg    660
ggggcagcaa gccccgggtc actaccccca ccgtggtgaa acacatccgg acctacaagc   720
agagagaccc cggcatcttc gcctgggaga tccgggaccg cctgctggcg gacgcgtgt    780 gcgacaagta caatgtgccc tccgtgagct ccatcagccg cattctgcgc aacaagatcg   840
gcaacttggc ccagcagggt cattacgact catacaagca gcaccagccg acgccgcagc   900
cagcgctgcc ctacaaccac atctactcgt accccagccc tatcacggcg gcggccgcca  960
aggtgcccac gccacccggg gtgc                                           984

<210> SEQ ID NO 55
<211> LENGTH: 545
<212> TYPE: DNA
<213> ORGANISM: Homo sapiens

<400> SEQUENCE: 55
aggaggcgca acgcgctgcc agggcggctt tatcctgccg ccacagggcg gggaccagcc     60
cggcagccgg gtgtccagcg ccgctcacgt gcctcgcctg gagcttagct ctcagactcc    120
gaagagggcg actgagactt gggcctggga gttggcttcg gggtacccaa ggcgacgaca    180
gctgagttgt accacgaagc tcaggccgag gcctcctccc ttgtctggcc ttcgaatcca    240
tactggcagc ctctcctctc aggcactccg cgggccgggc cactaggccc cctgctcctg    300
gagctgcgct atgatccggg tcttgagatg cgcgcgattc tctctgaacc ggtggagagg    360
aggctctgcc ccgcgcggag cgaggacagc ggcgcccgag cttcccgcgc ctctccaggg    420
cccaatggca agaacagcct ccgaagtgcg cggatgacga gaaagatct tcagttcttc     480 tgccgctaga gaagtgcggg atacaagcct ctattggatc cacaacctgg agtcctgcct   540
tcgga                                                                545

<210> SEQ ID NO 56
<211> LENGTH: 1533
<212> TYPE: DNA
<213> ORGANISM: Homo sapiens

<400> SEQUENCE: 56
atctgcgtgc ccttttctgg gcgagccctg ggagatccag ggagaactgg gcgctccaga     60
tggtgtatgt ctgtaccttc acagcaaggc ttcccttgga tttgaggctt cctattttgt   120
ctgggatcgg ggtttctcct tgtcccagtg gcagccccgc gttgcgggtt ccgggcgctg  180
```

| | |
|---|---|
| cgcggagccc aaggctgcat ggcagtgtgc agcgcccgcc agtcgggctg gtgggttgtg | 240 |
| cactccgtcg gcagctgcag aaaggtggga gtgcaggtct tgcctttcct caccgggcgg | 300 |
| ttggcttcca gcaccgaggc tgacctatcg tggcaagttt gcggccccg cagatcccca | 360 |
| gtggagaaag agggctcttc cgatgcgatc gagtgtgcgc ctccccgcaa agcaatgcag | 420 |
| accctaaatc actcaaggcc tggagctcca gtctcaaagg tggcagaaaa ggccagacct | 480 |
| aactcgagca cctactgcct tctgcttgcc ccgcagagcc ttcagggact gactgggacg | 540 |
| cccctggtgg cgggcagtcc catccgccat gagaacgccg tgcagggcag cgcagtggag | 600 |
| gtgcagacgt accagccgcc gtggaaggcg ctcagcgagt ttgccctcca gagcgacctg | 660 |
| gaccaacccg ccttccaaca gctggtgagg ccctgcccta cccgccccga cctcgggact | 720 |
| ctgcggggttg gggatttagc cacttagcct ggcagagagg ggaggggtg gccttgggct | 780 |
| gaggggctgg gtacagccct aggcggtggg ggaggggggaa cagtggcggg ctctgaaacc | 840 |
| tcacctcggc ccattacgcg ccctaaacca ggtctccctg gattaaagtg ctcacaagag | 900 |
| aggtcgcagg attaaccaac ccgctccccc gccctaatcc ccccctcgtg cgcctgggga | 960 |
| cctggcctcc ttctccgcag ggcttgctct cagctggcgg ccggtcccca agggacactt | 1020 |
| tccgactcga gcacgcggc cctggagcac cagctcgcgt gcctcttcac ctgcctcttc | 1080 |
| ccggtgtttc cgccgcccca ggtctccttc tccgagtccg gctccctagg caactcctcc | 1140 |
| ggcagcgacg tgacctccct gtcctcgcag ctccccgaca cccccaacag tatggtgccg | 1200 |
| agtcccgtgg agacgtgagg gggacccctc cctgccagcc cgcggacctc gcatgctccc | 1260 |
| tgcatgagac tcacccatgc tcaggccatt ccagttccga aagctctctc gccttcgtaa | 1320 |
| ttattctatt gttatttatg agagagtacc gagagacacg gtctggacag cccaaggcgc | 1380 |
| caggatgcaa cctgctttca ccagactgca gaccctgct ccgaggactc ttagtttttc | 1440 |
| aaaaccagaa tctgggactt accagggtta gctctgccct ctcctctcct ctctacgtgg | 1500 |
| ccgccgctct gtctctccac gccccacctg tgt | 1533 |

<210> SEQ ID NO 57
<211> LENGTH: 702
<212> TYPE: DNA
<213> ORGANISM: Homo sapiens

<400> SEQUENCE: 57

| | |
|---|---|
| aggtctcttc agactgccca ttctccgggc ctcgctgaat gcggggctc tatccacagc | 60 |
| gcgcggggcc gagctcaggc aggctggggc gaagatctga ttctttcctt cccgccgcca | 120 |
| aaccgaatta atcagtttct tcaacctgag ttactaagaa agaaaggtcc ttccaaataa | 180 |
| aactgaaaat cactgcgaat gacaatacta tactacaagt tcgttttggg gccggtgggt | 240 |
| gggatggagg agaaagggca cggataatcc cggagggccg cggagtgagg aggactatgg | 300 |
| tcgcggtgga atctctgttc cgctggcaca tccgcgcagg tgcggctctg agtgctggct | 360 |
| cggggttaca gacctcggca tccggctgca ggggcagaca gagacctcct ctgctagggc | 420 |
| gtgcggtagg catcgtatgg agcccagaga ctgccgagag cactgcgcac tcaccaagtg | 480 |
| ttaggggtgc ccgtgataga ccgccaggga aggggctggt tcggagggaa ttcccgctac | 540 |
| cgggaaggtc ggaactcggg gtgatcaaac aaggaatgca tctcacctcc gtgggtgctt | 600 |
| gtgctgcgca aggaattatt accggagcgg ttgcgatggc ctttgcccgg cgacccaaga | 660 |
| agagtaagca aactaccgtc cacccagcgg atcaggtcca at | 702 |

<210> SEQ ID NO 58
<211> LENGTH: 3180
<212> TYPE: DNA
<213> ORGANISM: Homo sapiens

<400> SEQUENCE: 58

```
gatgtcctgt tctagcagc ctccagagcc aagctaggcg agaggcgtag gaggcagaga      60
gagcgggcgc gggaggccag ggtccgcctg ggggcctgag gggacttcgt ggggtcccgg     120
gagtggccta gaaacaggga gctgggaggg ccgggaagag cttgaggctg agcggggac     180
gaacgggcag cgcaaagggg agatgaacgg aatggccgag gagccacgca ttcgccttgt     240
gtccgcggac ccttgttccc gacaggcgac caagccaagg ccctccggac tgacgcggcc     300
tgagcagcag cgagtgtgaa gtttggcacc tccggcggcg agacggcgcg ttctggcgcg     360
cggctcctgc gtccggctgg tggagctgct gcgccctatg cggcctgccg agggcgccgc     420
cgagggcccg cgagctccgt ggggtcgggg tgggggacc cgggagcgga cagcgcggcc     480
cgaggggcag gggcagggc gcgcctgcc tgggtgtgt ctgggccccg gctccgggct     540
cttgaaggac cgcgagcagg aggcttgcgc aatcccttgg ctgagcgtcc acggagaaag     600
aaaaagagca aaagcagagc gagagtggag cgagggatgg gggcgggcaa agagccatcc     660
gggtctccac caccgccctg acacgcgacc cggctgtctg ttggggaccg cacggggct     720
cgggcgagca ggggagggag gagcctgcgc ggggctcgtg ttcgcccagg aatcccggag     780
aagctcgaag acggtctggt gttgaacgca cacgtggact ccatttcatt accaccttgc     840
agctcttgcg ccacggaggc tgctgctgcc cggcggctgc tacccaccga acccacgtg      900
gcccctcccc aggggtgtag gggtgacggt tgtcttctgg tgacagcaga ggtgttgggt     960
ttgcgactga tctctaacga gcttgaggcg caaacctagg attccctgag tgttggggtg    1020
cggcggggg gcaagcaagg tgggacgacg cctgcctggt ttccctgact agttgcgggg    1080
ggtgggggcc ggctctcagg ggccaccaga agctgggtgg gtgtacagga aatatttttt    1140
ctcctgccgt gtttggcttt ttcctggcat ttttgcccag ggcgaagaac tgtcgcgcgg    1200
ggcagctcca ccgcggaggg agaggggtcg cgaggctggc gcgggaagcg ctgtaggtgg    1260
cagtcatccg tccacgccgc acaggccgtc tgcgccgtcg gaccatcggg aggtctgcag    1320
caactttgtc ccggccagtc cccttgtccg ggaaggggct gagcttcccg acactctacc    1380
ctccccctct tgaaaatccc ctggaaaatc tgtttgcaat gggtgtttcc gcggcgtcca    1440
ggtctgggct gccgggggag gccgagcggc tgctgcagcc tccctgctgc caggggcgtc    1500
ggactccgct tcgctcacta cgcccaggcc cctcaggggc ccacgctcag gacttcgggg    1560
ccacacagca ggaccggtg ccccgacgac gagtttgcgc aggacccggg ctgggccagc    1620
cgcggagctg gggaggaagg ggcgggggtc ggtgcagcgg atcttttctg ttgctgcctg    1680
tgcggcggca ggaagcgtct tgaggctccc caagactacc tgaggggccg cccaagcact    1740
tcagaagccc aaggagcccc cggccacccc cgctcctggc cttttgcca acgactttga    1800
aagtgaaatg cacaagcacc agcaattgac ttcccttccg tggttatta ttttgtcttt     1860
gtggatggtg ggcagatggg gagagaggcc cctacctaac ctcggtggct ggtccctaga    1920
ccaccctgc cagccggtgt ggggaggagc tcaggtccgc gggagagcga atgggcgcca    1980
ggaggtggga cagaatcctg ggaaggtaca gcggacgccc tggaagctcc cctgatgccc    2040
cagagggccc ttcctgggaa acctcccggg ggggtgcccc ataccatccc acccggctgt    2100
cttggcccct cccagggagc cgcaggagaa actagccta cacctgggat tcccagagcc    2160
```

```
ttctgctggg gctcctgccc ccgacttcgg ataaccagct ccgcacaggt ccccgagaag    2220
ggccgctggc ctgcttattt gatactgccc cctcccagac aggggctggt cgagcccctg    2280
gttctgctgc cagactgaag ccttccagac gccacctcgg tttgggcccc cagggccctc    2340
aggggcccca ggagaggaga gctgctatct agctcagcca caggctcgct cctggtgggg    2400
gccaggctga aggagtggac cctggagagg tcgggaacct tttaacagcc gtgggctgga    2460
gggtggctac taagtgttcg gtctgggaag aggcatgacc cgcaccatcc cggggaaata    2520
aacgacttct taagggaatc ttctcgctga gcggtgctc tgggccagga gattgccacc    2580
gccagcccac ggaacccaga tttgggctct gccttgagcg ggccgcctgt ggcttcccgg    2640
gtcgctcccc cgactcagaa agctctcaag ttggtatcgt tttcccggcc ctcggaggtg    2700
gattgcagat caccgagagg ggatttacca gtaaccacta cagaatctac ccgggcttta    2760
acaagcgctc atttctctcc cttgtcctta gaaaaacttc gcgctggcgt tgatcatatc    2820
gtacttgtag cggcagctta ggggcagcgg aactggtggg gttgtgcgtg caggggagg    2880 ctgtgaggga gccctgcact ccgcccctcc acccttctgg aggagtggct tgtttctaa    2940 gggtgccccc ccaaccccg ggtccccact tcaatgtttc tgctctttgt cccaccgccc    3000
gtgaaagctc ggctttcatt tggtcggcga agcctccgac gccccgagt cccaccctag    3060 cgggccgcgc ggcactgcag ccgggggttc ctgcggactg gcccgacagg gtgcgcggac    3120
ggggacgcgg gccccgagca ccgcgacgcc agggtccttt ggcagggccc aagcacccct    3180

<210> SEQ ID NO 59
<211> LENGTH: 1038
<212> TYPE: DNA
<213> ORGANISM: Homo sapiens

<400> SEQUENCE: 59
tggcggccgg cgggcacagc cggctcattg ttctgcacta caaccactcg ggccggctgg      60
ccgggcgcgg ggggccggag gatggcggcc tgggggcccct gcggggggctg tcggtggccg     120 ccagctgcct ggtggtgctg gagaacttgc tggtgctggc ggccatcacc agccacatgc     180
ggtcgcgacg ctgggtctac tattgcctgg tgaacatcac gctgagtgac ctgctcacgg     240
gcgcggccta cctggccaac gtgctgctgt cgggggcccg caccttccgt ctggcgcccg     300
cccagtggtt cctacgggag ggcctgctct tcaccgccct ggccgcctcc accttcagcc     360
tgctcttcac tgcaggggag cgctttgcca ccatggtgcg gccggtggcc gagagcgggg     420
ccaccaagac cagccgcgtc tacggcttca tcggcctctg ctggctgctg gccgcgctgc     480
tggggatgct gcctttgctg ggctggaact gcctgtgcgc ctttgaccgc tgctccagcc     540
ttctgcccct ctactccaag cgctacatcc tcttctgcct ggtgatcttc gccggcgtcc     600
tggccaccat catgggcctc tatgggccca tcttccgcct ggtgcaggcc agcgggcaga     660
aggccccacg cccagcggcc cgccgcaagg cccgccgcct gctgaagacg gtgctgatga     720
tcctgctggc cttcctggtg tgctgggggcc cactcttcgg gctgctgctg gccgacgtct     780
ttggctccaa cctctgggcc caggagtacc tgcggggcat ggactggatc ctggccctgg     840
ccgtcctcaa ctcggcggtc aaccccatca tctactcctt ccgcagcagg gaggtgtgca     900
gagccgtgct cagcttcctc tgctgcgggt gtcccggct gggcatgcga gggcccgggg     960
actgcctggc ccggggccgtc gaggctcact ccggagcttc caccaccgac agctctctga    1020
ggccaaggga cagcttc                                                    1038
```

```
<210> SEQ ID NO 60
<211> LENGTH: 374
<212> TYPE: DNA
<213> ORGANISM: Homo sapiens

<400> SEQUENCE: 60
tagtaaggca ccgaggggtg gctcctctcc ctgcagcggc tgtcgcttac catcctgtag      60
accgtgacct cctcacacag cgccaggacg aggatcgcgg tgagccagca ggtgactgcg     120
atcctggagc tggtcgcagc aggccatcct gcacgcggtg gaggcgcccc ctgcaggccg     180
cagcgcatcc ccagcttctg gacgcactgt gagcggttat gcagcagcac gctcatatga     240
gatgccccgc agggtgctat gcaggcccac gtccccacaa gcccatggc aggcgcccgg      300 gtgccggagc acgcacttgg ccccatggat ctctgtgccc agggctcagc caggcatctg     360
gccgctaaag gttt                                                       374

<210> SEQ ID NO 61
<211> LENGTH: 246
<212> TYPE: DNA
<213> ORGANISM: Homo sapiens

<400> SEQUENCE: 61
tctcatctga gcgctgtctt tcaccagagc tctgtaggac tgaggcagta gcgctggccc      60
gcctgcgaga gcccgaccgt ggacgatgcg tcgcgcccct cccatcgcgg cctgggcggg     120
cccgcctgcc ctcggctgag cccggtttcc ctaccccggg gcacctcccc tcgcccgcac     180
ccggccccag tccctcccag gcttgcgggt agagcctgtc tttgcccaga aggccgtctc     240
caagct                                                                246

<210> SEQ ID NO 62
<211> LENGTH: 222
<212> TYPE: DNA
<213> ORGANISM: Homo sapiens

<400> SEQUENCE: 62
cagtccccga ggccctcccc ggtgactcta accaggggatt tcagcgcgcg gcgcggggct     60
gcccccaggc gtgacctcac ccgtgctctc tccctgcaga atctcctacg acccggcgag     120
gtaccccagg tacctgcctg aagcctactg cctgtgccgg ggctgcctga ccgggctgtt     180
cggcgaggag gacgtgcgct tccgcagcgc ccctgtctac at                        222

<210> SEQ ID NO 63
<211> LENGTH: 2209
<212> TYPE: DNA
<213> ORGANISM: Homo sapiens

<400> SEQUENCE: 63
agagagacat tttccacgga ggccgagttg tggcgcttgg ggttgtgggc gaaggacggg      60
gacacggggg tgaccgtcgt ggtggaggag aaggtctcgg aactgtggcg gcggcggccc     120
ccctgcgggt ctgcgcggat gaccttggcg ccgcggtggg ggtccggggg ctggctggcc     180
tgcaggaagg cctcgactcc cgacacctgc tccatgaggc tcagcctctt cacgcccgac     240
gtcgggctgg ccacgcgggc agcttctggc ttcggggggg ccgcgatagg ttgcggcggg     300
gtggcggcca caccaaaagc catctcggtg tagtcaccat tgtccccggt gtccgaggac     360
aacgatgagg cggcgcccgg gccctgggcg gtggcaacgg ccgaggcggg gggcaggcgg     420
tacagctccc ccggggccgg cggcggtggc ggcggctgca gagacgacga cggggacgcg     480
```

-continued

| | |
|---|---|
| gacggacgcg ggggcaacgg cggatacggg gaggaggcct cggggggacag gaggccgtcc | 540 |
| aaggagccca cggggtggcc gctcggggcg cccggcttag gagacttggg ggagctgaag | 600 |
| tcgaggttca tgtagtcgga gagcggagac cgctgccggc tgtcgctgct ggtgcccggg | 660 |
| gtgcctgagc ccagcgacga ggccgggctg ctggcggaca agagcgagga ggacgaggcc | 720 |
| gccgacgcca gcagggggagg cgcgggcggc gacaggcggg ccccgggctc gccaaagtcg | 780 |
| atgttgatgt actcgccggg gctcttgggc tccggtggca gtgggtactc gtgcatgctg | 840 |
| ggcaggctgg gcagcccctc cagggacagg cgcgtgggcc tcaccgcccg gccgcgctgg | 900 |
| cccaagaagc cctccgggcg gccgccgcta ggccgcacgg gcgaaggcac tacagggtga | 960 |
| gggggctgcg tggggccggc cccgaaggcg ctggccgcct ggctgggccc tggcgtggcc | 1020 |
| tgaggctcca gacgctcctc ctccaggatg cgccccacgg gggagctcat gagcacgtac | 1080 |
| tggtcgctgt ccccgccaca ggtgtagggg gccttgtagg agcggggcaa ggagctgtag | 1140 |
| cagcagccgg gaacgcccct gagcggctcc ccgccggggt gcaggggctgc ggagaagaag | 1200 |
| tcgggcgggg tgcccgtggt gaccgcgtcg ctgggggaca cgttgaggta gtccccgttg | 1260 |
| ggcagcagct tgccatctgc atgctccatg gacagcttgg aaccgcacca catgcgcatg | 1320 |
| tacccactgt cctcggggga gctctcggcg ggcgagctgg ccttgtagcc gccccccgctc | 1380 |
| gccgggaatg tcctgcccgc cgcagaggtg ggtgctggcc ccgcaggccc cgcagaaggc | 1440 |
| acggcggcgg cggcggcggc ggcggccctg ggctgcaaga tctgcttggg ggcggacacg | 1500 |
| ctggcggggc tcatgggcat gtagtcgtcg ctcctgcagc tgccgctccc actgcccgcg | 1560 |
| agggccgcgc cgggcgtcat gggcatgtag ccgtcgtctg cccccaggtt gctgctggag | 1620 |
| ctcctgtggg agccgatctc gatgtctccg tagtcctctg ggtaggggtg gtaggccacc | 1680 |
| ttgggagagg acgcggggca ggacgggcag aggcggcccg cgctgcccga aaggtggcc | 1740 |
| cgcatcaggg tgtattcatc cagcgaggca gaggagggct ggggcaccgg ccgctgccgg | 1800 |
| gctggcgtgg tcagggagta ggtcctcttg cgcagccctc ggtccaggtc ctgggccgcg | 1860 |
| tcccccgaga cccggcggta ggagcggcca cagtggctca ggggcctgtc catggtcatg | 1920 |
| tacccgtaga actcaccgcc gccgccgccg tctcggggcg ggggcgtctc cgcgatggac | 1980 |
| tcgggcgtgt tgcttcggtg gctgcagaag gcgcgcaggt cgcctgggct ggagccgtac | 2040 |
| tcgtccaggg acatgaagcc ggggtcgctg ggggagcccg aggcggaggc gctgccgctg | 2100 |
| gagggccgct ggccggggcc gtggtgcagc ggatgcggca gaggcgggtg cgggccgggc | 2160 |
| ggcggcgggt aggagcccga gccgtggccg ctgctggacg acagggagc | 2209 |

<210> SEQ ID NO 64
<211> LENGTH: 149
<212> TYPE: DNA
<213> ORGANISM: Homo sapiens

<400> SEQUENCE: 64

| | |
|---|---|
| taacctaaag aatgaagtca tgccccggcc tgcacccggg aaactgcaca cagcgaaaga | 60 |
| tcgccactga gataaagagc tgaaagctat tccccaattc agctgtttca gccgtgcggt | 120 |
| ctcacaatgg gctcacagac ggcagcatc | 149 |

<210> SEQ ID NO 65
<211> LENGTH: 832
<212> TYPE: DNA
<213> ORGANISM: Homo sapiens

<400> SEQUENCE: 65

| gtttccacaa tccacctcgt agctggggcg tgccgcttgc ctcggcttgt cccggcagaa | 60 |
| cactcttacc tttaatggcg actgaaaagt tgccacgagt tcctgatcat tgtggtaggt | 120 |
| gctgcgtgaa gctgagacgt gcgtgagcca catcccaggg ggctttgagc ccccaccgcg | 180 |
| gcggcggctg aggggaggct tgtcgtactc gcacaggagg acacagggct gcagtgttca | 240 |
| ctccagggcc tcttatcatt gggatctgag gaattttccg agaggaagtg cgaattaaca | 300 |
| atgatgaaag gtttgtgagt gagtgacagg cacgttctat tgagcactgc atggggcatt | 360 |
| atgtgccacc agacggggg gcagaggtca agagccctcg agggctggga gagttcggag | 420 |
| gatagaagtc atcagagcac aatgaagcca gaccctgcag ccgccttccc cttcggggc | 480 |
| ttccttagaa tgcagcattg cggggactga gctgtcccag gtgaaggggg gccgtcacgg | 540 |
| tgtgtggacg cccctcggct cagccctcta agagactcgg cagccaggat gggctcaagg | 600 |
| catgagccct caaaggaggt taggaaggag cgagggagaa agatatgct tgtgtgacgt | 660 |
| cctggccgaa gtgagaacaa ttgtatcaga taatgagtca tgtcccattg agggtgccg | 720 |
| acaaggactc gggaggaggc cacggagccc tgtactgagg agacgcccac agggagcctc | 780 |
| gggggcccag cgtcccggga tcactggatg gtaaagccgc cctgcctggc gt | 832 |

<210> SEQ ID NO 66
<211> LENGTH: 256
<212> TYPE: DNA
<213> ORGANISM: Homo sapiens

<400> SEQUENCE: 66

| tccagctgca gcgagggcgg ccaggccccc ttctccgacc tgcaggggta gcgcggcctc | 60 |
| ggcgccggag acccgcgcgc tgtctggggc tgcggtggcg tggggagggc gcggccccg | 120 |
| gacgccccga ggaaggggca cctcaccgcc cccacccaga gcgcctggcc gtgcgggctg | 180 |
| cagaggaccc ctccggggca gaggcaggtt ccacggaaga ccccggcccg ctggggcttc | 240 |
| cccggagact ccagag | 256 |

<210> SEQ ID NO 67
<211> LENGTH: 184
<212> TYPE: DNA
<213> ORGANISM: Homo sapiens

<400> SEQUENCE: 67

| acttactgct tccaaaagcg ctgggcacag cctttatga ctgaccccgc ccccgagtcc | 60 |
| caggccgccc catgcaaccg cccaaccgcc caaccgccac tccaaaggtc accaaccact | 120 |
| gctccaggcc acgggctgcc tctccccacg gctctagggc ccttcccctc caccgcaggc | 180 |
| tgac | 184 |

<210> SEQ ID NO 68
<211> LENGTH: 118
<212> TYPE: DNA
<213> ORGANISM: Homo sapiens

<400> SEQUENCE: 68

| tgccacaccc aggtaccgcc cgcccgcgcg agagccgggc aggtgggccg cggatgctcc | 60 |
| cagaggccgg cccagcagag cgatggactt ggacaggcta agatggaagt gacctgag | 118 |

<210> SEQ ID NO 69
<211> LENGTH: 1534
<212> TYPE: DNA
<213> ORGANISM: Homo sapiens

<400> SEQUENCE: 69

| | | | | | |
|---|---|---|---|---|---|
| tcgccagcgc | agcgctggtc | catgcaggtg | ccacccgagg | tgagcgcgga | ggcaggcgac | 60 |
| gcggcagtgc | tgccctgcac | cttcacgcac | ccgcaccgcc | actacgacgg | gccgctgacg | 120 |
| gccatctggc | gcgcgggcga | gccctatgcg | ggcccgcagg | tgttccgctg | cgctgcggcg | 180 |
| cggggcagcg | agctctgcca | gacggcgctg | agcctgcacg | gccgcttccg | gctgctgggc | 240 |
| aacccgcgcc | gcaacgacct | ctcgctgcgc | gtcgagcgcc | tcgccctggc | tgacgaccgc | 300 |
| cgctacttct | gccgcgtcga | gttcgccggc | gacgtccatg | accgctacga | gagccgccac | 360 |
| ggcgtccggc | tgcacgtgac | aggcgaggcg | gcgtgggagc | gggtccccgg | cctcccttcc | 420 |
| cgccctcccg | cctgccccgc | cccaagggct | acgtgggtgc | caggcgctgt | gctgagccag | 480 |
| gaagggcaac | gagacccagc | cctctcctct | accccaggga | tctcacacct | ggggtagtt | 540 |
| taggaccacc | tgggagcttg | acacaaatgc | agaatccagg | tcccaggaag | ggctgaggtg | 600 |
| ggcccgggaa | taggcattgc | cgtgactctc | gtagagtgac | tgtccccagt | ggctctcaga | 660 |
| cgaagaggcg | agaaagacaa | gtgaatggca | atcctaaata | tgccaagagg | tgcaatgtgg | 720 |
| tgtgtgctac | cagcccggaa | agacactcgc | agccctcta | cccaggggtg | cacagacagc | 780 |
| ccaccaagta | gtgcctagca | cttttgccaga | ccctgatata | caaagatgcc | tgaaccaggg | 840 |
| tcccgtccct | agagcagtgg | ctctccactc | tagcccccac | cctgctctgc | gacaataatg | 900 |
| gccacttagc | atttgctagg | gagccgggac | ctagtccaag | cacccacaag | catgaatttg | 960 |
| ccaaatcttt | tcagcaacct | cttaaggcaa | ctgctatcat | gatcctcact | ttacacatgg | 1020 |
| agaagcagaa | gcagagatga | tagaatcttt | cgcccaaggc | cacatctgta | ttgggacggg | 1080 |
| ggcagcctgg | cacccaagtg | cccattcctc | ccttctgacc | agcccccacc | cctccggctc | 1140 |
| tggcgtccaa | agggctaagg | ggaggggtgc | ccttgtgaca | gtcacccgcc | ttctcccctg | 1200 |
| cagccgcgcc | gcgatcgtc | aacatctcgg | tgctgcccag | tccggctcac | gccttccgcg | 1260 |
| cgctctgcac | tgccgaaggg | gagccgccgc | ccgccctcgc | ctggtccggc | ccggccctgg | 1320 |
| gcaacagctt | ggcagccgtg | cggagcccgc | gtgagggtca | cggccaccta | gtgaccgccg | 1380 |
| aactgcccgc | actgacccat | gacggccgct | acacgtgtac | ggccgccaac | agcctgggcc | 1440 |
| gctccgaggc | cagcgtctac | ctgttccgct | tccatggcgc | cagcggggcc | tcgacggtcg | 1500 |
| ccctcctgct | cggcgctctc | ggcttcaagg | cgct | | | 1534 |

<210> SEQ ID NO 70
<211> LENGTH: 269
<212> TYPE: DNA
<213> ORGANISM: Homo sapiens

<400> SEQUENCE: 70

| | | | | | |
|---|---|---|---|---|---|
| atgaacttca | agggcgacat | catcgtggtc | tacgtcagcc | agacctcgca | ggagggcgcg | 60 |
| gcggcggctg | cggagcccat | gggccgcccg | gtgcaggagg | agaccctggc | gcgccgagac | 120 |
| tccttcgcgg | ggaacggccc | gcgcttcccg | gaccgtgcg | gcggcccga | ggggctgcgg | 180 |
| gagccggaga | aggcctcgag | gccggtgcag | gagcaaggcg | gggccaaggc | ttgagcgccc | 240 |
| cccatggctg | ggagcccgaa | gctcggagc | | | | 269 |

```
<210> SEQ ID NO 71
<211> LENGTH: 282
<212> TYPE: DNA
<213> ORGANISM: Homo sapiens

<400> SEQUENCE: 71
tcagtgttat gtggggagcg ctagatcgtg cacacagtag gcgtcaggaa gtgttttccc    60
cagtaattta ttctccatgg tactttgcta aagtcatgaa ataactcaga ttttgttttc   120
caaggaagga gaaaggccca gaatttaaga gcaggcagac acacaaccgg gcaccccag    180 accctggccc ttccagcagt caggaattga cttgccttcc aaagcccag cccggagctt    240 gaggaacgga ctttcctgcg caggggatc ggggcgcact cg                       282

<210> SEQ ID NO 72
<211> LENGTH: 142
<212> TYPE: DNA
<213> ORGANISM: Homo sapiens

<400> SEQUENCE: 72
gtggaaacac aacctgcctt ccattgtctg cgcctccaaa acacaccccc cgcgcatccg    60
tgaagctgtg tgtttctgtg ttactacagg ggccggctgt ggaaatccca cgctccagac   120
cgcgtgccgg gcaggcccag cc                                            142

<210> SEQ ID NO 73
<211> LENGTH: 741
<212> TYPE: DNA
<213> ORGANISM: Homo sapiens

<400> SEQUENCE: 73
tccacacctc gggcagtcac taggaaaagg gtcgccaact gaaaggcctg caggaaccag    60
gatgatacct gcgtcagtcc cgcggctgct gcgagtgcgc gctctcctgc caggggacc   120 tcagaccctc ctttacagca caccgagggc cctgcagaca cgcgagcggg ccttcagttt   180
gcaaaccctg aaagcgggcg cggtccacca ggacgatctg gcagggctct gggtgaggag   240
gccgcgtctt tatttggggt cctcgggcag ccacgttgca gctctggggg aagactgctt   300
aaggaacccg ctctgaactg cgcgctggtg tcctctccgg ccctcgcttc cccgaccccg   360
cacaggctaa cgggagacgc gcaggcccac cccaccggct ggagaccccg gcacggcccg   420
catccgccag gattgaagca gctggcttgg acgcgcgcag ttttcctttg gcgacattgc   480
agcgtcggtg cggccacaat ccgtccactg gttgtgggaa cggttggagg tcccccaaga   540
aggagacacg cagagctctc cagaaccgcc tacatgcgca tggggcccaa acagcctccc   600
aaggagcacc caggtccatg cacccgagcc caaaatcaca gacccgctac gggcttttgc   660
acatcagctc caaacacctg agtccacgtg cacaggctct cgcacagggg actcacgcac   720
ctgagttcgc gctcacagat c                                             741

<210> SEQ ID NO 74
<211> LENGTH: 4498
<212> TYPE: DNA
<213> ORGANISM: Homo sapiens

<400> SEQUENCE: 74
ctgccctcgc ggatctcccc cggcctcgcc ggcctccgcc tgtcctccca ccacccctctc    60 cgggccagta ccttgaaagc gatgggcagg gtcttgttgc agcgccagtg cgtaggcagc   120
acggagcaga ggaagttggg gctgtcggtg cgcaccagct cgcccgggtg gtcggccagc   180
```

| | |
|---|---|
| acctccacca tgctgcggtc gccgctcctc agcttgccgg ccagggcagc gccggcgtcc | 240 |
| ggggcgccca gcggcaacgc ctcgctcatc ttgcctgggc tcagcgcggt ggaaggcggc | 300 |
| gtgaagcggc ggctcgtgct ggcatctacg gggatacgca tcacaacaag ccgattgagt | 360 |
| taggaccctg caaacagctc ctaccagacg gcgacagggg cgcggatctt cagcaagcag | 420 |
| ctcccgggag accaacatac acgttcaggg gcctttatta ctgcgggggg tgggggggggg | 480 |
| cgggggtggt taggggagga gggagactaa gttactaaca gtccaggagg ggaaaacgtt | 540 |
| ctggttctgc ggatcggcct ctgacccagg atgggctcct agcaaccgat tgcttagtgc | 600 |
| attaaaaagt ggagactatc ttccacgaat cttgcttgca gaggttaagt tctgtctttg | 660 |
| gctgttagaa aagttcctga aggcaaaatt ctcatacact tcctaaaata tttatgcgaa | 720 |
| gagtaaaacg atcagcaaac acattatttg gaagttccag tagttaatgc ctgtcagttt | 780 |
| tttgcaggtg agttttgtct aaagtcccaa cagaacacaa ttatctcccg taacaaggcc | 840 |
| acttttatca tgcaaaactg gcttcagtcc cgaaaagcaa gagctgagac ttccaaaggt | 900 |
| agtgctacta atgtatgtgc acgtatatat aaatatatac atatgctcta cttcataaaa | 960 |
| tatttacaat acaatctgtg gagaatttaa acacaacaga aatccattaa tgtacgctgc | 1020 |
| agatttttttt aagtagcctt gaaaatcagc ttcagtagtt ggagcagtgc tgagctagaa | 1080 |
| gtacttgtca tgttctctgt tctctcaatg aattctgtca aaacgctcag tgcagaaaat | 1140 |
| tcagcgtttc agagatcttc agctaatctt aaaacaacaa tcataagaag gcccagtcga | 1200 |
| tgacactcag ggttctacag ctctcccaca tctgtgaact cgggtttggg gatgttggtt | 1260 |
| aagtttgtgg ctggtcctct ggtttgttgg gagttgagca gccgcagagt cacacacatg | 1320 |
| caaacacgca ctcttcggaa ggcagccact gtctacatca gctgggtgac tcagccctga | 1380 |
| ctcgggcagc agcgagacga tactcctcca ccgtcgccca gcacccgccg gttagctgct | 1440 |
| ccgaggcacg aacacccacg agcgccgcgt aaccgcagca ggtggagcgg gccttgaggg | 1500 |
| agggctccgc ggcgcagatc gaaacagatc gggcggctcg ggttacacac gcacgcacat | 1560 |
| cctgccacgc acactgccac gcacacgcaa cttcacggct cgcctcggac cacagagcac | 1620 |
| tttctccccc tgttgtaaaa ggaaaacaat tggggaaaag ttcgcagcca ggaaagaagt | 1680 |
| tgaaaacatc cagccaagaa gccagttaat tcaaaggaa gaaggggaa aaacaaaaaa | 1740 |
| aaacaacaaa aaaaggaagg tccaacgcag gccaaggaga agcagcagag gttgacttcc | 1800 |
| ttctggcgtc cctaggagcc ccggaaagaa gtgcctggcg gcgcagggcc gggcagcgtg | 1860 |
| gtgccctggc tgggtccggc cgcggggcgc ccgtcccgcc cgcgcccgct ggctctatga | 1920 |
| atgagagtgc ctggaaatga acgtgctttt actgtaagcc cggccggagg aattccattc | 1980 |
| cctcagctcg tttgcatagg ggcggccggc ggccaatcac aggcctttcc ggtatcagcc | 2040 |
| agggcgcggc tcgccgccgc cggctcctgg aattggcccg cgcgccccg ccgccgcgcc | 2100 |
| gcgcgctact gtacgcagcc cggcggggga gtcggaggcc accccgcgc cccgcatcca | 2160 |
| agcctgcatg ctggcccggg gccccgcccg cgtgcgaccc cctttccgca gccacacgca | 2220 |
| ggcttgtgcg gctccgcgag tggccacggt ccggagacct ggaaaaagaa agcaggcccc | 2280 |
| gccggcccga ggaggacccg gccggcgcgc cgcacccgga gaggcccggc cccgcgagcc | 2340 |
| gctgcaggca ggcgcagtgg ccgccacgag gctcccgaac cgggctgcag cccgcggacg | 2400 |
| gccccagatc ctgcgcggcc gcccagggc aggcctccgc ttccagggcg ggggtgcgat | 2460 |
| ttggccgcgg ggcccggggg agccactccg cgctcctgca ccgtccggct ggcagctgcg | 2520 |
| gcgaagcggc gctgattcct tgcatgaggc cggacggcgt ccgcgcgtgc cgtttgctct | 2580 |

```
cagcgtcttc ccttgggtcg gtttctgtaa tgggtgtttt ttaccgctgc gcccgggccg    2640
cggctcgatc cctccgcgcg tctcacttgc tgcgtgcgtc agcggccagc gaagagtttc    2700
ctagtcagga aagaccccaa gaacgcgcgg ctggaaggaa agttgaaagc agccacgcgg    2760
cttgctcccg ggccttgtag cgccggcacc cgcagcagcc ggacagcctg cccgggcccc    2820
gcgtctcccc tccggctccc cggaagcggc ccccgctcct ctccccgccc ccgtgcgctc    2880
gagcggcccc aggtgcggaa cccacccgg cttcgcgtgc gggcggccgc ttccccctgc    2940
gccggtcccc gcggtgctgc gggcattttc gcggagctcg gagggccccg cccccggtcc    3000
ggcgtgcgct gccaactccg accccgcccg gcggggctcc ctcccagcgg aggctgctcc    3060
cgtcaccatg agtccctcca cgccctccct gccgggccct gcacctcccg ggcctctca    3120 tccaccccgg ggctgcaacc cagtcccegg atcccggccc cgttccaccg cgggctgctt    3180
tgtggtcccc gcggagcccc tcaattaagc tccccggcgc ggggtccct cgccgacctc    3240 acggggcccc tgacgcccgc tcctccctcc cccagggcta gggtgctgtg gccgctgccg    3300
cgcagggact gtccccgggc gttgccgcgg gcccggacga aggaggggc cggggttgac    3360 tggcgtggag gcctttcccg ggcgggcccg gactgcgcgg agctgtcggg acgcgccgcg    3420
ggctctggcg gacgccaggg ggcagcagcc gccctccctg gacgccgcgc gcagtccccg    3480
gagctcccgg aacgccccg acggcgcggg gctgtgcggc ccgcctcgtg gccttcgggt    3540
cgcccgggaa gaactagcgt tcgaggataa aagacaggaa gccgccccag agcccacttg    3600
agctggaacg gccaaggcgc gtttccgagg ttccaatata gagtcgcagc cggccaggtg    3660
gggactctcg gaccaggcct ccccgctgtg cggcccggtc ggggtctctt cccgaagccc    3720
ctgttcctgg ggcttgactc gggccgctct tggctatctg tgcttcagga gcccgggctt    3780 ccgggggggct aaggcgggcg gcccgcggcc tcaaccctct ccgcctccgc tccccctggg    3840
cactgccagc acccgagttc agttttgttt taatggacct ggggtctcgg aaagaaaact    3900
tactacattt ttcttttaaa atgatttttt taagcctaat tccagttgta atccccccc    3960 tcccccccgcc caaacgtcca ctttctaact ctgtccctga aagagtgca tcgcgcgcgc    4020 ccgcccgccc gcaggggccg cagcgccttt gcctgcgggt tcggacgcgg cccgctctag    4080
aggcaagttc tgggcaaggg aaaccttttc gcctggtctc caatgcattt ccccgagatc    4140
ccacccaggg ctcctgggc cacccccacg tgcatccccc ggaaccccg agatgcggga    4200 gggagcacga gggtgtggcg gctccaaaag taggcttttg actccagggg aaatagcaga    4260
ctcgggtgat ttgcccctcg gaaaggtcca gggaggctcc tctgggtctc gggccgcttg    4320
cctaaaaccc taaaccccgc gacgggggct gcgagtcgga ctcgggctgc ggtctcccag    4380
gagggagtca agttccttta tcgagtaagg aaagttggtc ccagccttgc atgcaccgag    4440
tttagccgtc agaggcagcg tcgtgggagc tgctcagcta ggagtttcaa ccgataaa     4498
```

<210> SEQ ID NO 75
<211> LENGTH: 453
<212> TYPE: DNA
<213> ORGANISM: Homo sapiens

<400> SEQUENCE: 75

```
ttcggaagtg agagttctct gagtcccgca cagagcgagt ctctgtcccc agcccccaag      60
gcagctgccc tggtgggtga gtcaggccag gcccggagac ttcccgagag cgagggaggg    120
acagcagcgc ctccatcaca gggaagtgtc cctgcgggag gccctggccc tgattgggcg    180
ccggggcgga gcggcctttg ctctttgcgt ggtcgcgggg gtataacagc ggcgcgcgtg    240
```

```
gctcgcagac cggggagacg ggcgggcgca cagccggcgc ggaggcccca cagccccgcc      300
gggacccgag gccaagcgag gggctgccag tgtcccggga cccaccgcgt ccgccccagc      360
cccgggtccc cgcgcccacc ccatggcgac ggacgcggcg ctacgccggc ttctgaggct      420
gcaccgcacg gagatcgcgg tggccgtgga cag                                   453
```

<210> SEQ ID NO 76
<211> LENGTH: 560
<212> TYPE: DNA
<213> ORGANISM: Homo sapiens

<400> SEQUENCE: 76

```
acgcacactg ggggtgtgat ggaaagggg acgcgatgga taggggtggg cgcacactgg       60
gggacgcgac ggggagggggt gagcacacac tgggggtgtg atggagaggg cgacgcaata    120
gggaggggtg ggcgcacacc agggacgcga tgatgggggac gggtgggcgc acaccaggtg    180
gcatgatggg gaggagtggg tacacaccat gggggggcgtg atggggaggc gtgggcgtac    240
accggggggc gcgatgggga ggggtgggcg cacaccgggg gacgcgatgg aggcggtggg    300
tgcacacggg gcgcgatggg tgggagtagg tgcacactga gggcacgatt ggggagacac    360
gaaggagagg ggtgggcgca cactggggga gcgcgatggcc gggacacgat gcggagaagt    420
gggtgaatac cggggtcgcg atgggcgccc tggaaggacg gcagtgctgc tcacaggggc    480
caggcccctc agagcgcgcc ccttgggggt aaccccagac gcttgttccc gagccgactc    540
cgtgcactcg acacaggatc                                                  560
```

<210> SEQ ID NO 77
<211> LENGTH: 157
<212> TYPE: DNA
<213> ORGANISM: Homo sapiens

<400> SEQUENCE: 77

```
ccacagggtg gggtgcgccc acctgccctg tccatgtggc cttgggcctg cggggggagag     60 ggaatcagga cccacagggc gagccccctc cgtagcccgc ggcaccgact ggatctcagt    120
gaacacccgt cagcccatcc agaggctaga aggggga                              157
```

<210> SEQ ID NO 78
<211> LENGTH: 114
<212> TYPE: DNA
<213> ORGANISM: Homo sapiens

<400> SEQUENCE: 78

```
ttgaggtctc tgtgcatgct tgtgcgtacc ctggactttg ccgtgagggg tggccagtgc      60
tctgggtgcc tttgccagac aactggtctg ccgggccgag cattcatgct ggtc           114
```

<210> SEQ ID NO 79
<211> LENGTH: 104
<212> TYPE: DNA
<213> ORGANISM: Homo sapiens

<400> SEQUENCE: 79

```
tgacgcgccc ctctcccccgc agctccacct ggttgcgctc aacagccccc tgtcaggcgg     60
catgcggggc atccgcgggg ccgacttcca gtgcttccag cagg                      104
```

<210> SEQ ID NO 80
<211> LENGTH: 659
<212> TYPE: DNA
<213> ORGANISM: Homo sapiens

<400> SEQUENCE: 80

```
aacacactgt ctcgcactag gtgctcgcgg aagagcgcgg cgtcgatgct gcggctcagg      60
ttgatgggcg atggcggccg cagatccagc tcgctcagcg atggcgccgg tcccacaccg     120
ttgcgggaca gtcccgggcc accctggggt ccgcgaccca cgacgcagc cgagccccag     180
gcgcctgaac tgggcgtggc cagctgccca ctctccgccg ggttgcggat gaggctcttg     240
ctgatgtcca agctgcctgc accaacgttg ctgggccctg catagcagtt attgggtcgc     300
tccggcacct cgctctttcc tgacggcgcc gggcacgcca gacgcatcag cttagcccag     360
caagcgtgct ccgtgggcgg cctgggtctc gcggcagcca ccgcggccaa cgccagggcg     420
agcgcccatg tcagctccag gaggcgcagc cagaagtgga caccccacca ggcccacgag     480
aagcggccca cgcggcctgg gcccgggtac agcagagcg cagccgccag ctgcaagccg     540
ctagccagca gccccagcgc gcccgccaca gccaacagcc gagggcccgg gctggcatcc     600
cagccccgtg ggccgtccag caggcggcga cggcacaggc agagcgtgcc cagagccac     659
```

<210> SEQ ID NO 81
<211> LENGTH: 813
<212> TYPE: DNA
<213> ORGANISM: Homo sapiens

<400> SEQUENCE: 81

```
gtctgcacga agcccgcggc ggcctgcagg gggcccagcg actcgtccag ggaaccggtg      60
cgcaggagca gccgggggcg cggcgcgccg gccgcccttg ggggactctg gggccggggg     120
cgcagctcga tctgacgctt gggcactgtc cggggcctgg cgggcgcggc gccctcctcc     180
agagccacct ccacacactc gaactgcgct ggggcggcag gacttggccc acggggccgc     240
agctctaggt aggtggccca gcgggagcca ccatcgggga cctgggactg gcgtgggacc     300
gcggcgggag acgctggccc cggcggcaag gggctgatga aggccggctc cgtgaactgt     360
tgttgcgcct cgcgatcgtc tgcgccgag cagccgaaca ggggtccgac gccgaagatg     420
acttccatct cccccgacgg cagcgtgcgc agctggggct ggggtggccg tgggccggaa     480
cctgggcctc gcgggaaacc cgagccggc ccgtgccgct ggcggctatt ctgggcgctg     540
acggacaggc gaggctgcgc gcccgccccc cgcccaggag ccacccaggg ccaattcgct     600
gggccttcg cgtccggccc aacgtccggg ggctccggag aacctggagc cgtgtagtag     660
gagcctgacg aaccggagga gtcctggcgc cgcgcggggg ccgtgggcag ctgcctcggg     720
atcccaggca gggctggcgg ggcgagcgcg gtcagcatgg tggggccgga cgccgtgcac     780
tatctcccct gcattcgcct ccgctggtgg cgc                                  813
```

<210> SEQ ID NO 82
<211> LENGTH: 440
<212> TYPE: DNA
<213> ORGANISM: Homo sapiens

<400> SEQUENCE: 82

```
ctggagagaa ctatacgggc tgtgggagtc accgggcgac tatcaccggg cctcctttcc      60
acatcctcct ccgggaaggg acccgttcc gggcctcgac cggcgcagac tgggctgacc     120
cactttcttg ggcccactga gtcacctcga aacctccagg ccggtagcgg ggaggagagg     180
aggagcaggc gggggtgcca aggtgtgggc tgcgccctgg ttaggggcg agcccggctt     240
gtttatgagg aggagcgcgg aggaggatcc agacacacag gcttgcgcgc ccagactcgc     300
ccggccagcg gctggcggcc tccgacgtca ccaaaccggt tgggtgagag ggcagagagc     360
```

```
aggggggaagg gccgcagtcc cgcccgcgcc ccccggcacg caccgtacat cttgccctcg    420
tctgacagga tgatcttccg                                                 440

<210> SEQ ID NO 83
<211> LENGTH: 252
<212> TYPE: DNA
<213> ORGANISM: Homo sapiens

<400> SEQUENCE: 83
gagtgcggag tgaaggggtg cactgggcac tcagcgcggc ccttgggagg cagggccgcc     60
ccagcctgcc ctcctgtctg ggaaggccgt ccagaagcag gagccccggg gaaaacaact    120
ggctggacgg ggcggccttc agtgtctctc ccagcctgag agtcgcttcc caccacctgg    180
gcacgaacct gctctgcgat ctccggcaag ttcctgcgcc tcctgtcggt aaaatgcaga    240
tcgtggcgtc tt                                                        252

<210> SEQ ID NO 84
<211> LENGTH: 1539
<212> TYPE: DNA
<213> ORGANISM: Homo sapiens

<400> SEQUENCE: 84
tcttctttcc gccccctaggg ggcacaagcg ggcatgtcca agcgcctagg agcccgtacc     60 gctgggacc tcccccttccg cgaacccga gcgggtagac ccagagcaat ccgagtgtgg    120
aaacaatgga gagggggcgt gttgagctgg ggtctccatg cctcgttggg gagagggagg    180
tgagtttgtg tcttctggaa ggcgtgggggg ctgtgccctc gtgggggtag gaagtgctcc    240
cgtggggcgg ggtgcggatc ggagaggtga gtgggtgcgt ctgtccagcg gtccgcccgg    300
tgtggtcgtg cccggcccgc gtggggatgg gggtgtctct cccgctgggc aactatacca    360
gcgcaaccgg ggcgtcggcg cggcccacgc tagcggcgct gctccggcgg cggggggctgg    420 gcgtggcggt gatgctgggc gtggtggccg cgctgggcgt ggtggccgcg ctgccgccct    480 caccccgggca gccgtgctgg agaaggatgt cggcgcacag ctggcttcca gcctggcggg    540
cgtagaacag cgccgtgcgg ccctgggcgt cacgggccgc cacgtccgcg ccgtactaga    600
gggcggaaac ggccgcgtga ccgcgcgtcc cagggcgcc cacacccggc gccgcctccc    660
ccacatggcc aagcctactt ccggggtccc tctgggaatt cgggcttttc ccgcgccagg    720
cgttttccga gatgaagcct caaagacccc ctttcctccc cccagctcac gtacccacag    780
cagcagttgc gtgatgacga cgtgggcgag ctcggccgcc aggtggagtg gggagcgcag    840
ctgtgggtcc tctacgctgg tgtcgagcgg cccgtgtcgc gcatgggcca aaagcaggag    900
aacggtagcc acgtcctggg cctgcacggc ggcccacagc tggcggccca gcggctcctc    960
cgaggtgctc agcggcgcca ggaacagtag ctgctcgtac ttggcgcgaa tccacgactc   1020
gcgctcctcc ctgcaagacc agggatcaac ggaaaaggct ctaggacccc cagccagga   1080 cttctgcccc tacccacggg accgtctcag gttcgcacac cctcagcaac cctccccccg   1140
ctctgttccc tcacgcttac cgcgaagagt cccgcgaggg cttggcacgg cctcgcgtgt   1200
cgctttccca cacgcggttg gccgtgtcgt tgccaatagc cgtcagcacc agggtcagct   1260
cccgtggcca gtcgtccaag tccagcgagc gaacgcggga caggtgtgtg cccaggttgc   1320
ggtggatgcc agaacactcg atgcagatga gggcgcccag gttcaagctg cccacgtgg    1380 ggtctgcgga aggagcgtag aggtcggctc ccagccgggc agcacaggca ccccggcatt   1440
```

| | |
|---|---|
| cactacactc cctagcccct ccgctgcctc ctggcactca ctgggggccc cgcagtccac | 1500 |
| gcagattgaa ttcccttgg cgttccggat cgcctggat | 1539 |

<210> SEQ ID NO 85
<211> LENGTH: 2648
<212> TYPE: DNA
<213> ORGANISM: Homo sapiens

<400> SEQUENCE: 85

| | |
|---|---|
| agccaggtcc agccccgcg cctgacaccg gccggacgtt cccggggcgc cgcagctgcg | 60 |
| gcgggaactc tgggatccgg agccatctgc tcccacccgc tccggagcca aaccccgggg | 120 |
| gccgcctccg ctcccggacc cgcctcctct cccgggagtg tgagccgaac caagagtctc | 180 |
| ctgcctatct cctccagtag gaaaatagta ataataatag acaccctgcc cccgtaaaaa | 240 |
| acactacctt ccccgtaccg cctcccaagt ctcccggggt acggattgcc tttgcagcag | 300 |
| ttccgcccca cctgactcac tccagggtca gccccgggtg ggtttcaatg cggctctggg | 360 |
| gagggggtgg gcagtggggg aagtgaggct tcctatccgc cccctctcac ttcacattta | 420 |
| aatattctgc acgttccagc ccccgcggac tcgcgtaccg cccaatccgc cttcaccgca | 480 |
| cgaaaaacat cactagcctg ctctcagccc aggggacgac tagtccctgg cgagaagctg | 540 |
| cctgcaaggt cactgtcatg ccacctgccc caagtgctca ggggaaactg aggcttcctc | 600 |
| atccccttca ccttcaacgt cgctctaaac acggcaaagc cccgtttcca tgctcccaga | 660 |
| gttcagctga ggctggaagt ggggtcctgg gcttctctgg gagcaatttt ctagtcactc | 720 |
| tgatcaagga cgttactttc ccagaaagct ctgaggctga gtccctctga aatcaagtcc | 780 |
| tttctcctgt cgcacaatgt agctactcgc cccgcttcag gactcctatt ctttgcccca | 840 |
| atccttgaca gaggggtgag cttggttcat ccgcccaccc cagagaaaag cttccctagt | 900 |
| ttcctggacc tcgctcctcc accccaagct gagcattcca ggtacccttc cctccctgtt | 960 |
| ctcaagccct gactcaactc actagggaa gcgcggagct cggcgcccag cagctccctg | 1020 |
| gacccgctgc cagaagacag gctgggggt ccgggaaggg gccggagcc aggaggccct | 1080 |
| cctgtgctct tggtgaagat gccgctgata aacttgagca tcttgcggtc acgagtggat | 1140 |
| gctcggcccc cctcccggcc ccgtttcagc cccggagctg gaggctccag agtgattgga | 1200 |
| ggtgcaggcc cggggggctg cgcggaagca gcggtgacag cagtggctgg actcggagtt | 1260 |
| ggtgggaggg ttagcggagg aggagagccg gcaggcggtc ccggatgcaa gtcactgttg | 1320 |
| tccaaggtct tactcttgcc tttccgaggg gacaacttcc ctcgggctcc agccccagcc | 1380 |
| ccgaccccac cagaggtcga agctgtagag ccccctcccc cggcggcggc ggcggtggcg | 1440 |
| gcggcagaga ccgaagctcc agtcccggcg ctgctctttg acccttgac cctgggcttg | 1500 |
| ccctcgcttt cgggccatga caggcggcta cccgcgcccc tgccccgcc ggctttggct | 1560 |
| ccactcgtgg tcacggtctt gcaaggcttg ggagccggcg gaggaggcgc caccttgagc | 1620 |
| ctccggctgc cggtgccagg gtgcggagag gatgagccag gatgccgcc gcccgcccgg | 1680 |
| ccttcgggct ccgggccgcc ccagctcggg ctgctgagca ggggcgccg ggaggaggtg | 1740 |
| ggggcgcccc caggcttggg gtcggggctc agtccccgg agagcggggg tcccggaggg | 1800 |
| acggcccaga gggagaggcg gcggccggga gcggggaga ctgggcgggc cggactggcc | 1860 |
| ggagccgggg acagggctgg gggtccgcgc ccccggtgc ccgcgctgct cgtgctgatc | 1920 |
| cacagcgcat cctgccggtg gaagagacgt tcgtgccgct tcttgcccgg ctcctccgcg | 1980 |
| cctcgggggc tgccaggatc cccagtctcg gagcctctgg caccggcggc gccggccgcg | 2040 |

-continued

| | |
|---|---|
| gccgcagacg gagaaggcgg cggcggaggc accgactcga gcttaaccag ggtcagcgag | 2100 |
| atgaggtagg tcgttgtccg gcgctgaagc gcgcccgcgc cccggctcat ggggcccgga | 2160 |
| gaccccgag ctggggaggg gaggggactc ccccggactg cctcaggggg gcccggccat | 2220 |
| ggggccgccc tgctcgctgc ccccagcccc cggaccccgc tgagccccg gcccggctcc | 2280 |
| gctgtcgccg ccgcctccgc cgcctccgct tgcgccccc tcccatcaca tggggcgccc | 2340 |
| cctccccatg ctccccgccc tgcgccccca ccctcttgga gccccgggac cttggtgctg | 2400 |
| ctccaggag gcgcgccgga ccgtccaccc cggcctgggt gggggcgctg agatgggtgg | 2460 |
| gggagggcgg ggaggacagt agtgggggca aatgggggag agagaggaaa agggagcaga | 2520 |
| aaaggggacc ggaggctagg ggaaacgaac ctgtgcgggg gaggcagggg cggggaattg | 2580 |
| ggactcaagg gacaggggcc gcggatgcgg tcggaaagag ggtctagagg agggtgggaa | 2640 |
| gctagtgg | 2648 |

<210> SEQ ID NO 86
<211> LENGTH: 452
<212> TYPE: DNA
<213> ORGANISM: Homo sapiens

<400> SEQUENCE: 86

| | |
|---|---|
| aggagcgcaa ggcttgcagg gcatgctggg agagcgcagg gaacgctggg agagcgcggg | 60 |
| aaatactggg attggctccc gagggctgtg aggagggcac gaggggacac tccgatgaag | 120 |
| gcagggcacg cggggcgagc cgggagcgtc tcctgagggc agcgaggagg gagctgaggc | 180 |
| acgcgggctc tcaatcgacg ccccacagag accaagaggc ctggccttgg ggggcagctg | 240 |
| cttgaaggag gcagagcgga agcgagggag actgctggag gccctgccgc ccacccgccc | 300 |
| tttcctcccc ctgaggagac gcctgacgca tctgcagtgc aggaggccgt gggcgttaga | 360 |
| agtgttgctt ttccagtttg taagaccatt ttcctgattc tcttccccac ggttgcggag | 420 |
| gagcaggtca gggccgccat gagggcagga tc | 452 |

<210> SEQ ID NO 87
<211> LENGTH: 232
<212> TYPE: DNA
<213> ORGANISM: Homo sapiens

<400> SEQUENCE: 87

| | |
|---|---|
| tcgaccgcta ctattatgaa aacagcgacc agcccattga cttaaccaag tccaagaaca | 60 |
| agccgctggt gtccagcgtg gctgattcgg tggcatcacc tctgcgggag agcgcactca | 120 |
| tggacatctc cgacatggtg aaaaacctca caggccgcct gacgcccaag tcctccacgc | 180 |
| cctccacagt ttcagagaag tccgatgctg atggcagcag ctttgaggag gc | 232 |

<210> SEQ ID NO 88
<211> LENGTH: 221
<212> TYPE: DNA
<213> ORGANISM: Homo sapiens

<400> SEQUENCE: 88

| | |
|---|---|
| tgtgccgtcg cacacagacg ccctcaacgt cggagagctg tgagcggggc cgtgctcttg | 60 |
| ggatgggagc ccccgggaga gctgcccgcc aacaccactc cgacgtgatc catgctggac | 120 |
| ataaagtgct cttccctccg ctagtcatcg gccgagcggg cccctcgctc ctgggtgtaa | 180 |
| gttctttctg tgcgtccttc tcccatctcc gtgcagttca g | 221 |

```
<210> SEQ ID NO 89
<211> LENGTH: 477
<212> TYPE: DNA
<213> ORGANISM: Homo sapiens

<400> SEQUENCE: 89
ccatgcgccg ctgcgcgcgc gagttcgggc tgctgctgct gttcctctgc gtggccatgg      60
cgctcttcgc gccactggtg cacctggccg agcgcgagct gggcgcgcgc cgcgacttct     120
ccagcgtgcc cgccagctat tggtgggccg tcatctccat gaccaccgtg ggctacggcg     180
acatggtccc gcgcagcctg cccgggcagg tggtggcgct cagcagcatc ctcagcggca     240
tcctgctcat ggccttcccg gtcacctcca tcttccacac cttttcgcgc tcctactccg     300
agctcaagga gcagcagcag cgcgcggcca gccccgagcc ggccctgcag gaggacagca     360
cgcactcggc cacagccacc gaggacagct cgcaggccc cgacagcgcg ggcctggccg     420
acgactccgc ggatgcgctg tgggtgcggg cagggcgctg acgcctgcgc cgcccac       477

<210> SEQ ID NO 90
<211> LENGTH: 88
<212> TYPE: DNA
<213> ORGANISM: Homo sapiens

<400> SEQUENCE: 90
gattgacagt ttctccttcc ccagactggc caatcacagg caggaagatg aaggttctgt      60
gggctgcgtt gctggtcaca ttcctggc                                         88

<210> SEQ ID NO 91
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
acgttggatg ttgacagttt ctccttcccc                                       30

<210> SEQ ID NO 92
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
acgttggatg gaatgtgacc agcaacgcag                                       30

<210> SEQ ID NO 93
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
gcaggaagat gaaggtty                                                    18

<210> SEQ ID NO 94
<211> LENGTH: 88
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 94
gattgacagt ttctccttcc ccagactggc caatcacagg caggaagatg aaggttttgt        60
gggctgcgtt gctggtcaca ttcctggc                                          88

<210> SEQ ID NO 95
<211> LENGTH: 90
<212> TYPE: DNA
<213> ORGANISM: Homo sapiens

<400> SEQUENCE: 95
gagttttgga tagtaaaata agtttcgaac tctggcacct ttcaattttg tcgcactctc        60
cttgtttttg acaatgcaat catatgcttc                                        90

<210> SEQ ID NO 96
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
acgtggatag taaaataagt ttcgaactct g                                       31

<210> SEQ ID NO 97
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
gaagcatatg attgcattgt caaaaac                                            27

<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
atttcaattt tgtcgcacty                                                    20

<210> SEQ ID NO 99
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
gagttttgga tagtaaaata agtttcgaac tctggcacct ttcaattttg tcgcactttc        60
cttgtttttg acaatgcaat catatgcttc                                        90
```

-continued

<210> SEQ ID NO 100
<211> LENGTH: 97
<212> TYPE: DNA
<213> ORGANISM: Homo sapiens

<400> SEQUENCE: 100
gaactcctct tgtctctgc gtgcccggcg cgccccctc ccggtgggtg ataaacccac    60
tctggcgccg gccatgcgct gggtgattaa tttgcga                          97

<210> SEQ ID NO 101
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
acgttggatg tctttgtctc tgcgtgccc                                   29

<210> SEQ ID NO 102
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
acgttggatg ttaatcaccc agcgcatggc                                  30

<210> SEQ ID NO 103
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
cccctcccgg tgggtgataa ay                                          22

<210> SEQ ID NO 104
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
gaactcctct tgtctctgc gtgcccggcg cgccccctc ccggtgggtg ataaatccac    60
tctggcgccg gccatgcgct gggtgattaa tttgcga                          97

<210> SEQ ID NO 105
<211> LENGTH: 86
<212> TYPE: DNA
<213> ORGANISM: Homo sapiens

<400> SEQUENCE: 105
ccattggccg tccgccgtgg cagtgcgggc gggagcgcag ggagagaacc acagctggaa    60
tccgattccc accccaaaac ccagga                                        86

```
<210> SEQ ID NO 106
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
acgttggatg ccattggccg tccgccgtg                                    29

<210> SEQ ID NO 107
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
acgttggatg tcctgggttt tggggtggga a                                 31

<210> SEQ ID NO 108
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
ttccagctgt ggttctctc                                               19

<210> SEQ ID NO 109
<211> LENGTH: 86
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
ccattggccg tccgccgtgg cagtgcgggc gggagcgcag agagagaacc acagctggaa   60
tccgattccc accccaaaac ccagga                                       86

<210> SEQ ID NO 110
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
acgttggatg acatggtcgg ccccacggaa t                                 31

<210> SEQ ID NO 111
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
acgttggatg acccattggc cgtccgccgt                                   30
```

<210> SEQ ID NO 112
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 112
acgttggatg gaactcctct ttgtctctgc g                              31

<210> SEQ ID NO 113
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 113
acgttggatg cgcagcaacg ggaccgctac a                              31

<210> SEQ ID NO 114
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 114
acgttgcgta gcaacctgtt acatattaa                                 29

<210> SEQ ID NO 115
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 115
acgttggatg catagaggcc catgatggtg g                              31

<210> SEQ ID NO 116
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 116
acgttggatg gtgtggtcag ctcttccctt cat                            33

<210> SEQ ID NO 117
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 117
acgttggatg ctccttccta gtgtgagaac cg                             32

<210> SEQ ID NO 118
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 118
acgttggatg ttttggggtg ggaatcggat t                              31

<210> SEQ ID NO 119
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 119
acgttggatg tggcatggcc ggcgccaga                                 29

<210> SEQ ID NO 120
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 120
acgttggcat ctaggtaggt ctttgtagcc aa                             32

<210> SEQ ID NO 121
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 121
acgttggatc tgagcaaagg caatcaacac cc                             32

<210> SEQ ID NO 122
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 122
acgttggatg accttctgcc cctctactcc aa                             32

<210> SEQ ID NO 123
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 123
acgttggccc acatgtaatg tgttgaaaaa gca                            33

```
<210> SEQ ID NO 124
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
caggttccgg ggcttggg                                                 18

<210> SEQ ID NO 125
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
cgcagggaga gaaccacag                                                19

<210> SEQ ID NO 126
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
cccctcccgg tgggtgataa a                                             21

<210> SEQ ID NO 127
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
aaagctgtag gacaatcggg t                                             21

<210> SEQ ID NO 128
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128 cattttctcta catcctttgt tt                                           22

<210> SEQ ID NO 129
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
agaagatcac caggcagaag agg                                           23
```

```
<210> SEQ ID NO 130
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
acttggagaa caaaggacac cgtta                                          25

<210> SEQ ID NO 131
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
ggtcggcccc acggaatccc ggctctgtgt gcgcccaggt tccggggctt gggtgttgcc    60
ggttctcaca ctaggaagga g                                              81

<210> SEQ ID NO 132
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
ccattggccg tccgccgtgg cagtgcgggc gggagcgcag agagagaacc acagctggaa    60
tccgattccc accccaaaa                                                 79

<210> SEQ ID NO 133
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
gaactcctct ttgtctctgc gtgcccggcg cgccccctc ccggtgggtg ataaatccac     60
tctggcgccg gccatgc                                                   77

<210> SEQ ID NO 134
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
gcagcaacgg gaccgctaca gccactggac aaagccgtag acaatcggg taacattggc     60 tacaaagacc tacctagatg c                                              81

<210> SEQ ID NO 135
<211> LENGTH: 95
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 135
gcgtagcaac ctgttacata ttaaagtttt attatactac attttttctac atcctttgtt    60 tcagagtgtt gattgccttt gctcagtatc ttcag                               95

<210> SEQ ID NO 136
<211> LENGTH: 86
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
ccttctgccc ctctactcca agcgctacac cctcttctgc ctggtgatct ttgccggcgt    60
cctggccacc atcatgggcc tctatg                                        86

<210> SEQ ID NO 137
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
gtgtggtcag ctcttcccctt catcacatac ttggagaaca aggacaccg ttatccatgc    60 tttttcaaca cattacatgt ggg                                           83

<210> SEQ ID NO 138
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138
acgttggatg ttctgcccct ctactccaag                                    30

<210> SEQ ID NO 139
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
acgttggatg tcagctcttc ccttcatcac                                    30

<210> SEQ ID NO 140
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 140
acgttggatg ttgacagttt ctccttcccc                                    30
```

```
<210> SEQ ID NO 141
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
acgttggatg cggtcggccc cacggaat                                        28

<210> SEQ ID NO 142
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142
acgttggatg taaaataagt ttcgaactct g                                    31

<210> SEQ ID NO 143
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143
acgttggatg cacagctcac cgcagcaacg                                      30

<210> SEQ ID NO 144
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 144
acgttggatg tctttgtctc tgcgtgccc                                       29

<210> SEQ ID NO 145
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145
acgttggatg gactgagccc cagaactcg                                       29

<210> SEQ ID NO 146
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146
acgttggatg aagccaagtt tccctccgc                                       29
```

<210> SEQ ID NO 147
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 147
acgttagcgt agcaacctgt tacatattaa          30

<210> SEQ ID NO 148
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 148
acgttggatg catagaggcc catgatggtg          30

<210> SEQ ID NO 149
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 149
acgttggatg cctacctccc acatgtaatg t          31

<210> SEQ ID NO 150
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 150
acgttggatg gaatgtgacc agcaacgcag          30

<210> SEQ ID NO 151
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 151
acgttggatg ctccttccta gtgtgagaac cg          32

<210> SEQ ID NO 152
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 152
gaagcatatg attgcattgt caaaaac          27

```
<210> SEQ ID NO 153
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 153
acgttggatg ctaggtaggt ctttgtagcc aa                                    32

<210> SEQ ID NO 154
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 154
acgttggatg ttaatcaccc agcgcatggc                                       30

<210> SEQ ID NO 155
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 155
acgttggatg gtgggtttgt gctttccacg                                       30

<210> SEQ ID NO 156
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 156
acgttggatg cttttgcttt cccagccagg                                       30

<210> SEQ ID NO 157
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 157
acgttggatg ctgagcaaag gcaatcaaca                                       30

<210> SEQ ID NO 158
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 158
ttctgcctgg tgatctt                                                     17
```

<210> SEQ ID NO 159
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 159
aacaaaggac accgtta                                                17

<210> SEQ ID NO 160
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 160
gcaggaagat gaaggtt                                                17

<210> SEQ ID NO 161
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 161
aaggttccgg ggcttggg                                               18

<210> SEQ ID NO 162
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 162
atttcaattt tgtcgcact                                              19

<210> SEQ ID NO 163
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 163
agctgtagga caatcgggt                                              19

<210> SEQ ID NO 164
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 164
ccctcccggt gggtgataaa                                             20

```
<210> SEQ ID NO 165
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 165
agggccgggg tctgcgcgtg                                                 20

<210> SEQ ID NO 166
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 166
gaggcactgc ccggacaaac c                                               21

<210> SEQ ID NO 167
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 167
catttttcta catcctttgt tt                                              22

<210> SEQ ID NO 168
<211> LENGTH: 86
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
ccttctgccc ctctactcca agcgctacac cctcttctgc ctggtgatct ttgccggcgt     60
cctggccacc atcatgggcc tctatg                                          86

<210> SEQ ID NO 169
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
gtgtggtcag ctcttccctt catcacatac ttggagaaca aaggacaccg ttatccatgc     60
tttttcaaca cattacatgt gggaggtagg                                      90

<210> SEQ ID NO 170
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 170
gattgacagt ttctccttcc ccagactggc caatcacagg caggaagatg aaggttttgt    60
gggctgcgtt gctggtcaca ttcctggc                                      88

<210> SEQ ID NO 171
<211> LENGTH: 98
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
aaaaccagag attcgcggtc ggccccacgg aatcccggct ctgtgtgcgc ccaggttccg    60
gggcttgggt gttgccggtt ctcacactag gaaggagc                           98

<210> SEQ ID NO 172
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
gagttttgga tagtaaaata agtttcgaac tctggcacct ttcaattttg tcgcactttc    60
cttgtttttg acaatgcaat catatgcttc                                    90

<210> SEQ ID NO 173
<211> LENGTH: 95
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
gcagccagct caccgcagca acgggaccgc tacagccact ggacaaagct gtaggacaat    60
cgggtgacat tggctacaaa gacctaccta gatgc                              95

<210> SEQ ID NO 174
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174
gaactcctct ttgtctctgc gtgcccggcg cgcccccctc ccggtgggtg ataaatccac    60
tctggcgccg gccatgcgct gggtgattaa tttgcga                            97

<210> SEQ ID NO 175
<211> LENGTH: 86
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 175
gtgggtttgt gctttccacg cgtgcacaca cacgcgcaga ccccggccct tgccccgcct    60
acctccccga gttctggggc tcagtc                                          86

<210> SEQ ID NO 176
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
gcgccagctt ttgctttccc agccagggcg cggtgaggtt tgtccgggca gtgcctcgag    60
caactgggaa ggccaaggcg gagggaaac                                       89

<210> SEQ ID NO 177
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
gcgtagcaac ctgttacata ttaaagtttt attatactac atttttctac atcctttgtt    60
ttagggtgtt gattgccttt gctcagtatc ttcagc                              96

<210> SEQ ID NO 178
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
cgcaaccact                                                            10

<210> SEQ ID NO 179
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
cgcgaccact                                                            10
```